(12) United States Patent
Yamamura et al.

(10) Patent No.: US 7,446,187 B2
(45) Date of Patent: Nov. 4, 2008

(54) PLASMIDS AND UTILIZATION THEREOF

(75) Inventors: Eitora Yamamura, Takaoka (JP); Noboru Fujimoto, Takaoka (JP)

(73) Assignee: Daiichi Fine Chemical Co., Ltd., Takaoka-shi, Toyama (JP)

( * ) Notice: Subject to any disclaimer, the term of this patent is extended or adjusted under 35 U.S.C. 154(b) by 126 days.

(21) Appl. No.: 10/577,296

(22) PCT Filed: Oct. 29, 2004

(86) PCT No.: PCT/JP2004/016104

§ 371 (c)(1),
(2), (4) Date: Apr. 28, 2006

(87) PCT Pub. No.: WO2005/042739

PCT Pub. Date: May 12, 2005

(65) Prior Publication Data

US 2007/0031948 A1 Feb. 8, 2007

(30) Foreign Application Priority Data

Oct. 31, 2003 (JP) .............................. 2003-373476

(51) Int. Cl.
*C07H 21/02* (2006.01)
*C07H 21/04* (2006.01)
*C12N 15/63* (2006.01)
*C12P 13/00* (2006.01)

(52) U.S. Cl. .................... 536/23.1; 435/320.1; 435/128; 435/252.2; 536/23.2

(58) Field of Classification Search ........................ None
See application file for complete search history.

(56) References Cited

U.S. PATENT DOCUMENTS

| 4,920,054 A | 4/1990 | Kozlowski et al. |
| 2004/0091981 A1 | 5/2004 | Sakamoto et al. |
| 2004/0247583 A1 | 12/2004 | Sakamoto et al. |

FOREIGN PATENT DOCUMENTS

| EP | 0 482 426 | 4/1992 |
| EP | 0502476 | 9/1992 |
| EP | 0 757 101 | 2/1997 |
| EP | 1127943 | 8/2001 |
| JP | 4-148685 | 5/1992 |
| JP | 4-330287 | 11/1992 |
| JP | 9-28379 | 2/1997 |
| WO | 89/07151 | 8/1989 |
| WO | WO 01/73100 | 10/2001 |
| WO | 02/055709 | 7/2002 |
| WO | WO 02/070714 | 9/2002 |

OTHER PUBLICATIONS

"Construction of an Escherichia coli-Rhodococcus Shuttle Vector and Plasmid Transformation in Rhodococcus spp." As published Feb. 1988 Journal of Bacteriology, vol. 170, No. 2 pp. 638-645.
International Search Report for PCT/JP2004/016104 dated Dec. 28, 2004 (4 pages).
"Structural analysis of the 6 kb cryptic plasmid pFAJ2600 from Rhodococcus erythropolis N186/21 and construction of Escherichia coli-Rhodococcus shuttle vectors" As published in Microbiology, , vol. 143, 1997 pp. 3137 to 3147.
"A small cryptic plasmid from Rhodococcus erythropolis: characterization and utility for gene expression" As published in Appl. Microbiol. Biotechnol., vol. 62, No. 1, Jul. 2003 pp. 61 to 68.
English translation of PCT International Preliminary Report on Patentability, issued Aug. 3, 2006, during the prosecution of International Application No. PCT/JP2004/016104 (7 pages).
M.E. Vogt Singer et al., "Construction of an Escherichia coli-Rhodococcus Shuttle Vector and Plasmid Transformation in Rhodococcus spp."; Journal of Bacteriology, vol. 170, No. 2, p. 638-645 dated Feb. 1988, 8 pages.
European Search Report dated Mar. 4, 2008 issued in European Patent Application No. EP 04 79 3212, 7 pages.
Claude Denis-Larose, et al., "Characterization of the Basic Replicon of Rhodococcus Plasmid pSOX and Development of a Rhodococcus-Escherichia coli Shuttle Vector"; Applied and Environmental Microbiology, p. 4363-4367, Nov. 1998, 5 pages.

*Primary Examiner*—Rebecca E. Prouty
*Assistant Examiner*—MD. Younus Meah
(74) *Attorney, Agent, or Firm*—Osha · Liang LLP

(57) ABSTRACT

A shuttle vector is constructed by preparing a DNA region replicable in bacteria belonging to the genus *Rhodococcus* from a *Rhodococcus*-derived plasmid having the nucleotide sequence set forth as SEQ ID NO: 73 and a plasmid or its DNA fragment having the nucleotide sequence set forth as SEQ ID NO: 74, and a DNA region replicable in *E. coli* from an *E. coli*-derived plasmid or its DNA fragment. An aminoketone asymmetric reductase gene is inserted into the shuttle vector, transformants containing the vector are created, and the aminoketone asymmetric reductase and optically active aminoalcohols are produced.

6 Claims, 5 Drawing Sheets

SEQUENCE LISTING

<160> NUMBER OF SEQ ID NOS: 100

<210> SEQ ID NO 1
<211> LENGTH: 279
<212> TYPE: DNA
<213> ORGANISM: Rhodococcus erythropolis
<220> FEATURE:
<221> NAME/KEY: misc_feature
<223> OTHER INFORMATION: 202bp to 480bp pRET1100

<400> SEQUENCE: 1

```
atgactctga gggtggacga accggagtcg gtgagaatgc ttcatccgag cgcttccccg        60
gaagactgtg ccctggtcga gaccttcaag cctggtacct gccttttcga gaagccagga       120
gaaggccggc agattatgcg atgcgacttt gtcggcgagt acgggagata tgcgcgagcc       180
```

```
atcgagtctt cggatctgcg ttttctcgcc accctccagc aagaccaggc ccaacgcgaa      240
ttcttcgctg aggagttcgg tgtggtggat ccgtcatga                              279

<210> SEQ ID NO 2
<211> LENGTH: 243
<212> TYPE: DNA
<213> ORGANISM: Rhodococcus erythropolis
<220> FEATURE:
<221> NAME/KEY: misc_feature
<223> OTHER INFORMATION: 238bp to 480bp pRET1100

<400> SEQUENCE: 2
atgcttcatc cgagcgcttc cccggaagac tgtgccctgg tcgagacctt caagcctggt       60
acctgccttt tcgagaagcc aggagaaggc cggcagatta tgcgatgcga ctttgtcggc      120
gagtacggga gatatgcgcg agccatcgag tcttcggatc tgcgttttct cgccaccctc      180
cagcaagacc aggcccaacg cgaattcttc gctgaggagt tcggtgtggt ggatccgtca      240
tga                                                                    243

<210> SEQ ID NO 3
<211> LENGTH: 144
<212> TYPE: DNA
<213> ORGANISM: Rhodococcus erythropolis
<220> FEATURE:
<221> NAME/KEY: misc_feature
<223> OTHER INFORMATION: 337bp to 480bp pRET1100

<400> SEQUENCE: 3
atgcgatgcg actttgtcgg cgagtacggg agatatgcgc gagccatcga gtcttcggat       60
ctgcgttttc tcgccaccct ccagcaagac caggcccaac gcgaattctt cgctgaggag      120
ttcggtgtgg tggatccgtc atga                                             144

<210> SEQ ID NO 4
<211> LENGTH: 282
<212> TYPE: DNA
<213> ORGANISM: Rhodococcus erythropolis
<220> FEATURE:
<221> NAME/KEY: misc_feature
<223> OTHER INFORMATION: 477bp to 758bp pRET1100

<400> SEQUENCE: 4
atgactggac cacaggagag aaagcgcaag cggcgaagc cgtcgcggga gcctcagttg        60
aactgctgtg aacggacgt gccgaaacga gcaaaacagc ccccggttcc ctctacgttc       120
gacctgctca cggtgaagga gactgcgggg ctgctgagag tcagtcaggc aactctttac      180
cggctgcttc ggagtgggga aggacccaca tacacacgga tcggtggaca gatacgcgtt     240
caccgcgagt cgctgcgtcg gttcatcgaa ccgcgtggat aa                        282

<210> SEQ ID NO 5
<211> LENGTH: 1548
<212> TYPE: DNA
<213> ORGANISM: Rhodococcus erythropolis
<220> FEATURE:
<221> NAME/KEY: misc_feature
<223> OTHER INFORMATION: 862bp to 2409bp pRET1100

<400> SEQUENCE: 5
atgcacttcc acgataacgc agaggtcgga caagagggaa gaactgccgt tctctcgccg       60
ttgcgcggcg tagccgccaa gcgggacgtg tctgacgatg cagcgaagcg gagtcggcag     120
gcgcggcacg cgcctgggct tgttacatct gccacaactg tccgtgaatc tctgccagct     180
```

```
cctgaaaccg ctggtcaggg ccttgcggaa tccgtgaccg ctgatgattt ttggtctcat      240
tcgttccccc gcgctgacga tgtacgcggc gcagctgctt ccttccagtc ggtggctaac      300
tgggatgggc gtgagggtcc gaggccgcgt ttcgttgtcg cgcctggcgt tgtccgcttg      360
gaggtttgtg atctcgcacg ccgcgaacga acggctgaac gtgcgtatct ggctgctcgg      420
gctcgggtgg atatggcggc tgccaggcat aactcgccgt acgacttcga cgtgacgat       480 gaagagttgg cggaactggc ttctctgcaa ggcctcgagg acgacgacat tggggctgg       540 tctgcggaga gggaaatagt gggctggtct gctcgttctc ggtcacggat gatcttgcga      600
atggcagaac tcgactgggc tcccatgatg gatttgccgg gcattcctgc gatggtgacc      660
ctcacctatc cggggactg gcttacggtt gccccaccg gcgctgaggt caaaaaacat        720
ctccagacgt tcttcaaacg gttccaacgg gcctgggca ttgcctggat gggtgcgtgg       780
aaaatggagt ccaaagccg aggcgctccg cattttcacc tgtacatggt ccctcctcat      840
gggaaggcag gagactcgcg gaagctgcgg catgatgctg agctcttgaa atgggagata     900
gcacgtgcag agggtgaaga cccaggtcgc aggccgtatt ccgggaagc tccaagcgat      960 ggattgaagt ttcgtccgtg gctttctgcg gtgtgggccg acgtcgtaga tcatccggac     1020
cccaaggaaa aagaaaagca cgtcagtgcc ggcactggag tggactacgc ggagggcacg     1080
cgagggtcag atccgaaaag gcttgcggtg tacttctcca gcatggaac ctttgccgac      1140 aaggaatatc agcacgtagt tcctgctcaa tggcagaaaa cgggtgcggg acctggcagg     1200
ttctggggct accgcggttt gtcgccgcc acggctgcca ccgagatttc ctgggatgag      1260
tacctgcttt tatctcgcac gttgcgacga ttgtcagcgc gaacgaagat ctgggacccg     1320
gctttacgag gcgtagcgg cggccacaga tggactaagg cgatgatgcg acgcacggtt     1380
acccggcacc gcttggacct cgtgaccggt gagattctgg cacgaagac gcggaaggtt      1440 cgggcgccag tgaagaggtt tgtccggact tcggatacc tgtgtgtcaa tgacgggccc      1500
gcactggctc gaaccctcag ccgtcttcgt acaagctgcc tgagctag                    1548

<210> SEQ ID NO 6
<211> LENGTH: 1116
<212> TYPE: DNA
<213> ORGANISM: Rhodococcus erythropolis
<220> FEATURE:
<221> NAME/KEY: misc_feature
<223> OTHER INFORMATION: 1294bp to 2409bp pRET1100

<400> SEQUENCE: 6
atggcggctg ccaggcataa ctcgccgtac gacttcgacg tggacgatga agagttggcg        60
gaactggctt ctctgcaagg cctcgaggac gacgacattg gggctggtc tgcggagagg       120 gaaatagtgg gctggtctgc tcgttctcgg tcacggatga tcttgcgaat ggcagaactc      180
gactgggctc ccatgatgga tttgccggc attcctgcga tggtgaccct cacctatccg       240
ggggactggc ttacggttgc ccccaccggc gctgaggtca aaaaacatct ccagacgttc      300
ttcaaacggt tccaacgggc ctggggcatt gcctggatgg gtgcgtggaa aatggagttc      360
caaagccgag gcgctccgca ttttcacctg tacatggtcc ctcctcatgg gaaggcagga      420
gactcgcgga agctgcggca tgatgctgag ctcttgaaat gggagatagc acgtgcagag     480
ggtgaagacc caggtcgcag gccgtatttc gggaagctc aagcgatgg attgaagttt       540 cgtccgtggc tttctgcggt gtgggccgac gtcgtagatc atccggaccc caaggaaaaa     600
gaaaagcacg tcagtgccgg cactggagtg gactacgcgg agggcacgcg agggtcagat     660
```

| | |
|---|---|
| ccgaaaaggc ttgcggtgta cttctccaag catggaacct tgccgacaa ggaatatcag | 720 |
| cacgtagttc ctgctcaatg cagaaaacg ggtgcgggac ctggcaggtt ctggggctac | 780 |
| cgcggtttgt cgccggccac ggctgccacc gagatttcct gggatgagta cctgcttta | 840 |
| tctcgcacgt tgcgacgatt gtcagcgcga acgaagatct gggacccggc tttacgaggc | 900 |
| ggtagcggcg ccacagatg gactaagcg atgatgcgac gcacggttac ccggcaccgc | 960 |
| ttggacctcg tgaccggtga gattctgggc acgaagacgc ggaaggttcg ggcgccagtg | 1020 |
| aagaggtttg tccggacttc gggatacctg tgtgtcaatg acgggcccgc actggctcga | 1080 |
| accctcagcc gtcttcgtac aagctgcctg agctag | 1116 |

<210> SEQ ID NO 7
<211> LENGTH: 960
<212> TYPE: DNA
<213> ORGANISM: Rhodocuccus erythropolis
<220> FEATURE:
<221> NAME/KEY: misc_feature
<223> OTHER INFORMATION: 1450bp to 2409bp pRET1100

<400> SEQUENCE: 7

| | |
|---|---|
| atgatcttgc gaatggcaga actcgactgg gctcccatga tggatttgcc gggcattcct | 60 |
| gcgatggtga ccctcaccta tccgggggac tggcttacgg ttgcccccac cggcgctgag | 120 |
| gtcaaaaaac atctccagac gttcttcaaa cggttccaac gggcctgggg cattgcctgg | 180 |
| atgggtgcgt ggaaaatgga gttccaaagc cgaggcgctc cgcattttca cctgtacatg | 240 |
| gtccctcctc atgggaaggc aggagactcg cggaagctgc ggcatgatgc tgagctcttg | 300 |
| aaatgggaga tagcacgtgc agagggtgaa gacccaggtc gcaggccgta tttccgggaa | 360 |
| gctccaagcg atggattgaa gtttcgtccg tggctttctg cggtgtgggc cgacgtcgta | 420 |
| gatcatccgg accccaagga aaagaaaaag cacgtcagtg ccggcactgg agtggactac | 480 |
| gcggagggca cgcgagggtc agatccgaaa aggcttgcgg tgtacttctc caagcatgga | 540 |
| acctttgccg acaaggaata tcagcacgta gttcctgctc aatggcagaa acgggtgcg | 600 |
| ggacctggca ggttctgggg ctaccgcggt tgtcgccgg ccacggctgc caccgagatt | 660 |
| tcctgggatg agtacctgct tttatctcgc acgttgcgac gattgtcagc gcgaacgaag | 720 |
| atctgggacc cggctttacg aggcggtagc ggcggccaca gatggactaa ggcgatgatg | 780 |
| cgacgcacgg ttacccggca ccgcttggac ctcgtgaccg tgagattct gggcacgaag | 840 |
| acgcggaagg ttcgggcgcc agtgaagagg tttgtccgga cttcgggata cctgtgtgtc | 900 |
| aatgacgggc ccgcactggc tcgaaccctc agccgtcttc gtacaagctg cctgagctag | 960 |

<210> SEQ ID NO 8
<211> LENGTH: 948
<212> TYPE: DNA
<213> ORGANISM: Rhodococcus erythropolis
<220> FEATURE:
<221> NAME/KEY: misc_feature
<223> OTHER INFORMATION: 1462bp to 2409bp pRET1100

<400> SEQUENCE: 8

| | |
|---|---|
| atggcagaac tcgactgggc tcccatgatg gatttgccgg gcattcctgc gatggtgacc | 60 |
| ctcacctatc cggggactg gcttacggtt gcccccaccg cgctgaggt caaaaaacat | 120 |
| ctccagacgt tcttcaaacg gttccaacgg gcctggggca ttgcctggat gggtgcgtgg | 180 |
| aaaatggagt tccaaagccg aggcgctccg cattttcacc tgtacatggt ccctcctcat | 240 |

```
gggaaggcag gagactcgcg gaagctgcgg catgatgctg agctcttgaa atgggagata    300
gcacgtgcag agggtgaaga cccaggtcgc aggccgtatt ccgggaagc tccaagcgat     360 ggattgaagt tcgtccgtg gctttctgcg gtgtgggccg acgtcgtaga tcatccggac    420
cccaaggaaa aagaaaagca cgtcagtgcc ggcactggag tggactacgc ggagggcacg    480
cgagggtcag atccgaaaag gcttgcggtg tacttctcca agcatggaac ctttgccgac    540
aaggaatatc agcacgtagt tcctgctcaa tggcagaaaa cgggtgcggg acctggcagg    600
ttctggggct accgcggttt gtcgccggcc acggctgcca ccgagatttc ctgggatgag    660
tacctgcttt tatctcgcac gttgcgacga ttgtcagcgc gaacgaagat ctgggacccg    720
gctttacgag gcggtagcgg cggccacaga tggactaagg cgatgatgcg acgcacggtt    780
acccggcacc gcttggacct cgtgaccggt gagattctgg gcacgaagac gcggaaggtt    840
cgggcgccag tgaagaggtt tgtccggact cgggatacc tgtgtgtcaa tgacgggccc     900
gcactggctc gaaccctcag ccgtcttcgt acaagctgcc tgagctag                 948

<210> SEQ ID NO 9
<211> LENGTH: 924
<212> TYPE: DNA
<213> ORGANISM: Rhodoccus erythropolis
<220> FEATURE:
<221> NAME/KEY: misc_feature
<223> OTHER INFORMATION: 1486bp to 2409bp pRET1100

<400> SEQUENCE: 9
atgatggatt tgccgggcat tcctgcgatg gtgaccctca cctatccggg ggactggctt     60
acggttgccc ccaccggcgc tgaggtcaaa aacatctcc agacgttctt caaacggttc    120
caacgggcct ggggcattgc ctggatgggt gcgtggaaaa tggagttcca agccgaggc    180 gctccgcatt ttcacctgta catggtccct cctcatggga aggcaggaga ctcgcggaag    240
ctgcggcatg atgctgagct cttgaaatgg agatagcac gtgcagaggg tgaagaccca     300
ggtcgcaggc cgtatttccg ggaagctcca agcgatggat tgaagtttcg tccgtggctt    360
tctgcggtgt gggccgacgt cgtagatcat ccggacccca aggaaaaaga aaagcacgtc    420
agtgccggca ctggagtgga ctacgcggag gcacgcgag ggtcagatcc gaaaaggctt    480
gcggtgtact tctccaagca tggaaccttt gccgacaagg aatatcagca cgtagttcct    540
gctcaatggc agaaaacggg tgcgggacct ggcaggttct ggggctaccg cggtttgtcg    600
ccggccacgg ctgccaccga gatttcctgg gatgagtacc tgcttttatc tcgcacgttg    660
cgacgattgt cagcgcgaac gaagatctgg gacccggctt tacgaggcgg tagcggcggc    720
cacagatgga ctaaggcgat gatgcgacgc acggttaccc ggcaccgctt ggacctcgtg    780
accggtgaga ttctgggcac gaagacgcgg aaggttcggg cgccagtgaa gaggtttgtc    840
cggacttcgg gataccgtg tgtcaatgac gggcccgcac tggctcgaac cctcagccgt    900
cttcgtacaa gctgcctgag ctag                                           924

<210> SEQ ID NO 10
<211> LENGTH: 921
<212> TYPE: DNA
<213> ORGANISM: Rhodococcus erythropolis
<220> FEATURE:
<221> NAME/KEY: misc_feature
<223> OTHER INFORMATION: 1489bp to 2409bp pRET1100

<400> SEQUENCE: 10
atggatttgc cgggcattcc tgcgatggtg accctcacct atccggggga ctggcttacg     60
```

| | |
|---|---|
| gttgccccca ccggcgctga ggtcaaaaaa catctccaga cgttcttcaa acggttccaa | 120 |
| cgggcctggg gcattgcctg gatgggtgcg tggaaaatgg agttccaaag ccgaggcgct | 180 |
| ccgcattttc acctgtacat ggtccctcct catgggaagg caggagactc gcggaagctg | 240 |
| cggcatgatg ctgagctctt gaaatgggag atagcacgtg cagagggtga agacccaggt | 300 |
| cgcaggccgt atttccggga agctccaagc gatggattga agtttcgtcc gtggcttttct | 360 |
| gcggtgtggg ccgacgtcgt agatcatccg accccaagg aaaagaaaaa gcacgtcagt | 420 |
| gccggcactg gagtggacta cgcggagggc acgcgagggt cagatccgaa aaggcttgcg | 480 |
| gtgtacttct ccaagcatgg aacctttgcc gacaaggaat atcagcacgt agttcctgct | 540 |
| caatggcaga aaacgggtgc gggacctggc aggttctggg gctaccgcgg tttgtcgccg | 600 |
| gccacggctg ccaccgagat tcctgggat gagtacctgc ttttatctcg cacgttgcga | 660 |
| cgattgtcag cgcgaacgaa gatctgggac cggctttac gaggcggtag cggcggccac | 720 |
| agatggacta aggcgatgat gcgacgcacg gttacccggc accgcttgga cctcgtgacc | 780 |
| ggtgagattc tgggcacgaa gacgcggaag gttcgggcgc cagtgaagag gtttgtccgg | 840 |
| acttcgggat acctgtgtgt caatgacggg cccgcactgg ctcgaaccct cagccgtctt | 900 |
| cgtacaagct gcctgagcta g | 921 |

<210> SEQ ID NO 11
<211> LENGTH: 897
<212> TYPE: DNA
<213> ORGANISM: Rhodococcus erythropolis
<220> FEATURE:
<221> NAME/KEY: misc_feature
<223> OTHER INFORMATION: 1513bp to 2409bp pRET1100

<400> SEQUENCE: 11

| | |
|---|---|
| atggtgaccc tcacctatcc gggggactgg cttacggttg cccccaccgg cgctgaggtc | 60 |
| aaaaaacatc tccagacgtt cttcaaacgg ttccaacggg cctggggcat tgcctggatg | 120 |
| ggtgcgtgga aatggagtt ccaaagccga ggcgctccgc attttcacct gtacatggtc | 180 |
| cctcctcatg ggaaggcagg agactcgcgg aagctgcggc atgatgctga gctcttgaaa | 240 |
| tgggagatag cacgtgcaga gggtgaagac ccaggtcgca ggccgtattt ccgggaagct | 300 |
| ccaagcgatg gattgaagtt tcgtccgtgg ctttctgcgg tgtgggccga cgtcgtagat | 360 |
| catccggacc caaggaaaa agaaaagcac gtcagtgccg gcactggagt ggactacgcg | 420 |
| gagggcacgc gagggtcaga tccgaaaagg cttgcgtgt acttctccaa gcatggaacc | 480 |
| tttgccgaca aggaatatca gcacgtagtt cctgctcaat ggcagaaaac gggtgcggga | 540 |
| cctggcaggt tctggggcta ccgcggtttg tcgccggcca cggctgccac cgagatttcc | 600 |
| tgggatgagt acctgctttt atctcgcacg ttgcgacgat tgtcagcgcg aacgaagatc | 660 |
| tgggaccccg ctttacgagg cggtagcggc ggccacagat ggactaaggc gatgatgcga | 720 |
| cgcacggtta cccggcaccg cttggacctc gtgaccggtg agattctggg cacgaagacg | 780 |
| cggaaggttc gggcgccagt gaagaggttt gtccggactt cgggatacct gtgtgtcaat | 840 |
| gacgggcccg cactggctcg aaccctcagc cgtcttcgta caagctgcct gagctag | 897 |

<210> SEQ ID NO 12
<211> LENGTH: 780
<212> TYPE: DNA
<213> ORGANISM: Rhodococcus erythropolis
<220> FEATURE:
<221> NAME/KEY: misc_feature
<223> OTHER INFORMATION: 1630bp to 2409bp pRET1100

<400> SEQUENCE: 12

```
atgggtgcgt ggaaaatgga gttccaaagc cgaggcgctc cgcatttcca cctgtacatg      60
gtccctcctc atgggaaggc aggagactcg cggaagctgc ggcatgatgc tgagctcttg     120
aaatgggaga tagcacgtgc agagggtgaa gacccaggtc gcaggccgta tttccgggaa     180
gctccaagcg atggattgaa gtttcgtccg tggctttctg cggtgtgggc cgacgtcgta     240
gatcatccgg accccaagga aaagaaaaag cacgtcagtg ccggcactgg agtggactac     300
gcggagggca cgcgagggtc agatccgaaa aggcttgcgg tgtacttctc aagcatgga     360
acctttgccg acaaggaata tcagcacgta gttcctgctc aatggcagaa acgggtgcg     420
ggacctggca ggttctgggg ctaccgcggt tgtcgccgg ccacggctgc caccgagatt     480
tcctgggatg agtacctgct tttatctcgc acgttgcgac gattgtcagc gcgaacgaag     540
atctgggacc cggctttacg aggcggtagc ggcggccaca gatggactaa ggcgatgatg     600
cgacgcacgg ttacccggca ccgcttggac ctcgtgaccg tgagattct gggcacgaag     660
acgcggaagt tcgggcgcc agtgaagagg tttgtccgga cttcgggata cctgtgtgtc     720
aatgacgggc ccgcactggc tcgaaccctc agccgtcttc gtacaagctg cctgagctag     780
```

<210> SEQ ID NO 13
<211> LENGTH: 765
<212> TYPE: DNA
<213> ORGANISM: Rhodococcus erythropolis
<220> FEATURE:
<221> NAME/KEY: misc_feature
<223> OTHER INFORMATION: 1645bp to 2409bp pRET1100

<400> SEQUENCE: 13

```
atggagttcc aaagccgagg cgctccgcat tttcacctgt acatggtccc tcctcatggg      60
aaggcaggag actcgcggaa gctgcggcat gatgctgagc tcttgaaatg ggagatagca     120
cgtgcagagg gtgaagaccc aggtcgcagg ccgtatttcc gggaagctcc aagcgatgga     180
ttgaagtttc gtccgtggct ttctgcggtg tgggccgacg tcgtagatca tccgaccccc     240
aaggaaaaag aaaagcacgt cagtgccggc actggagtgg actacgcgga gggcacgcga     300
gggtcagatc cgaaaggct gcggtgtac ttctccaagc atggaacctt gccgacaag     360
gaatatcagc acgtagttcc tgctcaatgg cagaaacgg gtgcgggacc tggcaggttc     420
tggggctacc gcggtttgtc gccggccacg gctgccaccg agatttcctg ggatgagtac     480
ctgcttttat ctcgcacgtt gcgacgattg tcagcgcgaa cgaagatctg gacccggct     540
ttacgaggcg gtagcggcgg ccacagatgg actaaggcga tgatgcgacg cacggttacc     600
cggcaccgct tggacctcgt gaccggtgag attctgggca cgaagacgcg gaaggttcgg     660
gcgccagtga gaggtttgt ccggacttcg ggatacctgt gtgtcaatga cgggcccgca     720
ctggctcgaa ccctcagccg tcttcgtaca agctgcctga gctag                    765
```

<210> SEQ ID NO 14
<211> LENGTH: 723
<212> TYPE: DNA
<213> ORGANISM: Rhodococcus erythropolis
<220> FEATURE:
<221> NAME/KEY: misc_feature
<223> OTHER INFORMATION: 1687bp to 2409bp pRET1100

<400> SEQUENCE: 14

```
atggtccctc ctcatgggaa ggcaggagac tcgcggaagc tgcggcatga tgctgagctc      60
```

```
ttgaaatggg agatagcacg tgcagagggt gaagacccag gtcgcaggcc gtatttccgg    120
gaagctccaa gcgatggatt gaagtttcgt ccgtggcttt ctgcggtgtg ggccgacgtc    180
gtagatcatc cggaccccaa ggaaaaagaa agcacgtca gtgccggcac tggagtggac     240
tacgcggagg gcacgcgagg gtcagatccg aaaaggcttg cggtgtactt ctccaagcat    300
ggaacctttg ccgacaagga atatcagcac gtagttcctg ctcaatggca gaaaacgggt    360
gcgggacctg gcaggttctg gggctaccgc ggtttgtcgc cggccacggc tgccaccgag    420
atttcctggg atgagtacct gcttttatct cgcacgttgc gacgattgtc agcgcgaacg    480
aagatctggg acccggcttt acgaggcggt agcggcggcc acagatggac taaggcgatg    540
atgcgacgca cggttacccg gcaccgcttg gacctcgtga ccggtgagat tctgggcacg    600
aagacgcgga aggttcgggc gccagtgaag aggtttgtcc ggacttcggg atacctgtgt    660
gtcaatgacg ggcccgcact ggctcgaacc ctcagccgtc ttcgtacaag ctgcctgagc    720
tag                                                                  723

<210> SEQ ID NO 15
<211> LENGTH: 186
<212> TYPE: DNA
<213> ORGANISM: Rhodococcus erythropolis
<220> FEATURE:
<221> NAME/KEY: misc_feature
<223> OTHER INFORMATION: 2224bp to 2409bp pRET1100

<400> SEQUENCE: 15
atgatgcgac gcacggttac ccggcaccgc ttggacctcg tgaccggtga gattctgggc     60
acgaagacgc ggaaggttcg ggcgccagtg aagaggtttg tccggacttc gggatacctg    120
tgtgtcaatg acgggcccgc actggctcga accctcagcc gtcttcgtac aagctgcctg    180
agctag                                                               186

<210> SEQ ID NO 16
<211> LENGTH: 183
<212> TYPE: DNA
<213> ORGANISM: Rhodococcus erythropolis
<220> FEATURE:
<221> NAME/KEY: misc_feature
<223> OTHER INFORMATION: 2227bp to 2409bp pRET1100

<400> SEQUENCE: 16
atgcgacgca cggttacccg gcaccgcttg gacctcgtga ccggtgagat tctgggcacg     60
aagacgcgga aggttcgggc gccagtgaag aggtttgtcc ggacttcggg atacctgtgt    120
gtcaatgacg ggcccgcact ggctcgaacc ctcagccgtc ttcgtacaag ctgcctgagc    180
tag                                                                  183

<210> SEQ ID NO 17
<211> LENGTH: 432
<212> TYPE: DNA
<213> ORGANISM: Rhodococcus erythropolis
<220> FEATURE:
<221> NAME/KEY: misc_feature
<223> OTHER INFORMATION: 1875bp to 1444bp pRET1100

<400> SEQUENCE: 17
atgatctacg acgtcggccc acaccgcaga aagccacgga cgaaacttca atccatcgct     60
tggagcttcc cggaaatacg gcctgcgacc tgggtcttca ccctctgcac gtgctatctc    120
ccatttcaag agctcagcat catgccgcag cttccgcgag tctcctgcct tcccatgagg    180
```

```
agggaccatg tacaggtgaa atgcggagc gcctcggctt tggaactcca ttttccacgc    240
acccatccag gcaatgcccc aggcccgttg aaccgtttg aagaacgtct ggagatgttt    300
tttgacctca gcgccggtgg gggcaaccgt aagccagtcc cccggatagg tgagggtcac    360
catcgcagga atgcccggca aatccatcat gggagcccag tcgagttctg ccattcgcaa    420
gatcatccgt ga                                                       432
```

```
<210> SEQ ID NO 18
<211> LENGTH: 291
<212> TYPE: DNA
<213> ORGANISM: Rhodococcus erythropolis
<220> FEATURE:
<221> NAME/KEY: misc_feature
<223> OTHER INFORMATION: 1734bp to 1444bp pRET1100

<400> SEQUENCE: 18
atgccgcagc ttccgcgagt ctcctgcctt cccatgagga gggaccatgt acaggtgaaa    60
atgcggagcg cctcggcttt ggaactccat tttccacgca cccatccagg caatgcccca   120
ggcccgttgg aaccgtttga agaacgtctg gagatgtttt ttgacctcag cgccggtggg   180
ggcaaccgta agccagtccc ccggataggt gagggtcacc atcgcaggaa tgcccggcaa   240
atccatcatg ggagcccagt cgagttctgc cattcgcaag atcatccgtg a            291
```

```
<210> SEQ ID NO 19
<211> LENGTH: 258
<212> TYPE: DNA
<213> ORGANISM: Rhodococcus erythropolis
<220> FEATURE:
<221> NAME/KEY: misc_feature
<223> OTHER INFORMATION: 1701bp to 1444bp pRET1100

<400> SEQUENCE: 19
atgaggaggg accatgtaca ggtgaaaatg cggagcgcct cggctttgga actccatttt    60
ccacgcaccc atccaggcaa tgccccaggc ccgttggaac cgtttgaaga acgtctggag   120 atgtttttg acctcagcgc cggtgggggc aaccgtaagc cagtcccccg gataggtgag   180
ggtcaccatc gcaggaatgc ccggcaaatc catcatggga gcccagtcga gttctgccat   240
tcgcaagatc atccgtga                                                 258
```

```
<210> SEQ ID NO 20
<211> LENGTH: 231
<212> TYPE: DNA
<213> ORGANISM: Rhodococcus erythropolis
<220> FEATURE:
<221> NAME/KEY: misc_feature
<223> OTHER INFORMATION: 1674bp to 1444bp pRET1100

<400> SEQUENCE: 20
atgcggagcg cctcggcttt ggaactccat tttccacgca cccatccagg caatgcccca    60
ggcccgttgg aaccgtttga agaacgtctg gagatgtttt ttgacctcag cgccggtggg   120
ggcaaccgta agccagtccc ccggataggt gagggtcacc atcgcaggaa tgcccggcaa   180
atccatcatg ggagcccagt cgagttctgc cattcgcaag atcatccgtg a            231
```

```
<210> SEQ ID NO 21
<211> LENGTH: 138
<212> TYPE: DNA
<213> ORGANISM: Rhodococcus erythropolis
<220> FEATURE:
<221> NAME/KEY: misc_feature
```

<223> OTHER INFORMATION: 1581bp to 1444bp pRET1100

<400> SEQUENCE: 21

```
atgtttttg acctcagcgc cggtgggggc aaccgtaagc cagtcccccg gataggtgag      60
ggtcaccatc gcaggaatgc ccggcaaatc catcatggga gcccagtcga gttctgccat     120
tcgcaagatc atccgtga                                                   138
```

<210> SEQ ID NO 22
<211> LENGTH: 423
<212> TYPE: DNA
<213> ORGANISM: Rhodococcus erythropolis
<220> FEATURE:
<221> NAME/KEY: misc_feature
<223> OTHER INFORMATION: 2828bp to 2406bp pRET1100

<400> SEQUENCE: 22

```
atggtgggag gcaacactc ccaatacgct tcagttatga atgaagacag agacaacatc      60
atcgccaggt tccgcgtcga atgctccgc tcaatcgagg atgcaattca tttagccgca     120
ctctccgcga acgacgaaaa ccgttatgcc gcaacagaag acaatcgacc cgtgcggaca    180
caactatcgc aacaacagca ggttgtcctg accgagctga cattggccga ccacatggaa    240
aagctcgcgc gggagcacct cgtttaccta gccgacagag cgcgggagat gaattgcacc    300
tgggtagaga taggtcagtc gttgggtctc tctcccacg gagcgcagca gcgcatcacc     360
agaagccgcc aaaacccgc catccagcaa aagacaaagc cgaaaggcgt tccgcgcgtc    420
tag                                                                   423
```

<210> SEQ ID NO 23
<211> LENGTH: 387
<212> TYPE: DNA
<213> ORGANISM: Rhodococcus erythropolis
<220> FEATURE:
<221> NAME/KEY: misc_feature
<223> OTHER INFORMATION: 2792bp to 2406bp pRET1100

<400> SEQUENCE: 23

```
atgaatgaag acagagacaa catcatcgcc aggttccgcg tcgaaatgct ccgctcaatc      60
gaggatgcaa ttcatttagc cgcactctcc gcgaacgacg aaaaccgtta tgccgcaaca    120
gaagacaatc gacccgtgcg gacacaacta tcgcaacaac agcaggttgt cctgaccgag    180
ctgacattgg ccgaccacat ggaaaagctc gcgcgggagc acctcgttta cctagccgac    240
agagcgcggg agatgaattg cacctgggta gagataggtc agtcgttggg tctctctccc    300
cacggagcgc agcagcgcat caccagaagc cgcccaaaac ccgccatcca gcaaaagaca    360
aagccgaaag gcgttccgcg cgtctag                                         387
```

<210> SEQ ID NO 24
<211> LENGTH: 342
<212> TYPE: DNA
<213> ORGANISM: Rhodococcus erythropolis
<220> FEATURE:
<221> NAME/KEY: misc_feature
<223> OTHER INFORMATION: 2747bp to 2406bp pRET1100

<400> SEQUENCE: 24

```
atgctccgct caatcgagga tgcaattcat ttagccgcac tctccgcgaa cgacgaaaac      60
cgttatgccg caacagaaga caatcgaccc gtgcggacac aactatcgca acaacagcag    120
gttgtcctga ccgagctgac attggccgac cacatggaaa agctcgcgcg ggagcacctc    180
```

-continued

```
gtttacctag ccgacagagc gcgggagatg aattgcacct gggtagagat aggtcagtcg    240
ttgggtctct ctccccacgg agcgcagcag cgcatcacca gaagccgccc aaaacccgcc    300
atccagcaaa agacaaagcc gaaaggcgtt ccgcgcgtct ag                       342
```

<210> SEQ ID NO 25
<211> LENGTH: 189
<212> TYPE: DNA
<213> ORGANISM: Rhodococcus erythropolis
<220> FEATURE:
<221> NAME/KEY: misc_feature
<223> OTHER INFORMATION: 2594bp to 2406bp pRET1100

<400> SEQUENCE: 25

```
atggaaaagc tcgcgcggga gcacctcgtt tacctagccg acagagcgcg ggagatgaat    60
tgcacctggg tagagatagg tcagtcgttg gtctctctc cccacggagc gcagcagcgc    120
atcaccagaa gccgcccaaa acccgccatc agcaaaaga caaagccgaa aggcgttccg    180
cgcgtctag                                                           189
```

<210> SEQ ID NO 26
<211> LENGTH: 135
<212> TYPE: DNA
<213> ORGANISM: Rhodococcus erythropolis
<220> FEATURE:
<221> NAME/KEY: misc_feature
<223> OTHER INFORMATION: 2540bp to 2406bp pRET1100

<400> SEQUENCE: 26

```
atgaattgca cctgggtaga gataggtcag tcgttgggtc tctctcccca cggagcgcag    60
cagcgcatca ccagaagccg cccaaaaccc gccatccagc aaaagacaaa gccgaaaggc    120
gttccgcgcg tctag                                                    135
```

<210> SEQ ID NO 27
<211> LENGTH: 336
<212> TYPE: DNA
<213> ORGANISM: Rhodococcus erythropolis
<220> FEATURE:
<221> NAME/KEY: misc_feature
<223> OTHER INFORMATION: 2971bp to 3306bp pRET1100

<400> SEQUENCE: 27

```
atggctttga agctgctgg caacgtgatt cctgattcct ccgcgtacga gtaccgggcg    60
gttcaggtcg agccgaagat ggtcagaaaa gacccggaag acccgaactc tgagcagttc    120
cagaagcaga aggacggcac gccggtgtgg tcgatcgact gcattcgggt cgaccgggca    180
tcaggcaaca aggcaatcgt gaccgtgacg gttccggacg tgatggaacc ggatgttgcg    240
gggccggtgg agttctccga gatgattgcc ggtttctggg tttcgcgcag tggttcgggc    300
atgtggtttt cggcaagcgc cgtcgcttct ctctga                             336
```

<210> SEQ ID NO 28
<211> LENGTH: 258
<212> TYPE: DNA
<213> ORGANISM: Rhodococcus erythropolis
<220> FEATURE:
<221> NAME/KEY: misc_feature
<223> OTHER INFORMATION: 3049bp to 3306bp pRET1100

<400> SEQUENCE: 28

```
atggtcagaa agacccgga agacccgaac tctgagcagt tccagaagca gaaggacggc    60
acgccggtgt ggtcgatcga ctgcattcgg gtcgaccggg catcaggcaa caaggcaatc    120
```

```
gtgaccgtga cggttccgga cgtgatggaa ccggatgttg cggggccggt ggagttctcc    180
gagatgattg ccggtttctg ggtttcgcgc agtggttcgg gcatgtggtt ttcggcaagc    240
gccgtcgctt ctctctga                                                  258

<210> SEQ ID NO 29
<211> LENGTH: 525
<212> TYPE: DNA
<213> ORGANISM: Rhodococcus erythropolis
<220> FEATURE:
<221> NAME/KEY: misc_feature
<223> OTHER INFORMATION: 3577bp to 3053bp pRET1100

<400> SEQUENCE: 29
atgtcgatgt actgccctcc gctgaacggc cccagctctt ccggagagag aacgaggcac     60
ccggcaacgt ccgagaacac cccgttttcc acttcggat cggccggcac tctcagcggc    120
acagcttcgg actgtgaacg atcactgaac acgttcgccg cttgccaacc tgccgcaacc    180
agcacaaaca cgagcacgag ggcacccaca cccagcgcaa cgccttttcc tttggacatt    240
tccgaacctt tcgaggggcg acgatcagcg atcagagaga agcgacggcg cttgccgaaa    300
accacatgcc cgaaccactg cgcgaaaccc agaaaccggc aatcatctcg gagaactcca    360
ccggccccgc aacatccggt tccatcacgt ccggaaccgt cacggtcacg attgccttgt    420
tgcctgatgc ccggtcgacc cgaatgcagt cgatcgacca caccggcgtg ccgtccttct    480
gcttctggaa ctgctcagag ttcgggtctt ccgggtcttt tctga                    525

<210> SEQ ID NO 30
<211> LENGTH: 519
<212> TYPE: DNA
<213> ORGANISM: Rhodococcus erythropolis
<220> FEATURE:
<221> NAME/KEY: misc_feature
<223> OTHER INFORMATION: 3571bp to 3053bp pRET1100

<400> SEQUENCE: 30
atgtactgcc ctccgctgaa cggccccagc tcttccggag agagaacgag gcacccggca     60
acgtccgaga cacccccgtt tcccacttc ggatcggccg gcactctcag cggcacagct    120
tcggactgtg aacgatcact gaacacgttc gccgcttgcc aacctgccgc aaccagcaca    180
aacacgagca cgagggcacc cacacccagc gcaacgcctt ttcctttgga catttccgaa    240
cctttcgagg ggcgacgatc agcgatcaga gagaagcgac ggcgcttgcc gaaaaccaca    300
tgcccgaacc actgcgcgaa acccagaaac cggcaatcat ctcggagaac tccaccggcc    360
ccgcaacatc cggttccatc acgtccggaa ccgtcacggt cacgattgcc ttgttgcctg    420
atgcccggtc gacccgaatg cagtcgatcg accacaccgg cgtgccgtcc ttctgcttct    480
ggaactgctc agagttcggg tcttccgggt cttttctga                           519

<210> SEQ ID NO 31
<211> LENGTH: 564
<212> TYPE: DNA
<213> ORGANISM: Rhodococcus erythropolis
<220> FEATURE:
<221> NAME/KEY: misc_feature
<223> OTHER INFORMATION: 3339bp to 3902bp pRET1100

<400> SEQUENCE: 31
atgtccaaag gaaaaggcgt tgcgctgggt gtgggtgccc tcgtgctcgt gtttgtgctg     60
gttgcggcag gttggcaagc ggcgaacgtg ttcagtgatc gttcacagtc cgaagctgtg    120
```

```
ccgctgagag tgccggccga tccgaagtgg gaaaacgggg tgttctcgga cgttgccggg       180
tgcctcgttc tctctccgga agagctgggg ccgttcagcg gagggcagta catcgacata       240
gtgaggccag ttgagccgga gaggttggag cgcgactggg tgaggtcggc tgagtgcgtt       300
tcggcgtcga tgaatgtctc tgacctgttg gtttctgctc ttccagagtc cacccgtccc       360
cccggcgatt tcgttcgttc gtggaaagtg gcgagtgatg attactgcta tgagggtgat       420
aacccgcaag gctgcacttc tcgtatgccg gtttgggtct ctgcaaaaaa ctggtggtgc       480
acagaacccg tactcgatcc gctcgttcgt cgctgtgagg tctttcctgc aaggcaaatc       540
gttgtgccgg aagggggttttc gtga                                             564
```

<210> SEQ ID NO 32
<211> LENGTH: 255
<212> TYPE: DNA
<213> ORGANISM: Rhodococcus erythropolis
<220> FEATURE:
<221> NAME/KEY: misc_feature
<223> OTHER INFORMATION: 3648bp to 3902bp pRET1100

<400> SEQUENCE: 32

```
atgaatgtct ctgacctgtt ggtttctgct cttccagagt ccacccgtcc ccccggcgat       60
ttcgttcgtt cgtggaaagt ggcgagtgat gattactgct atgagggtga taacccgcaa      120
ggctgcactt ctcgtatgcc ggtttgggtc tctgcaaaaa actggtggtg cacagaaccc      180
gtactcgatc cgctcgttcg tcgctgtgag gtctttcctg caaggcaaat cgttgtgccg      240 gaagggggttt cgtga                                                       255
```

<210> SEQ ID NO 33
<211> LENGTH: 669
<212> TYPE: DNA
<213> ORGANISM: Rhodococcus erythropolis
<220> FEATURE:
<221> NAME/KEY: misc_feature
<223> OTHER INFORMATION: 4366bp to 5034bp pRET1100

<400> SEQUENCE: 33

```
atgggcaccc cacgcccaag taaccgctgg tgcgctggat atttcggcgg tggtctcgtg       60
agcggggaga agcggcacag cgaggccggc ccggtagaaa tcatcttttt gatgctggca      120
gtcagggcgg gggactacat cgtcgccgtg actgcggttc tcgcggtcgg gttcttcgcg      180
gtcgcggttg agggttttctg gttcctggtc gtcgcagtca tcgctgcacc ggcgtggtgg      240
tttctgcgcg actgggaatc gaagcggagg gccgtacggg tctttgaacg ggcatggaag      300
gggacacctg aatcccccgg tattgctctc tcccttggcc tgtcgaacgt ggcgggtct       360 ctgccgaggt tgaggaagtt tgaaactggt tcggggatac gcacactcgt gtttttcttg      420
ccgcccggag tcactgccga gagctttgag aaagttcgcc ctgcgctggc agacgcgatg      480
gggggtcacc gctgccaagt agagaaggtg gcccccggac aggtccgcgt cagagtgatt      540
gatgaggatt cgatgaagac gccgcgtgat gcgggatggg cgaaagatgt tgtgctggaa      600
gaggatacgt tcgacggtct tccgggcgag acgcgatcct ggttcgagca agaggggccg      660
gcatcatga                                                              669
```

<210> SEQ ID NO 34
<211> LENGTH: 558
<212> TYPE: DNA
<213> ORGANISM: Rhodococcus erythropolis
<220> FEATURE:

<221> NAME/KEY: misc_feature
<223> OTHER INFORMATION: 4477bp to 5034bp pRET1100

<400> SEQUENCE: 34

```
atgctggcag tcagggcggg ggactacatc gtcgccgtga ctgcggttct cgcggtcggg      60
ttcttcgcgg tcgcggttga gggtttctgg ttcctggtcg tcgcagtcat cgctgcaccg     120
gcgtggtggt ttctgcgcga ctgggaatcg aagcggaggg ccgtacgggt cttttgaacgg   180
gcatggaagg ggacacctga atccccggt attgctctct cccttggcct gtcgaacgtg     240
gcggggtctc tgccgaggtt gaggaagttt gaaactggtt cggggatacg cacactcgtg    300
ttttctttgc cgcccggagt cactgccgag agctttgaga agttcgccc tgcgctggca     360
gacgcgatgg ggggtcaccg ctgccaagta gagaaggtgg cccccggaca ggtccgcgtc    420
agagtgattg atgaggattc gatgaagacg ccgcgtgatg cgggatgggc gaaagatgtt    480
gtgctggaag aggatacgtt cgacggtctt ccgggcgaga cgcgatcctg gttcgagcaa    540
gaggggccgg catcatga                                                  558
```

<210> SEQ ID NO 35
<211> LENGTH: 791
<212> TYPE: DNA
<213> ORGANISM: Rhodococcus erythropolis
<220> FEATURE:
<221> NAME/KEY: misc_feature
<223> OTHER INFORMATION: 2410bp to 3200bp pRET1100

<400> SEQUENCE: 35

```
acgcgcggaa cgcctttcgg cttttgtcttt tgctggatgg cgggttttgg gcggcttctg   60
gtgatgcgct gctgcgctcc gtggggagag agacccaacg actgacctat ctctacccag   120
gtgcaattca tctcccgcgc tctgtcggct aggtaaacga ggtgctcccg cgcgagcttt   180
tccatgtggt cggccaatgt cagctcggtc aggacaacct gctgttgttg cgatagttgt    240
gtccgcacgg gtcgattgtc ttctgttgcg gcataacggt tttcgtcgtt cgcggagagt    300
gcggctaaat gaattgcatc ctcgattgag cggagcattt cgacgcggaa cctggcgatg    360
atgttgtctc tgtcttcatt cataactgaa gcgtattggg agtgttgccc tcccaccatg    420
tgtgccaatg caggtgtgaa ctgagtcaca gtttctcaat agactccaag tttgtgatcc    480
ttttactccc aaaatggggc atgatgtgtg cgtgcctcgg ttcagggggcg aaagttcgac   540
acctcgaaag aaggcctcga catggctttg aaagctgctg caacgtgat tcctgattcc     600
tccgcgtacg agtaccgggc ggttcaggtc gagccgaaga tggtcagaaa agaccccggaa  660
gacccgaact ctgagcagtt ccagaagcag aaggacggca cgccggtgtg gtcgatcgac    720
tgcattcggg tcgaccgggc atcaggcaac aaggcaatcg tgaccgtgac ggttccggac    780
gtgatggaac c                                                         791
```

<210> SEQ ID NO 36
<211> LENGTH: 501
<212> TYPE: DNA
<213> ORGANISM: Rhodococcus erythropolis
<220> FEATURE:
<221> NAME/KEY: misc_feature
<223> OTHER INFORMATION: 1000bp to 1500bp pRET1100

<400> SEQUENCE: 36

```
cttgttacat ctgccacaac tgtccgtgaa tctctgccag ctcctgaaac cgctggtcag    60
ggccttgcgg aatccgtgac cgctgatgat ttttggtctc attcgttccc ccgcgctgac   120
```

-continued

```
gatgtacgcg gcgcagctgc ttccttccag tcggtggcta actgggatgg gcgtgagggt      180
ccgaggccgc gtttcgttgt cgcgcctggc gttgtccgct tggaggtttg tgatctcgca      240
cgccgcgaac gaacggctga acgtgcgtat ctggctgctc gggctcgggt ggatatggcg      300
gctgccaggc ataactcgcc gtacgacttc gacgtggacg atgaagagtt ggcggaactg      360
gcttctctgc aaggcctcga ggacgacgac attgggggct ggtctgcgga gagggaaata      420
gtgggctggt ctgctcgttc tcggtcacgg atgatcttgc gaatggcaga actcgactgg      480
gctcccatga tggatttgcc g                                                501
```

<210> SEQ ID NO 37
<211> LENGTH: 945
<212> TYPE: DNA
<213> ORGANISM: Rhodococcus erythropolis
<220> FEATURE:
<221> NAME/KEY: misc_feature
<223> OTHER INFORMATION: 5000bp to 500bp pRET1100

<400> SEQUENCE: 37

```
gatcctggtt cgagcaagag gggccggcat catgagaaaa tcggcgggag tatctcggat       60
tcctatccgt ctcgggcgct ctcagtacgg ggaagacgtt ggattcgatc tcgctgcgga      120
cgccgctcac atcgccatgc agggcaaaac ccgatccggc aaaagtcagg cgacgtacaa      180
cgtgttagct caggcagcag cgaacgcggc ggttcgagtc gtagggtccg acccgacaca      240
cgtactcctg gagcccttca acatcgagg ggtgtccgag ccttacgtgg tttcgggact      300
gaatgcgcag gccacggtgg acatgctggg ctgggtcaag cgtgagtctg atcgtcgcat      360
cgaccagatg tggcccctgc gtaccgacaa gttttccgag ttcggggctt cgttcccgct      420
gatactcgtc gtgctcgaag agtttcccgg gatcctcgag ggggcagcgg acgaagacgc      480
cgcgttaggc cgaaaacctg ccgagcgtct cgcaccccgc atttcggcct acgtgcgtca      540
gatagcagcg cagtcggcaa aggctggaat tcgccttctc ctgctctcgc aacgagcgga      600
ggcctcgatc attggcggca atgcgcgttc gaatttcggg gtcaagatga ctctgagggt      660
ggacgaaccg gagtcggtga gaatgcttca tccgagcgct tccccggaag actgtgccct      720
ggtcgagacc ttcaagcctg gtacctgcct tttcgagaag ccaggagaag gccggcagat      780
tatgcgatgc gactttgtcg gcgagtacgg gagatatgcg cgagccatcg agtcttcgga      840
tctgcgtttt ctcgccaccc tccagcaaga ccaggcccaa cgcgaattct tcgctgagga      900
gttcggtgtg gtggatccgt catgactgga ccacaggaga gaaag                      945
```

<210> SEQ ID NO 38
<211> LENGTH: 939
<212> TYPE: DNA
<213> ORGANISM: Rhodococcus rhodnii
<220> FEATURE:
<221> NAME/KEY: misc_feature
<223> OTHER INFORMATION: 3350bp to 2412bp pRET1000

<400> SEQUENCE: 38

```
atggttgcgg tggaagagca cacaggcggc gcctgggaac agctgtggct accgctgtgg       60
ccactggcaa ccgacgattt cctcgacggc gtctaccgga tgcggcgatc agacgcactg      120
gatcgccgct acatcgagtc gaaccccgcag gcattgagca acctgctcgt cgtggacgtt      180
gaccacccgg acgccgcgct gcgggcgctg tcggcggccg ggaatcatcc tctgccgaac      240
gcgatcgtgg agaaccccccg taacgggcac gcacacgctg tgtgggcgct ggcagagccg      300
ttcacccgca ccgagtacgc ccgtcgtaag ccgctcgcct atgcggccgc cgtcaccgaa      360
```

```
ggcctccggc gcgccgtcca gggggacaag ggctattcgg gcctgatgac caagaacccg   420
actcacggtg actgggacac ccattggctg cacaccgagc ggcgatccct cgccgagctc   480
gaggcggaac tcggcatcca catgccgcca acgcgctggc ggcaaacccg atcgcgccgt   540
gagaacccga tcggcctcgg ccgaaactgc gccctgttcg aaaccgcacg cacctgggcc   600
taccgcgaaa tccgcttcca ctggggcgac ccgaccggcc tcggggccgc gatctatgcg   660
gaagccgcac agatcaacgc cacgttcagg aacccggtca caggcaggcc cgatccactg   720
ccagcaagcg agctacgcgc cgtcgcggcc tccattaccc gctggatcac tacaaagtcc   780
cggatgtggg ccgacggccc tgctgtctac gaggccacat tcatcgccat acaagccgca   840
cgcggtcgca agatgagtga agaagagcg gaggcaaacc ggaaacgagc gacgaaggtc   900
gaccggaacg cattgtggga ggcagaccgt gggcgctga                          939
```

<210> SEQ ID NO 39
<211> LENGTH: 840
<212> TYPE: DNA
<213> ORGANISM: Rhodococcus rhodnii
<220> FEATURE:
<221> NAME/KEY: misc_feature
<223> OTHER INFORMATION: 3251bp to 2412bp pRET1000

<400> SEQUENCE: 39

```
atgcggcgat cagacgcact ggatcgccgc tacatcgagt cgaacccgca ggcattgagc   60
aacctgctcg tcgtggacgt tgaccacccg gacgccgcgc tgcgggcgct gtcggcggcc   120
gggaatcatc ctctgccgaa cgcgatcgtg gagaaccccc gtaacgggca cgcacacgct   180
gtgtgggcgc tggcagagcc gttcaccgcc accgagtacg cccgtcgtaa gccgctcgcc   240
tatgcggccg ccgtcaccga aggcctccgg cgcgccgtcc agggggacaa gggctattcg   300
ggcctgatga ccaagaaccc gactcacggt gactgggaca cccattggct gcacaccgag   360
cggcgatccc tcgccgagct cgaggcggaa ctcggcatcc acatgccgcc aacgcgctgg   420
cggcaaaccc gatcgcgccg tgagaacccg atcggcctcg gccgaaactg cgccctgttc   480
gaaaccgcac gcacctgggc ctaccgcgaa atccgcttcc actggggcga cccgaccggc   540
ctcggggccg cgatctatgc ggaagccgca cagatcaacg ccacgttcag gaacccggtc   600
acaggcaggc ccgatccact gccagcaagc gagctacgcg ccgtcgcggc ctccattacc   660
cgctggatca ctacaaagtc ccggatgtgg gccgacggcc ctgctgtcta cgaggccaca   720
ttcatcgcca tacaagccgc acgcggtcgc aagatgagtg agaagaagcg cgaggcaaac   780
cggaaacgag cgacgaaggt cgaccggaac gcattgtggg aggcagaccg tgggcgctga   840
```

<210> SEQ ID NO 40
<211> LENGTH: 534
<212> TYPE: DNA
<213> ORGANISM: Rhodococcus rhodnii
<220> FEATURE:
<221> NAME/KEY: misc_feature
<223> OTHER INFORMATION: 2945bp to 2412bp pRET1000

<400> SEQUENCE: 40

```
atgaccaaga acccgactca cggtgactgg gacacccatt ggctgcacac cgagcggcga   60
tccctcgccg agctcgaggc ggaactcggc atccacatgc cgccaacgcg ctggcggcaa   120
acccgatcgc gccgtgagaa cccgatcggc ctcggccgaa actgcgccct gttcgaaacc   180
gcacgcacct gggcctaccg cgaaatccgc ttccactggg gcgacccgac cggcctcggg   240
```

```
gccgcgatct atgcggaagc cgcacagatc aacgccacgt tcaggaaccc ggtcacaggc    300
aggcccgatc cactgccagc aagcgagcta cgcgccgtcg cggcctccat tacccgctgg    360
atcactacaa agtcccggat gtgggccgac ggccctgctg tctacgaggc cacattcatc    420
gccatacaag ccgcacgcgg tcgcaagatg agtgagaaga agcgcgaggc aaaccggaaa    480
cgagcgacga aggtcgaccg gaacgcattg tgggaggcag accgtgggcg ctga           534
```

```
<210> SEQ ID NO 41
<211> LENGTH: 438
<212> TYPE: DNA
<213> ORGANISM: Rhodococcus rhodnii
<220> FEATURE:
<221> NAME/KEY: misc_feature
<223> OTHER INFORMATION: 2849bp to 2412bp pRET1000

<400> SEQUENCE: 41
atgccgccaa cgcgctggcg gcaaacccga tcgcgccgtg agaacccgat cggcctcggc      60
cgaaactgcg ccctgttcga aaccgcacgc acctgggcct accgcgaaat ccgcttccac     120
tggggcgacc cgaccggcct cggggccgcg atctatgcgg aagccgcaca gatcaacgcc     180
acgttcagga acccggtcac aggcaggccc gatccactgc cagcaagcga gctacgcgcc     240
gtcgcggcct ccattacccg ctggatcact acaaagtccc ggatgtgggc cgacggccct     300
gctgtctacg aggccacatt catcgccata caagccgcac gcggtcgcaa gatgagtgag     360
aagaagcgcg aggcaaaccg gaaacgagcg acgaaggtcg accggaacgc attgtgggag     420
gcagaccgtg ggcgctga                                                   438
```

```
<210> SEQ ID NO 42
<211> LENGTH: 207
<212> TYPE: DNA
<213> ORGANISM: Rhodococcus rhodnii
<220> FEATURE:
<221> NAME/KEY: misc_feature
<223> OTHER INFORMATION: 2365bp to 2159bp pRET1000

<400> SEQUENCE: 42
atgggggcct ccacgcgcac gatccagcgc atcatggccg agccgcggga ccagttcctc      60
gcacgggcag ccgagaaccg tcgccgggcc gtcgagctgc gcgagcaggg cctgaagtac     120
cgcgagatcg ccgaggagat gggaatctcc accggaacgg tgggaaagct cctgcacgac     180
gcacgcaagt acgcggtcag ctcctag                                         207
```

```
<210> SEQ ID NO 43
<211> LENGTH: 174
<212> TYPE: DNA
<213> ORGANISM: Rhodococcus rhodnii
<220> FEATURE:
<221> NAME/KEY: misc_feature
<223> OTHER INFORMATION: 2332bp to 2159bp pRET1000

<400> SEQUENCE: 43
atggccgagc cgcgggacca gttcctcgca cgggcagccg agaaccgtcg ccgggccgtc      60
gagctgcgcg agcagggcct gaagtaccgc gagatcgccg aggagatggg aatctccacc     120
ggaacggtgg gaaagctcct gcacgacgca cgcaagtacg cggtcagctc ctag           174
```

```
<210> SEQ ID NO 44
<211> LENGTH: 330
<212> TYPE: DNA
<213> ORGANISM: Rhodococcus rhodnii
<220> FEATURE:
```

```
<221> NAME/KEY: misc_feature
<223> OTHER INFORMATION: 3197bp to 3526bp pRET1000

<400> SEQUENCE: 44
atgcctgcgg gttcgactcg atgtagcggc gatccagtgc gtctgatcgc cgcatccggt    60
agacgccgtc gaggaaatcg tcggttgcca gtggccacag cggtagccac agctgttccc   120
aggcgccgcc tgtgtgctct ccaccgcaa ccatggggaa cacactcaca cacaagatcg    180
atttattccg gtacgacacg ccagccaagt cagatgtttc ggtttctgga gcggtcctcc   240
agacctttga gatccgctcc agaaacgtcc acaaattatt ggggtacgtc gaaccaagcc   300
ttatcaggta tcccggggtt ccggggggtga                                   330

<210> SEQ ID NO 45
<211> LENGTH: 357
<212> TYPE: DNA
<213> ORGANISM: Rhodococcus rhodnii
<220> FEATURE:
<221> NAME/KEY: misc_feature
<223> OTHER INFORMATION: 4035bp to 3679bp pRET1000

<400> SEQUENCE: 45
atggggtggt tattgcttgt tgcgtcgggg gccgtggcga tggtggccgg tgtggtctta    60
ccgcgccggg atcgtctcgg gccggcacca ggatttccct ggttctgggt ggtgttccca   120
tccacgtgca ttgccatcgc tgccgcggtg ggtgtcttcg cttggcccca agcggttacc   180
ggcacgggga gctactggtg ggatccgccc agcgcgagct caccgaccct gcagttcctg   240
tcaaacgagc agtaccggcg cctcgtgaca ctgcgccggt tgcaggggc gctaccggtg    300 gtgtccctcg tgggaagcgg attgtgcgtg tgggcctggc gtcgacgccg cttctga      357

<210> SEQ ID NO 46
<211> LENGTH: 318
<212> TYPE: DNA
<213> ORGANISM: Rhodococcus rhodnii
<220> FEATURE:
<221> NAME/KEY: misc_feature
<223> OTHER INFORMATION: 3996bp to 3679bp pRET1000

<400> SEQUENCE: 46
atggtggccg gtgtggtctt accgcgccgg gatcgtctcg ggccggcacc aggatttccc    60
tggttctggg tggtgttccc atccacgtgc attgccatcg ctgccgcggt gggtgtcttc   120
gcttggcccc aagcggttac cggcacgggg agctactggt gggatccgcc cagcgcgagc   180
tcaccgaccc tgcagttcct gtcaaacgag cagtaccggc gcctcgtgac actgcgccgg   240
ttgcaggggg cgctaccggt ggtgtccctc gtgggaagcg gattgtgcgt gtgggcctgg   300
cgtcgacgcc gcttctga                                                 318

<210> SEQ ID NO 47
<211> LENGTH: 450
<212> TYPE: DNA
<213> ORGANISM: Rhodococcus  rhodnii
<220> FEATURE:
<221> NAME/KEY: misc_feature
<223> OTHER INFORMATION: 4381bp to 4830bp pRET1000

<400> SEQUENCE: 47
atggccgctg acgctgcatc tgacgaccgg cggaccgagg tccgcgccgc tgcttcgcgg    60
gccgctgacg cggccccggc gaagcgcacc cgcaccgtgg cggtgcggct gaccgatggg   120
gaggaggccg cgtggatcga cgccgcgctg gccgatggcc accggcagct cggggcgtgg   180
```
gtgcgtgagc gggcggtggc cggctatctc gggaaggtcc gcccgaagac cggcagtgga    240
atgtcggcgg aggcggccgc ggaggtcgcc gcgatgcggc agcagatgac gaaggtgggg    300
aacaacctga accagatcgc gagggcgatc aacgccgggc aggtgccgtc gcagatggcc    360
gagtccctgc agaaggggtg gctggagagg tgggggcagg agttggggcg gatggcggat    420
cggctcgacg cgctcgacga ccagggctga                                     450

<210> SEQ ID NO 48
<211> LENGTH: 210
<212> TYPE: DNA
<213> ORGANISM: Rhodococcus rhodnii
<220> FEATURE:
<221> NAME/KEY: misc_feature
<223> OTHER INFORMATION: 4621bp to 4830bp pRET1000

<400> SEQUENCE: 48
atgtcggcgg aggcggccgc ggaggtcgcc gcgatgcggc agcagatgac gaaggtgggg     60
aacaacctga accagatcgc gagggcgatc aacgccgggc aggtgccgtc gcagatggcc    120
gagtccctgc agaaggggtg gctggagagg tgggggcagg agttggggcg gatggcggat    180
cggctcgacg cgctcgacga ccagggctga                                     210

<210> SEQ ID NO 49
<211> LENGTH: 177
<212> TYPE: DNA
<213> ORGANISM: Rhodococcus rhodnii
<220> FEATURE:
<221> NAME/KEY: misc_feature
<223> OTHER INFORMATION: 4654bp to 4830bp pRET1000

<400> SEQUENCE: 49
atgcggcagc agatgacgaa ggtggggaac aacctgaacc agatcgcgag ggcgatcaac     60
gccgggcagg tgccgtcgca gatggccgag tccctgcaga aggggtggct ggagaggtgg    120 ggcaggagt tggggcggat ggcggatcgg ctcgacgcgc tcgacgacca gggctga        177

<210> SEQ ID NO 50
<211> LENGTH: 165
<212> TYPE: DNA
<213> ORGANISM: Rhodococcus rhodnii
<220> FEATURE:
<221> NAME/KEY: misc_feature
<223> OTHER INFORMATION: 4666bp to 4830bp pRET1000

<400> SEQUENCE: 50
atgacgaagg tggggaacaa cctgaaccag atcgcgaggg cgatcaacgc cgggcaggtg     60
ccgtcgcaga tggccgagtc cctgcagaag gggtggctgg agaggtgggg gcaggagttg    120 ggcggatgg cggatcggct cgacgcgctc gacgaccagg gctga                     165

<210> SEQ ID NO 51
<211> LENGTH: 453
<212> TYPE: DNA
<213> ORGANISM: Rhodococcus rhodnii
<220> FEATURE:
<221> NAME/KEY: misc_feature
<223> OTHER INFORMATION: 5161bp to 4709bp pRET1000

<400> SEQUENCE: 51
atgactctcg aagcccatcc gctcggcgac cgtctgcgcg atgtccgcga actcggtatc     60
ggtcagccgc cgatccccgg gcgcgcaccg cagcgagcaa tgccacaccg gcttacccac    120

```
ccgcgcgttc gtcgcggcgg cccgctcgaa gtcccgcccc caccgggtcg ggttttggc    180 ggtgacctgc accgatcccg cgatcaccgt cccgccggca atcagccggc cgcctcggt    240 gcggtagctg tgcggggtgg ccttccccgg cccgtgcaga tacgccgcca acccttcgg    300 gtcgctgccc gtgctgatct tcgcgatcac gtcagccctg gtcgtcgagc gcgtcgagcc    360
gatccgccat ccgccccaac tcctgccccc acctctccag ccacccctc tgcagggact    420 cggccatctg cgacggcacc tgcccggcgt tga                                453

<210> SEQ ID NO 52
<211> LENGTH: 354
<212> TYPE: DNA
<213> ORGANISM: Rhodococcus rhodnii
<220> FEATURE:
<221> NAME/KEY: misc_feature
<223> OTHER INFORMATION: 5062bp to 4709bp pRET1000

<400> SEQUENCE: 52
atgccacacc ggcttaccca cccgcgcgtt cgtcgcggcg gcccgctcga agtcccgccc     60
ccaccgggtc gggttttttgg cggtgacctg caccgatccc gcgatcaccg tcccgccggc    120
aatcagccgg cccgcctcgg tgcggtagct gtgcggggtg gccttccccg gcccgtgcag    180
atacgccgcc aacccttcg gtcgctgccc cgtgctgatc ttcgcgatca cgtcagccct    240
ggtcgtcgag cgcgtcgagc cgatccgcca tccgccccaa ctcctgcccc acctctcca    300 gccacccctt ctgcagggac tcggccatct gcgacggcac ctgcccggcg ttga          354

<210> SEQ ID NO 53
<211> LENGTH: 288
<212> TYPE: DNA
<213> ORGANISM: Rhodococcus rhodnii
<220> FEATURE:
<221> NAME/KEY: misc_feature
<223> OTHER INFORMATION: 2331bp to 2618bp pRET1000

<400> SEQUENCE: 53
atgatgcgct ggatcgtgcg cgtggaggcc cccatcttct cggccagctc gcagctgtc     60 tgcttgcggc ggatcggtcg ttcagcgccc acggtctgcc tcccacaatg cgttccggtc    120
gaccttcgtc gctcgtttcc ggtttgcctc gcgcttcttc tcactcatct tgcgaccgcg    180
tgcggcttgt atggcgatga atgtggcctc gtagacagca gggccgtcgg cccacatccg    240
ggactttgta gtgatccagc gggtaatgga ggccgcgacg gcgcgtag               288

<210> SEQ ID NO 54
<211> LENGTH: 285
<212> TYPE: DNA
<213> ORGANISM: Rhodococcus rhodnii
<220> FEATURE:
<221> NAME/KEY: misc_feature
<223> OTHER INFORMATION: 2334bp to 2618bp pRET1000

<400> SEQUENCE: 54
atgcgctgga tcgtgcgcgt ggaggccccc atcttctcgg ccagctcgcg agctgtctgc     60
ttgcggcgga tcggtcgttc agcgcccacg gtctgcctcc acaatgcgt tccggtcgac    120 cttcgtcgct cgtttccggt ttgcctcgcg cttcttctca tcatcttgc gaccgcgtgc    180 ggcttgtatg gcgatgaatg tggcctcgta gacagcaggg ccgtcggccc acatccggga    240
ctttgtagtg atccagcggg taatggaggc cgcgacggcg cgtag                   285

<210> SEQ ID NO 55
```

```
<211> LENGTH: 336
<212> TYPE: DNA
<213> ORGANISM: Rhodococcus rhodnii
<220> FEATURE:
<221> NAME/KEY: misc_feature
<223> OTHER INFORMATION: 2907bp to 3242bp pRET1000

<400> SEQUENCE: 55
atgggtgtcc cagtcaccgt gagtcgggtt cttggtcatc aggcccgaat agcccttgtc      60
cccctggacg gcgcgccgga ggccttcggt gacggcggcc gcataggcga gcggcttacg     120
acgggcgtac tcggtgcggg tgaacggctc tgccagcgcc acacagcgt gtgcgtgccc     180 gttacggggg ttctccacga tcgcgttcgg cagaggatga ttcccggccg ccgacagcgc     240
ccgcagcgcg cgtccgggt ggtcaacgtc acgacgagc aggttgctca atgcctgcgg     300
gttcgactcg atgtagcggc gatccagtgc gtctga                              336

<210> SEQ ID NO 56
<211> LENGTH: 513
<212> TYPE: DNA
<213> ORGANISM: Rhodococcus rhodnii
<220> FEATURE:
<221> NAME/KEY: misc_feature
<223> OTHER INFORMATION: 1650bp to 2162bp pRET1000

<400> SEQUENCE: 56
atgcggattg aactagttca tttggggaac gatgacctga tgaccgggga tcgtgaccta      60
cccatgctga ccatcgccga ggcggtggac gcgacgcaga ccagtgagag cacgatcaag     120
cgccgcctgc ggtcgggcgc gttcccgaac gcggtccgca ctgccgacgg aagtggatg     180 attcccctcg gtgacctatc agcggcaggg ctgagaccag ggaaaatggc gaaacctgac     240
ccggtgaccc cttcaaatga ccgggtccgt gacctggcag ctgagaacgc cgagctccgt     300
cagcgcctgg ccgtggccga agccctggcc agcgaacgca atcggatcat cgacgtgcag     360
caacagatgc tccggatgct cgaagcccgg ccggtgtcgg ccctggagcc cgcggcggtt     420
ccagtggcgg gtccgccgcc gcccgtcccg gccgccgatg gtcgggcagc tacgggcgcc     480
ctggcccgga tacgtcgacg gcttctcggc tag                                 513

<210> SEQ ID NO 57
<211> LENGTH: 474
<212> TYPE: DNA
<213> ORGANISM: Rhodococcus rhodnii
<220> FEATURE:
<221> NAME/KEY: misc_feature
<223> OTHER INFORMATION: 1689bp to 2162bp pRET1000

<400> SEQUENCE: 57
atgaccgggg atcgtgacct acccatgctg accatcgccg aggcggtgga cgcgacgcag      60
accagtgaga gcacgatcaa gcgccgcctg cggtcgggcg cgttcccgaa cgcggtccgc     120
actgccgacg ggaagtggat gattcccctc ggtgacctat cagcggcagg gctgagacca     180
gggaaaatgg cgaaacctga cccggtgacc ccttcaaatg accgggtccg tgacctggca     240
gctgagaacg ccgagctccg tcagcgcctg gccgtggccg aagccctggc cagcgaacgc     300
aatcggatca tcgacgtgca gcaacagatg ctccggatgc tcgaagcccg gccggtgtcg     360
gccctggagc ccgcggcggt tccagtggcg gtccgccgcc gcccgtccc ggccgccgat     420 ggtcgggcag ctacgggcgc cctggcccgg atacgtcgac ggcttctcgg ctag          474

<210> SEQ ID NO 58
```

<211> LENGTH: 450
<212> TYPE: DNA
<213> ORGANISM: Rhodococcus rhodnii
<220> FEATURE:
<221> NAME/KEY: misc_feature
<223> OTHER INFORMATION: 1713bp to 2162bp pRET1000

<400> SEQUENCE: 58

```
atgctgacca tcgccgaggc ggtggacgcg acgcagacca gtgagagcac gatcaagcgc      60
cgcctgcggt cgggcgcgtt cccgaacgcg gtccgcactg ccgacgggaa gtggatgatt    120
cccctcggtg acctatcagc ggcagggctg agaccaggga aaatggcgaa acctgacccg    180
gtgacccctt caaatgaccg ggtccgtgac ctggcagctg agaacgccga gctccgtcag    240
cgcctggccg tggccgaagc cctggccagc gaacgcaatc ggatcatcga cgtgcagcaa    300
cagatgctcc ggatgctcga agcccggccg gtgtcggccc tggagcccgc ggcggttcca    360
gtggcgggtc cgccgccgcc cgtcccggcc gccgatggtc gggcagctac gggcgccctg    420
gccccggatac gtcgacggct ctcggctag                                     450
```

<210> SEQ ID NO 59
<211> LENGTH: 336
<212> TYPE: DNA
<213> ORGANISM: Rhodococcus rhodnii
<220> FEATURE:
<221> NAME/KEY: misc_feature
<223> OTHER INFORMATION: 1827bp to 2162bp pRET1000

<400> SEQUENCE: 59

```
atgattcccc tcggtgacct atcagcggca gggctgagac cagggaaaat ggcgaaacct      60
gacccggtga ccccttcaaa tgaccgggtc cgtgacctgg cagctgagaa cgccgagctc    120
cgtcagcgcc tggccgtggc cgaagccctg ccagcgaac gcaatcggat catcgacgtg    180
cagcaacaga tgctccggat gctcgaagcc cggccggtgt cggccctgga gcccgcggcg    240
gttccagtgg cgggtccgcc gccgcccgtc ccggccgccg atggtcgggc agctacgggc    300
gccctggccc ggatacgtcg acggcttctc ggctag                              336
```

<210> SEQ ID NO 60
<211> LENGTH: 288
<212> TYPE: DNA
<213> ORGANISM: Rhodococcus rhodnii
<220> FEATURE:
<221> NAME/KEY: misc_feature
<223> OTHER INFORMATION: 1875bp to 2162bp pRET1000

<400> SEQUENCE: 60

```
atggcgaaac ctgacccggt gaccccttca aatgaccggg tccgtgacct ggcagctgag      60
aacgccgagc tccgtcagcg cctggccgtg gccgaagccc tggccagcga acgcaatcgg    120
atcatcgacg tgcagcaaca gatgctccgg atgctcgaag cccggccggt gtcggccctg    180
agcccgcgg cggttccagt ggcgggtccg ccgccgcccg tcccggccgc cgatggtcg    240
gcagctacgg gcgccctggc ccggatacgt cgacggcttc tcggctag                288
```

<210> SEQ ID NO 61
<211> LENGTH: 264
<212> TYPE: DNA
<213> ORGANISM: Rhodococcus rhodnii
<220> FEATURE:
<221> NAME/KEY: misc_feature
<223> OTHER INFORMATION: 1906bp to 2169bp pRET1000

<400> SEQUENCE: 61

```
atgaccgggt ccgtgacctg gcagctgaga acgccgagct ccgtcagcgc ctggccgtgg      60
ccgaagccct ggccagcgaa cgcaatcgga tcatcgacgt gcagcaacag atgctccgga     120
tgctcgaagc ccggccggtg tcggccctgg agcccgcggc ggttccagtg gcgggtccgc     180
cgccgcccgt cccggccgcc gatggtcggg cagctacggg cgccctggcc cggatacgtc     240
gacggcttct cggctaggag ctga                                            264

<210> SEQ ID NO 62
<211> LENGTH: 258
<212> TYPE: DNA
<213> ORGANISM: Rhodococcus rhodnii
<220> FEATURE:
<221> NAME/KEY: misc_feature
<223> OTHER INFORMATION: 810bp to 553bp pRET1000

<400> SEQUENCE: 62
atgctatggg aggtatgcac ctttcgcgcg ttatgtacgc atcctgggca ccctgggcac      60
gaccgacctt ctagcgatcg atggtgttct tggacatgct tcgccaggcc tgcgtctgtt     120
ccctacgctc cacgaaagcc ttctcgctct ctgctcacag tcccattccg gattctcgac     180
ctcggtcgcg gccgggtggc tgataccccg gggccgactg cggcatggtt ggtccctggc     240
ggcgggccgg gggtttga                                                   258

<210> SEQ ID NO 63
<211> LENGTH: 540
<212> TYPE: DNA
<213> ORGANISM: Rhodococcus rhodnii
<220> FEATURE:
<221> NAME/KEY: misc_feature
<223> OTHER INFORMATION: 117bp to 656bp pRET1000

<400> SEQUENCE: 63
atgggaggcc acccgacacc gctacgggac atgctcgccg cccaggagca gcgccggaag      60
ccgtggactc cggagcagaa cgccagtac gcgaccgcaa agcccaagc agaacgcgcc       120 gcgaaggcca aggacgccgc gaaatggacc gaggtcgccg gcggcggcta ccagcgggac     180
gtgcgcggga tgaacctgcg actgtgggtg gctgaggacg gcgcctggtc gatcacctcg     240
aagaaggacc ccgaccgcca gtacgccgca ggtcaggccc acaccgtcgc gcaggcccaa     300
gccgcggcca cggccacagc gaaaacgcag gcccaggcga tgtggaagca ggtcccggcc     360
gacaagcgca ccgagtcagc caccagagcg gtccggcgcg tgatcgcgga tctcacccccc   420 accaaacccg ccgaggtcaa accccccggcc cgccgccagg accaaccat gccgcagtcg    480 gccccgggt atcagccacc cggccgcgac cgaggtcgag aatccggaat gggactgtga     540

<210> SEQ ID NO 64
<211> LENGTH: 510
<212> TYPE: DNA
<213> ORGANISM: Rhodococcus rhodnii
<220> FEATURE:
<221> NAME/KEY: misc_feature
<223> OTHER INFORMATION: 147bp to 656bp pRET1000

<400> SEQUENCE: 64
atgctcgccg cccaggagca gcgccggaag ccgtggactc cggagcagaa cgccagtac      60 gcgaccgcaa agcccaagc agaacgcgcc gcgaaggcca aggacgccgc gaaatggacc     120
gaggtcgccg gcggcggcta ccagcgggac gtgcgcggga tgaacctgcg actgtgggtg     180
gctgaggacg gcgcctggtc gatcacctcg aagaaggacc ccgaccgcca gtacgccgca     240
```

```
ggtcaggccg acaccgtcgc gcaggcccaa gccgcggcca cggccacagc gaaaacgcag      300
gcccaggcga tgtggaagca ggtcccggcc gacaagcgca ccgagtcagc caccagagcg      360
gtccggcgcg tgatcgcgga tctcaccccc accaaacccg ccgaggtcaa accccggcc       420 cgccgccagg gaccaaccat gccgcagtcg gccccggggt atcagccacc cggccgcgac      480
cgaggtcgag aatccggaat gggactgtga                                      510

<210> SEQ ID NO 65
<211> LENGTH: 351
<212> TYPE: DNA
<213> ORGANISM: Rhodococcus rhodnii
<220> FEATURE:
<221> NAME/KEY: misc_feature
<223> OTHER INFORMATION: 306bp to 656bp pRET1000

<400> SEQUENCE: 65
atgaacctgc gactgtgggt ggctgaggac ggcgcctggt cgatcacctc gaagaaggac       60
cccgaccgcc agtacgccgc aggtcaggcc gacaccgtcg cgcaggccca gccgcggcc       120 acggccacag cgaaaacgca ggcccaggcg atgtggaagc aggtcccggc cgacaagcgc      180
accgagtcag ccaccagagc ggtccggcgc gtgatcgcgg atctcaccccc accaaaccc    240 gccgaggtca aaccccggc ccgccgccag ggaccaacca tgccgcagtc ggccccgggg      300
tatcagccac ccggccgcga ccgaggtcga gaatccggaa tgggactgtg a              351

<210> SEQ ID NO 66
<211> LENGTH: 201
<212> TYPE: DNA
<213> ORGANISM: Rhodococcus rhodnii
<220> FEATURE:
<221> NAME/KEY: misc_feature
<223> OTHER INFORMATION: 456bp to 656bp pRET1000

<400> SEQUENCE: 66
atgtggaagc aggtcccggc cgacaagcgc accgagtcag ccaccagagc ggtccggcgc       60
gtgatcgcgg atctcaccccc accaaaccc gccgaggtca aaccccggc ccgccgccag      120 ggaccaacca tgccgcagtc ggccccgggg tatcagccac ccggccgcga ccgaggtcga      180
gaatccggaa tgggactgtg a                                               201

<210> SEQ ID NO 67
<211> LENGTH: 1326
<212> TYPE: DNA
<213> ORGANISM: Rhodococcus rhodnii
<220> FEATURE:
<221> NAME/KEY: misc_feature
<223> OTHER INFORMATION: 5144bp to 656bp pRET1000

<400> SEQUENCE: 67
atgggcttcg agagtcatcc gtgggtggcg gtgcggcacg acgacgacca catccacctg       60
gctgtctccc gggtcgattt tcagggcgtg acctggaaga cagcaacga ccggtggaag      120 gtcgtcgagg tgatgcgcga ggtcgaacgc gcgcacggcc tgatcgaggt ggcgagcccg      180
gagcgggccc gtggccggca agccagcagc ggcgagcaac gccgcgcggt gcggaccggc      240
aaggtggcgc agcgggacgg tctgagggaa attgtgaccg ccgccgcga catcgccgca      300 ggccagggtg tgggggcgtt cgaagtggcg ctcgtacaga accgattac ccgagtgcag      360 gtgcggcgca acgtcgcgaa gacgggccgg atgaatggct acagcttcaa cctgcccggc      420
tacgtcgacg ccgccgggga gccgatctgg ttgccggcct ccaaactcga ccggggtttg      480
```

```
tcctggtcac agctggaaaa gacgctgacc agaccccgcc cggaccgcct cgccggcgag    540
gagacggtgc cgcggaagcg gctcgagcgc gccgccgcgt gggagcagcg ccgccgcgag    600
gtcggcggcg agcagttcgc agctgcccgc tgggagcagg cccgcgcgaa tgttggtgag    660
acggccgggc ggatccgcgc cgaacagtcc gcggacacga agtggaagca ggtgaacgag    720
gcgttgacca gccaagaccg ggccgaggag caggctgccg aggcagcgcg ggtcgcctcc    780
gctgtcatgg gaggccaccc gacaccgcta cgggacatgc tcgccgccca ggagcagcgc    840
cggaagccgt ggactccgga gcagaaacgc cagtacgcga ccgcaaaagc ccaagcagaa    900
cgcgccgcga aggccaagga cgccgcgaaa tggaccgagg tcgccggcgg cggctaccag    960
cgggacgtgc gcgggatgaa cctgcgactg tgggtggctg aggacggcgc ctggtcgatc   1020
acctcgaaga aggaccccga ccgccagtac gccgcaggtc aggccgacac cgtcgcgcag   1080
gcccaagccg cggccacggc cacagcgaaa acgcaggccc aggcgatgtg gaagcaggtc   1140
ccggccgaca gcgcaccga gtcagccacc agagcggtcc ggcgcgtgat cgcggatctc   1200 accccacca aacccgccga ggtcaaaccc ccggcccgcc gccagggacc aaccatgccg   1260
cagtcggccc cggggtatca gccacccggc cgcgaccgag gtcgagaatc cggaatggga   1320
ctgtga                                                             1326

<210> SEQ ID NO 68
<211> LENGTH: 1194
<212> TYPE: DNA
<213> ORGANISM: Rhodococcus rhodnii
<220> FEATURE:
<221> NAME/KEY: misc_feature
<223> OTHER INFORMATION: 5276bp to 656bp pRET1000

<400> SEQUENCE: 68
atgcgcgagg tcgaacgcgc gcacggcctg atcgaggtgg cgagcccgga gcgggcccgt     60
ggccggcaag ccagcagcgg cgagcaacgc cgcgcggtgc ggaccggcaa ggtggcgcag    120
cgggacggtc tgagggaaat tgtgaccgcc gcccgcgaca tcgccgcagg ccagggtgtg    180
ggggcgttcg aagtggcgct cgtacagaac ccgattaccc gagtgcaggt gcggcgcaac    240
gtcgcgaaga cgggccggat gaatggctac agcttcaacc tgcccggcta cgtcgacgcc    300
gccggggagc cgatctggtt gccggcctcc aaactcgacc ggggtttgtc ctggtcacag    360
ctggaaaaga cgctgaccag accccgcccg gaccgcctcg ccggcgagga gacggtgccg    420
cggaagcggc tcgagcgcgc cgccgcgtgg gagcagcgcc gccgcgaggt cggcggcgag    480
cagttcgcag ctgcccgctg ggagcaggcc cgcgcgaatg ttggtgagac ggccgggcgg    540
atccgcgccc aacagtccgc ggacacgaag tggaagcagg tgaacgaggc gttgaccagc    600
caagaccggg ccgaggagca ggctgccgag gcagcgcggg tcgcctccgc tgtcatggga    660
ggccacccga caccgctacg ggacatgctc gccgccagg agcagcgccg gaagccgtgg    720
actccggagc agaaacgcca gtacgcgacc gcaaaagccc aagcagaacg cgccgcgaag    780
gccaaggacg ccgcgaaatg gaccgaggtc gccggcggcg gctaccagcg ggacgtgcgc    840
gggatgaacc tgcgactgtg ggtggctgag gacggcgcct ggtcgatcac ctcgaagaag    900
gaccccgacc gccagtacgc cgcaggtcag gccgacaccc tcgcgcaggc caagccgcg     960 gccacggcca cagcgaaaac gcaggccag gcgatgtgga agcaggtccc ggccgacaag   1020
cgcaccgagt cagccaccag agcggtccgg cgcgtgatcg cggatctcac ccccaccaaa   1080
cccgccgagg tcaaaccccc ggcccgccgc cagggaccaa ccatgccgca gtcggccccg   1140
```
gggtatcagc cacccggccg cgaccgaggt cgagaatccg gaatgggact gtga    1194

<210> SEQ ID NO 69
<211> LENGTH: 936
<212> TYPE: DNA
<213> ORGANISM: Rhodococcus rhodnii
<220> FEATURE:
<221> NAME/KEY: misc_feature
<223> OTHER INFORMATION: 5534bp to 656bp pRET1000

<400> SEQUENCE: 69

```
atgaatggct acagcttcaa cctgcccggc tacgtcgacg ccgccgggga gccgatctgg    60
ttgccggcct ccaaactcga ccggggtttg tcctggtcac agctggaaaa gacgctgacc   120
agaccccgcc cggaccgcct cgccggcgag gagacggtgc cgcggaagcg gctcgagcgc   180
gccgccgcgt gggagcagcg ccgccgcgag gtcggcggcg agcagttcgc agctgcccgc   240
tgggagcagg cccgcgcgaa tgttggtgag acggccgggc ggatccgcgc cgaacagtcc   300
gcggacacga agtggaagca ggtgaacgag gcgttgacca gccaagaccg ggccgaggag   360
caggctgccg aggcagcgcg ggtcgcctcc gctgtcatgg gaggccaccc gacaccgcta   420
cgggacatgc tcgccgccca ggagcagcgc cggaagccgt ggactccgga gcagaaacgc   480
cagtacgcga ccgcaaaagc ccaagcagaa cgcgccgcga aggccaagga cgccgcgaaa   540
tggaccgagg tcgccggcgg cggctaccag cgggacgtgc gcgggatgaa cctgcgactg   600
tgggtggctg aggacggcgc ctggtcgatc acctcgaaga aggaccccga ccgccagtac   660
gccgcaggtc aggccgacac cgtcgcgcag gcccaagccg cggccacggc cacagcgaaa   720
acgcaggccc aggcgatgtg gaagcaggtc ccggccgaca gcgcaccga gtcagccacc   780
agagcggtcc ggcgcgtgat cgcggatctc acccccacca aacccgccga ggtcaaaccc   840
ccggcccgcc gccagggacc aaccatgccg cagtcggccc cggggtatca gccacccggc   900
cgcgaccgag gtcgagaatc cggaatggga ctgtga                             936
```

<210> SEQ ID NO 70
<211> LENGTH: 153
<212> TYPE: DNA
<213> ORGANISM: Rhodococcus rhodnii
<220> FEATURE:
<221> NAME/KEY: misc_feature
<223> OTHER INFORMATION: 3355bp to 3507bp pRET1000

<400> SEQUENCE: 70

```
aacacactca cacacaagat cgatttattc cggtacgaca cgccagccaa gtcagatgtt    60
tcggtttctg gagcggtcct ccagaccttt gagatccgct ccagaaacgt ccacaaatta   120
ttggggtacg tcgaaccaag ccttatcagg tat                                153
```

<210> SEQ ID NO 71
<211> LENGTH: 61
<212> TYPE: DNA
<213> ORGANISM: Rhodococcus rhodnii
<220> FEATURE:
<221> NAME/KEY: misc_feature
<223> OTHER INFORMATION: 4290bp to 4350bp pRET1000

<400> SEQUENCE: 71

```
gagctatgcc cagggttgcg cagtgacttc gtcactgcgt aaccctgggc gctcgcctcc    60
c                                                                    61
```

<210> SEQ ID NO 72
<211> LENGTH: 325
<212> TYPE: DNA
<213> ORGANISM: Rhodococcus rhodnii
<220> FEATURE:
<221> NAME/KEY: misc_feature
<223> OTHER INFORMATION: 3570bp to 3894bp pRET1000

<400> SEQUENCE: 72

```
ccgctcgaag tccttgagtc agtgacagga ccactgctgg gctcccagcg cagaaggcaa        60
gtgaaggcag acgactgcgg gaggtaagtc gggtacggca tgaggtcctt cagaagcggc       120
gtcgacgcca ggcccacacg cacaatccgc ttcccacgag ggacaccacc ggtagcgccc       180
cctgcaaccg gcgcagtgtc acgaggcgcc ggtactgctc gtttgacagg aactgcaggg       240
tcggtgagct cgcgctgggc ggatcccacc agtagctccc cgtgccggta accgcttggg       300
gccaagcgaa gacacccacc gcggc                                             325
```

<210> SEQ ID NO 73
<211> LENGTH: 5444
<212> TYPE: DNA
<213> ORGANISM: Rhodococcus erythropolis
<220> FEATURE:
<221> NAME/KEY: misc_feature
<223> OTHER INFORMATION: pRET1100 Full Length

<400> SEQUENCE: 73

```
cccgggatcc tcgaggggc agcggacgaa gacgccgcgt taggccgaaa acctgccgag         60
cgtctcgcac cccgcatttc ggcctacgtg cgtcagatag cagcgcagtc ggcaaaggct       120
ggaattcgcc ttctcctgct ctcgcaacga gcggaggcct cgatcattgg cggcaatgcg       180
cgttcgaatt tcgggtcaa gatgactctg agggtggacg aaccggagtc ggtgagaatg        240
cttcatccga gcgcttcccc ggaagactgt gccctggtcg agaccttcaa gcctggtacc       300 tgcctttttcg agaagccagg agaaggccgg cagattatgc gatgcgactt tgtcggcgag     360
tacgggagat atgcgcgagc catcgagtct tcggatctgc gttttctcgc caccctccag       420
caagaccagg cccaacgcga attcttcgct gaggagttcg gtgtggtgga tccgtcatga       480
ctggaccaca ggagagaaag cgcaaggcgg cgaagccgtc gcgggagcct cagttgaact       540
gctgtgaagc ggacgtgccg aaacgagcaa aacagccccc ggttccctct acgttcgacc       600
tgctcacggt gaaggagact gcggggctgc tgagagtcag tcaggcaact ctttaccggc       660
tgcttcggag tgggaagga cccacataca cacggatcgg tggacagata cgcgttcacc        720
gcgagtcgct gcgtcggttc atcgaaccgc gtggataacg tcacagagac agcgaaaacg       780
cctcccctgg gtcaatccgg ttaccgccgg actgggggag gcgcttcgac acctacatcc       840
gtcgcccctc gaaaggctca gatgcacttc cacgataacg cagaggtcgg acaagaggga       900
agaactgccg ttctctcgcc gttgcgcggc gtagccgcca agcgggacgt gtctgacgat       960
gcagcgaagc ggagtcggca ggcgcggcac gcgcctgggc ttgttacatc tgccacaact      1020
gtccgtgaat ctctgccagc tcctgaaacc gctggtcagg gccttgcgga atccgtgacc      1080
gctgatgatt tttggtctca ttcgttcccc cgcgctgacg atgtacgcgg cgcagctgct      1140
tccttccagt cggtggctaa ctgggatggg cgtgagggtc cgaggccgcg tttcgttgtc      1200
gcgcctggcg ttgtccgctt ggaggtttgt gatctcgcac gccgcgaacg aacggctgaa      1260
cgtgcgtatc tggctgctcg ggctcggggt gatatggcgg ctgccaggca taactcgccg      1320
tacgacttcg acgtggacga tgaagagttg gcggaactgg cttctctgca aggcctcgag      1380
```

-continued

```
gacgacgaca ttgggggctg gtctgcggag agggaaatag tgggctggtc tgctcgttct   1440
cggtcacgga tgatcttgcg aatggcagaa ctcgactggg ctcccatgat ggatttgccg   1500
ggcattcctg cgatggtgac cctcacctat ccgggggact ggcttacggt tgcccccacc   1560
ggcgctgagg tcaaaaaaca tctccagacg ttcttcaaac ggttccaacg ggcctggggc   1620
attgcctgga tgggtgcgtg gaaaatggag ttccaaagcc gaggcgctcc gcattttcac   1680
ctgtacatgg tccctcctca tgggaaggca ggagactcgc ggaagctgcg gcatgatgct   1740
gagctcttga aatgggagat agcacgtgca gagggtgaag acccaggtcg caggccgtat   1800
ttccgggaag ctccaagcga tggattgaag tttcgtccgt ggctttctgc ggtgtgggcc   1860
gacgtcgtag atcatccgga ccccaaggaa aagaaaagc acgtcagtgc cggcactgga   1920
gtggactacg cggagggcac gcgagggtca gatccgaaaa ggcttgcggt gtacttctcc   1980
aagcatggaa cctttgccga caaggaatat cagcacgtag ttcctgctca atggcagaaa   2040
acgggtgcgg gacctggcag gttctggggc taccgcggtt tgtcgccggc cacgctgcc    2100 accgagattt cctgggatga gtacctgctt ttatctcgca cgttgcgacg attgtcagcg   2160
cgaacgaaga tctgggaccc ggctttacga ggcggtagcg gcggccacag atggactaag   2220
gcgatgatgc gacgcacggt tacccggcac cgcttggacc tcgtgaccgg tgagattctg   2280
ggcacgaaga cgcggaaggt tcgggcgcca gtgaagaggg ttgtccggac ttcgggatac   2340
ctgtgtgtca atgacgggcc cgcactggct cgaaccctca gccgtcttcg tacaagctgc   2400
ctgagctaga cgcgcggaac gcctttcggc tttgtctttt gctggatggc gggttttggg   2460
cggcttctgg tgatgcgctg ctgcgctccg tggggagaga gacccaacga ctgacctatc   2520
tctacccagg tgcaattcat ctcccgcgct ctgtcggcta ggtaaacgag gtgctcccgc   2580
gcgagctttt ccatgtggtc ggccaatgtc agctcggtca ggacaacctg ctgttgttgc   2640
gatagttgtg tccgcacggg tcgattgtct tctgttgcgg cataacggtt ttcgtcgttc   2700
gcggagagtg cggctaaatg aattgcatcc tcgattgagc ggagcatttc gacgcggaac   2760
ctggcgatga tgttgtctct gtcttcattc ataactgaag cgtattggga gtgttgccct   2820
cccaccatgt gtgccaatgc aggtgtgaac tgagtcacag tttctcaata gactccaagt   2880
ttgtgatcct tttactccca aaatggggca tgatgtgtgc gtgcctcggt tcaggggcga   2940
aagttcgaca cctcgaaaga aggcctcgac atggctttga aagctgctgg caacgtgatt   3000
cctgattcct ccgcgtacga gtaccggcg gttcaggtcg agccgaagat ggtcagaaaa   3060
gacccggaag acccgaactc tgagcagttc cagaagcaga aggacggcac gccggtgtgg   3120
tcgatcgact gcattcgggt cgaccgggca tcaggcaaca aggcaatcgt gaccgtgacg   3180
gttccggacg tgatggaacc ggatgttgcg gggccggtgg agttctccga gatgattgcc   3240
ggtttctggg tttcgcgcag tggttcgggc atgtggtttt cggcaagcgc cgtcgcttct   3300
ctctgatcgc tgatcgtcgc ccctcgaaag gttcggaaat gtccaaagga aaggcgttg   3360 cgctgggtgt gggtgccctc gtgctcgtgt ttgtgctggt tgcggcaggt tggcaagcgg   3420
cgaacgtgtt cagtgatcgt tcacagtccg aagctgtgcc gctgagagtg ccggccgatc   3480
cgaagtggga aaacggggtg ttctcggacg ttgccgggtg cctcgttctc tctccggaag   3540
agctggggcc gttcagcgga gggcagtaca tcgacatagt gaggccagtt gagccggaga   3600
ggttggagcg cgactgggtg aggtcggctg agtgcgtttc ggcgtcgatg aatgtctctg   3660
acctgttggt ttctgctctt ccagagtcca cccgtccccc cggcgatttc gttcgttcgt   3720
ggaaagtggc gagtgatgat tactgctatg agggtgataa cccgcaaggc tgcacttctc   3780
```

```
gtatgccggt tgggtctct gcaaaaaact ggtggtgcac agaacccgta ctcgatccgc   3840
tcgttcgtcg ctgtgaggtc tttcctgcaa ggcaaatcgt tgtgccggaa ggggtttcgt   3900
gatgtttctc cgagcgtttt ttcgttccaa gttggtcatg gtggctcttg tcctggtcgc   3960
tggcctgttt ctctacaacg cctgctcttc ttctgacgca aaggaagaga tcggcagcag   4020
tctgaatctc tctcctgtca ctgctcgttc gaatccgtat gagggcgtcc agcccacgat   4080
gagcgaaaaa agccctgttc ccgtccctgt cgtttccggc acaggatttt cggggggtggc  4140 atcgtgcggg acggattacg ccgggaagcc tgccggtgacg ctggaagctg tgtggatttc   4200
gtccgactcg gtgaactaca cactcgataa gaggcattgc ctggtgacga ccggcccgct   4260
gtggaaacaa gcgatccgta aagcgtcagg gtcagagatt cggcctgagg gcgggagctg   4320 gatacggtg gtgcttgcca tgcctgacgg caatttcagg gcaggatggg caccccacgc    4380
ccaagtaacc gctggtgcgc tggatatttc ggcggtggtc tcgtgagcgg ggagaagcgg   4440
cacagcgagg ccggcccggt agaaatcatc ttttgatgc tggcagtcag ggcggggac     4500 tacatcgtcg ccgtgactgc ggttctcgcg gtcgggttct tcgcggtcgc ggttgagggt   4560
ttctggttcc tggtcgtcgc agtcatcgct gcaccggcgt ggtggtttct gcgcgactgg   4620
gaatcgaagc ggagggccgt acgggtcttt gaacgggcat ggaaggggac acctgaatcc   4680
cccggtattg ctctctccct tggcctgtcg aacgtggcgg ggtctctgcc gaggttgagg   4740
aagtttgaaa ctggttcggg gatacgcaca ctcgtgttt ctttgccgcc cggagtcact    4800
gccgagagct ttgagaaagt tcgccctgcg ctggcagacg cgatgggggg tcaccgctgc   4860
caagtagaga aggtggcccc cggacaggtc cgcgtcagag tgattgatga ggattcgatg   4920
aagacgccgc gtgatgcggg atgggcgaaa gatgttgtgc tggaagagga tacgttcgac   4980
ggtcttccgg gcgagacgcg atcctggttc gagcaagagg ggccggcatc atgagaaaat   5040
cggcgggagt atctcggatt cctatccgtc tcgggcgctc tcagtacggg gaagacgttg   5100
gattcgatct cgctgcggac gccgctcaca tcgccatgca gggcaaaacc cgatccggca   5160
aaagtcaggc gacgtacaac gtgttagctc aggcagcagc gaacgcggcg gttcgagtcg   5220
tagggtccga cccgacacac gtactcctgg agcccttcaa acatcgaggg gtgtccgagc   5280
cttacgtggt tcgggactg aatgcgcagg ccacggtgga catgctgggc tgggtcaagc    5340
gtgagtctga tcgtcgcatc gaccagatgt ggcccctgcg taccgacaag ttttccgagt   5400
tcggggcttc gttcccgctg atactcgtcg tgctcgaaga gttt                    5444
```

<210> SEQ ID NO 74
<211> LENGTH: 5813
<212> TYPE: DNA
<213> ORGANISM: Rhodococcus rhodnii
<220> FEATURE:
<221> NAME/KEY: misc_feature
<223> OTHER INFORMATION: pRET1000 Full Length

<400> SEQUENCE: 74

```
ggatccgcgc cgaacagtcc gcggacacga agtggaagca ggtgaacgag gcgttgacca     60
gccaagaccg ggccgaggag caggctgccg aggcagcgcg ggtcgcctcc gctgtcatgg    120
gaggccaccc gacaccgcta cgggacatgc tcgccgccca ggagcagcgc cggaagccgt    180
ggactccgga gcagaaacgc cagtacgcga ccgcaaaagc ccaagcagaa cgcgccgcga    240
aggccaagga cgccgcgaaa tggaccgagg tcgccggcgg cggctaccag cgggacgtgc    300
gcgggatgaa cctgcgactg tgggtggctg aggacggcgc ctggtcgatc acctcgaaga    360
```

-continued

```
aggaccccga ccgccagtac gccgcaggtc aggccgacac cgtcgcgcag gcccaagccg    420
cggccacggc cacagcgaaa acgcaggccc aggcgatgtg gaagcaggtc ccggccgaca    480
agcgcaccga gtcagccacc agagcggtcc ggcgcgtgat cgcggatctc accccccacca   540 aacccgccga ggtcaaaccc ccggcccgcc gccagggacc aaccatgccg cagtcggccc    600
cggggtatca gccacccggc cgcgaccgag gtcgagaatc cggaatggga ctgtgagcag    660
agagcgagaa ggctttcgtg gagcgtaggg aacagacgca ggcctggcga agcatgtcca    720
agaacaccat cgatcgctag aaggtcggtc gtgcccaggg tgcccaggat gcgtacataa    780
cgcgcgaaag gtgcatacct cccatagcat cggcgcgtat ggtagggaaa atgatcttca    840
aacgtattgc tgtggtcgtg ctcgctggtg gggctttggt agtgggaggc agccaggttg    900
ctggtgctac cacggtttca gctccacagc cgagtccttc agcagcggtg gtgccgacgg    960
ttcttccacc agtcactttc accgccgctt ctgcgcactg cgaggcccag tacgcgtcgg    1020
attcccggcg atgccgtctg attccacttc cacagggccg agcgatctgc tgggcggcag    1080
ccgctgcccg ttacgcagcg tgccgcgccg gaaactaggt agaacgtgag catggacgag    1140
cttcccacct tcatcgccga cgacatcgtg atggccagaa cgttcgacag ccctaacggc    1200
caggtggtgc tcgaggtgaa cactccgcgg ccgttcgatg ctgcggcccc ggagggtgac    1260
tactgctgca ccttccggat cagcgggaac atggatgccc cttacgacgg attcggtggc    1320
ggcgtcgacg cagtgcaggc gctgctactc gcattggcca tggcacacga ggaacttcgt    1380
caaacttcgc cagagttgac gtttctaggc gagacgaacc tcggtctacc ggtcttgaac    1440
atcaagcccg acaacgcgat cgaagccgtg gtctcattcc ccgctccctg atgtgacgca    1500 cttttcacccc tggcactcat gtaccgaagc tgggactgag aaagggctgc cgcgtcaccg    1560
cttcgcgttg acttgccact gaacggggc gtgtcccggt cagggcgggg tgtgacctgg    1620
gttcatgaca ccgctaacac gctgcggaaa tgcggattga actagttcat ttggggaacg    1680
atgacctgat gaccggggat cgtgacctac ccatgctgac catcgccgag gcggtggacg    1740
cgacgcagac cagtgagagc acgatcaagc gccgcctgcg gtcgggcgcg ttcccgaacg    1800
cggtccgcac tgccgacggg aagtggatga ttcccctcgg tgacctatca gcggcagggc    1860
tgagaccagg gaaaatggcg aaacctgacc cggtgaccc ttcaaatgac cgggtccgtg     1920
acctggcagc tgagaacgcc gagctccgtc agcgcctggc cgtggccgaa gccctggcca    1980
gcgaacgcaa tcggatcatc gacgtgcagc aacagatgct ccggatgctc gaagcccggc    2040
cggtgtcggc cctggagccc gcggcggttc cagtggcggg tccgccgccg cccgtcccgg    2100
ccgccgatgg tcgggcagct acgggcgccc tggcccggat acgtcgacgg cttctcggct    2160
aggagctgac cgcgtacttg cgtgcgtcgt gcaggagctt cccaccgtt ccggtggaga     2220 ttcccatctc ctcggcgatc tcgcggtact caggccctg ctcgcgcagc tcgacggccc     2280
ggcgacggtt ctcggctgcc cgtgcgagga actggtcccg cggctcggcc atgatgcgct    2340
ggatcgtgcg cgtggaggcc cccatcttct cggccagctc gcgagctgtc tgcttgcggc    2400
ggatcggtcg ttcagcgccc acggtctgcc tcccacaatg cgttccggtc gaccttcgtc    2460 gctcgttttcc ggtttgcctc gcgcttcttc tcactcatct tgcgaccgcg tgcggcttgt    2520
atggcgatga atgtggcctc gtagacagca gggccgtcgg cccacatccg ggactttgta    2580
gtgatccagc gggtaatgga ggccgcgacg gcgcgtagct cgcttgctgg cagtggatcg    2640
ggcctgcctg tgaccgggtt cctgaacgtg gcgttgatct gtgcggcttc cgcatagatc    2700
```

```
gcggccccga ggccggtcgg gtcgcccag tggaagcgga tttcgcggta ggcccaggtg    2760
cgtgcggttt cgaacagggc gcagtttcgg ccgaggccga tcgggttctc acggcgcgat    2820
cgggtttgcc gccagcgcgt tggcggcatg tggatgccga gttccgcctc gagctcggcg    2880
agggatcgcc gctcggtgtg cagccaatgg gtgtcccagt caccgtgagt cgggttcttg    2940
gtcatcaggc ccgaatagcc cttgtccccc tggacggcgc gccggaggcc ttcggtgacg    3000
gcggccgcat aggcgagcgg cttacgacgg gcgtactcgg tgcgggtgaa cggctctgcc    3060
agcgcccaca cagcgtgtgc gtgcccgtta cggggttct ccacgatcgc gttcggcaga    3120
ggatgattcc cggccgccga cagcgcccgc agcgcggcgt ccggtggtc aacgtccacg    3180 acgagcaggt tgctcaatgc ctgcgggttc gactcgatgt agcggcgatc cagtgcgtct    3240
gatcgccgca tccggtagac gccgtcgagg aaatcgtcgg ttgccagtgg ccacagcggt    3300
agccacagct gttcccaggc gccgcctgtg tgctcttcca ccgcaaccat ggggaacaca    3360
ctcacacaca agatcgattt attccggtac gacacgccag ccaagtcaga tgtttcggtt    3420
tctggagcgg tcctccagac ctttgagatc cgctccagaa acgtccacaa attattgggg    3480
tacgtcgaac caagccttat caggtatccc ggggttccgg gggtgaacac caccctccga    3540
ccggtccaga atccgtcgat ctcacctatc cgctcgaagt ccttgagtca gtgacaggac    3600
cactgctggg ctcccagcgc agaaggcaag tgaaggcaga cgactgcggg aggtaagtcg    3660
ggtacggcat gaggtccttc agaagcggcg tcgacgccag gcccacacgc acaatccgct    3720
tcccacgagg gacaccaccg gtagcgcccc ctgcaaccgg cgcagtgtca cgaggcgccg    3780
gtactgctcg tttgacagga actgcagggt cggtgagctc gcgctgggcg gatcccacca    3840
gtagctcccc gtgccggtaa ccgcttgggg ccaagcgaag acaccaccg cggcagcgat    3900 ggcaatgcac gtggatggga acaccaccca gaaccaggga aatcctggtg ccggcccgag    3960
acgatcccgg cgcggtaaga ccacaccggc caccatcgcc acggccccg acgcaacaag    4020 caataaccac cccatgagcg gacggtacaa gcgccgacgc cgggtggccg ttaggtgcgc    4080
gccagcccgt gaccggaccg gcgaagcgtg ccgctgggcg gccgccgtg gcgcccgtcc    4140 cgtgcccgtt ctgaccggtg gtctcggtcg ctcgttcctc gcgtcctcac ctgccggtca    4200
gcccgtgacc gtgccgtcca ccacccggtg cctggtctgc gtctccctcg gctcgttcct    4260
cgcctatcct ggtgaccaga caccggagcg agctatgccc agggttgcgc agtgacttcg    4320
tcactgcgta accctgggcg ctcgcctccc attcgcttcg ctcacaggag ggggccgtcg    4380
atggccgctg acgctgcatc tgacgaccgg cggaccgagg tccgcgccgc tgcttcgcgg    4440
gccgctgacg cggccccggc gaagcgcacc cgcaccgtgg cggtgcggct gaccgatggg    4500
gaggaggccg cgtggatcga cgccgcgctg gccgatggcc accggcagct cggggcgtgg    4560
gtgcgtgagc gggcggtggc cggctatctc gggaaggtcc gcccgaagac cggcagtgga    4620
atgtcggcga aggcggccgc ggaggtcgcc gcgatgcggc agcagatgac gaaggtgggg    4680
aacaacctga accagatcgc gagggcgatc aacgccgggc aggtgccgtc gcagatggcc    4740
gagtccctgc agaaggggtg gctggagagg tgggggcagg agttggggcg gatggcggat    4800
cggctcgacg cgctcgacga ccagggctga cgtgatcgcg aagatcagca cgggcagcga    4860
cccgaagggg ttggcggcgt atctgcacgg gccggggaag gccaccccgc acagctaccg    4920
caccgaggcg ggccggctga ttgccggcgg gacggtgatc gcgggatcgg tgcaggtcac    4980
cgccaaaaac ccgaccccgt gggggcggga cttcagcggg gccgccgcga cgaacgcgcg    5040
ggtgggtaag ccggtgtggc attgctcgct gcggtgcgcg cccggggatc ggcggctgac    5100
```

```
cgataccgag ttcgcggaca tcgcgcagac ggtcgccgag cggatgggct tcgagagtca     5160
tccgtgggtg gcggtgcggc acgacgacga ccacatccac ctggctgtct cccgggtcga     5220
ttttcagggc gtgacctgga agaacagcaa cgaccggtgg aaggtcgtcg aggtgatgcg     5280
cgaggtcgaa cgcgcgcacg gcctgatcga ggtggcgagc ccggagcggg cccgtggccg     5340
gcaagccagc agcggcgagc aacgccgcgc ggtgcggacc ggcaaggtgg cgcagcggga     5400
cggtctgagg gaaattgtga ccgccgcccg cgacatcgcc gcaggccagg gtgtgggggc     5460
gttcgaagtg gcgctcgtac agaacccgat tacccgagtg caggtgcggc gcaacgtcgc     5520
gaagacgggc cggatgaatg gctacagctt caacctgccc ggctacgtcg acgccgccgg     5580
ggagccgatc tggttgccgg cctccaaact cgaccggggt ttgtcctggt cacagctgga     5640
aaagacgctg accagacccc gcccggaccg cctcgccgga gaggagacgg tgccgcggaa     5700
gcggctcgag cgcgccgccg cgtgggagca gcgccgccgc gaggtcggcg gcgagcagtt     5760
cgcagctgcc cgctgggagc aggcccgcgc gaatgttggt gagacggccg ggc           5813

<210> SEQ ID NO 75
<211> LENGTH: 80
<212> TYPE: DNA
<213> ORGANISM: Rhodococcus rhodnii
<220> FEATURE:
<221> NAME/KEY: misc_feature
<223> OTHER INFORMATION: 4260bp to 4339bp pRET1000

<400> SEQUENCE: 75
tcgcctatcc tggtgaccag acaccggagc gagctatgcc cagggttgcg cagtgacttc       60
gtcactgcgt aaccctgggc                                                  80

<210> SEQ ID NO 76
<211> LENGTH: 108
<212> TYPE: DNA
<213> ORGANISM: Rhodococcus erythropolis
<220> FEATURE:
<221> NAME/KEY: misc_feature
<223> OTHER INFORMATION: 761bp to 868bp pRET1100

<400> SEQUENCE: 76
tcacagagac agcgaaaacg cctcccctgg gtcaatccgg ttaccgccgg actgggggag       60
gcgcttcgac acctacatcc gtcgcccctc gaaaggctca gatgcact                  108

<210> SEQ ID NO 77
<211> LENGTH: 556
<212> TYPE: DNA
<213> ORGANISM: Rhodococcus erythropolis

<400> SEQUENCE: 77
gaagcaacac cgcatccgcc cattgccgat cgctcagcac gccccccgtt gcggatttca       60
tggggcaact gtgcccgccc acatcaacta ttcgagtccg acgcgccgag gctatatgga     120
aaattattcg actacgcaaa acaaagccat atcaggtatc ccggcgacac cccccaaaac     180
ctcctcccca ccaacccctg cttttttgaac cttgccgcgc tggatcgttc gatttcttct     240
ggaaccctgc gagcggaaag ccacggtcgg caccttggtg caagaggtgt gctcgggttg     300
ggctttgcgt cggtggatgg tgagcacagg cgggtgagta cggcggtact cccggagct     360 gcttcgagct gcgggaggta ggtcgggtac ggcgcgcaga gcggaagcgt ggtcggtggt     420
tgttcactct tctgctcggc cgaatcgagc gccggccgaa tcgagcgccg gccgaatcga     480
```

```
gcgccggccg aatcgagcgc cggccgaatc gagcgccggc cgaatcgtta gtgcggtgtg    540
cgtgcgtggt ggtcga                                                    556
```

<210> SEQ ID NO 78
<211> LENGTH: 259
<212> TYPE: PRT
<213> ORGANISM: Rhodococcus erythropolis

<400> SEQUENCE: 78

```
Met Phe Asn Ser Ile Glu Gly Arg Ser Val Val Thr Gly Gly Ser
 1               5                  10                  15

Lys Gly Ile Gly Leu Gly Met Val Arg Val Phe Ala Arg Ala Gly
                20                  25                  30

Asn Val Leu Met Thr Ala Arg Asp Ala Leu Thr Leu Glu Arg Ala Ala
             35                  40                  45

Glu Gly Leu Asn Gly Leu Pro Gly Ala Val Ser Thr Leu Gln Val Asp
     50                  55                  60

Val Thr Asn Pro Asp Ser Leu Ala Gly Met Ala Glu Val Ala Ala Glu
 65                  70                  75                  80

Arg His Gly Gly Ile Asp Val Leu Cys Ala Asn Ala Gly Ile Phe Pro
                 85                  90                  95

Ser Lys Arg Leu Gly Glu Met Thr Ser Glu Asp Met Asp Ser Val Phe
            100                 105                 110

Gly Val Asn Val Lys Gly Thr Ile His Ala Val Gln Ala Cys Met Pro
        115                 120                 125

Trp Leu Glu Thr Ser Gly Arg Gly Arg Val Val Thr Ser Ser Ile
    130                 135                 140

Thr Gly Pro Val Thr Gly Tyr Pro Gly Trp Ser His Tyr Gly Ala Ser
145                 150                 155                 160

Lys Ala Ala Gln Met Gly Phe Ile Arg Thr Ala Ala Ile Glu Leu Ala
                165                 170                 175

Pro Lys Arg Ile Thr Ile Asn Ala Val Leu Pro Gly Asn Val Ile Thr
            180                 185                 190

Glu Gly Leu Asp Gly Leu Gly Gln Glu Tyr Leu Asp Gln Met Ala Ser
        195                 200                 205

Ser Val Pro Ala Gly Ser Leu Gly Ser Val Glu Asp Ile Ala Asn Ala
    210                 215                 220

Ala Leu Phe Phe Ala Leu Asp Glu Ala Ala Tyr Ile Thr Gly Gln Ser
225                 230                 235                 240

Leu Ile Val Asp Gly Gln Val Leu Pro Glu Ser Ala Met Ala Leu
                245                 250                 255

Gly Glu Leu
```

<210> SEQ ID NO 79
<211> LENGTH: 780
<212> TYPE: DNA
<213> ORGANISM: Rhodococcus erythropolis

<400> SEQUENCE: 79

```
atgttcaact ccattgaagg tcgttcggtc gtcgtcaccg gcggtagcaa gggcatcggc    60
ttgggaatgg tccgggtatt cgcgcgcgca ggggccaatg tgctcatgac cgcgcgagac   120
gctctgactc tcgaacgtgc cgcggagggt ttgaatggtc ttcctggcgc ggtctccaca   180
cttcaagtcg acgtcacgaa tcctgactcc ttggccggta tggcagaagt tgcggccgag   240
cgacacggag gaatcgacgt gttgtgcgcg aacgctggga tcttcccgtc gaagcggttg   300
```

```
ggagagatga cctcggagga catggacagc gtattcggcg tcaacgtcaa ggggaccatc      360
cacgccgtgc aagcgtgcat gccgtggctc gaaacttctg ggcgtggaag ggttgtcgtg      420
acatcgtcga tcaccggacc cgtaaccggt tatccgggtt ggtcgcacta cggggcaagc      480
aaggctgcgc agatgggctt catccgaact gctgccattg agttggcacc gaagaggatc      540
acgatcaacg ccgtcttgcc cggcaacgtg atcaccgagg ggctcgacgg tttgggacag      600
gaatatctcg accaaatggc gtccagcgtc ccggccggca gtctgggcag cgtcgaggat      660
atcgccaatg ccgcactgtt ctttgcactg gacgaagccg cgtacatcac cggtcagtcg      720
ttgatcgtag atggtggaca ggttcttccg gagtcggcga tggcgctcgg cgaactgtaa      780
```

<210> SEQ ID NO 80
<211> LENGTH: 28
<212> TYPE: DNA
<213> ORGANISM: Artificial
<220> FEATURE:
<223> OTHER INFORMATION: primer (MAK F1)

<400> SEQUENCE: 80

```
gaatcttctc gttgatgcag atcaggtc                                         28
```

<210> SEQ ID NO 81
<211> LENGTH: 26
<212> TYPE: DNA
<213> ORGANISM: Artificial
<220> FEATURE:
<223> OTHER INFORMATION: primer (MAK R2)

<400> SEQUENCE: 81

```
ctgactccgt agtgttctgc cagttc                                           26
```

<210> SEQ ID NO 82
<211> LENGTH: 34
<212> TYPE: DNA
<213> ORGANISM: Artificial
<220> FEATURE:
<223> OTHER INFORMATION: primer (MAK Pst F)

<400> SEQUENCE: 82

```
gaccactgca gatcaatcaa ctctgatgag gtcc                                  34
```

<210> SEQ ID NO 83
<211> LENGTH: 34
<212> TYPE: DNA
<213> ORGANISM: Artificial
<220> FEATURE:
<223> OTHER INFORMATION: primer (MAK His Bgl II R)

<400> SEQUENCE: 83

```
cgcttagatc tcagttcgcc gagcgccatc gccg                                  34
```

<210> SEQ ID NO 84
<211> LENGTH: 35
<212> TYPE: DNA
<213> ORGANISM: Artificial
<220> FEATURE:
<223> OTHER INFORMATION: primer (P1200rep-Pst5195)

<400> SEQUENCE: 84

```
agccgctgca gaagcaacac cgcatccgcc cattg                                 35
```

<210> SEQ ID NO 85

```
<211> LENGTH: 24
<212> TYPE: DNA
<213> ORGANISM: Artificial
<220> FEATURE:
<223> OTHER INFORMATION: primer (P7)

<400> SEQUENCE: 85
cgccagggtt tcccagtca cgac                                                 24

<210> SEQ ID NO 86
<211> LENGTH: 30
<212> TYPE: DNA
<213> ORGANISM: Artificial
<220> FEATURE:
<223> OTHER INFORMATION: primer (pQE70 F1)

<400> SEQUENCE: 86
ggcgtatcac gaggcccttt cgtcttcacc                                          30

<210> SEQ ID NO 87
<211> LENGTH: 35
<212> TYPE: DNA
<213> ORGANISM: Artificial
<220> FEATURE:
<223> OTHER INFORMATION: primer (pQE70 R1135Bm)

<400> SEQUENCE: 87
ggttggatcc gtcatcaccg aaacgcgcga ggcag                                    35

<210> SEQ ID NO 88
<211> LENGTH: 34
<212> TYPE: DNA
<213> ORGANISM: Artificial
<220> FEATURE:
<223> OTHER INFORMATION: primer ( P1204rep-Ec2958)

<400> SEQUENCE: 88
cgcggaattc gaccaccacg cacgcacacc gcac                                     34

<210> SEQ ID NO 89
<211> LENGTH: 8134
<212> TYPE: DNA
<213> ORGANISM: Artificial
<220> FEATURE:
<223> OTHER INFORMATION: pRET1101

<400> SEQUENCE: 89
gggtaccgag ctcgaattcg taatcatggt catagctgtt tcctgtgtga aattgttatc         60
cgctcacaat tccacacaac atacgagccg aagcataaa gtgtaaagcc tggggtgcct         120
aatgagtgag ctaactcaca ttaattgcgt tgcgctcact gcccgctttc cagtcggaa         180 acctgtcgtg ccagctgcat taatgaatcg ccaacgcgc ggggagaggc ggtttgcgta         240
ttgggcgctc ttccgcttcc tcgctcactg actcgctgcg ctcggtcgtt cggctgcggc         300
gagcggtatc agctcactca aaggcggtaa tacggttatc cacagaatca ggggataacg         360
caggaaagaa catgtgagca aaaggccagc aaaaggccag gaaccgtaaa aaggccgcgt         420
tgctggcgtt tttccatagg ctccgccccc ctgacgagca tcacaaaaat cgacgctcaa         480
gtcagaggtg gcgaaacccg acaggactat aaagatacca ggcgtttccc cctggaagct         540
ccctcgtgcg ctctcctgtt ccgaccctgc cgcttaccgg atacctgtcc gcctttctcc         600
cttcgggaag cgtggcgctt tctcatagct cacgctgtag gtatctcagt tcggtgtagg         660
tcgttcgctc caagctgggc tgtgtgcacg aaccccccgt tcagcccgac cgctgcgcct         720
```

```
tatccggtaa ctatcgtctt gagtccaacc cggtaagaca cgacttatcg ccactggcag      780
cagccactgg taacaggatt agcagagcga ggtatgtagg cggtgctaca gagttcttga      840
agtggtggcc taactacggc tacactagaa ggacagtatt tggtatctgc gctctgctga      900
agccagttac cttcggaaaa agagttggta gctcttgatc cggcaaacaa accaccgctg      960
gtagcggtgg ttttttttgtt tgcaagcagc agattacgcg cagaaaaaaa ggatctcaag     1020
aagatccttt gatcttttct acggggtctg acgctcagtg aacgaaaac tcacgttaag       1080 ggattttggt catgagatta tcaaaaagga tcttcaccta gatccttttta aattaaaaat     1140 gaagttttaa atcaatctaa agtatatatg agtaaacttg gtctgacagt taccaatgct     1200
taatcagtga ggcacctatc tcagcgatct gtctatttcg ttcatccata gttgcctgac     1260
tccccgtcgt gtagataact acgatacggg agggcttacc atctggcccc agtgctgcaa     1320
tgataccgcg agacccacgc tcaccggctc cagatttatc agcaataaac cagccagccg     1380
gaagggccga gcgcagaagt ggtcctgcaa ctttatccgc ctccatccag tctattaatt     1440
gttgccggga agctagagta agtagttcgc cagttaatag tttgcgcaac gttgttgcca     1500
ttgctacagg catcgtggtg tcacgctcgt cgtttggtat ggcttcattc agctccggtt     1560
cccaacgatc aaggcgagtt acatgatccc ccatgttgtg caaaaaagcg gttagctcct     1620
tcggtcctcc gatcgttgtc agaagtaagt tggccgcagt gttatcactc atggttatgg     1680
cagcactgca taattctctt actgtcatgc catccgtaag atgcttttct gtgactggtg     1740
agtactcaac caagtcattc tgagaatagt gtatgcggcg accgagttgc tcttgcccgg     1800
cgtcaatacg ggataatacc gcgccacata gcagaacttt aaaagtgctc atcattggaa     1860
aacgttcttc ggggcgaaaa ctctcaagga tcttaccgct gttgagatcc agttcgatgt     1920
aacccactcg tgcacccaac tgatcttcag catcttttac tttcaccagc gtttctgggt     1980
gagcaaaaac aggaaggcaa aatgccgcaa aaaagggaat aagggcgaca cggaaatgtt     2040
gaatactcat actcttcctt tttcaatatt attgaagcat ttatcagggt tattgtctca     2100
tgagcggata catatttgaa tgtatttaga aaaataaaca aataggggtt ccgcgcacat     2160
ttccccgaaa agtgccacct gacgtctaag aaaccattat tatcatgaca ttaacctata     2220
aaaataggcg tatcacgagg ccctttcgtc tcgcgcgttt cggtgatgac ggtgaaaacc     2280
tctgacacat gcagctcccg gagacggtca cagcttgtct gtaagcggat gccgggagca     2340
gacaagcccg tcagggcgcg tcagcgggtg ttggcgggtg tcggggctgg cttaactatg     2400
cggcatcaga gcagattgta ctgagagtgc accatatgcg gtgtgaaata ccgcacagat     2460
gcgtaaggag aaaataccgc atcaggcgcc attcgccatt caggctgcgc aactgttggg     2520
aagggcgatc ggtgcgggcc tcttcgctat tacgccagct ggcgaaaggg ggatgtgctg     2580
caaggcgatt aagttgggta acgccagggt tttcccagtc acgacgttgt aaaacgacgg     2640
ccagtgccaa gcttgcatgc ctgcaggtcg actctagagg atcccctgca cagaacccgt     2700
actcgatccg ctcgttcgtc gctgtgaggt ctttcctgca aggcaaatcg ttgtgccgga     2760
aggggtttcg tgatgtttct ccgagcgttt tttcgttcca agttggtcat ggtggctctt     2820
gtcctggtcg ctggcctgtt tctctacaac gcctgctctt cttctgacgc aaaggaagag     2880
atcggcagca gtctgaatct ctctcctgtc actgctcgtt cgaatccgta tgagggcgtc     2940
cagcccacga tgagcgaaaa aagccctgtt cccgtccctg tcgtttccgg cgacaggatt     3000 tcggggggtgg catcgtgcgg gacggattac gccgggaagc ctgcggtgac gctggaagct     3060
```

-continued

```
gtgtggattt cgtccgactc ggtgaactac acactcgata agaggcattg cctggtgacg    3120
accggcccgc tgtggaaaca agcgatccgt aaagcgtcag ggtcagagat tcggcctgag    3180
ggcgggagct ggatacgggt ggtgcttgcc atgcctgacg gcaatttcag ggcaggatgg    3240
gcaccccacg cccaagtaac cgctggtgcg ctggatattt cggcggtggt ctcgtgagcg    3300
gggagaagcg gcacagcgag gccggcccgg tagaaatcat cttttgatg ctggcagtca     3360 gggcggggga ctacatcgtc gccgtgactg cggttctcgc ggtcgggttc ttcgcggtcg    3420
cggttgaggg tttctggttc ctggtcgtcg cagtcatcgc tgcaccggcg tggtggtttc    3480
tgcgcgactg ggaatcgaag cggagggccg tacgggtctt tgaacgggca tggaagggga    3540
cacctgaatc ccccggtatt gctctctccc ttggcctgtc gaacgtggcg gggtctctgc    3600
cgaggttgag gaagtttgaa actggttcgg ggatacgcac actcgtgttt tctttgccgc    3660
ccggagtcac tgccgagagc tttgagaaag ttcgccctgc gctggcagac gcgatggggg    3720
gtcaccgctg ccaagtagag aaggtggccc cggacaggt ccgcgtcaga gtgattgatg     3780
aggattcgat gaagacgccg cgtgatgcgg gatgggcgaa agatgttgtg ctggaagagg    3840
atacgttcga cggtcttccg ggcgagacgc gatcctggtt cgagcaagag gggccggcat    3900
catgagaaaa tcggcgggag tatctcggat tcctatccgt ctcgggcgct ctcagtacgg    3960
ggaagacgtt ggattcgatc tcgctgcgga cgccgctcac atcgccatgc agggcaaaac    4020
ccgatccggc aaaagtcagg cgacgtacaa cgtgttagct caggcagcag cgaacgcggc    4080
ggttcgagtc gtagggtccg acccgacaca cgtactcctg gagcccttca acatcgagg    4140 ggtgtccgag ccttacgtgg tttcgggact gaatgcgcag gccacggtgg acatgctggg    4200
ctgggtcaag cgtgagtctg atcgtcgcat cgaccagatg tggcccctgc gtaccgacaa    4260
gttttccgag ttcggggctt cgttcccgct gatactcgtc gtgctcgaag agtttcccgg    4320
gatcctcgag ggggcagcgg acgaagacgc gcgttaggc cgaaaacctg ccgagcgtct     4380
cgcaccccgc atttcggcct acgtgcgtca gatagcagcg cagtcggcaa aggctggaat    4440
tcgccttctc ctgctctcgc aacgagcgga ggcctcgatc attggcggca atgcgcgttc    4500
gaatttcggg gtcaagatga ctctgagggt ggacgaaccg gagtcggtga aatgcttca    4560 tccgagcgct tccccggaag actgtgccct ggtcgagacc ttcaagcctg gtacctgcct    4620
tttcgagaag ccaggagaag gccggcagat tatgcgatgc gactttgtcg gcgagtacgg    4680
gagatatgcg cgagccatcg agtcttcgga tctgcgtttt ctcgccaccc tccagcaaga    4740
ccaggcccaa cgcgaattct tcgctgagga gttcggtgtg gtggatccgt catgactgga    4800
ccacaggaga gaaagcgcaa ggcggcgaag ccgtcgcggg agcctcagtt gaactgctgt    4860
gaagcggacg tgccgaaacg agcaaaacag ccccgttc cctctacgtt cgacctgctc       4920
acggtgaagg agactgcggg gctgctgaga gtcagtcagg caactctta ccggctgctt      4980 cggagtgggg aaggacccac atacacacg atcggtggac agatacgcgt tcaccgcgag     5040
tcgctgcgtc ggttcatcga accgcgtgga taacgtcaca gagacagcga aaacgcctcc    5100
cctgggtcaa tccggttacc gccggactgg gggaggcgct tcgacaccta catccgtcgc    5160
ccctcgaaag gctcagatgc acttccacga taacgcagag gtcggacaag agggaagaac    5220
tgccgttctc tcgccgttgc gcggcgtagc cgccaagcgg gacgtgtctg acgatgcagc    5280
gaagcggagt cggcaggcgc ggcacgcgcc tgggcttgtt acatctgcca caactgtccg    5340
tgaatctctg ccagctcctg aaaccgctgg tcagggcctt gcggaatccg tgaccgctga    5400 tgattttgg tctcattcgt tccccgcgc tgacgatgta cgcggcgcag ctgcttcctt       5460
```

```
ccagtcggtg gctaactggg atgggcgtga gggtccgagg ccgcgtttcg ttgtcgcgcc    5520
tggcgttgtc cgcttggagg tttgtgatct cgcacgccgc gaacgaacgg ctgaacgtgc    5580
gtatctggct gctcgggctc gggtggatat ggcggctgcc aggcataact cgccgtacga    5640
cttcgacgtg gacgatgaag agttggcgga actggcttct ctgcaaggcc tcgaggacga    5700
cgacattggg ggctggtctg cggagaggga aatagtgggc tggtctgctc gttctcggtc    5760
acggatgatc ttgcgaatgg cagaactcga ctgggctccc atgatggatt tgccgggcat    5820
tcctgcgatg gtgaccctca cctatccggg ggactggctt acggttgccc ccaccggcgc    5880
tgaggtcaaa aaacatctcc agacgttctt caaacggttc caacgggcct ggggcattgc    5940
ctggatgggt gcgtggaaaa tggagttcca aagccgaggc gctccgcatt ttcacctgta    6000
catggtccct cctcatggga aggcaggaga ctcgcggaag ctgcggcatg atgctgagct    6060
cttgaaatgg gagatagcac gtgcagaggg tgaagaccca ggtcgcaggc cgtatttccg    6120
ggaagctcca agcgatggat tgaagtttcg tccgtggctt tctgcggtgt gggccgacgt    6180
cgtagatcat ccggaccccca aggaaaaaga aaagcacgtc agtgccggca ctggagtgga    6240
ctacgcggag ggcacgcgag ggtcagatcc gaaaaggctt gcggtgtact tctccaagca    6300
tggaaccttt gccgacaagg aatatcagca cgtagttcct gctcaatggc agaaaacggg    6360
tgcgggacct ggcaggttct ggggctaccg cggtttgtcg ccggccacgg ctgccaccga    6420
gatttcctgg gatgagtacc tgcttttatc tcgcacgttg cgacgattgt cagcgcgaac    6480
gaagatctgg gacccggctt tacgaggcgg tagcggcggc cacagatgga ctaaggcgat    6540
gatgcgacgc acggttaccc ggcaccgctt ggacctcgtg accggtgaga ttctgggcac    6600
gaagacgcgc aaggttcggg cgccagtgaa gaggtttgtc cggacttcgg gatacctgtg    6660
tgtcaatgac gggcccgcac tggctcgaac cctcagccgt cttcgtacaa gctgcctgag    6720
ctagacgcgc ggaacgcctt tcggctttgt cttttgctgg atggcgggtt ttgggcggct    6780
tctggtgatg cgctgctgcg ctccgtgggg agagagaccc aacgactgac ctatctctac    6840
ccaggtgcaa ttcatctccc gcgctctgtc ggctaggtaa acgaggtgct cccgcgcgag    6900
cttttccatg tggtcggcca atgtcagctc ggtcaggaca acctgctgtt gttgcgatag    6960
ttgtgtccgc acgggtcgat tgtccttctgt tgccggcataa cggttttcgt cgttcgcgga    7020
gagtgcggct aaatgaattg catcctcgat tgagcggagc atttcgacgc ggaacctggc    7080
gatgatgttg tctctgtctt cattcataac tgaagcgtat tgggagtgtt gccctcccac    7140
catgtgtgcc aatgcaggtg tgaactgagt cacagtttct caatagactc caagtttgtg    7200
atccttttac tcccaaaatg gggcatgatg tgtgcgtgcc tcggttcagg ggcgaaagtt    7260
cgacacctcg aaagaaggcc tcgacatggc tttgaaagct gctggcaacg tgattcctga    7320
ttcctccgcg tacgagtacc gggcggttca gtcgagccg aagatggtca gaaaagaccc    7380
ggaagacccg aactctgagc agttccagaa gcagaaggac ggcacgccgg tgtggtcgat    7440
cgactgcatt cgggtcgacc gggcatcagg caacaaggca atcgtgaccg tgacggttcc    7500
ggacgtgatg gaaccggatg ttgcggggcc ggtggagttc tccgagatga ttgccggttt    7560
ctgggtttcg cgcagtggtt cgggcatgtg gttttcggca agcgccgtcg cttctctctg    7620
atcgctgatc gtcgcccctc gaaaggttcg gaaatgtcca aggaaaaagg cgttgcgctg    7680
ggtgtgggtg ccctcgtgct cgtgtttgtg ctggttgcgg caggttggca agcggcgaac    7740
gtgttcagtg atcgttcaca gtccgaagct gtgccgctga gagtgccggc cgatccgaag    7800
```

```
tgggaaaacg gggtgttctc ggacgttgcc gggtgcctcg ttctctctcc ggaagagctg    7860
gggccgttca gcggagggca gtacatcgac atagtgaggc cagttgagcc ggagaggttg    7920
gagcgcgact gggtgaggtc ggctgagtgc gtttcggcgt cgatgaatgt ctctgacctg    7980
ttggtttctg ctcttccaga gtccacccgt ccccccggcg atttcgttcg ttcgtggaaa    8040
gtggcgagtg atgattactg ctatgagggt gataacccgc aaggctgcac ttctcgtatg    8100
ccggtttggg tctctgcaaa aaactggtgg tgca                                8134

<210> SEQ ID NO 90
<211> LENGTH: 8124
<212> TYPE: DNA
<213> ORGANISM: Artificial
<220> FEATURE:
<223> OTHER INFORMATION: pRET1102

<400> SEQUENCE: 90
gacctgcagg catgcaagct tggcgtaatc atggtcatag ctgtttcctg tgtgaaattg      60
ttatccgctc acaattccac acaacatacg agccggaagc ataaagtgta aagcctgggg     120
tgcctaatga gtgagctaac tcacattaat tgcgttgcgc tcactgcccg ctttccagtc     180
gggaaacctg tcgtgccagc tgcattaatg aatcggccaa cgcgcgggga gaggcggttt     240
gcgtattggc gaactttttgc tgagttgaag gatcagatca cgcatcttcc cgacaacgca     300
gaccgttccg tggcaaagca aaagttcaaa atcagtaacc gtcagtgccg ataagttcaa     360
agttaaacct ggtgttgata ccaacattga acgctgatc gaaaacgcgc tgaaaaacgc     420
tgctgaatgt gcgagcttct tccgcttcct cgctcactga ctcgctgcgc tcggtcgttc     480
ggctgcggcg agcggtatca gctcactcaa aggcggtaat acggttatcc acagaatcag     540
gggataacgc aggaaagaac atgtgagcaa aaggccagca aaaggccagg aaccgtaaaa     600
aggccgcgtt gctggcgttt ttccataggc tccgccccc tgacgagcat cacaaaaatc     660
gacgctcaag tcagaggtgg cgaaacccga caggactata aagataccag gcgtttcccc     720
ctggaagctc cctcgtgcgc tctcctgttc cgaccctgcc gcttaccgga tacctgtccg     780
cctttctccc ttcgggaagc gtggcgcttt ctcaatgctc acgctgtagg tatctcagtt     840
cggtgtaggt cgttcgctcc aagctgggct gtgtgcacga accccccgtt cagcccgacc     900
gctgcgcctt atccggtaac tatcgtcttg agtccaaccc ggtaagacac gacttatcgc     960
cactggcagc agccactggt aacaggatta gcagagcgag gtatgtaggc ggtgctacag    1020
agttcttgaa gtggtggcct aactacggct acactagaag gacagtattt ggtatctgcg    1080
ctctgctgaa gccagttacc ttcggaaaaa gagttggtag ctcttgatcc ggcaaacaaa    1140
ccaccgctgg tagcggtggt ttttttgttt gcaagcagca gattacgcgc agaaaaaaag    1200
gatctcaaga agatcctttg atcttttcta cggggtctga cgctcagtgg aacgatccgt    1260
cgagaggtct gcctcgtgaa gaaggtgttg ctgactcata ccaggcctga atcgccccat    1320
catccagcca gaaagtgagg gagccacggt tgatgagagc tttgttgtag gtggaccagt    1380
tggtgatttt gaacttttgc tttgccacgg aacggtctgc gttgtcggga agatgcgtga    1440
tctgatcctt caactcagca aaagttcgat ttattcaaca agccacgtt gtgtctcaaa    1500 atctctgatg ttacattgca caagataaaa atatatcatc atgaacaata aaactgtctg    1560
cttacataaa cagtaataca aggggtgtta tgagccatat tcaacgggaa acgtcttgct    1620
cgaagccgcg attaaattcc aacatggatg ctgatttata tgggtataaa tgggctcgcg    1680
ataatgtcgg gcaatcaggt gcgacaatct atcgattgta tgggaagccc gatgcgccag    1740
```

```
agttgtttct gaaacatggc aaaggtagcg ttgccaatga tgttacagat gagatggtca   1800
gactaaactg gctgacggaa tttatgcctc ttccgaccat caagcatttt atccgtactc   1860
ctgatgatgc atggttactc accactgcga tccccgggaa aacagcattc caggtattag   1920
aagaatatcc tgattcaggt gaaaatattg ttgatgcgct ggcagtgttc ctgcgccggt   1980
tgcattcgat tcctgtttgt aattgtcctt ttaacagcga tcgcgtattt cgtctcgctc   2040
aggcgcaatc acgaatgaat aacggtttgg ttgatgcgag tgattttgat gacgagcgta   2100
atggctggcc tgttgaacaa gtctggaaag aaatgcataa gcttttgcca ttctcaccgg   2160
attcagtcgt cactcatggt gatttctcac ttgataacct tattttgac gaggggaaat   2220
taataggttg tattgatgtt ggacgagtcg aatcgcaga ccgataccag gatcttgcca   2280
tcctatggaa ctgcctcggt gagttttctc cttcattaca gaaacggctt tttcaaaaat   2340
atggtattga taatcctgat atgaataaat tgcagtttca tttgatgctc gatgagtttt   2400
tctaatcaga attggttaat tggttgtaac actggcagag cattacgctg acttgacggg   2460
acggcggctt tgttgaataa atcgcattcg ccattcaggc tgcgcaactg ttgggaaggg   2520
cgatcggtgc gggcctcttc gctattacgc cagctggcga aaggggatg tgctgcaagg   2580
cgattaagtt gggtaacgcc agggttttcc cagtcacgac gttgtaaaac gacggccagt   2640
gaattcgagc tcggtacccg gggatcctct agagtctgca cagaacccgt actcgatccg   2700
ctcgttcgtc gctgtgaggt ctttcctgca aggcaaatcg ttgtgccgga aggggtttcg   2760
tgatgttctc cgagcgtttt tttcgttcca agttggtcat ggtggctctt gtcctggtcg   2820
ctggcctgtt tctctacaac gcctgctctt cttctgacgc aaaggaagag atcggcagca   2880
gtctgaatct ctctcctgtc actgctcgtt cgaatccgta tgagggcgtc cagcccacga   2940
tgagcgaaaa aagccctgtt cccgtccctg tcgtttccgg cgacaggatt tcggggtgg   3000
catcgtgcgg gacggattac gccgggaagc ctgcggtgac gctggaagct gtgtggattt   3060
cgtccgactc ggtgaactac acactcgata gaggcattg cctggtgacg accggcccgc   3120
tgtgaaaca agcgatccgt aaagcgtcag ggtcagagat tcggcctgag ggcgggagct   3180
ggatacgggt ggtgcttgcc atgcctgacg gcaatttcag ggcaggatgg gcaccccacg   3240
cccaagtaac cgctggtgcg ctggatattt cggcggtggt ctcgtgagcg gggagaagcg   3300
gcacagcgag gccggcccgg tagaaatcat ctttttgatg ctggcagtca gggcggggga   3360
ctacatcgtc gccgtgactg cggttctcgc ggtcgggttc ttcgcggtcg cggttgaggg   3420
tttctggttc ctggtcgtcg cagtcatcgc tgcaccggcg tggtggtttc tgcgcgactg   3480
ggaatcgaag cggagggccg tacgggtctt tgaacgggca tggaagggga cacctgaatc   3540
ccccggtatt gctctctccc ttggcctgtc gaacgtggcg gggtctctgc cgaggttgag   3600
gaagtttgaa actggttcgg ggatacgcac actcgtgttt tctttgccgc ccggagtcac   3660
tgccgagagc tttgagaaag ttcgccctgc gctggcagac gcgatggggg gtcaccgctg   3720
ccaagtagag aaggtggccc ccggacaggt ccgcgtcaga gtgattgatg aggattcgat   3780
gaagacgccg cgtgatgcgg gatgggcgaa agatgttgtg ctggaagagg atacgttcga   3840
cggtcttccg ggcgagacgc gatcctggtt cgagcaagag gggccggcat catgagaaaa   3900
tcggcgggag tatctcggat tcctatccgt ctcgggcgct ctcagtacgg ggaagacgtt   3960
ggattcgatc tcgctgcgga cgccgctcac atcgccatgc agggcaaaac ccgatccggc   4020
aaaagtcagg cgacgtacaa cgtgttagct caggcagcag cgaacgcggc ggttcgagtc   4080
```

```
gtagggtccg acccgacaca cgtactcctg gagcccttca aacatcgagg ggtgtccgag   4140
ccttacgtgg tttcgggact gaatgcgcag gccacggtgg acatgctggg ctgggtcaag   4200
cgtgagtctg atcgtcgcat cgaccagatg tggcccctgc gtaccgacaa gttttccgag   4260
ttcggggctt cgttcccgct gatactcgtc gtgctcgaag agtttcccgg gatcctcgag   4320
ggggcagcgg acgaagacgc cgcgttaggc cgaaaacctg ccgagcgtct cgcaccccgc   4380
atttcggcct acgtgcgtca gatagcagcg cagtcggcaa aggctggaat tcgccttctc   4440
ctgctctcgc aacgagcgga ggcctcgatc attggcggca atgcgcgttc gaatttcggg   4500
gtcaagatga ctctgagggt ggacgaaccg gagtcggtga gaatgcttca tccgagcgct   4560
tccccggaag actgtgccct ggtcgagacc ttcaagcctg gtacctgcct tttcgagaag   4620
ccaggagaag gccggcagat tatgcgatgc gactttgtcg gcgagtacgg gagatatgcg   4680
cgagccatcg agtcttcgga tctgcgtttt ctcgccaccc tccagcaaga ccaggcccaa   4740
cgcgaattct tcgctgagga gttcggtgtg gtggatccgt catgactgga ccacaggaga   4800
gaaagcgcaa ggcggcgaag ccgtcgcggg agcctcagtt gaactgctgt gaagcggacg   4860
tgccgaaacg agcaaaacag cccccggttc cctctacgtt cgacctgctc acggtgaagg   4920
agactgcggg gctgctgaga gtcagtcagg caactctttta ccggctgctt cggagtgggg   4980
aaggacccac atacacacgg atcggtggac agatacgcgt tcaccgcgag tcgctgcgtc   5040
ggttcatcga accgcgtgga taacgtcaca gagacagcga aaacgcctcc cctgggtcaa   5100
tccggttacc gccggactgg gggaggcgct tcgacaccta catccgtcgc ccctcgaaag   5160
gctcagatgc acttccacga taacgcagag gtcggacaag agggaagaac tgccgttctc   5220
tcgccgttgc gcggcgtagc cgccaagcgg gacgtgtctg acgatgcagc gaagcggagt   5280
cggcaggcgc ggcacgcgcc tgggcttgtt acatctgcca caactgtccg tgaatctctg   5340
ccagctcctg aaaccgctgg tcagggcctt gcggaatccg tgaccgctga tgattttttgg   5400
tctcattcgt tcccccgcgc tgacgatgta cgcggcgcag ctgcttcctt ccagtcggtg   5460
gctaactggg atgggcgtga gggtccgagg ccgcgtttcg ttgtcgcgcc tggcgttgtc   5520
cgcttggagg tttgtgatct cgcacgccgc gaacgaacgg ctgaacgtgc gtatctggct   5580
gctcgggctc gggtggatat ggcggctgcc aggcataact cgccgtacga cttcgacgtg   5640
gacgatgaag agttggcgga actggcttct ctgcaaggcc tcgaggacga cgacattggg   5700
ggctggtctg cggagaggga aatagtgggc tggtctgctc gttctcggtc acggatgatc   5760
ttgcgaatgg cagaactcga ctgggctccc atgatggatt tgccgggcat tcctgcgatg   5820
gtgaccctca cctatccggg ggactggctt acggttgccc ccaccggcgc tgaggtcaaa   5880
aaacatctcc agacgttctt caaacggttc caacgggcct ggggcattgc ctggatgggt   5940
gcgtggaaaa tggagttcca aagccgaggc gctccgcatt ttcacctgta catggtccct   6000
cctcatggga aggcaggaga ctcgcggaag ctgcggcatg atgctgagct cttgaaatgg   6060
gagatagcac gtgcagaggg tgaagaccca ggtcgcaggc cgtatttccg ggaagctcca   6120
agcgatggat tgaagtttcg tccgtggctt tctgcggtgt gggccgacgt cgtagatcat   6180
ccggacccca aggaaaaaga aaagcacgtc agtgccggca ctggagtgga ctacgcggag   6240
ggcacgcgag ggtcagatcc gaaaaggctt gcggtgtact tctccaagca tggaaccttt   6300
gccgacaagg aatatcagca cgtagttcct gctcaatggc agaaaacggg tgcgggacct   6360
ggcaggttct ggggctaccg cggtttgtcg ccggccacgg ctgccaccga gatttcctgg   6420
gatgagtacc tgctttttatc tcgcacgttg cgacgattgt cagcgcgaac gaagatctgg   6480
```

-continued

```
gacccggctt tacgaggcgg tagcggcggc cacagatgga ctaaggcgat gatgcgacgc    6540
acggttaccc ggcaccgctt ggacctcgtg accggtgaga ttctgggcac gaagacgcgg    6600
aaggttcggg cgccagtgaa gaggtttgtc cggacttcgg gatacctgtg tgtcaatgac    6660
gggcccgcac tggctcgaac cctcagccgt cttcgtacaa gctgcctgag ctagacgcgc    6720
ggaacgcctt tcggctttgt cttttgctgg atggcgggtt ttgggcggct tctggtgatg    6780
cgctgctgcg ctccgtgggg agagagaccc aacgactgac ctatctctac ccaggtgcaa    6840
ttcatctccc gcgctctgtc ggctaggtaa acgaggtgct cccgcgcgag cttttccatg    6900
tggtcggcca atgtcagctc ggtcaggaca acctgctgtt gttgcgatag ttgtgtccgc    6960
acgggtcgat tgtcttctgt tgcggcataa cggttttcgt cgttcgcgga gagtgcggct    7020
aaatgaattg catcctcgat tgagcggagc atttcgacgc ggaacctggc gatgatgttg    7080
tctctgtctt cattcataac tgaagcgtat tgggagtgtt gccctcccac catgtgtgcc    7140
aatgcaggtg tgaactgagt cacagtttct caatagactc caagtttgtg atccttttac    7200
tcccaaaatg gggcatgatg tgtgcgtgcc tcggttcagg ggcgaaagtt cgacacctcg    7260
aaagaaggcc tcgacatggc tttgaaagct gctggcaacg tgattcctga ttcctccgcg    7320
tacgagtacc gggcggttca ggtcgagccg aagatggtca gaaagaccc ggaagacccg     7380
aactctgagc agttccagaa gcagaaggac ggcacgccgg tgtggtcgat cgactgcatt    7440
cgggtcgacc gggcatcagg caacaaggca atcgtgaccg tgacggttcc ggacgtgatg    7500
gaaccggatg ttgcggggcc ggtggagttc tccgagatga ttgccggttt ctgggtttcg    7560
cgcagtggtt cgggcatgtg gttttcggca agcgccgtcg cttctctctg atcgctgatc    7620
gtcgcccctc gaaaggttcg gaaatgtcca aggaaaagg cgttgcgctg ggtgtgggtg     7680
ccctcgtgct cgtgtttgtg ctggttgcgg caggttggca agcggcgaac gtgttcagtg    7740
atcgttcaca gtccgaagct gtgccgctga gagtgccggc cgatccgaag tgggaaaacg    7800
gggtgttctc ggacgttgcc gggtgcctcg ttctctctcc ggaagagctg gggccgttca    7860
gcggagggca gtacatcgac atagtgaggc cagttgagcc ggagaggttg gagcgcgact    7920
gggtgaggtc ggctgagtgc gtttcggcgt cgatgaatgt ctctgacctg ttggttctg     7980
ctcttccaga gtccacccgt cccccgcgcg atttcgttcg ttcgtggaaa gtggcgagtg    8040
atgattactg ctatgagggt gataacccgc aaggctgcac ttctcgtatg ccggtttggg    8100
tctctgcaaa aaactggtgg tgca                                           8124
```

<210> SEQ ID NO 91
<211> LENGTH: 7675
<212> TYPE: DNA
<213> ORGANISM: Artificial
<220> FEATURE:
<223> OTHER INFORMATION: pRET1103

<400> SEQUENCE: 91

```
gacctgcagg catgcaagct tggcactggc cgtcgtttta caacgtcgtg actgggaaaa      60
ccctggcgtt acccaactta atcgccttgc agcacatccc cctttcgcca gctggcgtaa    120
tagcgaagag gcccgcaccg atcgcccttc ccaacagttg cgcagcctga atggcgaatg    180
agcttcttcc gcttcctcgc tcactgactc gctgcgctcg tcgttcggc tgcggcgagc      240
ggtatcagct cactcaaagg cggtaatacg gttatccaca gaatcagggg ataacgcagg    300
aaagaacatg tgagcaaaag gccagcaaaa ggccaggaac cgtaaaaagg ccgcgttgct    360
```

```
ggcgttttc  cataggctcc  gccccctga   cgagcatcac  aaaaatcgac  gctcaagtca   420
gaggtggcga  aacccgacag  gactataaag  ataccaggcg  tttcccctg   gaagctccct   480
cgtgcgctct  cctgttccga  ccctgccgct  taccggatac  ctgtccgcct  ttctcccttc   540
gggaagcgtg  gcgctttctc  aatgctcacg  ctgtaggtat  ctcagttcgg  tgtaggtcgt   600
tcgctccaag  ctgggctgtg  tgcacgaacc  ccccgttcag  cccgaccgct  gcgccttatc   660
cggtaactat  cgtcttgagt  ccaacccggt  aagacacgac  ttatcgccac  tggcagcagc   720
cactggtaac  aggattagca  gagcgaggta  tgtaggcggt  gctacagagt  tcttgaagtg   780
gtggcctaac  tacggctaca  ctagaaggac  agtatttggt  atctgcgctc  tgctgaagcc   840
agttaccttc  ggaaaaagag  ttggtagctc  ttgatccggc  aaacaaacca  ccgctggtag   900
cggtggtttt  tttgtttgca  agcagcagat  tacgcgcaga  aaaaaggat   ctcaagaaga   960
tcctttgatc  ttttctacgg  ggtctgacgc  tcagtggaac  tccgtcgaac  ggaagatcac  1020
ttcgcagaat  aaataaatcc  tggtgtccct  gttgataccg  ggaagccctg  gccaacttt   1080
tggcgaaaat  gagacgttga  tcggcacgta  agaggttcca  actttcacca  taatgaaata  1140
agatcactac  cgggcgtatt  ttttgagtta  tcgagatttt  caggagctaa  ggaagctaaa  1200
atggagaaaa  aaatcactgg  atataccacc  gttgatatat  cccaatggca  tcgtaaagaa  1260
catttttgagg  catttcagtc  agttgctcaa  tgtacctata  accagaccgt  tcagctggat  1320
attacggcct  ttttaaagac  cgtaaagaaa  aataagcaca  agttttatcc  ggcctttatt  1380
cacattcttg  cccgcctgat  gaatgctcat  ccggaattc   gtatggcaat  gaaagacggt  1440
gagctggtga  tatgggatag  tgttcaccct  tgttacaccg  ttttccatga  gcaaactgaa  1500
acgttttcat  cgctctggag  tgaataccac  gacgatttcc  ggcagtttct  acacatatat  1560
tcgcaagatg  tggcgtgtta  cggtgaaaac  ctggcctatt  tccctaaagg  gtttattgag  1620
aatatgtttt  tcgtctcagc  caatccctgg  gtgagtttca  ccagttttga  tttaaacgtg  1680
gccaatatgg  acaacttctt  cgcccccgtt  ttcaccatgg  gcaaatatta  tacgcaaggc  1740
gacaaggtgc  tgatgccgct  ggcgattcag  gttcatcatg  ccgtctgtga  tggcttccat  1800
gtcggcagaa  tgcttaatga  attacaacag  tactgcgatg  agtggcaggg  cggggcgtaa  1860
ttttttttaag  gcagttattg  gtgcccttaa  acgcctggtg  ctacgcctga  ataagtgata  1920
ataagcggat  gaatggcaga  aattcagctt  ggcccagtgc  caagctccaa  tacgcaaacc  1980
gcctctcccc  gcgcgttggc  cgattcatta  atgcagctgg  cacgacaggt  ttcccgactg  2040
gaaagcgggc  agtgagcgca  acgcaattaa  tgtgagttag  ctcactcatt  aggcacccca  2100
ggctttacac  tttatgcttc  cggctcgtat  gttgtgtgga  attgtgagcg  ataacaatt   2160
tcacacagga  aacagctatg  accatgatta  cgaattcgag  ctcggtaccc  ggggatcctc  2220
tagagtctgc  acagaacccg  tactcgatcc  gctcgttcgt  cgctgtgagg  tctttcctgc  2280
aaggcaaatc  gttgtgccgg  aaggggtttc  gtgatgtttc  tccgagcgtt  ttttcgttcc  2340
aagttggtca  tggtggctct  tgtcctggtc  gctggcctgt  ttctctacaa  cgcctgctct  2400
tcttctgacg  caaaggaaga  gatcggcagc  agtctgaatc  tctctcctgt  cactgctcgt  2460
tcgaatccgt  atgagggcgt  ccagcccacg  atgagcgaaa  aaagccctgt  tcccgtccct  2520
gtcgtttccg  gcgacaggat  ttcggggtg   gcatcgtgcg  ggacggatta  cgccgggaag  2580
cctgcggtga  cgctggaagc  tgtgtggatt  tcgtccgact  cggtgaacta  cacactcgat  2640
aagaggcatt  gcctggtgac  gaccggcccg  ctgtggaaaa  aagcgatccg  taaagcgtca  2700
gggtcagaga  ttcggcctga  gggcgggagc  tggatacggg  tggtgcttgc  catgcctgac  2760
```

-continued

```
ggcaatttca gggcaggatg ggcaccccac gcccaagtaa ccgctggtgc gctggatatt    2820
tcggcggtgg tctcgtgagc ggggagaagc ggcacagcga ggccggcccg gtagaaatca    2880 tcttttgat gctggcagtc agggcggggg actacatcgt cgccgtgact gcggttctcg     2940
cggtcgggtt cttcgcggtc gcggttgagg gtttctggtt cctggtcgtc gcagtcatcg    3000
ctgcaccggc gtggtggttt ctgcgcgact gggaatcgaa gcgagggcc gtacgggtct     3060 ttgaacgggc atggaagggg acacctgaat cccccggtat tgctctctcc cttggcctgt    3120
cgaacgtggc ggggtctctg ccgaggttga ggaagtttga aactggttcg gggatacgca    3180
cactcgtgtt ttctttgccg cccggagtca ctgccgagag ctttgagaaa gttcgccctg    3240
cgctggcaga cgcgatgggg ggtcaccgct gccaagtaga aaggtggcc cccggacagg     3300 tccgcgtcag agtgattgat gaggattcga tgaagacgcc gcgtgatgcg ggatgggcga    3360
aagatgttgt gctggaagag gatacgttcg acggtcttcc gggcgagacg cgatcctggt    3420
tcgagcaaga ggggccggca tcatgagaaa atcggcggga gtatctcgga ttcctatccg    3480
tctcgggcgc tctcagtacg gggaagacgt tggattcgat ctcgctgcgg acgccgctca    3540
catcgccatg cagggcaaaa cccgatccgg caaaagtcag gcgacgtaca acgtgttagc    3600
tcaggcagca gcgaacgcgg cggttcgagt cgtagggtcc gacccgacac acgtactcct    3660
ggagcccttc aaacatcgag gggtgtccga gccttacgtg gtttcgggac tgaatgcgca    3720
ggccacggtg gacatgctgg gctgggtcaa gcgtgagtct gatcgtcgca tcgaccagat    3780
gtggcccctg cgtaccgaca gttttccga gttcggggct tcgttcccgc tgatactcgt     3840
cgtgctcgaa gagtttcccg ggatcctcga ggggcagcg gacgaagacg ccgcgttagg     3900
ccgaaaacct gccgagcgtc tcgcaccccg catttcggcc tacgtgcgtc agatagcagc    3960
gcagtcggca aaggctggaa ttcgccttct cctgctctcg caacgagcgg aggcctcgat    4020 cattggcgg aatgcgcgtt cgaatttcgg ggtcaagatg actctgaggg tggacgaacc     4080
ggagtcggtg agaatgcttc atccgagcgc ttccccggaa gactgtgccc tggtcgagac    4140
cttcaagcct ggtacctgcc ttttcgagaa gccaggagaa ggccggcaga ttatgcgatg    4200
cgactttgtc ggcgagtacg ggagatatgc gcgagccatc gagtcttcgg atctgcgttt    4260
tctcgccacc ctccagcaag accagggccca acgcgaattc ttcgctgagg agttcggtgt    4320
ggtggatccg tcatgactgg accacaggag agaaagcgca aggcggcgaa gccgtcgcgg    4380
gagcctcagt tgaactgctg tgaagcggac gtgccgaaac gagcaaaaca gccccggtt    4440 ccctctacgt tcgacctgct cacggtgaag gagactgcgg ggctgctgag agtcagtcag    4500
gcaactcttt accggctgct tcggagtggg aaggaccca catacacacg gatcggtgga    4560
cagatacgcg ttcaccgcga gtcgctgcgt cggttcatcg aaccgcgtgg ataacgtcac    4620
agagacagcg aaaacgcctc ccctgggtca atccggttac cgccggactg ggggaggcgc    4680
ttcgacacct acatccgtcg cccctcgaaa ggctcagatg cacttccacg ataacgcaga    4740
ggtcggacaa gagggaagaa ctgccgttct ctcgccgttg cgcggcgtag ccgccaagcg    4800
ggacgtgtct gacgatgcag cgaagcggag tcggcaggcg cggcacgcgc ctgggcttgt    4860
tacatctgcc acaactgtcc gtgaatctct gccagctcct gaaaccgctg gtcagggcct    4920
tgcggaatcc gtgaccgctg atgatttttg gtctcattcg ttccccgcg ctgacgatgt     4980 acgcggcgca gctgcttcct tccagtcggt ggctaactgg gatgggcgtg agggtccgag    5040
gccgcgtttc gttgtcgcgc ctggcgttgt ccgcttggag gtttgtgatc tcgcacgccg    5100
```

```
cgaacgaacg gctgaacgtg cgtatctggc tgctcgggct cgggtggata tggcggctgc    5160
caggcataac tcgccgtacg acttcgacgt ggacgatgaa gagttggcgg aactggcttc    5220
tctgcaaggc ctcgaggacg acgacattgg gggctggtct gcggagaggg aaatagtggg    5280
ctggtctgct cgttctcggt cacggatgat cttgcgaatg gcagaactcg actgggctcc    5340
catgatggat ttgccgggca ttcctgcgat ggtgaccctc acctatccgg gggactggct    5400
tacggttgcc cccaccggcg ctgaggtcaa aaaacatctc cagacgttct tcaaacggtt    5460
ccaacgggcc tggggcattg cctggatggg tgcgtggaaa atggagttcc aaagccgagg    5520
cgctccgcat tttcacctgt acatggtccc tcctcatggg aaggcaggag actcgcggaa    5580
gctgcggcat gatgctgagc tcttgaaatg ggagatagca cgtgcagagg gtgaagaccc    5640
aggtcgcagg ccgtatttcc gggaagctcc aagcgatgga ttgaagtttc gtccgtggct    5700
ttctgcggtg tgggccgacg tcgtagatca tccggacccc aaggaaaaag aaaagcacgt    5760
cagtgccggc actggagtgg actacgcgga gggcacgcga gggtcagatc cgaaaaggct    5820
tgcggtgtac ttctccaagc atggaacctt tgccgacaag gaatatcagc acgtagttcc    5880
tgctcaatgg cagaaaacgg gtgcgggacc tggcaggttc tggggctacc gcggtttgtc    5940
gccggccacg gctgccaccg agatttcctg ggatgagtac ctgcttttat ctcgcacgtt    6000
gcgacgattg tcagcgcgaa cgaagatctg ggacccggct ttacgaggcg gtagcggcgg    6060
ccacagatgg actaaggcga tgatgcgacg cacggttacc cggcaccgct tggacctcgt    6120
gaccggtgag attctgggca cgaagacgcg gaaggttcgg gcgccagtga agaggtttgt    6180
ccggacttcg ggatacctgt gtgtcaatga cgggcccgca ctggctcgaa ccctcagccg    6240
tcttcgtaca agctgcctga gctagacgcg cggaacgcct tcggcttttg tcttttgctg    6300
gatggcgggt tttgggcggc ttctggtgat gcgctgctgc gctccgtggg gagagagacc    6360
caacgactga cctatctcta cccaggtgca attcatctcc cgcgctctgt cggctaggta    6420
aacgaggtgc tcccgcgcga gcttttccat gtggtcggcc aatgtcagct cggtcaggac    6480
aacctgctgt tgttgcgata gttgtgtccg cacgggtcga ttgtcttctg ttgcggcata    6540
acggttttcg tcgttcgcgg agagtgcggc taaatgaatt gcatcctcga ttgagcggag    6600
catttcgacg cggaacctgg cgatgatgtt gtctctgtct tcattcataa ctgaagcgta    6660
ttgggagtgt tgccctccca ccatgtgtgc caatgcaggt gtgaactgag tcacagtttc    6720
tcaatagact ccaagtttgt gatccttta ctcccaaaat ggggcatgat gtgtgcgtgc    6780
ctcggttcag gggcgaaagt tcgacacctc gaaagaaggc ctcgacatgg ctttgaaagc    6840
tgctggcaac gtgattcctg attcctccgc gtacgagtac cgggcggttc aggtcgagcc    6900
gaagatggtc agaaaagacc cggaagaccc gaactctgag cagttccaga agcagaagga    6960
cggcacgccg tgtggtcga tcgactgcat tcgggtcgac cgggcatcag gcaacaaggc    7020
aatcgtgacc gtgacggttc cggacgtgat ggaaccggat gttgcggggc cggtggagtt    7080
ctccgagatg attgccggtt tctgggtttc gcgcagtggt tcgggcatgt ggttttcggc    7140
aagcgccgtc gcttctctct gatcgctgat cgtcgcccct cgaaaggttc ggaaatgtcc    7200
aaaggaaaag gcgttgcgct gggtgtgggt gccctcgtgc tcgtgtttgt gctggttgcg    7260
gcaggttggc aagcggcgaa cgtgttcagt gatcgttcac agtccgaagc tgtgccgctg    7320
agagtgccgg ccgatccgaa gtgggaaaac ggggtgttct cggacgttgc cgggtgcctc    7380
gttctctctc cggaagagct ggggccgttc agcggagggc agtacatcga catagtgagg    7440
ccagttgagc cggagaggtt ggagcgcgac tgggtgaggt cggctgagtg cgtttcggcg    7500
```

```
tcgatgaatg tctctgacct gttggtttct gctcttccag agtccacccg tcccccggc    7560 gatttcgttc gttcgtggaa agtggcgagt gatgattact gctatgaggg tgataacccg    7620
caaggctgca cttctcgtat gccggtttgg gtctctgcaa aaaactggtg gtgca          7675

<210> SEQ ID NO 92
<211> LENGTH: 8134
<212> TYPE: DNA
<213> ORGANISM: Artificial
<220> FEATURE:
<223> OTHER INFORMATION: pRET1101Rv

<400> SEQUENCE: 92
ggggatcctc tagagtcgac ctgcaggcat gcaagcttgg cactggccgt cgttttacaa      60
cgtcgtgact gggaaaaccc tggcgttacc caacttaatc gccttgcagc acatccccct    120
ttcgccagct ggcgtaatag cgaagaggcc cgcaccgatc gcccttccca acagttgcgc    180
agcctgaatg gcgaatggcg cctgatgcgg tattttctcc ttacgcatct gtgcggtatt    240
tcacaccgca tatggtgcac tctcagtaca atctgctctg atgccgcata gttaagccag    300
ccccgacacc cgccaacacc cgctgacgcg ccctgacggg cttgtctgct cccggcatcc    360
gcttacagac aagctgtgac cgtctccggg agctgcatgt gtcagaggtt ttcaccgtca    420
tcaccgaaac gcgcgagacg aaagggcctc gtgatacgcc tatttttata ggttaatgtc    480
atgataataa tggtttctta gacgtcaggt ggcactttc ggggaaatgt gcgcggaacc    540
cctatttgtt tattttccta aatacattca aatatgtatc cgctcatgag acaataaccc    600
tgataaatgc ttcaataata ttgaaaaagg aagagtatga gtattcaaca tttccgtgtc    660
gcccttattc cctttttgc ggcatttgc cttcctgttt ttgctcaccc agaaacgctg    720
gtgaaagtaa aagatgctga agatcagttg ggtgcacgag tgggttacat cgaactggat    780
ctcaacagcg gtaagatcct tgagagtttt cgccccgaag aacgttttcc aatgatgagc    840
acttttaaag ttctgctatg tggcgcggta ttatcccgta ttgacgccgg gcaagagcaa    900
ctcggtcgcc gcatacacta ttctcagaat gacttggttg agtactcacc agtcacagaa    960
aagcatctta cggatggcat gacagtaaga gaattatgca gtgctgccat aaccatgagt   1020
gataacactg cggccaactt acttctgaca acgatcggag gaccgaagga gctaaccgct   1080
tttttgcaca acatggggga tcatgtaact cgccttgatc gttgggaacc ggagctgaat   1140
gaagccatac caaacgacga gcgtgacacc acgatgcctg tagcaatggc aacaacgttg   1200
cgcaaactat taactggcga actacttact ctagcttccc ggcaacaatt aatagactgg   1260
atggaggcgg ataaagttgc aggaccactt ctgcgctcgg cccttccggc tggctggttt   1320
attgctgata atctggagc cggtgagcgt gggtctcgcg gtatcattgc agcactgggg   1380
ccagatggta agccctcccg tatcgtagtt atctacacga cggggagtca ggcaactatg   1440
gatgaacgaa atagacagat cgctgagata ggtgcctcac tgattaagca ttggtaactg   1500
tcagaccaag tttactcata tatactttag attgatttaa aacttcattt ttaatttaaa   1560
aggatctagg tgaagatcct ttttgataat ctcatgacca aaatccctta acgtgagttt   1620
tcgttccact gagcgtcaga ccccgtagaa aagatcaaag gatcttcttg agatcctttt   1680
tttctgcgcg taatctgctg cttgcaaaca aaaaaaccac cgctaccagc ggtggtttgt   1740
ttgccggatc aagagctacc aactcttttt ccgaaggtaa ctggcttcag cagagcgcag   1800
ataccaaata ctgtccttct agtgtagccg tagttaggcc accacttcaa gaactctgta   1860
```

```
gcaccgccta catacctcgc tctgctaatc ctgttaccag tggctgctgc cagtggcgat    1920
aagtcgtgtc ttaccgggtt ggactcaaga cgatagttac cggataaggc gcagcggtcg    1980
ggctgaacgg ggggttcgtg cacacagccc agcttggagc gaacgaccta caccgaactg    2040
agatacctac agcgtgagct atgagaaagc gccacgcttc ccgaagggag aaaggcggac    2100
aggtatccgg taagcggcag ggtcggaaca ggagagcgca cgaggagct tccagggga    2160 aacgcctggt atctttatag tcctgtcggg tttcgccacc tctgacttga gcgtcgattt    2220
ttgtgatgct cgtcagggg gcggagccta tggaaaaacg ccagcaacgc ggcctttta    2280 cggttcctgg ccttttgctg ccttttgct cacatgttct ttcctgcgtt atccctgat    2340 tctgtggata accgtattac cgcctttgag tgagctgata ccgctcgccg cagccgaacg    2400
accgagcgca gcgagtcagt gagcgaggaa gcggaagagc gcccaatacg caaaccgcct    2460
ctccccgcgc gttggccgat tcattaatgc agctggcacg acaggtttcc cgactggaaa    2520
gcgggcagtg agcgcaacgc aattaatgtg agttagctca ctcattaggc accccaggct    2580
ttacacttta tgcttccggc tcgtatgttg tgtggaattg tgagcggata acaatttcac    2640
acaggaaaca gctatgacca tgattacgaa ttcgagctcg gtaccctgca cagaacccgt    2700
actcgatccg ctcgttcgtc gctgtgaggt cttttcctgca aggcaaatcg ttgtgccgga    2760
aggggtttcg tgatgtttct ccgagcgttt tttcgttcca agttggtcat ggtggctctt    2820
gtcctggtcg ctggcctgtt tctctacaac gcctgctctt cttctgacgc aaaggaagag    2880
atcggcagca gtctgaatct ctctcctgtc actgctcgtt cgaatccgta tgagggcgtc    2940
cagcccacga tgagcgaaaa aagccctgtt cccgtccctg tcgtttccgg cgacaggatt    3000 tcggggtgtgg catcgtgcgg gacggattac gccgggaagc ctgcggtgac gctgaagct    3060 gtgtggattt cgtccgactc ggtgaactac acactcgata agaggcattg cctggtgacg    3120
accggcccgc tgtggaaaca agcgatccgt aaagcgtcag ggtcagagat tcggcctgag    3180
ggcgggagct ggatacgggt ggtgcttgcc atgcctgacg gcaatttcag ggcaggatgg    3240
gcaccccacg cccaagtaac cgctggtgcg ctggatattt cggcggtggt ctcgtgagcg    3300
gggagaagcg gcacagcgag gccggcccgg tagaaatcat cttttttgatg ctggcagtca    3360 gggcgggga ctacatcgtc gccgtgactg cggttctcgc ggtcgggttc ttcgcggtcg    3420
cggttgaggg tttctggttc ctggtcgtcg cagtcatcgc tgcaccggcg tggtggtttc    3480
tgcgcgactg ggaatcgaag cggagggccg tacgggtctt tgaacgggca tggaagggga    3540
cacctgaatc ccccggtatt gctctctccc ttggcctgtc gaacgtggcg gggtctctgc    3600
cgaggttgag gaagtttgaa actggttcgg ggatacgcac actcgtgttt tctttgccgc    3660
ccggagtcac tgccgagagc tttgagaaag ttcgccctgc gctggcagac gcgatggggg    3720
gtcaccgctg ccaagtagag aaggtggccc ccggacaggt ccgcgtcaga gtgattgatg    3780
aggattcgat gaagacgccg cgtgatgcgg gatgggcgaa agatgttgtg ctggaagagg    3840
atacgttcga cggtcttccg ggcgagacgc gatcctggtt cgagcaagag gggccggcat    3900
catgagaaaa tcggcgggag tatctcggat tcctatccgt ctcgggcgct tcagtacgg    3960 ggaagacgtt ggattcgatc tcgctgcgga cgccgctcac atcgccatgc agggcaaaac    4020
ccgatccggc aaaagtcagg cgacgtacaa cgtgttagct caggcagcag cgaacgcggc    4080
ggttcgagtc gtagggtccg acccgacaca cgtactcctg gagcccttca acatcgagg    4140 ggtgtccgag ccttacgtgg tttcgggact gaatgcgcag gccacggtgg acatgctggg    4200
ctgggtcaag cgtgagtctg atcgtcgcat cgaccagatg tggcccctgc gtaccgacaa    4260
```

```
gttttccgag ttcggggctt cgttcccgct gatactcgtc gtgctcgaag agtttcccgg   4320
gatcctcgag ggggcagcgg acgaagacgc cgcgttaggc cgaaaacctg ccgagcgtct   4380
cgcaccccgc atttcggcct acgtgcgtca gatagcagcg cagtcggcaa aggctggaat   4440
tcgccttctc ctgctctcgc aacgagcgga ggcctcgatc attggcggca atgcgcgttc   4500
gaatttcggg gtcaagatga ctctgagggt ggacgaaccg gagtcggtga gaatgcttca   4560
tccgagcgct tccccggaag actgtgccct ggtcgagacc ttcaagcctg gtacctgcct   4620
tttcgagaag ccaggagaag gccggcagat tatgcgatgc gactttgtcg gcgagtacgg   4680
gagatatgcg cgagccatcg agtcttcgga tctgcgtttt ctcgccaccc tccagcaaga   4740
ccaggcccaa cgcgaattct tcgctgagga gttcggtgtg gtggatccgt catgactgga   4800
ccacaggaga gaaagcgcaa ggcggcgaag ccgtcgcggg agcctcagtt gaactgctgt   4860
gaagcggacg tgccgaaacg agcaaaacag ccccggttc cctctacgtt cgacctgctc    4920
acggtgaagg agactgcggg gctgctgaga gtcagtcagg caactcttta ccggctgctt   4980
cggagtgggg aaggacccac atacacacg atcggtggac agatacgcgt tcaccgcgag    5040
tcgctgcgtc ggttcatcga accgcgtgga taacgtcaca gagacagcga aaacgcctcc   5100
cctgggtcaa tccggttacc gccggactgg gggaggcgct tcgacaccta catccgtcgc   5160
ccctcgaaag gctcagatgc acttccacga taacgcagag gtcggacaag agggaagaac   5220
tgccgttctc tcgccgttgc gcggcgtagc cgccaagcgg gacgtgtctg acgatgcagc   5280
gaagcggagt cggcaggcgc ggcacgcgcc tgggcttgtt acatctgcca caactgtccg   5340
tgaatctctg ccagctcctg aaaccgctgg tcagggcctt gcggaatccg tgaccgctga   5400
tgattttggg tctcattcgt tcccccgcgc tgacgatgta cgcggcgcag ctgcttcctt   5460
ccagtcggtg gctaactggg atgggcgtga gggtccgagg ccgcgtttcg ttgtcgcgcc   5520
tggcgttgtc cgcttggagg tttgtgatct cgcacgccgc gaacgaacgg ctgaacgtgc   5580
gtatctggct gctcgggctc gggtggatat ggcggctgcc aggcataact cgccgtacga   5640
cttcgacgtg gacgatgaag agttggcgga actggcttct ctgcaaggcc tcgaggacga   5700
cgacattggg ggctggtctg cggagaggga aatagtgggc tggtctgctc gttctcggtc   5760
acggatgatc ttgcgaatgg cagaactcga ctgggctccc atgatggatt tgccgggcat   5820
tcctgcgatg gtgaccctca cctatccggg ggactggctt acggttgccc ccaccggcgc   5880
tgaggtcaaa aaacatctcc agacgttctt caaacggttc caacgggcct ggggcattgc   5940
ctggatgggt gcgtggaaaa tggagttcca agccgaggc gctccgcatt ttcacctgta    6000
catggtccct cctcatggga aggcaggaga ctcgcggaag ctgcggcatg atgctgagct   6060
cttgaaatgg gagatagcac gtgcagaggg tgaagaccca ggtcgcaggc cgtatttccg   6120
ggaagctcca agcgatggat tgaagtttcg tccgtggctt tctgcggtgt gggccgacgt   6180
cgtagatcat ccggacccca aggaaaaaga aaagcacgtc agtgccggca ctggagtgga   6240
ctacgcggag ggcacgcgag ggtcagatcc gaaaaggctt gcggtgtact tctccaagca   6300
tggaaccttt gccgacaagg aatatcagca cgtagttcct gctcaatggc agaaaacggg   6360
tgcgggacct gcaggttct ggggctaccg cggtttgtcg ccggccacgg ctgccaccga    6420
gatttcctgg gatgagtacc tgcttttatc tcgcacgttg cgacgattgt cagcgcgaac   6480
gaagatctgg gacccggctt acgaggcgg tagcggcgc cacagatgga ctaaggcgat    6540
gatgcgacgc acggttaccc ggcaccgctt ggacctcgtg accggtgaga ttctgggcac   6600
```

-continued

| | |
|---|---|
| gaagacgcgg aaggttcggg cgccagtgaa gaggtttgtc cggacttcgg gatacctgtg | 6660 |
| tgtcaatgac gggcccgcac tggctcgaac cctcagccgt cttcgtacaa gctgcctgag | 6720 |
| ctagacgcgc ggaacgcctt tcggctttgt cttttgctgg atggcgggtt ttgggcggct | 6780 |
| tctggtgatg cgctgctgcg ctccgtgggg agagagaccc aacgactgac ctatctctac | 6840 |
| ccaggtgcaa ttcatctccc gcgctctgtc ggctaggtaa acgaggtgct cccgcgcgag | 6900 |
| cttttccatg tggtcggcca atgtcagctc ggtcaggaca acctgctgtt gttgcgatag | 6960 |
| ttgtgtccgc acgggtcgat tgtcttctgt tgcggcataa cggttttcgt cgttcgcgga | 7020 |
| gagtgcggct aaatgaattg catcctcgat tgagcggagc atttcgacgc ggaacctggc | 7080 |
| gatgatgttg tctctgtctt cattcataac tgaagcgtat tgggagtgtt gccctcccac | 7140 |
| catgtgtgcc aatgcaggtg tgaactgagt cacagtttct caatagactc caagtttgtg | 7200 |
| atccttttac tcccaaaatg gggcatgatg tgtgcgtgcc tcggttcagg ggcgaaagtt | 7260 |
| cgacacctcg aaagaaggcc tcgacatggc tttgaaagct gctggcaacg tgattcctga | 7320 |
| ttcctccgcg tacgagtacc gggcggttca ggtcgagccg aagatggtca gaaaagaccc | 7380 |
| ggaagacccg aactctgagc agttccagaa gcagaaggac ggcacgccgg tgtggtcgat | 7440 |
| cgactgcatt cgggtcgacc gggcatcagg caacaaggca atcgtgaccg tgacggttcc | 7500 |
| ggacgtgatg gaaccggatg ttgcggggcc ggtggagttc tccgagatga ttgccggttt | 7560 |
| ctgggtttcg cgcagtggtt cggcatgtg gttttcggca agcgccgtcg cttctctctg | 7620 |
| atcgctgatc gtcgcccctc gaaaggttcg gaaatgtcca aggaaaagg cgttgcgctg | 7680 |
| ggtgtgggtg ccctcgtgct cgtgtttgtg ctggttgcgg caggttggca agcggcgaac | 7740 |
| gtgttcagtg atcgttcaca gtccgaagct gtgccgctga gagtgccggc cgatccgaag | 7800 |
| tgggaaaacg gggtgttctc ggacgttgcc gggtgcctcg ttctctctcc ggaagagctg | 7860 |
| gggccgttca gcggagggca gtacatcgac atagtgaggc cagttgagcc ggagaggttg | 7920 |
| gagcgcgact gggtgaggtc ggctgagtgc gtttcggcgt cgatgaatgt ctctgacctg | 7980 |
| ttggtttctg ctcttccaga gtccacccgt cccccggcg atttcgttcg ttcgtggaaa | 8040 |
| gtggcgagtg atgattactg ctatgagggt gataacccgc aaggctgcac ttctcgtatg | 8100 |
| ccggtttggg tctctgcaaa aaactggtgg tgca | 8134 |

<210> SEQ ID NO 93
<211> LENGTH: 8124
<212> TYPE: DNA
<213> ORGANISM: Artificial
<220> FEATURE:
<223> OTHER INFORMATION: pRET1102Rv

<400> SEQUENCE: 93

| | |
|---|---|
| gactctagag gatccccggg taccgagctc gaattcactg gccgtcgttt tacaacgtcg | 60 |
| tgactgggaa aaccctggcg ttacccaact taatcgcctt gcagcacatc cccctttcgc | 120 |
| cagctggcgt aatagcgaag aggcccgcac cgatcgccct tcccaacagt tgcgcagcct | 180 |
| gaatggcgaa tgcgatttat tcaacaaagc cgccgtcccg tcaagtcagc gtaatgctct | 240 |
| gccagtgtta caaccaatta accaattctg attagaaaaa ctcatcgagc atcaaatgaa | 300 |
| actgcaattt attcatatca ggattatcaa taccatattt tgaaaaagc cgtttctgta | 360 |
| atgaaggaga aaactcaccg aggcagttcc ataggatggc aagatcctgg tatcggtctg | 420 |
| cgattccgac tcgtccaaca tcaatacaac ctattaattt cccctcgtca aaataaggt | 480 |
| tatcaagtga gaaatcacca tgagtgacga ctgaatccgg tgagaatggc aaaagcttat | 540 |

```
gcatttctttt ccagacttgt tcaacaggcc agccattacg ctcgtcatca aaatcactcg    600
catcaaccaa accgttattc attcgtgatt gcgcctgagc gagacgaaat acgcgatcgc    660
tgttaaaagg acaattacaa acaggaatcg aatgcaaccg gcgcaggaac actgccagcg    720
catcaacaat attttcacct gaatcaggat attcttctaa tacctggaat gctgttttcc    780
cggggatcgc agtggtgagt aaccatgcat catcaggagt acggataaaa tgcttgatgg    840
tcggaagagg cataaattcc gtcagccagt ttagtctgac catctcatct gtaacatcat    900
tggcaacgct acctttgcca tgtttcagaa acaactctgg cgcatcgggc ttcccataca    960
atcgatagat tgtcgcacct gattgcccga cattatcgcg agcccattta tacccatata   1020
aatcagcatc catgttggaa tttaatcgcg gcttcgagca agacgtttcc cgttgaatat   1080
ggctcataac accccttgta ttactgttta tgtaagcaga cagttttatt gttcatgatg   1140 atatatttt atcttgtgca atgtaacatc agagattttg agacacaacg tggctttgtt   1200
gaataaatcg aacttttgct gagttgaagg atcagatcac gcatcttccc gacaacgcag   1260
accgttccgt ggcaaagcaa aagttcaaaa tcaccaactg gtccacctac aacaaagctc   1320
tcatcaaccg tggctccctc actttctggc tggatgatgg ggcgattcag gcctggtatg   1380
agtcagcaac accttcttca cgaggcagac ctctcgacgg atcgttccac tgagcgtcag   1440
accccgtaga aaagatcaaa ggatcttctt gagatccttt ttttctgcgc gtaatctgct   1500
gcttgcaaac aaaaaaacca ccgctaccag cggtggtttg tttgccggat caagagctac   1560
caactctttt tccgaaggta actggcttca gcagagcgca gataccaaat actgtccttc   1620
tagtgtagcc gtagttaggc caccacttca agaactctgt agcaccgcct acatacctcg   1680
ctctgctaat cctgttacca gtggctgctg ccagtggcga taagtcgtgt cttaccgggt   1740
tggactcaag acgatagtta ccggataagg cgcagcggtc gggctgaacg ggggggttcgt   1800 gcacacagcc cagcttggag cgaacgacct acaccgaact gagatcccta cagcgtgagc   1860
attgagaaag cgccacgctt cccgaaggga gaaaggcgga caggtatccg gtaagcggca   1920
gggtcggaac aggagagcgc acgagggagc ttcagggggg aaacgcctgg tatctttata   1980
gtcctgtcgg gtttcgccac ctctgacttg agcgtcgatt tttgtgatgc tcgtcagggg   2040
ggcggagcct atggaaaaac gccagcaacg cggccttttt acggttcctg gccttttgct   2100
ggccttttgc tcacatgttc tttcctgcgt tatcccctga ttctgtggat aaccgtatta   2160
ccgcctttga gtgagctgat accgctcgcc gcagccgaac gaccgagcgc agcgagtcag   2220
tgagcgagga agcggaagaa gctcgcacat tcagcagcgt ttttcagcgc gttttcgatc   2280
agcgtttcaa tgttggtatc aacaccaggt ttaactttga acttatcggc actgacggtt   2340
actgattttg aacttttgct ttgccacgga acggtctgcg ttgtcgggaa gatgcgtgat   2400
ctgatccttc aactcagcaa aagttcgcca atacgcaaac cgcctctccc cgcgcgttgg   2460
ccgattcatt aatgcagctg gcacgacagg tttcccgact ggaaagcggg cagtgagcgc   2520
aacgcaatta atgtgagtta gctcactcat taggcacccc aggctttaca ctttatgctt   2580
ccggctcgta tgttgtgtgg aattgtgagc ggataacaat ttcacacagg aaacagctat   2640
gaccatgatt acgccaagct tgcatgcctg caggtctgca cagaacccgt actcgatccg   2700
ctcgttcgtc gctgtgaggt cttttcctgca aggcaaatcg ttgtgccgga aggggtttcg   2760
tgatgtttct ccgagcgttt tttcgttcca agttggtcat ggtggctctt gtcctggtcg   2820
ctggcctgtt tctctacaac gcctgctctt cttctgacgc aaaggaagag atcggcagca   2880
```

```
gtctgaatct ctctcctgtc actgctcgtt cgaatccgta tgagggcgtc cagcccacga    2940
tgagcgaaaa aagccctgtt cccgtccctg tcgtttccgg cgacaggatt tcggggggtgg   3000 catcgtgcgg gacggattac gccgggaagc ctgcggtgac gctggaagct gtgtggattt    3060
cgtccgactc ggtgaactac acactcgata agaggcattg cctggtgacg accggcccgc    3120
tgtggaaaca agcgatccgt aaagcgtcag ggtcagagat tcggcctgag ggcgggagct    3180
ggatacgggt ggtgcttgcc atgcctgacg gcaatttcag ggcaggatgg gcaccccacg    3240
cccaagtaac cgctggtgcg ctggatattt cggcggtggt ctcgtgagcg gggagaagcg    3300
gcacagcgag gccggcccgg tagaaatcat cttttttgatg ctggcagtca gggcggggga   3360
ctacatcgtc gccgtgactg cggttctcgc ggtcgggttc ttcgcggtcg cggttgaggg    3420
tttctggttc ctggtcgtcg cagtcatcgc tgcaccggcg tggtggtttc tgcgcgactg    3480
ggaatcgaag cggagggccg tacgggtctt tgaacgggca tggaagggga cacctgaatc    3540
ccccggtatt gctctctccc ttggcctgtc gaacgtggcg gggtctctgc cgaggttgag    3600
gaagtttgaa actggttcgg ggatacgcac actcgtgttt tctttgccgc ccggagtcac    3660
tgccgagagc tttgagaaag ttcgcccctgc gctggcagac gcgatggggg gtcaccgctg   3720
ccaagtagag aaggtggccc ccggacaggt ccgcgtcaga gtgattgatg aggattcgat    3780
gaagacgccg cgtgatgcgg gatgggcgaa agatgttgtg ctggaagagg atacgttcga    3840
cggtcttccg ggcgagacgc gatcctggtt cgagcaagag gggccggcat catgagaaaa    3900
tcggcgggag tatctcggat tcctatccgt ctcgggcgct ctcagtacgg ggaagacgtt    3960
ggattcgatc tcgctgcgga cgccgctcac atcgccatgc agggcaaaac ccgatccggc    4020
aaaagtcagg cgacgtacaa cgtgttagct caggcagcag cgaacgcggc ggttcgagtc    4080
gtagggtccg acccgacaca cgtactcctg gagcccttca acatcgagg ggtgtccgag     4140 ccttacgtgg tttcgggact gaatgcgcag gccacggtgg acatgctggg ctgggtcaag    4200
cgtgagtctg atcgtcgcat cgaccagatg tggcccctgc gtaccgacaa gttttccgag    4260 ttcgggctt cgttcccgct gatactcgtc gtgctcgaag agtttccggg gatcctcgag     4320
ggggcagcgg acgaagacgc cgcgttaggc cgaaaacctg ccgagcgtct cgcaccccgc    4380
atttcggcct acgtgcgtca gatagcgcgc cagtcggcaa aggctggaat tcgccttctc    4440
ctgctctcgc aacgagcgga ggcctcgatc attggcggca atgcgcgttc gaatttcggg    4500
gtcaagatga ctctgagggt ggacgaaccg gagtcggtga gaatgcttca tccgagcgct    4560 tcccccggaag actgtgccct ggtcgagacc ttcaagcctg gtacctgcct tttcgagaag   4620
ccaggagaag gccggcagat tatgcgatgc gactttgtcg gcgagtacgg gagatatgcg    4680
cgagccatcg agtcttcgga tctgcgtttt ctcgccaccc tccagcaaga ccaggcccaa    4740
cgcgaattct tcgctgagga gttcggtgtg gtggatccgt catgactgga ccacaggaga    4800
gaaagcgcaa ggcggcgaag ccgtcgcggg agcctcagtt gaactgctgt gaagcggacg    4860
tgccgaaacg agcaaaacag ccccccggttc cctctacgtt cgacctgctc acggtgaagg    4920
agactgcggg gctgctgaga gtcagtcagg caactctttta ccggctgctt cggagtgggg    4980
aaggacccac atacacacgg atcggtggac agatacgcgt tcaccgcgag tcgctgcgtc    5040
ggttcatcga accgcgtgga taacgtcaca gagacagcga aaacgcctcc cctgggtcaa    5100
tccggttacc gccggactgg gggaggcgct tcgacaccta catccgtcgc ccctcgaaag    5160
gctcagatgc acttccacga taacgcagag gtcggacaag agggaagaac tgccgttctc    5220
tcgccgttgc gcggcgtagc cgccaagcgg gacgtgtctg acgatgcagc gaagcggagt    5280
```

```
cggcaggcgc ggcacgcgcc tgggcttgtt acatctgcca caactgtccg tgaatctctg   5340
ccagctcctg aaaccgctgg tcagggcctt gcggaatccg tgaccgctga tgatttttgg   5400
tctcattcgt tcccccgcgc tgacgatgta cgcggcgcag ctgcttcctt ccagtcggtg   5460
gctaactggg atgggcgtga gggtccgagg ccgcgtttcg ttgtcgcgcc tggcgttgtc   5520
cgcttggagg tttgtgatct cgcacgccgc gaacgaacgg ctgaacgtgc gtatctggct   5580
gctcgggctc gggtggatat ggcggctgcc aggcataact cgccgtacga cttcgacgtg   5640
gacgatgaag agttggcgga actggcttct ctgcaaggcc tcgaggacga cgacattggg   5700
ggctggtctg cggagaggga aatagtgggc tggtctgctc gttctcggtc acggatgatc   5760
ttgcgaatgg cagaactcga ctgggctccc atgatggatt tgccgggcat tcctgcgatg   5820
gtgaccctca cctatccggg ggactggctt acggttgccc ccaccggcgc tgaggtcaaa   5880
aaacatctcc agacgttctt caaacggttc aacggggcct ggggcattgc ctggatgggt   5940
gcgtggaaaa tggagttcca agccgaggc gctccgcatt ttcacctgta catggtccct   6000
cctcatggga aggcaggaga ctcgcggaag ctgcggcatg atgctgagct cttgaaatgg   6060
gagatagcac gtgcagaggg tgaagaccca ggtcgcaggc cgtatttccg ggaagctcca   6120
agcgatggat tgaagtttcg tccgtggctt tctgcggtgt gggccgacgt cgtagatcat   6180
ccggacccca aggaaaaaga aaagcacgtc agtgccggca ctggagtgga ctacgcggag   6240
ggcacgcgag ggtcagatcc gaaaaggctt gcggtgtact tctccaagca tggaaccttt   6300
gccgacaagg aatatcagca cgtagttcct gctcaatggc agaaaacggg tgcgggacct   6360
ggcaggttct ggggctaccg cggtttgtcg ccggccacgg ctgccaccga gatttcctgg   6420
gatgagtacc tgcttttatc tcgcacgttg cgacgattgt cagcgcgaac gaagatctgg   6480
gacccggctt tacgaggcgg tagcggcggc cacagatgga ctaaggcgat gatgcgacgc   6540
acggttaccc ggcaccgctt ggacctcgtg accggtgaga ttctgggcac gaagacgcgg   6600
aaggttcggg cgccagtgaa gaggtttgtc cggacttcgg gatacctgtg tgtcaatgac   6660 gggccccgcac tggctcgaac cctcagccgt cttcgtacaa gctgcctgag ctagacgcgc   6720
ggaacgcctt tcggctttgt cttttgctgg atggcgggtt ttgggcggct tctggtgatg   6780
cgctgctgcg ctccgtgggg agagagaccc aacgactgac ctatctctac ccaggtgcaa   6840
ttcatctccc gcgctctgtc ggctaggtaa acgaggtgct cccgcgcgag cttttccatg   6900
tggtcggcca atgtcagctc ggtcaggaca acctgctgtt gttgcgatag ttgtgtccgc   6960
acgggtcgat tgtcttctgt tgcggcataa cggttttcgt cgttcgcgga gagtgcggct   7020
aaatgaattg catcctcgat tgagcggagc atttcgacgc ggaacctggc gatgatgttg   7080
tctctgtctt cattcataac tgaagcgtat tgggagtgtt gccctcccac catgtgtgcc   7140
aatgcaggtg tgaactgagt cacagtttct caatagactc caagtttgtg atccttttac   7200
tcccaaaatg gggcatgatg tgtgcgtgcc tcggttcagg ggcgaaagtt cgacacctcg   7260
aaagaaggcc tcgacatggc tttgaaagct gctggcaacg tgattcctga ttcctccgcg   7320
tacgagtacc gggcggttca ggtcgagccg aagatggtca gaaaagaccc ggaagacccg   7380
aactctgagc agttccagaa gcagaaggac ggcacgccgg tgtggtcgat cgactgcatt   7440
cgggtcgacc gggcatcagg caacaaggca atcgtgaccg tgacggttcc ggacgtgatg   7500
gaaccggatg ttgcgggcc ggtggagttc tccgagatga ttgccggttt ctgggtttcg   7560
cgcagtggtt cgggcatgtg gttttcggca agcgccgtcg cttctctctg atcgctgatc   7620
```

```
gtcgcccctc gaaaggttcg gaaatgtcca aggaaaagg cgttgcgctg ggtgtgggtg    7680
ccctcgtgct cgtgtttgtg ctggttgcgg caggttggca agcggcgaac gtgttcagtg    7740
atcgttcaca gtccgaagct gtgccgctga gagtgccggc cgatccgaag tgggaaaacg    7800
gggtgttctc ggacgttgcc gggtgcctcg ttctctctcc ggaagagctg gggccgttca    7860
gcggagggca gtacatcgac atagtgaggc cagttgagcc ggagaggttg gagcgcgact    7920
gggtgaggtc ggctgagtgc gtttcggcgt cgatgaatgt ctctgacctg ttggtttctg    7980
ctcttccaga gtccacccgt ccccccggcg atttcgttcg ttcgtggaaa gtggcgagtg    8040
atgattactg ctatgagggt gataacccgc aaggctgcac ttctcgtatg ccggtttggg    8100
tctctgcaaa aaactggtgg tgca                                           8124

<210> SEQ ID NO 94
<211> LENGTH: 7675
<212> TYPE: DNA
<213> ORGANISM: Artificial
<220> FEATURE:
<223> OTHER INFORMATION: pRET1103Rv

<400> SEQUENCE: 94
gactctagag gatccccggg taccgagctc gaattcgtaa tcatggtcat agctgtttcc      60
tgtgtgaaat tgttatccgc tcacaattcc acacaacata cgagccggaa gcataaagtg     120
taaagcctgg ggtgcctaat gagtgagcta actcacatta attgcgttgc gctcactgcc     180
cgctttccag tcgggaaacc tgtcgtgcca gctgcattaa tgaatcggcc aacgcgcggg     240
gagaggcggt ttgcgtattg gagcttggca ctgggccaag ctgaatttct gccattcatc     300
cgcttattat cacttattca ggcgtagcac caggcgttta agggcaccaa taactgcctt     360
aaaaaaatta cgccccgccc tgccactcat cgcagtactg ttgtaattca ttaagcattc     420
tgccgacatg gaagccatca cagacggcat gatgaacctg aatcgccagc ggcatcagca     480
ccttgtcgcc ttgcgtataa tatttgccca tggtgaaaac ggggggcgaag aagttgtcca     540 tattggccac gtttaaatca aaactggtga actcacccca gggattggct gagacgaaaa     600
acatattctc aataaaccct ttagggaaat aggccaggtt ttcaccgtaa cacgccacat     660
cttgcgaata tatgtgtaga aactgccgga atcgtcgtg gtattcactc cagagcgatg     720
aaaacgtttc agtttgctca tggaaaacgg tgtaacaagg gtgaacacta tcccatatca     780
ccagctcacc gtctttcatt gccatacgaa attccggatg agcattcatc aggcgggcaa     840
gaatgtgaat aaaggccgga taaaacttgt gcttattttt ctttacggtc tttaaaaagg     900
ccgtaatatc cagctgaacg gtctggttat aggtacattg agcaactgac tgaaatgcct     960
caaaatgttc tttacgatgc cattgggata tatcaacggt ggtatatcca gtgatttttt    1020
tctccatttt agcttcctta gctcctgaaa atctcgataa ctcaaaaaat acgcccggta    1080
gtgatcttat ttcattatgg tgaaagttgg aacctcttac gtgccgatca acgtctcatt    1140
ttcgccaaaa gttggcccag ggcttcccgg tatcaacagg gacaccagga tttatttatt    1200
ctgcgaagtg atcttccgtt cgacggagtt ccactgagcg tcagaccccg tagaaaagat    1260
caaaggatct tcttgagatc ctttttttct gcgcgtaatc tgctgcttgc aaacaaaaaa    1320
accaccgcta ccagcggtgg tttgtttgcc ggatcaagag ctaccaactc tttttccgaa    1380
ggtaactggc ttcagcagag cgcagatacc aaatactgtc cttctagtgt agccgtagtt    1440
aggccaccac ttcaagaact ctgtagcacc gcctacatac ctcgctctgc taatcctgtt    1500
accagtggct gctgccagtg gcgataagtc gtgtcttacc gggttggact caagacgata    1560
```

```
gttaccggat aaggcgcagc ggtcgggctg aacgggggt tcgtgcacac agcccagctt    1620
ggagcgaacg acctacaccg aactgagata cctacagcgt gagcattgag aaagcgccac    1680
gcttcccgaa gggagaaagg cggacaggta tccggtaagc ggcagggtcg aacaggaga    1740
gcgcacgagg gagcttccag ggggaaacgc ctggtatctt tatagtcctg tcgggtttcg    1800
ccacctctga cttgagcgtc gattttttgtg atgctcgtca gggggcgga gcctatggaa    1860
aaacgccagc aacgcggcct ttttacggtt cctggccttt tgctggcctt ttgctcacat    1920
gttctttcct gcgttatccc ctgattctgt ggataaccgt attaccgcct ttgagtgagc    1980
tgataccgct cgccgcagcc gaacgaccga gcgcagcgag tcagtgagcg aggaagcgga    2040
agaagctcat cgccattca ggctgcgcaa ctgttgggaa gggcgatcgg tgcgggcctc     2100
ttcgctatta cgccagctgg cgaaagggg atgtgctgca aggcgattaa gttgggtaac    2160
gccaggtttt cccagtcac gacgttgtaa aacgacggcc agtgccaagc ttgcatgcct     2220
gcaggtctgc acagaacccg tactcgatcc gctcgttcgt cgctgtgagg tctttcctgc    2280
aaggcaaatc gttgtgccgg aaggggtttc gtgatgtttc tccgagcgtt ttttcgttcc    2340
aagttggtca tggtggctct tgtcctggtc gctggcctgt ttctctacaa cgcctgctct    2400
tcttctgacg caaaggaaga gatcggcagc agtctgaatc tctctcctgt cactgctcgt    2460
tcgaatccgt atgagggcgt ccagcccacg atgagcgaaa aaagcccctgt tcccgtccct    2520
gtcgtttccg cgacaggat tcgggggtg gcatcgtgcg ggacggatta cgccgggaag     2580
cctgcggtga cgctggaagc tgtgtggatt tcgtccgact cggtgaacta cacactcgat    2640
aagaggcatt gcctggtgac gaccggcccg ctgtggaaac aagcgatccg taaagcgtca    2700
gggtcagaga ttcggcctga gggcgggagc tggatacggg tggtgcttgc catgcctgac    2760
ggcaatttca gggcaggatg ggcacccac gcccaagtaa ccgctggtgc gctggatatt     2820
tcggcggtgg tctcgtgagc ggggagaagc ggcacagcga ggccggcccg gtagaaatca    2880
tcttttgat gctggcagtc agggcggggg actacatcgt cgccgtgact gcggttctcg    2940
cggtcgggtt cttcgcggtc gcggttgagg gtttctggtt cctggtcgtc gcagtcatcg    3000
ctgcaccggc gtggtggttt ctgcgcgact gggaatcgaa gcggagggcc gtacgggtct    3060
ttgaacgggc atggaagggg acacctgaat ccccggtat tgctctctcc cttgcctgt     3120
cgaacgtggc ggggtctctg ccgaggttga ggaagtttga aactggttcg gggatacgca    3180
cactcgtgtt tcttttgccg cccggagtca ctgccgagag cttttgagaaa gttcgccctg    3240
cgctggcaga cgcgatgggg ggtcaccgct gccaagtaga aaggtggcc cccggacagg     3300
tccgcgtcag agtgattgat gaggattcga tgaagacgcc gcgtgatgcg ggatgggcga    3360
aagatgttgt gctggaagag gatacgttcg acggtcttcc gggcgagacg cgatcctggt    3420
tcgagcaaga ggggccggca tcatgagaaa atcggcggga gtatctcgga ttcctatccg    3480
tctcgggcgc tctcagtacg gggaagacgt tggattcgat ctcgctgcgg acgccgctca    3540
catcgccatg cagggcaaaa cccgatccgg caaaagtcag gcgacgtaca acgtgttagc    3600
tcaggcagca gcgaacgcgg cggttcgagt cgtagggtcc gacccgacac acgtactcct    3660
ggagcccttc aaacatcgag gggtgtccga gccttacgtg gtttcgggac tgaatgcgca    3720
ggccacggtg gacatgctgg gctgggtcaa gcgtgagtct gatcgtcgca tcgaccagat    3780
gtggcccctg cgtaccgaca agttttccga gttcggggct tcgttcccgc tgatactcgt    3840
cgtgctcgaa gagtttcccg ggatcctcga ggggcagcg gacgaagacg ccgcgttagg    3900
```

```
ccgaaaacct gccgagcgtc tcgcaccccg catttcggcc tacgtgcgtc agatagcagc   3960
gcagtcggca aaggctggaa ttcgccttct cctgctctcg caacgagcgg aggcctcgat   4020
cattggcggc aatgcgcgtt cgaatttcgg ggtcaagatg actctgaggg tggacgaacc   4080
ggagtcggtg agaatgcttc atccgagcgc ttccccggaa gactgtgccc tggtcgagac   4140
cttcaagcct ggtacctgcc ttttcgagaa gccaggagaa ggccggcaga ttatgcgatg   4200
cgactttgtc ggcgagtacg ggagatatgc gcgagccatc gagtcttcgg atctgcgttt   4260
tctcgccacc ctccagcaag accaggccca acgcgaattc ttcgctgagg agttcggtgt   4320
ggtggatccg tcatgactgg accacaggag agaaagcgca aggcggcgaa gccgtcgcgg   4380
gagcctcagt tgaactgctg tgaagcggac gtgccgaaac gagcaaaaca gcccccggtt   4440
ccctctacgt tcgacctgct cacggtgaag gagactgcgg ggctgctgag agtcagtcag   4500
gcaactcttt accggctgct tcggagtggg gaaggaccca catacacacg gatcggtgga   4560
cagatacgcg ttcaccgcga gtcgctgcgt cggttcatcg aaccgcgtgg ataacgtcac   4620
agagacagcg aaaacgcctc ccctgggtca atccggttac cgccggactg ggggaggcgc   4680
ttcgacacct acatccgtcg cccctcgaaa ggctcagatg cacttccacg ataacgagga   4740
ggtcggacaa gagggaagaa ctgccgttct ctcgccgttg cgcggcgtag ccgccaagcg   4800
ggacgtgtct gacgatgcag cgaagcggag tcggcaggcg cggcacgcgc tgggcttgt    4860
tacatctgcc acaactgtcc gtgaatctct gccagctcct gaaaccgctg gtcagggcct   4920
tgcggaatcc gtgaccgctg atgattttttg gtctcattcg ttcccccgcg ctgacgatgt   4980
acgcggcgca gctgcttcct tccagtcggt ggctaactgg gatgggcgtg agggtccgag   5040
gccgcgtttc gttgtcgcgc ctggcgttgt ccgcttggag gtttgtgatc tcgcacgccg   5100
cgaacgaacg gctgaacgtg cgtatctggc tgctcgggct cgggtggata tggcggctgc   5160
caggcataac tcgccgtacg acttcgacgt ggacgatgaa gagttggcgg aactggcttc   5220
tctgcaaggc ctcgaggacg acgacattgg gggctggtct gcggagaggg aaatagtggg   5280
ctggtctgct cgttctcggt cacgatgat cttgcgaatg gcagaactcg actgggctcc   5340
catgatggat ttgccgggca ttcctgcgat ggtgaccctc acctatccgg gggactggct   5400
tacggttgcc cccaccggcg ctgaggtcaa aaaacatctc cagacgttct tcaaacggtt   5460
ccaacgggcc tgggggcattg cctggatggg tgcgtggaaa atggagttcc aaagccgagg   5520
cgctccgcat tttcacctgt acatggtccc tcctcatggg aaggcaggag actcgcggaa   5580
gctgcggcat gatgctgagc tcttgaaatg ggagatagca cgtgcagagg gtgaagaccc   5640
aggtcgcagg ccgtatttcc gggaagctcc aagcgatgga ttgaagtttc gtccgtggct   5700
ttctgcggtg tgggccgacg tcgtagatca tccggacccc aaggaaaaag aaaagcacgt   5760
cagtgccggc actggagtgg actacgcgga gggcacgcga gggtcagatc cgaaaaggct   5820
tgcggtgtac ttctccaagc atggaaacctt tgccgacaag gaatatcagc acgtagttcc   5880
tgctcaatgg cagaaaacgg gtgcgggacc tggcaggttc tggggctacc gcggtttgtc   5940
gccgccacg gctgccaccg agatttcctg ggatgagtac ctgctttat ctcgcacgtt    6000
gcgacgattg tcagcgcgaa cgaagatctg ggacccggct ttacgaggcg gtagcggcgg   6060
ccacagatgt actaaggcga tgatgcgacg cacggttacc cggcaccgct tggacctcgt   6120
gaccggtgag attctgggca cgaagacgcg gaaggttcgg gcgccagtga agaggtttgt   6180
ccggacttcg ggatacctgt gtgtcaatga cgggcccgca ctggctcgaa ccctcagccg   6240
tcttcgtaca agctgcctga gctagacgcg cggaacgcct ttcggctttg tcttttgctg   6300
```

-continued

```
gatggcgggt tttgggcggc ttctggtgat gcgctgctgc gctccgtggg gagagagacc    6360
caacgactga cctatctcta cccaggtgca attcatctcc cgcgctctgt cggctaggta    6420
aacgaggtgc tcccgcgcga gcttttccat gtggtcggcc aatgtcagct cggtcaggac    6480
aacctgctgt tgttgcgata gttgtgtccg cacgggtcga ttgtcttctg ttgcggcata    6540
acggttttcg tcgttcgcgg agagtgcggc taaatgaatt gcatcctcga ttgagcggag    6600
catttcgacg cggaacctgg cgatgatgtt gtctctgtct tcattcataa ctgaagcgta    6660
ttgggagtgt tgccctccca ccatgtgtgc caatgcaggt gtgaactgag tcacagtttc    6720
tcaatagact ccaagtttgt gatcctttta ctcccaaaat ggggcatgat gtgtgcgtgc    6780
ctcggttcag gggcgaaagt tcgacacctc gaaagaaggc ctcgacatgg ctttgaaagc    6840
tgctggcaac gtgattcctg attcctccgc gtacgagtac cgggcggttc aggtcgagcc    6900
gaagatggtc agaaaagacc cggaagaccc gaactctgag cagttccaga agcagaagga    6960
cggcacgccg gtgtggtcga tcgactgcat tcgggtcgac cgggcatcag gcaacaaggc    7020
aatcgtgacc gtgacggttc cggacgtgat ggaaccggga gttgcggggc cggtggagtt    7080
ctccgagatg attgccggtt tctgggtttc gcgcagtggt tcgggcatgt ggttttcggc    7140
aagcgccgtc gcttctctct gatcgctgat cgtcgcccct cgaaaggttc ggaaatgtcc    7200
aaaggaaaag gcgttgcgct gggtgtgggt gccctcgtgc tcgtgtttgt gctggttgcg    7260
gcaggttggc aagcggcgaa cgtgttcagt gatcgttcac agtccgaagc tgtgccgctg    7320
agagtgccgg ccgatccgaa gtgggaaaac ggggtgttct cggacgttgc cggtgcctc    7380 gttctctctc cggaagagct ggggccgttc agcggagggc agtacatcga catagtgagg    7440
ccagttgagc cggagaggtt ggagcgcgac tgggtgaggt cggctgagtg cgtttcggcg    7500
tcgatgaatg tctctgacct gttggtttct gctcttccag agtccacccg tcccccggc    7560 gatttcgttc gttcgtggaa agtggcgagt gatgattact gctatgaggg tgataacccg    7620
caaggctgca cttctcgtat gccggtttgg gtctctgcaa aaaactggtg gtgca         7675
```

<210> SEQ ID NO 95
<211> LENGTH: 8497
<212> TYPE: DNA
<213> ORGANISM: Artificial
<220> FEATURE:
<223> OTHER INFORMATION: pRET1001

<400> SEQUENCE: 95

```
ccgtccacca cccggtgcct ggtctgcgtc tccctcggct cgttcctcgc ctatcctggt      60
gaccagacac cggagcgagc tatgcccagg gttgcgcagt gacttcgtca ctgcgtaacc     120
ctgggcgctc gcctcccatt cgcttcgctc acaggagggg gccgtcgatg gccgctgacg     180
ctgcatctga cgaccggcgg accgaggtcc gcgccgctgc ttcgcgggcc gctgacgcgg     240
ccccggcgaa gcgcacccgc accgtggcgg tgcggctgac cgatggggag gaggccgcgt     300
ggatcgacgc cgcgctggcc gatgccaccg gcagctcgg ggcgtggtg cgtgagcggg      360 cggtggccgg ctatctcggg aaggtccgcc cgaagaccgg cagtggaatg tcggcggagg     420
cggccgcgga ggtcgccgcg atgcggcagc agatgacgaa ggtggggaac aacctgaacc     480
agatcgcgag ggcgatcaac gccgggcagg tgccgtcgca gatggccgag tccctgcaga     540
aggggtggct ggagaggtgg gggcaggagt tggggcggat ggcggatcgg ctcgacgcgc     600
tcgacgacca gggctgacgt gatcgcgaag atcagcacgg gcagcgaccc gaaggggttg     660
```

-continued

```
gcggcgtatc tgcacgggcc ggggaaggcc accccgcaca gctaccgcac cgaggcgggc    720
cggctgattg ccggcgggac ggtgatcgcg ggatcggtgc aggtcaccgc caaaaacccg    780
acccggtggg ggcgggactt cgagcgggcc gccgcgacga acgcgcgggt gggtaagccg    840
gtgtggcatt gctcgctgcg gtgcgcgccc ggggatcggc ggctgaccga taccgagttc    900
gcggacatcg cgcagacggt cgccgagcgg atgggcttcg agagtcatcc gtgggtggcg    960
gtgcggcacg acgacgacca catccacctg gctgtctccc gggtcgattt tcagggcgtg   1020
acctggaaga cagcaacga ccggtggaag gtcgtcgagg tgatgcgcga ggtcgaacgc   1080
gcgcacggcc tgatcgaggt ggcgagcccg gagcgggccc gtggccggca agccagcagc   1140
ggcgagcaac gccgcgcggt gcggaccggc aaggtggcgc agcgggacgg tctgagggaa   1200
attgtgaccg ccgcccgcga catcgccgca ggccagggtg tgggggcgtt cgaagtggcg   1260
ctcgtacaga acccgattac ccgagtgcag gtgcggcgca acgtcgcgaa gacgggccgg   1320
atgaatggct acagcttcaa cctgcccggc tacgtcgacg ccgccgggga gccgatctgg   1380
ttgccggcct ccaaactcga ccggggtttg tcctggtcac agctggaaaa gacgctgacc   1440
agacccccgcc cggaccgcct cgccggcgag gagacggtgc cgcggaagcg gctcgagcgc   1500
gccgccgcgt gggagcagcg ccgccgcgag gtcggcggcg agcagttcgc agctgcccgc   1560
tgggagcagg cccgcgcgaa tgttggtgag acggccgggc ggatccgcgc cgaacagtcc   1620
gcggacacga agtggaagca ggtgaacgag gcgttgacca gccaagaccg ggccgaggag   1680
caggctgccg aggcagcgcg ggtcgcctcc gctgtcatgg gaggccaccc gacaccgcta   1740
cgggacatgc tcgccgccca ggagcagcgc cggaagccgt ggactccgga gcagaaacgc   1800
cagtacgcga ccgcaaaagc ccaagcagaa cgcgccgcga aggccaagga cgccgcgaaa   1860
tggaccgagg tcgccggcgg cggctaccag cgggacgtgc gcgggatgaa cctgcgactg   1920
tgggtggctg aggacggcgc ctggtcgatc acctcgaaga aggaccccga ccgccagtac   1980
gccgcaggtc aggccgacac cgtcgcgcag gcccaagccg cggccacggc cacagcgaaa   2040
acgcaggccc aggcgatgtg gaagcaggtc ccggccgaca agcgcaccga gtcagccacc   2100
agagcggtcc ggcgcgtgat cgcggatctc acccccacca aacccgccga ggtcaaaccc   2160
ccggcccgcc gccagggacc aaccatgccg cagtcggccc cggggtatca gccacccggc   2220
cgcgaccgag gtcgagaatc cggaatggga ctgtgagcag agagcgagaa ggctttcgtg   2280
gagcgtaggg aacagacgca ggcctggcga agcatgtcca agaacaccat cgatcgctag   2340
aaggtcggtc gtgcccaggg tgcccaggat gcgtacataa cgcgcgaaag gtgcatacct   2400
cccatagcat cggcgcgtat ggtagggaaa atgatcttca aacgtattgc tgtggtcgtg   2460
ctcgctggtg gggctttggt agtgggaggc agccaggttc tggtgctac cacggtttca   2520
gctccacagc cgagtccttc agcagcggtg gtgccgacgg ttcttccacc agtcactttc   2580
accgccgctt ctgcgcactg cgaggcccag tacgcgtcgg attcccggcg atgccgtctg   2640
attccacttc cacagggccg agcgatctgc tgggcggcag ccgctgcccg ttacgcagcg   2700
tgccgcgccg gaaactaggt agaacgtgag catggacgag cttcccacct tcatcgccga   2760
cgacatcgtg atggccagaa cgttcgacag ccctaacggc caggtggtgc tcgaggtgaa   2820
cactccgcgc ccgttcgatg ctgcggcccc ggagggtgac tactgctgca ccttccggat   2880
cagcgggaac atggatgccc cttacgacgg attcggtggc ggcgtcgacg cagtgcaggc   2940
gctgctactc gcattggcca tggcacacga ggaacttcgt caaacttcgc cagagttgac   3000
gtttctaggc gagacgaacc tcggtctacc ggtcttgaac atcaagcccg acaacgcgat   3060
```

-continued

```
cgaagccgtg gtctcattcc ccgctccctg atgtgacgca ctttcacccc tggcactcat    3120
gtaccgaagc tgggactgag aaagggctgc cgcgtcaccg cttcgcgttg acttgccact    3180
gaacgggggc gtgtcccggt cagggcgggg tgtgacctgg gttcatgaca ccgctaacac    3240
gctgcggaaa tgcggattga actagttcat ttggggaacg atgacctgat gaccggggat    3300
cgtgacctac ccatgctgac catcgccgag gcggtggacg cgacgcagac cagtgagagc    3360
acgatcaagc gccgcctgcg gtcgggcgcg ttcccgaacg cggtccgcac tgccgacggg    3420
aagtggatga ttcccctcgg tgacctatca gcggcagggc tgagaccagg gaaaatggcg    3480
aaacctgacc cggtgacccc ttcaaatgac cgggtccgtg acctggcagc tgagaacgcc    3540
gagctccgtc agcgcctggc cgtggccgaa gccctggcca cgaacgcaa tcggatcatc     3600
gacgtgcagc aacagatgct ccggatgctc gaagcccggc cggtgtcggc cctggagccc    3660
gcggcggttc cagtggcggg tccgccgccg cccgtcccgg ccgccgatgg tcgggcagct    3720
acgggcgccc tggcccggat acgtcgacgg cttctcggct aggagctgac cgcgtacttg    3780
cgtgcgtcgt gcaggagctt tcccaccgtt ccggtggaga ttcccatctc ctcggcgatc    3840
tcgcggtact tcaggccctg ctcgcgcagc tcgacggccc ggcgacggtt ctcggctgcc    3900
cgtgcgagga actggtcccg cggctcggcc atgatgcgct ggatcgtgcg cgtggaggcc    3960
cccatcttct cggccagctc gcgagctgtc tgcttgcggc ggatcggtcg ttcagcgccc    4020
acggtctgcc tcccacaatg cgttccggtc gaccttcgtc gctcgtttcc ggtttgcctc    4080
gcgcttcttc tcactcatct tgcgaccgcg tgcggcttgt atggcgatga atgtggcctc    4140
gtagacagca gggccgtcgg cccacatccg ggactttgta gtgatccagc gggtaatgga    4200
ggccgcgacg gcgcgtagct cgcttgctgg cagtggatcg ggcctgcctg tgaccgggtt    4260
cctgaacgtg gcgttgatct gtgcggcttc cgcatagatc gcggccccga ggccggtcgg    4320
gtcgccccag tggaagcgga tttcgcggta ggcccaggtg cgtgcggttt cgaacagggc    4380
gcagtttcgg ccgaggccga tcgggttctc acggcgcgat cgggtttgcc gccagcgcgt    4440
tggcggcatg tggatgccga gttccgcctc gagctcggcg agggatcgcc gctcggtgtg    4500
cagccaatgg gtgtcccagt caccgtgagt cgggttcttg gtcatcaggc ccgaatagcc    4560
cttgtccccc tggacggcgc gccggaggcc ttcggtgacg cgggccgcat aggcgagcgg    4620
cttacgacgg gcgtactcgg tgcgggtgaa cggctctgcc agcgcccaca cagcgtgtgc    4680
gtgcccgtta cggggggttct ccacgatcgc gttcggcaga ggatgattcc cggccgccga    4740
cagcgcccgc agcgcggcgt ccgggtggtc aacgtccacg acgagcaggt tgctcaatgc    4800
ctgcgggttc gactcgatgt agcggcgatc cagtgcgtct gatcgccgca tccggtagac    4860
gccgtcgagg aaatcgtcgg ttgccagtgg ccacagcggt agccacagct gttcccaggc    4920
gccgcctgtg tgctcttcca ccgcaaccat ggggaacaca ctcacacaca agatcgattt    4980
attccggtac gacacgccag ccaagtcaga tgtttcggtt tctggagcgg tcctccagac    5040
ctttgagatc cgctccagaa acgtccacaa attattgggg tacgtcgaac caagccttat    5100
caggtatccc ggggttccgg gggtgaacac caccctccga ccggtccaga atccgtcgat    5160
ctcacctatc cgctcgaagt ccttgagtca gtgacaggac cactgctggg ctcccagcgc    5220
agaaggcaag tgaaggcaga cgactgcggg aggtaagtcg ggtacggcat gaggtccttc    5280
agaagcggcg tcgacgccag gcccacacgc acaatccgct tcccacgagg acaccaccg     5340
gtagcgcccc ctgcaaccgg cgcagtgtca cgaggcgccg gtactgctcg tttgacagga    5400
```

```
actgcagggt cggtgagctc gcgctgggcg gatcccacca gtagctcccc gtgccggtaa    5460
ccgcttgggg ccaagcgaag acacccaccg cggcagcgat ggcaatgcac gtggatggga    5520
acaccaccca gaaccaggga aatcctggtg ccggcccgag acgatcccgg cgcggtaaga    5580
ccacaccggc caccatcgcc acggcccccg acgcaacaag caataaccac cccatgagcg    5640
gacggtacaa gcgccgacgc cgggtggccg ttaggtgcgc gccagcccgt gaccggaccg    5700
gcgaagcgtg ccgctgggcg gcccgccgtg gcgcccgtcc cgtgcccgtt ctgaccggtg    5760
gtctcggtcg ctcgttcctc gcgtcctcac ctgccggtca gcccgtgacc ggacctgcag    5820
gcatgcaagc ttggcactgg ccgtcgtttt acaacgtcgt gactgggaaa accctggcgt    5880
tacccaactt aatcgccttg cagcacatcc ccctttcgcc agctggcgta atagcgaaga    5940
ggcccgcacc gatcgccctt cccaacagtt gcgcagcctg aatggcgaat ggcgcctgat    6000
gcggtatttt ctccttacgc atctgtgcgg tatttcacac cgcatatggt gcactctcag    6060
tacaatctgc tctgatgccg catagttaag ccagccccga cacccgccaa cacccgctga    6120
cgcgccctga cgggcttgtc tgctcccggc atccgcttac agacaagctg tgaccgtctc    6180
cgggagctga atgtgtcaga ggttttcacc gtcatcaccg aaacgcgcga gacgaaaggg    6240
cctcgtgata cgcctatttt tataggttaa tgtcatgata ataatggttt cttagacgtc    6300
aggtggcact tttcggggaa atgtgcgcgg aaccccctatt tgtttatttt tctaaataca    6360
ttcaaatatg tatccgctca tgagacaata accctgataa atgcttcaat aatattgaaa    6420
aaggaagagt atgagtattc aacatttccg tgtcgccctt attcccttt ttgcggcatt    6480 ttgccttcct gtttttgctc acccagaaac gctggtgaaa gtaaagatg ctgaagatca    6540 gttgggtgca cgagtgggtt acatcgaact ggatctcaac agcggtaaga tccttgagag    6600
ttttcgcccc gaagaacgtt ttccaatgat gagcactttt aaagttctgc tatgtggcgc    6660
ggtattatcc cgtattgacg ccgggcaaga gcaactcggt cgccgcatac actattctca    6720
gaatgacttg gttgagtact caccagtcac agaaaagcat cttacggatg gcatgacagt    6780
aagagaatta tgcagtgctg ccataaccat gagtgataac actgcggcca acttacttct    6840
gacaacgatc ggaggaccga aggagctaac cgcttttttg cacaacatgg gggatcatgt    6900
aactcgcctt gatcgttggg aaccggagct gaatgaagcc ataccaaacg acgagcgtga    6960
caccacgatg cctgtagcaa tggcaacaac gttgcgcaaa ctattaactg gcgaactact    7020
tactctagct tcccggcaac aattaataga ctggatggag gcggataaag ttgcaggacc    7080
acttctgcgc tcggcccttc cggctggctg gtttattgct gataaatctg gagccggtga    7140
gcgtgggtct cgcggtatca ttgcagcact ggggccagat ggtaagccct cccgtatcgt    7200
agttatctac acgacgggga gtcaggcaac tatggatgaa cgaaatagac agatcgctga    7260
gataggtgcc tcactgatta agcattggta actgtcagac caagtttact catatatact    7320
ttagattgat ttaaaacttc atttttaatt taaaaggatc taggtgaaga tccttttga    7380 taatctcatg accaaaatcc cttaacgtga gttttcgttc cactgagcgt cagacccgt    7440 agaaaagatc aaaggatctt cttgagatcc ttttttctg cgcgtaatct gctgcttgca    7500
aacaaaaaaa ccaccgctac cagcggtggt ttgtttgccg gatcaagagc taccaactct    7560
ttttccgaag gtaactggct tcagcagagc gcagatacca aatactgtcc ttctagtgta    7620
gccgtagtta ggccaccact tcaagaactc tgtagcaccg cctacatacc tcgctctgct    7680
aatcctgtta ccagtggctg ctgccagtgg cgataagtcg tgtcttaccg ggttggactc    7740
aagacgatag ttaccggata aggcgcagcg gtcgggctga acggggggtt cgtgcacaca    7800
```

-continued

| | | | | |
|---|---|---|---|---|
| gcccagcttg | gagcgaacga | cctacaccga | actgagatac | ctacagcgtg agctatgaga | 7860 |
| aagcgccacg | cttcccgaag | ggagaaaggc | ggacaggtat | ccggtaagcg gcagggtcgg | 7920 |
| aacaggagag | cgcacgaggg | agcttccagg | gggaaacgcc | tggtatcttt atagtcctgt | 7980 |
| cgggtttcgc | cacctctgac | ttgagcgtcg | attttgtga | tgctcgtcag ggggcggag | 8040 |
| cctatggaaa | aacgccagca | acgcggcctt | tttacggttc | ctggccttt gctggccttt | 8100 |
| tgctcacatg | ttctttcctg | cgttatcccc | tgattctgtg | ataaccgta ttaccgcctt | 8160 |
| tgagtgagct | gataccgctc | gccgcagccg | aacgaccgag | cgcagcgagt cagtgagcga | 8220 |
| ggaagcggaa | gagcgcccaa | tacgcaaacc | gcctctcccc | gcgcgttggc cgattcatta | 8280 |
| atgcagctgg | cacgacaggt | ttcccgactg | aaagcgggc | agtgagcgca acgcaattaa | 8340 |
| tgtgagttag | ctcactcatt | aggcaccca | ggctttacac | tttatgcttc cggctcgtat | 8400 |
| gttgtgtgga | attgtgagcg | gataacaatt | tcacacagga | aacagctatg accatgatta | 8460 |
| cgaattcgag | ctcggtaccc | ggggatcctc | tagagtc | | 8497 |

<210> SEQ ID NO 96
<211> LENGTH: 8487
<212> TYPE: DNA
<213> ORGANISM: Artificial
<220> FEATURE:
<223> OTHER INFORMATION: pRET1002

<400> SEQUENCE: 96

| | | | | |
|---|---|---|---|---|
| ccgtccacca | cccggtgcct | ggtctgcgtc | tccctcggct | cgttcctcgc ctatcctggt | 60 |
| gaccagacac | cggagcgagc | tatgcccagg | gttgcgcagt | gacttcgtca ctgcgtaacc | 120 |
| ctgggcgctc | gcctcccatt | cgcttcgctc | acaggagggg | gccgtcgatg gccgctgacg | 180 |
| ctgcatctga | cgaccggcgg | accgaggtcc | gcgccgctgc | ttcgcgggcc gctgacgcgg | 240 |
| ccccggcgaa | gcgcacccgc | accgtggcgg | tgcggctgac | cgatgggag gaggccgcgt | 300 |
| ggatcgacgc | cgcgctggcc | gatggccacc | ggcagctcgg | ggcgtgggtg cgtgagcggg | 360 |
| cggtggccgc | ctatctcggg | aaggtccgcc | cgaagaccgg | cagtggaatg tcggcggagg | 420 |
| cggccgcgga | ggtcgccgcg | atgcggcagc | agatgacgaa | ggtggggaac aacctgaacc | 480 |
| agatcgcgag | ggcgatcaac | gccgggcagg | tgccgtcgca | gatggccgag tccctgcaga | 540 |
| aggggtggct | ggagaggtgg | gggcaggagt | tggggcggat | ggcggatcgg ctcgacgcgc | 600 |
| tcgacgacca | gggctgacgt | gatcgcgaag | atcagcacgg | gcagcgaccc gaaggggttg | 660 |
| gcggcgtatc | tgcacgggcc | ggggaaggcc | accccgcaca | gctaccgcac cgaggcgggc | 720 |
| cggctgattg | ccggcgggac | ggtgatcgcg | ggatcggtgc | aggtcaccgc caaaaacccg | 780 |
| acccggtggg | ggcgggactt | cgagcgggcc | gccgcgacga | acgcgcgggt gggtaagccg | 840 |
| gtgtggcatt | gctcgctgcg | gtgcgcgccc | gggatcggc | ggctgaccga taccgagttc | 900 |
| gcggacatcg | cgcagacggt | cgccgagcgg | atgggcttcg | agagtcatcc gtgggtggcg | 960 |
| gtgcggcacg | acgacgacca | catccacctg | gctgtctccc | gggtcgattt tcagggcgtg | 1020 |
| acctggaaga | acagcaacga | ccggtggaag | gtcgtcgagg | tgatgcgcga ggtcgaacgc | 1080 |
| gcgcacggcc | tgatcgaggt | ggcgagcccg | gagcgggccc | gtggccggca agccagcagc | 1140 |
| ggcgagcaac | gccgcgcggt | gcggaccggc | aaggtggcgc | agcgggacgg tctgagggaa | 1200 |
| attgtgaccg | ccgccgcga | catcgccgca | ggccagggtg | tggggcgtt cgaagtggcg | 1260 |
| ctcgtacaga | acccgattac | ccgagtgcag | gtgcggcgca | acgtcgcgaa gacgggccgg | 1320 |

-continued

```
atgaatggct acagcttcaa cctgcccggc tacgtcgacg ccgccgggga gccgatctgg    1380
ttgccggcct ccaaactcga ccggggtttg tcctggtcac agctggaaaa gacgctgacc    1440
agacccgcc cggaccgcct cgccggcgag gagacggtgc cgcggaagcg gctcgagcgc    1500
gccgccgcgt gggagcagcg ccgccgcgag gtcggcggcg agcagttcgc agctgcccgc    1560
tgggagcagg cccgcgcgaa tgttggtgag acggccgggc ggatccgcgc cgaacagtcc    1620
gcggacacga agtggaagca ggtgaacgag gcgttgacca gccaagaccg ggccgaggag    1680
caggctgccg aggcagcgcg ggtcgcctcc gctgtcatgg gaggccaccc gacaccgcta    1740
cgggacatgc tcgccgccca ggagcagcgc cggaagccgt ggactccgga gcagaaacgc    1800
cagtacgcga ccgcaaaagc ccaagcagaa cgcgccgcga aggccaagga cgccgcgaaa    1860
tggaccgagg tcgccggcgg cggctaccag cgggacgtgc gcgggatgaa cctgcgactg    1920
tgggtggctg aggacggcgc ctggtcgatc acctcgaaga aggaccccga ccgccagtac    1980
gccgcaggtc aggccgacac cgtcgcgcag gcccaagccg cggccacggc cacagcgaaa    2040
acgcaggccc aggcgatgtg gaagcaggtc ccggccgaca agcgcaccga gtcagccacc    2100
agagcggtcc ggcgcgtgat cgcggatctc accccacca aacccgccga ggtcaaaccc    2160
ccggcccgcc gccagggacc aaccatgccg cagtcggccc cggggtatca gccacccggc    2220
cgcgaccgag gtcgagaatc cggaatggga ctgtgagcag agagcgagaa ggctttcgtg    2280
gagcgtaggg aacagacgca ggcctggcga agcatgtcca agaacaccat cgatcgctag    2340
aaggtcggtc gtgcccaggg tgcccaggat gcgtacataa cgcgcgaaag gtgcatacct    2400
cccatagcat cggcgcgtat ggtagggaaa atgatcttca aacgtattgc tgtggtcgtg    2460
ctcgctggtg gggcttttggt agtgggaggc agccaggttg ctggtgctac cacggtttca    2520
gctccacagc cgagtccttc agcagcggtg gtgccgacgg ttcttccacc agtcactttc    2580
accgccgctt ctgcgcactg cgaggcccag tacgcgtcgg attcccggcg atgccgtctg    2640
attccacttc cacagggccg agcgatctgc tgggcggcag ccgctgcccg ttacgcagcg    2700
tgccgcgccg gaaactaggt agaacgtgag catggacgag cttcccaacct tcatcgccga    2760
cgacatcgtg atggccagaa cgttcgacag ccctaacggc caggtggtgc tcgaggtgaa    2820
cactccgcgg ccgttcgatg ctgcggcccc ggagggtgac tactgctgca ccttccggat    2880
cagcgggaac atggatgccc cttacgacgg attcggtggc ggcgtcgacg cagtgcaggc    2940
gctgctactc gcattggcca tggcacacga ggaacttcgt caaacttcgc cagagttgac    3000
gtttctaggc gagacgaacc tcggtctacc ggtcttgaac atcaagcccg acaacgcgat    3060
cgaagccgtg gtctcattcc ccgctccctg atgtgacgca ctttcacccc tggcactcat    3120
gtaccgaagc tgggactgag aaagggctgc cgcgtcaccg cttcgcgttg acttgccact    3180
gaacgggggc gtgtcccggt cagggcgggg tgtgacctgg gttcatgaca ccgctaacac    3240
gctgcgaaa tgcggattga actagttcat ttggggaacg atgacctgat gaccgggat    3300
cgtgacctac ccatgctgac catcgccgag gcggtggacg cgacgcagac cagtgagagc    3360
acgatcaagc gccgcctgcg gtcgggcgcg ttcccgaacg cggtccgcac tgccgacggg    3420
aagtggatga ttcccctcgg tgacctatca gcggcagggc tgagaccagg gaaaatggcg    3480
aaacctgacc cggtgacccc ttcaaatgac cgggtccgtg acctggcagc tgagaacgcc    3540
gagctccgtc agcgcctggc cgtggccgaa gccctggcca gcgaacgcaa tcggatcatc    3600
gacgtgcagc aacagatgct ccggatgctc gaagcccggc cggtgtcggc cctggagccc    3660
gcggcggttc cagtggcggg tccgccgccg cccgtcccgg ccgccgatgg tcgggcagct    3720
```

```
acgggcgccc tggcccggat acgtcgacgg cttctcggct aggagctgac cgcgtacttg    3780
cgtgcgtcgt gcaggagctt tcccaccgtt ccggtggaga ttcccatctc ctcggcgatc    3840
tcgcggtact tcaggccctg ctcgcgcagc tcgacggccc ggcgacggtt ctcggctgcc    3900
cgtgcgagga actggtcccg cggctcggcc atgatgcgct ggatcgtgcg cgtggaggcc    3960
cccatcttct cggccagctc gcgagctgtc tgcttgcggc ggatcggtcg ttcagcgccc    4020
acggtctgcc tcccacaatg cgttccggtc gaccttcgtc gctcgtttcc ggtttgcctc    4080
gcgcttcttc tcactcatct tgcgaccgcg tgcggcttgt atggcgatga atgtggcctc    4140
gtagacagca gggccgtcgg cccacatccg ggactttgta gtgatccagc gggtaatgga    4200
ggccgcgacg gcgcgtagct cgcttgctgg cagtggatcg ggcctgcctg tgaccgggtt    4260
cctgaacgtg gcgttgatct gtgcggcttc gcatagatc gcggccccga ggccggtcgg    4320
gtcgccccag tggaagcgga tttcgcggta ggcccaggtg cgtgcggttt cgaacagggc    4380
gcagtttcgg ccgaggccga tcgggttctc acggcgcgat cgggtttgcc gccagcgcgt    4440
tggcggcatg tggatgccga gttccgcctc gagctcggcg agggatcgcc gctcggtgtg    4500
cagccaatgg gtgtcccagt caccgtgagt cgggttcttg gtcatcaggc ccgaatagcc    4560
cttgtccccc tggacggcgc gccggaggcc ttcggtgacg gcggccgcat aggcgagcgg    4620
cttacgacgg gcgtactcgg tgcgggtgaa cggctctgcc agcgcccaca cagcgtgtgc    4680
gtgcccgtta cggggttct ccacgatcgc gttcggcaga ggatgattcc cggccgccga    4740
cagcgcccgc agcgcggcgt ccgggtggtc aacgtccacg acgagcaggt tgctcaatgc    4800
ctgcgggttc gactcgatgt agcggcgatc cagtgcgtct gatcgccgca tccggtagac    4860
gccgtcgagg aaatcgtcgg ttgccagtgg ccacagcggt agccacagct gttcccaggc    4920
gccgcctgtg tgctcttcca ccgcaaccat ggggaacaca ctcacacaca agatcgattt    4980
attccggtac gacacgccag ccaagtcaga tgtttcggtt tctggagcgg tcctccagac    5040
ctttgagatc cgctccagaa acgtccacaa attattgggg tacgtcgaac caagccttat    5100
caggtatccc ggggttccgg gggtgaacac caccctccga ccgtccaga atccgtcgat    5160
ctcacctatc cgctcgaagt ccttgagtca gtgacaggac cactgctggg ctcccagcgc    5220
agaaggcaag tgaaggcaga cgactgcggg aggtaagtcg ggtacggcat gaggtccttc    5280
agaagcggcg tcgacgccag gcccacacgc acaatccgct tcccacgagg gacaccaccg    5340
gtagcgcccc ctgcaaccgg cgcagtgtca cgaggcgccg gtactgctcg tttgacagga    5400
actgcagggt cggtgagctc gcgctgggcg gatcccacca gtagctcccc gtgccggtaa    5460
ccgcttgggg ccaagcgaag acacccaccg cggcagcgat ggcaatgcac gtggatggga    5520
acaccaccca gaaccaggga aatcctggtg ccggcccgag acgatcccgg cgcggtaaga    5580
ccacaccggc caccatcgcc acggcccccg acgcaacaag caataaccac cccatgagcg    5640
gacggtacaa gcgccgacgc cgggtggccg ttaggtgcgc gccagcccgt gaccggaccg    5700
gcgaagcgtg ccgctgggcg gcccgccgtg gcgcccgtcc cgtgcccgtt ctgaccggtg    5760
gtctcggtcg ctcgttcctc gcgtcctcac ctgccggtca gcccgtgacc ggacctgcag    5820
gcatgcaagc ttggcgtaat catggtcata gctgtttcct gtgtgaaatt gttatccgct    5880
cacaattcca cacaacatac gagccggaag cataaagtgt aaagcctggg gtgcctaatg    5940
agtgagctaa ctcacattaa ttgcgttgcg ctcactgccc gctttccagt cgggaaacct    6000
gtcgtgccag ctgcattaat gaatcggcca acgcgcgggg agaggcggtt tgcgtattgg    6060
```

```
cgaacttttg ctgagttgaa ggatcagatc acgcatcttc ccgacaacgc agaccgttcc   6120
gtggcaaagc aaaagttcaa aatcagtaac cgtcagtgcc gataagttca aagttaaacc   6180
tggtgttgat accaacattg aaacgctgat cgaaaacgcg ctgaaaaacg ctgctgaatg   6240
tgcgagcttc ttccgcttcc tcgctcactg actcgctgcg ctcggtcgtt cggctgcggc   6300
gagcggtatc agctcactca aaggcggtaa tacggttatc cacagaatca ggggataacg   6360
caggaaagaa catgtgagca aaaggccagc aaaaggccag gaaccgtaaa aaggccgcgt   6420
tgctggcgtt tttccatagg ctccgccccc ctgacgagca tcacaaaaat cgacgctcaa   6480
gtcagaggtg gcgaaacccg acaggactat aaagatacca ggcgtttccc cctggaagct   6540
ccctcgtgcg ctctcctgtt ccgaccctgc cgcttaccgg atacctgtcc gcctttctcc   6600
cttcgggaag cgtggcgctt tctcaatgct cacgctgtag gtatctcagt tcggtgtagg   6660
tcgttcgctc caagctgggc tgtgtgcacg aaccccccgt tcagcccgac cgctgcgcct   6720
tatccggtaa ctatcgtctt gagtccaacc cggtaagaca cgacttatcg ccactggcag   6780
cagccactgg taacaggatt agcagagcga ggtatgtagg cggtgctaca gagttcttga   6840
agtggtggcc taactacggc tacactagaa ggacagtatt tggtatctgc gctctgctga   6900
agccagttac cttcggaaaa agagttggta gctcttgatc cggcaaacaa accaccgctg   6960
gtagcggtgg tttttttgtt tgcaagcagc agattacgcg cagaaaaaaa ggatctcaag   7020
aagatccttt gatcttttct acggggtctg acgctcagtg gaacgatccg tcgagaggtc   7080
tgcctcgtga agaaggtgtt gctgactcat accaggcctg aatcgcccca tcatccagcc   7140
agaaagtgag ggagccacgg ttgatgagag ctttgttgta ggtggaccag ttggtgattt   7200
tgaacttttg ctttgccacg gaacggtctg cgttgtcggg aagatgcgtg atctgatcct   7260
tcaactcagc aaaagttcga tttattcaac aaagccacgt tgtgtctcaa aatctctgat   7320
gttacattgc acaagataaa aatatatcat catgaacaat aaaactgtct gcttacataa   7380
acagtaatac aaggggtgtt atgagccata ttcaacggga aacgtcttgc tcgaagccgc   7440
gattaaattc caacatggat gctgatttat atgggtataa atgggctcgc gataatgtcg   7500
ggcaatcagg tgcgacaatc tatcgattgt atgggaagcc cgatgcgcca gagttgtttc   7560
tgaaacatgg caaaggtagc gttgccaatg atgttacaga tgagatggtc agactaaact   7620
ggctgacgga atttatgcct cttccgacca tcaagcattt tatccgtact cctgatgatg   7680
catggttact caccactgcg atccccggga aaacagcatt ccaggtatta gaagaatatc   7740
ctgattcagg tgaaaatatt gttgatgcgc tggcagtgtt cctgcgccgg ttgcattcga   7800
ttcctgtttg taattgtcct tttaacagcg atcgcgtatt tcgtctcgct caggcgcaat   7860
cacgaatgaa taacggtttg gttgatgcga gtgattttga tgacgagcgt aatggctggc   7920
ctgttgaaca gtctggaaa gaaatgcata gcttttgcc attctcaccg gattcagtcg   7980
tcactcatgg tgatttctca cttgataacc ttattttga cgaggggaaa ttaataggtt   8040
gtattgatgt tggacgagtc ggaatcgcag accgatacca ggatcttgcc atcctatgga   8100
actgcctcgg tgagttttct ccttcattac agaaacggct ttttcaaaaa tatggtattg   8160
ataatcctga tatgaataaa ttgcagtttc atttgatgct cgatgagttt ttctaatcag   8220
aattggttaa ttggttgtaa cactggcaga gcattacgct gacttgacgg gacgcggct   8280 ttgttgaata atcgcattc gccattcagg ctgcgcaact gttgggaagg gcgatcggtg   8340
cgggcctctt cgctattacg ccagctgcg aaaggggat gtgctgcaag gcgattaagt   8400
tgggtaacgc cagggttttc ccagtcacga cgttgtaaaa cgacggccag tgaattcgag   8460
```

```
<210> SEQ ID NO 97
<211> LENGTH: 8038
<212> TYPE: DNA
<213> ORGANISM: Artificial
<220> FEATURE:
<223> OTHER INFORMATION: pRET1003

<400> SEQUENCE: 97
ctcggtaccc ggggatcctc tagagtc                                         8487 ccgtccacca cccggtgcct ggtctgcgtc tccctcggct cgttcctcgc ctatcctggt       60
gaccagacac cggagcgagc tatgcccagg gttgcgcagt gacttcgtca ctgcgtaacc      120
ctgggcgctc gcctcccatt cgcttcgctc acaggagggg gccgtcgatg gccgctgacg      180
ctgcatctga cgaccggcgg accgaggtcc gcgccgctgc ttcgcgggcc gctgacgcgg      240
ccccggcgaa gcgcacccgc accgtggcgg tgcggctgac cgatggggag gaggccgcgt      300
ggatcgacgc gcgctggcc gatggccacc ggcagctcgg ggcgtgggtg cgtgagcggg      360
cggtggccgg ctatctcggg aaggtccgcc gaagaccgg cagtgaatg tcggcggagg       420 cggccgcgga ggtcgccgcg atgcggcagc agatgacgaa ggtggggaac aacctgaacc      480
agatcgcgag ggcgatcaac gccgggcagg tgccgtcgca gatggccgag tccctgcaga      540
aggggtggct ggagaggtgg gggcaggagt tgggcggat ggcggatcgg ctcgacgcgc       600
tcgacgacca gggctgacgt gatcgcgaag atcagcacgg gcagcgaccc gaagggttg       660 gcggcgtatc tgcacgggcc ggggaaggcc accccgcaca gctaccgcac cgaggcgggc      720
cggctgattg ccggcgggac ggtgatcgcg ggatcggtgc aggtcaccgc caaaaacccg      780
acccggtggg ggcgggactt cgagcgggcc gccgcgacga cgcgcgggt gggtaagccg       840 gtgtggcatt gctcgctgcg gtgcgcgccc ggggatcggc ggctgaccga taccgagttc      900
gcggacatcg cgcagacggt cgccgagcgg atgggcttcg agagtcatcc gtgggtggcg      960
gtgcggcacg acgacgacca catccacctg gctgtctccc gggtcgattt tcagggcgtg     1020
acctggaaga acagcaacga ccggtggaag gtcgtcgagg tgatgcgcga ggtcgaacgc     1080
gcgcacggcc tgatcgaggt ggcgagcccg gagcgggccc gtggccggca agccagcagc     1140
ggcgagcaac gccgcgcgt gcggaccggc aagtggcgc agcgggacgg tctgagggaa       1200
attgtgaccg ccgcccgcga catcgccgca ggccagggtg tgggggcgtt cgaagtggcg     1260
ctcgtacaga acccgattac ccgagtgcag gtgcggcgca acgtcgcgaa gacgggccgg     1320
atgaatggct acagcttcaa cctgcccggc tacgtcgacg ccgccgggga gccgatctgg     1380
ttgccggcct ccaaactcga ccggggtttg tcctggtcac agctggaaaa gacgctgacc     1440
agaccccgcc cggaccgcct cgccggcgag gagacggtgc gcggaagcg gctcgagcgc     1500 gccgccgcgt gggagcagcg ccgcgcgag gtcggcggcg agcagttcgc agctgcccgc     1560
tgggagcagg cccgcgcgaa tgttggtgag acggccgggc ggatccgcgc cgaacagtcc     1620
gcggacacga agtggaagca ggtgaacgag gcgttgacca gccaagaccg ggccgaggag     1680
caggctgccg aggcagcgcg ggtcgcctcc gctgtcatgg gaggccaccc gacaccgcta     1740
cgggacatgc tcgccgccca ggagcagcgc cggaagccgt ggactccgga gcagaaacgc     1800
cagtacgcga ccgcaaaagc ccaagcagaa cgcgccgcga aggccaagga cgccgcgaaa     1860
tggaccgagg tcgccggcgg cggctaccag cgggacgtgc gcgggatgaa cctgcgactg     1920
tgggtggctg aggacggcgc ctggtcgatc acctcgaaga aggaccccga ccgccagtac     1980
```

```
gccgcaggtc aggccgacac cgtcgcgcag gcccaagccg cggccacggc cacagcgaaa    2040
acgcaggccc aggcgatgtg gaagcaggtc ccggccgaca agcgcaccga gtcagccacc    2100
agagcggtcc ggcgcgtgat cgcggatctc acccccacca aacccgccga ggtcaaaccc    2160
ccggcccgcc gccagggacc aaccatgccg cagtcggccc cggggtatca gccacccggc    2220
cgcgaccgag gtcgagaatc cggaatggga ctgtgagcag agagcgagaa ggctttcgtg    2280
gagcgtaggg aacagacgca ggcctggcga agcatgtcca agaacaccat cgatcgctag    2340
aaggtcggtc gtgcccaggg tgcccaggat gcgtacataa cgcgcgaaag gtgcatacct    2400
cccatagcat cggcgcgtat ggtagggaaa atgatcttca aacgtattgc tgtggtcgtg    2460
ctcgctggtg gggctttggt agtgggaggc agccaggttg ctggtgctac cacggtttca    2520
gctccacagc cgagtccttc agcagcgtg gtgccgacgg ttcttccacc agtcactttc      2580
accgccgctt ctgcgcactg cgaggcccag tacgcgtcgg attcccggcg atgccgtctg    2640
attccacttc cacagggccg agcgatctgc tgggcggcag ccgctgcccg ttacgcagcg    2700
tgccgcgccg gaaactaggt agaacgtgag catggacgag cttcccacct tcatcgccga    2760
cgacatcgtg atggccagaa cgttcgacag ccctaacggc caggtggtgc tcgaggtgaa    2820
cactccgcgg ccgttcgatg ctgcggcccc ggagggtgac tactgctgca ccttccggat    2880
cagcgggaac atggatgccc cttacgacgg attcggtggc ggcgtcgacg cagtgcaggc    2940
gctgctactc gcattggcca tggcacacga ggaacttcgt caaacttcgc cagagttgac    3000
gtttctaggc gagacgaacc tcggtctacc ggtcttgaac atcaagcccg acaacgcgat    3060
cgaagccgtg gtctcattcc ccgctccctg atgtgacgca ctttcacccc tggcactcat    3120
gtaccgaagc tgggactgag aaagggctgc gcgtcaccg cttcgcgttg acttgccact      3180
gaacgggggc gtgtcccggt cagggcgggg tgtgacctgg gttcatgaca ccgctaacac    3240
gctgcgaaaa tgcggattga actagttcat ttggggaacg atgacctgat gaccggggat    3300
cgtgacctac ccatgctgac catcgccgag gcggtggacg cgacgcagac cagtgagagc    3360
acgatcaagc gccgcctgcg gtcgggcgcg ttcccgaacg cggtccgcac tgccgacggg    3420
aagtggatga ttcccctcgg tgacctatca gcggcagggc tgagaccagg gaaaatggcg    3480
aaacctgacc cggtgacccc ttcaaatgac cgggtccgtg acctggcagc tgagaacgcc    3540
gagctccgtc agcgcctggc cgtggccgaa gccctggcca gcgaacgcaa tcggatcatc    3600
gacgtgcagc aacagatgct ccggatgctc gaagcccggc cggtgtcggc cctggagccc    3660
gcggcggttc cagtggcggg tccgccgccg cccgtcccgg ccgccgatgg tcgggcagct    3720
acgggcgccc tggcccggat acgtcgacgg cttctcggct aggagctgac cgcgtacttg    3780
cgtgcgtcgt gcaggagctt tcccaccgtt ccggtggaga ttcccatctc ctcggcgatc    3840
tcgcggtact tcaggccctg ctcgcgcagc tcgacggccc ggcgacggtt ctcggctgcc    3900
cgtgcgagga actggtcccg cggctcggcc atgatgcgct ggatcgtgcg cgtggaggcc    3960
cccatcttct cggccagctc gcgagctgtc tgcttgcggc ggatcggtcg ttcagcgccc    4020
acggtctgcc tcccacaatg cgttccggtc gaccttcgtc gctcgtttcc ggtttgcctc    4080
gcgcttcttc tcactcatct tgcgaccgcg tgcggcttgt atggcgatga atgtggcctc    4140
gtagacagca gggccgtcgg cccacatccg ggactttgta gtgatccagc gggtaatgga    4200
ggccgcgacg gcgcgtagct cgcttgctgg cagtggatcg ggcctgcctg tgaccgggtt    4260
cctgaacgtg gcgttgatct gtgcggcttc cgcatagatc gcggcccga ggccggtcgg      4320 gtcgccccag tggaagcgga tttcgcggta ggccaggtg cgtgcggttt cgaacagggc      4380
```

```
gcagtttcgg ccgaggccga tcgggttctc acggcgcgat cgggtttgcc gccagcgcgt    4440
tggcggcatg tggatgccga gttccgcctc gagctcggcg agggatcgcc gctcggtgtg    4500
cagccaatgg gtgtcccagt caccgtgagt cgggttcttg gtcatcaggc ccgaatagcc    4560
cttgtccccc tggacggcgc gccggaggcc ttcggtgacg gcggccgcat aggcgagcgg    4620
cttacgacgg gcgtactcgg tgcgggtgaa cggctctgcc agcgcccaca cagcgtgtgc    4680
gtgcccgtta cgggggttct ccacgatcgc gttcggcaga ggatgattcc cggccgccga    4740
cagcgcccgc agcgcggcgt ccgggtggtc aacgtccacg acgagcaggt tgctcaatgc    4800
ctgcgggttc gactcgatgt agcggcgatc cagtgcgtct gatcgccgca tccggtagac    4860
gccgtcgagg aaatcgtcgg ttgccagtgg ccacagcggt agccacagct gttcccaggc    4920
gccgcctgtg tgctcttcca ccgcaaccat ggggaacaca ctcacacaca agatcgattt    4980
attccggtac gacacgccag ccaagtcaga tgtttcggtt tctggagcgg tcctccagac    5040 cttttgagatc cgctccagaa acgtccacaa attattgggg tacgtcgaac caagccttat    5100
caggtatccc ggggttccgg gggtgaacac caccctccga ccggtccaga atccgtcgat    5160
ctcacctatc cgctcgaagt ccttgagtca gtgacaggac cactgctggg ctcccagcgc    5220
agaaggcaag tgaaggcaga cgactgcggg aggtaagtcg ggtacggcat gaggtccttc    5280
agaagcggcg tcgacgccag gcccacacgc acaatccgct tcccacgagg acaccaccg    5340 gtagcgcccc ctgcaaccgg cgcagtgtca cgaggcgccg gtactgctcg tttgacagga    5400
actgcagggt cggtgagctc gcgctgggcg gatcccacca gtagctcccc gtgccggtaa    5460
ccgcttgggg ccaagcgaag acacccaccg cggcagcgat ggcaatgcac gtggatggga    5520
acaccaccca gaaccaggga aatcctggtg ccggcccgag acgatcccgg cgcggtaaga    5580
ccacaccggc caccatcgcc acggcccccg acgcaacaag caataaccac cccatgagcg    5640
gacggtacaa gcgccgacgc cgggtggccg ttaggtgcgc gccagcccgt gaccggaccg    5700
gcgaagcgtg ccgctgggcg gcccgccgtg gcgcccgtcc cgtgcccgtt ctgaccggtg    5760
gtctcggtcg ctcgttcctc gcgtcctcac ctgccggtca gcccgtgacc ggacctgcag    5820
gcatgcaagc ttggcactgg ccgtcgtttt acaacgtcgt gactgggaaa accctggcgt    5880
tacccaactt aatcgccttg cagcacatcc ccctttcgcc agctggcgta atagcgaaga    5940
ggcccgcacc gatcgccctt cccaacagtt gcgcagcctg aatggcgaat gagcttcttc    6000
cgcttcctcg ctcactgact cgctgcgctc ggtcgttcgg ctgcggcgag cggtatcagc    6060
tcactcaaag gcggtaatac ggttatccac agaatcaggg gataacgcag gaaagaacat    6120
gtgagcaaaa ggccagcaaa aggccaggaa ccgtaaaaag gccgcgttgc tggcgttttt    6180
ccataggctc cgcccccctg acgagcatca aaaaatcga cgctcaagtc agaggtggcg    6240
aaacccgaca ggactataaa gataccaggc gtttccccct ggaagctccc tcgtgcgctc    6300
tcctgttccg accctgccgc ttaccggata cctgtccgcc tttctccctt cgggaagcgt    6360
ggcgctttct caatgctcac gctgtaggta tctcagttcg gtgtaggtcg ttcgctccaa    6420
gctgggctgt gtgcacgaac cccccgttca gcccgaccgc tgcgccttat ccggtaacta    6480
tcgtcttgag tccaacccgg taagacacga cttatcgcca ctggcagcag ccactggtaa    6540
caggattagc agagcgaggt atgtaggcgg tgctacagag ttcttgaagt ggtggcctaa    6600
ctacggctac actagaagga cagtatttgg tatctgcgct ctgctgaagc cagttacctt    6660
cggaaaaaga gttggtagct cttgatccgg caaacaaacc accgctggta gcggtggttt    6720
```

```
ttttgtttgc aagcagcaga ttacgcgcag aaaaaaagga tctcaagaag atcctttgat    6780
cttttctacg gggtctgacg ctcagtggaa ctccgtcgaa cggaagatca cttcgcagaa    6840
taaataaatc ctggtgtccc tgttgatacc gggaagccct gggccaactt ttggcgaaaa    6900
tgagacgttg atcggcacgt aagaggttcc aactttcacc ataatgaaat aagatcacta    6960
ccgggcgtat tttttgagtt atcgagattt tcaggagcta aggaagctaa atggagaaaa    7020
aaaatcactg gatataccac cgttgatata tcccaatggc atcgtaaaga acattttgag    7080
gcatttcagt cagttgctca atgtacctat aaccagaccg ttcagctgga tattacggcc    7140
tttttaaaga ccgtaaagaa aaataagcac aagtttatcc ggcctttatt cacattctt     7200 gcccgcctga tgaatgctca tccggaattt cgtatggcaa tgaaagacgg tgagctggtg    7260
atatgggata gtgttcaccc ttgttacacc gttttccatg agcaaactga acgttttca     7320 tcgctctgga gtgaatacca cgacgatttc cggcagtttc tacacatata ttcgcaagat    7380
gtggcgtgtt acggtgaaaa cctggcctat ttccctaaag ggtttattga gaatatgttt    7440
ttcgtctcag ccaatccctg ggtgagtttc accagttttg atttaaacgt ggccaatatg    7500
gacaacttct tcgcccccgt tttcaccatg ggcaaatatt atacgcaagg cgacaaggtg    7560
ctgatgccgc tggcgattca ggttcatcat gccgtctgtg atggcttcca tgtcggcaga    7620
atgcttaatg aattacaaca gtactgcgat gagtggcagg gcggggcgta atttttttaa    7680
ggcagttatt ggtgccctta aacgcctggt gctacgcctg aataagtgat aataagcgga    7740
tgaatggcag aaattcagct ggcccagtgc caagctcca atacgcaaac cgcctctccc     7800
cgcgcgttgg ccgattcatt aatgcagctg gcacgacagg tttcccgact ggaaagcggg    7860
cagtgagcgc aacgcaatta atgtgagtta gctcactcat taggcacccc aggctttaca    7920
ctttatgctt ccggctcgta tgttgtgtgg aattgtgagc ggataacaat ttcacacagg    7980
aaacagctat gaccatgatt acgaattcga gctcggtacc cggggatcct ctagagtc      8038

<210> SEQ ID NO 98
<211> LENGTH: 8497
<212> TYPE: DNA
<213> ORGANISM: Artificial
<220> FEATURE:
<223> OTHER INFORMATION: pRET1001Rv

<400> SEQUENCE: 98
ccgtccacca cccggtgcct ggtctgcgtc tccctcggct cgttcctcgc ctatcctggt      60
gaccagacac cggagcgagc tatgcccagg gttgcgcagt gacttcgtca ctgcgtaacc     120
ctgggcgctc gcctcccatt cgcttcgctc acaggagggg gccgtcgatg gccgctgacg     180
ctgcatctga cgaccggcgg accgaggtcc gcgccgctgc ttcgcgggcc gctgacgcgg     240
ccccggcgaa gcgcacccgc accgtggcgg tgcggctgac cgatggggag gaggccgcgt     300
ggatcgacgc cgcgctggcc gatggccacc ggcagctcgg ggcgtgggtg cgtgagcggg     360
cggtggccgg ctatctcggg aaggtccgcc cgaagaccgg cagtggaatg tcggcggagg     420
cggccgcgga ggtcgccgcg atgcggcagc agatgacgaa ggtggggaac aacctgaacc     480
agatcgcgag ggcgatcaac gccgggcagg tgccgtcgca gatggccgag tccctgcaga     540
aggggtggct ggagaggtgg gggcaggagt tgggcggat ggcggatcgg ctcgacgcgc      600
tcgacgacca gggctgacgt gatcgcgaag atcagcacgg gcagcgaccc gaagggggttg    660 gcggcgtatc tgcacgggcc ggggaaggcc accccgcaca gctaccgcac cgaggcgggc    720
cggctgattg ccggcgggac ggtgatcgcg ggatcggtgc aggtcaccgc caaaaacccg     780
```

-continued

```
acccggtggg ggcgggactt cgagcgggcc gccgcgacga acgcgcgggt gggtaagccg      840
gtgtggcatt gctcgctgcg gtgcgcgccc ggggatcggc ggctgaccga taccgagttc      900
gcggacatcg cgcagacggt cgccgagcgg atgggcttcg agagtcatcc gtgggtggcg      960
gtgcggcacg acgacgacca catccacctg gctgtctccc gggtcgattt tcagggcgtg     1020
acctggaaga acagcaacga ccggtggaag gtcgtcgagg tgatgcgcga ggtcgaacgc     1080
gcgcacggcc tgatcgaggt ggcgagcccg gagcgggccc gtggccggca agccagcagc     1140
ggcgagcaac gccgcgcggt gcggaccggc aaggtggcgc agcgggacgg tctgagggaa     1200
attgtgaccg ccgcccgcga catcgccgca ggccagggtg tgggggcgtt cgaagtggcg     1260
ctcgtacaga acccgattac ccgagtgcag gtgcggcgca acgtcgcgaa gacgggccgg     1320
atgaatggct acagcttcaa cctgcccggc tacgtcgacg ccgccgggga gccgatctgg     1380
ttgccggcct ccaaactcga ccggggtttg tcctggtcac agctggaaaa gacgctgacc     1440
agaccccgcc cggaccgcct cgccggcgag gagacggtgc cgcggaagcg gctcgagcgc     1500
gccgccgcgt gggagcagcg ccgccgcgag gtcggcggcg agcagttcgc agctgcccgc     1560
tgggagcagg cccgcgcgaa tgttggtgag acggccgggc ggatccgcgc cgaacagtcc     1620
gcggacacga agtggaagca ggtgaacgag gcgttgacca gccaagaccg ggccgaggag     1680
caggctgccg aggcagcgcg ggtcgcctcc gctgtcatgg gaggccaccc gacaccgcta     1740
cgggacatgc tcgccgccca ggagcagcgc cggaagccgt ggactccgga gcagaaacgc     1800
cagtacgcga ccgcaaaagc ccaagcagaa cgcgccgcga aggccaagga cgccgcgaaa     1860
tggaccgagg tcgccggcgg cggctaccag cgggacgtgc gcgggatgaa cctgcgactg     1920
tgggtggctg aggacggcgc ctggtcgatc acctcgaaga aggaccccga ccgccagtac     1980
gccgcaggtc aggccgacac cgtcgcgcag gcccaagccg cggccacggc cacagcgaaa     2040
acgcaggccc aggcgatgtg gaagcaggtc ccggccgaca agcgcaccga gtcagccacc     2100
agagcggtcc ggcgcgtgat cgcggatctc acccccacca aacccgccga ggtcaaaccc     2160
ccggcccgcc gccagggacc aaccatgccg cagtcggccc cggggtatca gccaccggc     2220
cgcgaccgag gtcgagaatc cggaatggga ctgtgagcag agagcgagaa ggctttcgtg     2280
gagcgtaggg aacagacgca ggcctggcga agcatgtcca agaacaccat cgatcgctag     2340
aaggtcggtc gtgcccaggg tgcccaggat gcgtacataa cgcgcgaaag gtgcatacct     2400
cccatagcat cggcgcgtat ggtagggaaa atgatcttca aacgtattgc tgtggtcgtg     2460
ctcgctggtg gggctttggt agtgggaggc agccaggttg ctggtgctac cacggtttca     2520
gctccacagc cgagtccttc agcagcggtg gtgccgacgg ttcttccacc agtcactttc     2580
accgccgctt ctgcgcactg cgaggcccag tacgcgtcgg attcccggcg atgccgtctg     2640
attccacttc cacagggccg agcgatctgc tgggcggcag ccgctgcccg ttacgcagcg     2700
tgccgcgccg gaaactaggt agaacgtgag catggacgag cttcccacct tcatcgccga     2760
cgacatcgtg atggccagaa cgttcgacag ccctaacggc caggtggtgc tcgaggtgaa     2820
cactccgcgg ccgttcgatg ctgcggcccc ggagggtgac tactgctgca ccttccggat     2880
cagcgggaac atggatgccc cttacgacgg attcggtggc ggcgtcgacg cagtgcaggc     2940
gctgctactc gcattggcca tggcacacga ggaacttcgt caaacttcgc cagagttgac     3000
gtttctaggc gagacgaacc tcggtctacc ggtcttgaac atcaagcccg acaacgcgat     3060
cgaagccgtg gtctcattcc ccgctcccctg atgtgacgca ctttcacccc tggcactcat     3120
```

```
gtaccgaagc tgggactgag aaagggctgc cgcgtcaccg cttcgcgttg acttgccact   3180 gaacggggggc gtgtcccggt cagggcgggg tgtgacctgg gttcatgaca ccgctaacac   3240
gctgcggaaa tgcggattga actagttcat ttggggaacg atgacctgat gaccggggat   3300
cgtgacctac ccatgctgac catcgccgag gcggtggacg cgacgcagac cagtgagagc   3360
acgatcaagc gccgcctgcg gtcgggcgcg ttcccgaacg cggtccgcac tgccgacggg   3420
aagtggatga ttccctcgg tgacctatca gcggcaggc tgagaccagg gaaaatggcg   3480
aaacctgacc cggtgacccc ttcaaatgac cgggtccgtg acctggcagc tgagaacgcc   3540
gagctccgtc agcgcctggc cgtggccgaa gccctggcca cgaacgcaa tcggatcatc   3600 gacgtgcagc aacagatgct ccggatgctc gaagcccggc cggtgtcggc cctggagccc   3660
gcggcggttc cagtggcggg tccgccgccg cccgtcccgg ccgccgatgg tcgggcagct   3720
acgggcgccc tggcccggat acgtcgacgg cttctcggct aggagctgac cgcgtacttg   3780
cgtgcgtcgt gcaggagctt tcccaccgtt ccggtggaga ttcccatctc ctcggcgatc   3840
tcgcggtact tcaggccctg ctcgcgcagc tcgacggccc ggcgacggtt ctcggctgcc   3900
cgtgcgagga actggtcccg cggctcggcc atgatgcgct ggatcgtgcg cgtggaggcc   3960
cccatcttct cggccagctc gcgagctgtc tgcttgcggc ggatcggtcg ttcagcgccc   4020
acggtctgcc tccacaatg cgttccggtc gaccttcgtc gctcgttttcc ggtttgcctc   4080 gcgcttcttc tcactcatct tgcgaccgcg tgcggcttgt atggcgatga atgtggcctc   4140
gtagacagca gggccgtcgg cccacatccg ggactttgta gtgatccagc gggtaatgga   4200
ggccgcgacg gcgcgtagct cgcttgctgg cagtggatcg ggcctgcctg tgaccgggtt   4260
cctgaacgtg gcgttgatct gtgcggcttc gcatagatc gcggccccga ggccggtcgg   4320
gtcgccccag tggaagcgga tttcgcggta ggcccaggtg cgtgcggttt cgaacagggc   4380
gcagtttcgg ccgaggccga tcgggttctc acggcgcgat cgggtttgcc gccagcgcgt   4440
tggcggcatg tggatgccga gttccgcctc gagctcggcg agggatcgcc gctcggtgtg   4500
cagccaatgg gtgtcccagt caccgtgagt cgggttcttg gtcatcaggc ccgaatagcc   4560
cttgtccccc tggacggcgc gccggaggcc ttcggtgacg cggccgcat aggcgagcgg   4620 cttacgacgg gcgtactcgg tgcgggtgaa cggctctgcc agcgcccaca cagcgtgtgc   4680
gtgcccgtta cggggggttct ccacgatcgc gttcggcaga ggatgattcc cggccgccga   4740
cagcgcccgc agcgcggcgt ccgggtggtc aacgtccacg acgagcaggt tgctcaatgc   4800
ctgcgggttc gactcgatgt agcggcgatc cagtgcgtct gatcgccgca tccggtagac   4860
gccgtcgagg aaatcgtcgg ttgccagtgg ccacagcggt agccacagct gttcccaggc   4920
gccgcctgtg tgctcttcca ccgcaaccat ggggaacaca ctcacacaca agatcgattt   4980
attccggtac gacacgccag ccaagtcaga tgtttcggtt tctggagcgg tcctccagac   5040 cttttgagatc cgctccagaa acgtccacaa attattgggg tacgtcgaac caagccttat   5100
caggtatccc ggggttccgg gggtgaacac caccctccga ccggtccaga atccgtcgat   5160
ctcacctatc cgctcgaagt ccttgagtca gtgacaggac cactgctggg ctcccagcgc   5220
agaaggcaag tgaaggcaga cgactgcggg aggtaagtcg ggtacggcat gaggtccttc   5280
agaagcggcg tcgacgccag gcccacacgc acaatccgct tcccacgagg acaccaccg   5340 gtagcgcccc ctgcaaccgg cgcagtgtca cgaggcgccg gtactgctcg tttgacagga   5400
actgcagggt cggtgagctc gcgctgggcg gatcccacca gtagctcccc gtgccggtaa   5460
ccgcttgggg ccaagcgaag acacccaccg cggcagcgat ggcaatgcac gtggatggga   5520
```

```
acaccaccca gaaccaggga atcctggtg ccggcccgag acgatcccgg cgcggtaaga    5580
ccacaccggc caccatcgcc acggcccccg acgcaacaag caataaccac cccatgagcg    5640
gacggtacaa gcgccgacgc cgggtggccg ttaggtgcgc gccagcccgt gaccggaccg    5700
gcgaagcgtg ccgctgggcg gcccgccgtg gcgcccgtcc cgtgcccgtt ctgaccggtg    5760
gtctcggtcg ctcgttcctc gcgtcctcac ctgccggtca gcccgtgacc ggactctaga    5820
ggatccccgg gtaccgagct cgaattcgta atcatggtca tagctgtttc ctgtgtgaaa    5880
ttgttatccg ctcacaattc cacacaacat acgagccgga agcataaagt gtaaagcctg    5940
gggtgcctaa tgagtgagct aactcacatt aattgcgttg cgctcactgc ccgctttcca    6000
gtcgggaaac ctgtcgtgcc agctgcatta atgaatcggc caacgcgcgg ggagaggcgg    6060
tttgcgtatt gggcgctctt ccgcttcctc gctcactgac tcgctgcgct cggtcgttcg    6120
gctgcggcga gcggtatcag ctcactcaaa ggcggtaata cggttatcca cagaatcagg    6180
ggataacgca ggaaagaaca tgtgagcaaa aggccagcaa aaggccagga accgtaaaaa    6240
ggccgcgttg ctggcgtttt tccataggct ccgcccccct gacgagcatc acaaaaatcg    6300
acgctcaagt cagaggtggc gaaacccgac aggactataa agataccagg cgtttccccc    6360
tggaagctcc ctcgtgcgct ctcctgttcc gaccctgccg cttaccggat acctgtccgc    6420
ctttctccct tcgggaagcg tggcgctttc tcatagctca cgctgtaggt atctcagttc    6480
ggtgtaggtc gttcgctcca agctgggctg tgtgcacgaa ccccccgttc agcccgaccg    6540
ctgcgcctta tccggtaact atcgtcttga gtccaacccg gtaagacacg acttatcgcc    6600
actggcagca gccactggta acaggattag cagagcgagg tatgtaggcg gtgctacaga    6660
gttcttgaag tggtggccta actacggcta cactagaagg acagtatttg gtatctgcgc    6720
tctgctgaag ccagttacct tcggaaaaag agttggtagc tcttgatccg gcaaacaaac    6780
caccgctggt agcggtggtt tttttgtttg caagcagcag attacgcgca gaaaaaaagg    6840
atctcaagaa gatcctttga tcttttctac ggggtctgac gctcagtgga acgaaaactc    6900
acgttaaggg attttggtca tgagattatc aaaaaggatc ttcacctaga tccttttaaa    6960
ttaaaaatga agttttaaat caatctaaag tatatatgag taaacttggt ctgacagtta    7020
ccaatgctta atcagtgagg cacctatctc agcgatctgt ctatttcgtt catccatagt    7080
tgcctgactc cccgtcgtgt agataactac gatacgggag ggcttaccat ctggccccag    7140
tgctgcaatg ataccgcgag acccacgctc accggctcca gatttatcag caataaacca    7200
gccagccgga agggccgagc gcagaagtgg tcctgcaact ttatccgcct ccatccagtc    7260
tattaattgt tgccgggaag ctagagtaag tagttcgcca gttaatagtt tgcgcaacgt    7320
tgttgccatt gctacaggca tcgtggtgtc acgctcgtcg tttggtatgg cttcattcag    7380
ctccggttcc caacgatcaa ggcgagttac atgatccccc atgttgtgca aaaaagcggt    7440
tagctccttc ggtcctccga tcgttgtcag aagtaagttg gccgcagtgt tatcactcat    7500
ggttatggca gcactgcata attctcttac tgtcatgcca tccgtaagat gcttttctgt    7560
gactggtgag tactcaacca agtcattctg agaatagtgt atgcggcgac cgagttgctc    7620
ttgcccggcg tcaatacggg ataataccgc gccacatagc agaactttaa aagtgctcat    7680
cattggaaaa cgttcttcgg ggcgaaaact ctcaaggatc ttaccgctgt tgagatccag    7740
ttcgatgtaa cccactcgtg cacccaactg atcttcagca tcttttactt tcaccagcgt    7800
ttctgggtga gcaaaaacag gaaggcaaaa tgccgcaaaa aagggaataa gggcgacacg    7860
```

| | |
|---|---|
| gaaatgttga atactcatac tcttcctttt tcaatattat tgaagcattt atcagggtta | 7920 |
| ttgtctcatg agcggataca tatttgaatg tatttagaaa aataaacaaa tagggggttcc | 7980 |
| gcgcacattt ccccgaaaag tgccacctga cgtctaagaa accattatta tcatgacatt | 8040 |
| aacctataaa aataggcgta tcacgaggcc ctttcgtctc gcgcgtttcg gtgatgacgg | 8100 |
| tgaaaacctc tgacacatgc agctcccgga cacggtcaca gcttgtctgt aagcggatgc | 8160 |
| cgggagcaga caagcccgtc agggcgcgtc agcgggtgtt ggcgggtgtc ggggctggct | 8220 |
| taactatgcg gcatcagagc agattgtact gagagtgcac catatgcggt gtgaaatacc | 8280 |
| gcacagatgc gtaaggagaa aataccgcat caggcgccat cgccattcca ggctgcgcaa | 8340 |
| ctgttgggaa gggcgatcgg tgcgggcctc ttcgctatta cgccagctgg cgaaaggggg | 8400 |
| atgtgctgca aggcgattaa gttgggtaac gccagggttt tcccagtcac gacgttgtaa | 8460 |
| aacgacggcc agtgccaagc ttgcatgcct gcaggtc | 8497 |

<210> SEQ ID NO 99
<211> LENGTH: 8487
<212> TYPE: DNA
<213> ORGANISM: Artificial
<220> FEATURE:
<223> OTHER INFORMATION: pRET1002Rv

<400> SEQUENCE: 99

| | |
|---|---|
| ccgtccacca cccggtgcct ggtctgcgtc tccctcggct cgttcctcgc ctatcctggt | 60 |
| gaccagacac cggagcgagc tatgcccagg gttgcgcagt gacttcgtca ctgcgtaacc | 120 |
| ctgggcgctc gcctcccatt cgcttcgctc acaggagggg gccgtcgatg gccgctgacg | 180 |
| ctgcatctga cgaccggcgg accgaggtcc gcgccgctgc ttcgcgggcc gctgacgcgg | 240 |
| ccccggcgaa gcgcacccgc accgtggcgg tgcggctgac cgatggggag gaggccgcgt | 300 |
| ggatcgacgc cgcgctggcc gatgccaccg gcagctcgg ggcgtgggtg cgtgagcggg | 360 |
| cggtggccgg ctatctcggg aaggtccgcc cgaagaccgg cagtggaatg tcggcggagg | 420 |
| cggccgcgga ggtcgccgcg atgcggcagc agatgacgaa ggtggggaac aacctgaacc | 480 |
| agatcgcgag ggcgatcaac gccgggcagg tgccgtcgca gatggccgag tccctgcaga | 540 |
| aggggtggct ggagaggtgg gggcaggagt tgggcggat ggcggatcgg ctcgacgcgc | 600 |
| tcgacgacca gggctgacgt gatcgcgaag atcagcacgg gcagcgaccc gaagggggttg | 660 |
| gcggcgtatc tgcacgggcc ggggaaggcc accccgcaca gctaccgcac cgaggcgggc | 720 |
| cggctgattg ccgcgggac ggtgatcgcg ggatcggtgc aggtcaccgc caaaaacccg | 780 |
| acccggtggg ggcgggactt cgagcgggcc gccgcgacga acgcgcgggt gggtaagccg | 840 |
| gtgtggcatt gctcgctgcg gtgcgcgccc gggatcggc ggctgaccga taccgagttc | 900 |
| gcggacatcg cgcagacggt cgccgagcgg atgggcttcg agagtcatcc gtgggtggcg | 960 |
| gtgcggcacg acgacgacca catccacctg gctgtctccc gggtcgattt tcagggcgtg | 1020 |
| acctggaaga acagcaacga ccggtggaag gtcgtcgagg tgatgcgcga ggtcgaacgc | 1080 |
| gcgcacggcc tgatcgaggt ggcgagcccg gagcgggccc gtggccggca agccagcagc | 1140 |
| ggcgagcaac gccgcgcggt gcggaccggc aaggtggcgc agcgggacgg tctgagggaa | 1200 |
| attgtgaccg ccgcccgcga catcgccgca ggccagggtg tgggggcgtt cgaagtggcg | 1260 |
| ctcgtacaga acccgattac ccgagtgcag gtgcggcgca acgtcgcgaa gacgggccgg | 1320 |
| atgaatggct acagcttcaa cctgcccggc tacgtcgacg ccgccgggga gccgatctgg | 1380 |
| ttgccggcct ccaaactcga ccggggtttg tcctggtcac agctggaaaa gacgctgacc | 1440 |

-continued

```
agacccgcc cggaccgcct cgccggcgag gagacggtgc cgcggaagcg gctcgagcgc    1500
gccgccgcgt gggagcagcg ccgccgcgag gtcggcggcg agcagttcgc agctgcccgc    1560
tgggagcagg cccgcgcgaa tgttggtgag acggccgggc ggatccgcgc cgaacagtcc    1620
gcggacacga agtggaagca ggtgaacgag gcgttgacca gccaagaccg ggccgaggag    1680
caggctgccg aggcagcgcg ggtcgcctcc gctgtcatgg gaggccaccc gacaccgcta    1740
cgggacatgc tcgccgccca ggagcagcgc cggaagccgt ggactccgga gcagaaacgc    1800
cagtacgcga ccgcaaaagc ccaagcagaa cgcgccgcga aggccaagga cgccgcgaaa    1860
tggaccgagg tcgccggcgg cggctaccag cgggacgtgc gcgggatgaa cctgcgactg    1920
tgggtggctg aggacggcgc ctggtcgatc acctcgaaga aggaccccga ccgccagtac    1980
gccgcaggtc aggccgacac cgtcgcgcag gcccaagccg cggccacggc cacagcgaaa    2040
acgcaggccc aggcgatgtg gaagcaggtc ccggccgaca agcgcaccga gtcagccacc    2100
agagcggtcc ggcgcgtgat cgcggatctc acccccacca aacccgccga ggtcaaaccc    2160
ccggcccgcc gccagggacc aaccatgccg cagtcggccc cggggtatca gccaccgggc    2220
cgcgaccgag gtcgagaatc cggaatggga ctgtgagcag agagcgagaa ggctttcgtg    2280
gagcgtaggg aacagacgca ggcctggcga agcatgtcca agaacaccat cgatcgctag    2340
aaggtcggtc gtgcccaggg tgcccaggat gcgtacataa cgcgcgaaag gtgcatacct    2400
cccatagcat cggcgcgtat ggtagggaaa atgatcttca aacgtattgc tgtggtcgtg    2460
ctcgctggtg gggctttggt agtgggaggc agccaggttg ctggtgctac cacggtttca    2520
gctccacagc cgagtccttc agcagcggtg gtgccgacgg ttcttccacc agtcactttc    2580
accgccgctt ctgcgcactg cgaggcccag tacgcgtcgg attcccggcg atgccgtctg    2640
attccacttc cacagggccg agcgatctgc tgggcggcag ccgctgcccg ttacgcagcg    2700
tgccgcgccg gaaactaggt agaacgtgag catggacgag cttcccacct tcatcgccga    2760
cgacatcgtg atggccagaa cgttcgacag ccctaacggc caggtggtgc tcgaggtgaa    2820
cactccgcgg ccgttcgatg ctgcggcccc ggagggtgac tactgctgca ccttccggat    2880
cagcgggaac atggatgccc cttacgacgg attcggtggc ggcgtcgacg cagtgcaggc    2940
gctgctactc gcattggcca tggcacacga ggaacttcgt caaacttcgc cagagttgac    3000
gtttctaggc gagacgaacc tcggtctacc ggtcttgaac atcaagcccg acaacgcgat    3060
cgaagccgtg gtctcattcc ccgctcctg atgtgacgca ctttcacccc tggcactcat    3120
gtaccgaagc tgggactgag aaagggctgc cgcgtcaccg cttcgcgttg acttgccact    3180
gaacgggggc gtgtccccggt cagggcgggg tgtgacctgg gttcatgaca ccgctaacac    3240
gctgcggaaa tgcggattga actagttcat ttggggaacg atgacctgat gaccggggat    3300
cgtgacctac ccatgctgac catcgccgag gcggtggacg cgacgcagac cagtgagagc    3360
acgatcaagc gccgcctgcg gtcgggcgcg ttcccgaacg cggtccgcac tgccgacggg    3420
aagtggatga ttcccctcgg tgacctatca gcggcagggc tgagaccagg aaaatggcg    3480 aaacctgacc cggtgacccc ttcaaatgac cgggtccgtg acctggcagc tgagaacgcc    3540
gagctccgtc agcgcctggc cgtggccgaa gccctggcca gcgaacgcaa tcggatcatc    3600
gacgtgcagc aacagatgct ccggatgctc gaagcccggc cggtgtcggc cctggagccc    3660
gcggcggttc cagtggcggg tccgccgccg ccgtcccgg ccgccgatgg tcgggcagct    3720
acgggcgccc tggcccggat acgtcgacgg cttctcggct aggagctgac cgcgtacttg    3780
```

```
cgtgcgtcgt gcaggagctt tcccaccgtt ccggtggaga ttcccatctc ctcggcgatc   3840
tcgcggtact tcaggccctg ctcgcgcagc tcgacgccc ggcgacggtt ctcggctgcc    3900
cgtgcgagga actggtcccg cggctcggcc atgatgcgct ggatcgtgcg cgtggaggcc   3960
cccatcttct cggccagctc gcgagctgtc tgcttgcggc ggatcggtcg ttcagcgccc   4020
acggtctgcc tcccacaatg cgttccggtc gaccttcgtc gctcgtttcc ggtttgcctc   4080
gcgcttcttc tcactcatct tgcgaccgcg tgcggcttgt atggcgatga atgtggcctc   4140
gtagacagca gggccgtcgg cccacatccg ggactttgta gtgatccagc gggtaatgga   4200
ggccgcgacg gcgcgtagct cgcttgctgg cagtggatcg ggcctgcctg tgaccgggtt   4260
cctgaacgtg gcgttgatct gtgcggcttc cgcatagatc gcggccccga ggccggtcgg   4320
gtcgccccag tggaagcgga tttcgcggta ggcccaggtg cgtgcggttt cgaacagggc   4380
gcagtttcgg ccgaggccga tcgggttctc acggcgcgat cgggtttgcc gccagcgcgt   4440
tggcggcatg tggatgccga gttccgcctc gagctcggcg agggatcgcc gctcggtgtg   4500
cagccaatgg gtgtcccagt caccgtgagt cgggttcttg gtcatcaggc ccgaatagcc   4560
cttgtccccc tggacggcgc gccggaggcc ttcggtgacg gcggccgcat aggcgagcgg   4620
cttacgacgg gcgtactcgg tgcgggtgaa cggctctgcc agcgcccaca cagcgtgtgc   4680
gtgcccgtta cggggttct ccacgatcgc gttcggcaga ggatgattcc cggccgccga    4740
cagcgcccgc agcgcggcgt ccgggtggtc aacgtccacg acgagcaggt tgctcaatgc   4800
ctgcgggttc gactcgatgt agcggcgatc cagtgcgtct gatcgccgca tccggtagac   4860
gccgtcgagg aaatcgtcgg ttgccagtgg ccacagcggt agccacagct gttcccaggc   4920
gccgcctgtg tgctcttcca ccgcaaccat ggggaacaca ctcacacaca agatcgattt   4980
attccggtac gacacgccag ccaagtcaga tgtttcggtt tctggagcgg tcctccagac   5040 cttttgagatc cgctccagaa acgtccacaa attattgggg tacgtcgaac caagccttat   5100
caggtatccc ggggttccgg gggtgaacac caccctccga ccggtccaga atccgtcgat   5160
ctcacctatc cgctcgaagt ccttgagtca gtgacaggac cactgctggg ctcccagcgc   5220
agaaggcaag tgaaggcaga cgactgcggg aggtaagtcg ggtacggcat gaggtccttc   5280
agaagcggcg tcgacgccag gcccacacgc acaatccgct tcccacgagg acaccaccg    5340 gtagcgcccc ctgcaaccgg cgcagtgtca cgaggcgccg gtactgctcg tttgacagga   5400
actgcagggt cggtgagctc gcgctgggcg gatcccacca gtagctcccc gtgccggtaa   5460
ccgcttgggg ccaagcgaag acacccaccg cggcagcgat ggcaatgcac gtggatggga   5520
acaccaccca gaaccaggga atcctggtg ccggcccgag acgatcccgg cgcggtaaga    5580
ccacaccggc caccatcgcc acggcccccg acgcaacaag caataaccac cccatgagcg   5640
gacggtacaa gcgccgacgc cgggtggccg ttaggtgcgc gccagcccgt gaccggaccg   5700
gcgaagcgtg ccgctgggcg gcccgccgtg gcgcccgtcc cgtgcccgtt ctgaccggtg   5760
gtctcggtcg ctcgttcctc gcgtcctcac ctgccggtca gcccgtgacc ggactctaga   5820 ggatcccgg gtaccgagct cgaattcact ggccgtcgtt ttacaacgtc gtgactggga    5880
aaaccctggc gttacccaac ttaatcgcct tgcagcacat ccccctttcg ccagctggcg   5940
taatagcgaa gaggcccgca ccgatcgccc ttcccaacag ttgcgcagcc tgaatggcga   6000
atgcgattta ttcaacaaag ccgccgtccc gtcaagtcag cgtaatgctc tgccagtgtt   6060
acaaccaatt aaccaattct gattagaaaa actcatcgag catcaaatga aactgcaatt   6120
tattcatatc aggattatca ataccatatt tttgaaaaag ccgtttctgt aatgaaggag   6180
```

```
aaaactcacc gaggcagttc cataggatgg caagatcctg gtatcggtct gcgattccga    6240
ctcgtccaac atcaatacaa cctattaatt tcccctcgtc aaaaataagg ttatcaagtg    6300
agaaatcacc atgagtgacg actgaatccg gtgagaatgg caaaagctta tgcatttctt    6360
tccagacttg ttcaacaggc cagccattac gctcgtcatc aaaatcactc gcatcaacca    6420
aaccgttatt cattcgtgat tgcgcctgag cgagacgaaa tacgcgatcg ctgttaaaag    6480
gacaattaca aacaggaatc gaatgcaacc ggcgcaggaa cactgccagc gcatcaacaa    6540
tattttcacc tgaatcagga tattcttcta atacctggaa tgctgttttc ccggggatcg    6600
cagtggtgag taaccatgca tcatcaggag tacggataaa atgcttgatg gtcggaagag    6660
gcataaattc cgtcagccag tttagtctga ccatctcatc tgtaacatca ttggcaacgc    6720
tacctttgcc atgtttcaga acaactctg gcgcatcggg cttcccatac aatcgataga    6780
ttgtcgcacc tgattgcccg acattatcgc gagcccattt ataccatat aaatcagcat    6840
ccatgttgga atttaatcgc ggcttcgagc aagacgtttc ccgttgaata tggctcataa    6900
caccccttgt attactgttt atgtaagcag acagttttat tgttcatgat gatatatttt    6960
tatcttgtgc aatgtaacat cagagatttt gagacacaac gtggctttgt tgaataaatc    7020
gaacttttgc tgagttgaag gatcagatca cgcatcttcc cgacaacgca gaccgttccg    7080
tggcaaagca aagttcaaa atcaccaact ggtccaccta acaaagct ctcatcaacc       7140
gtggctccct cactttctgg ctggatgatg gggcgattca ggcctggtat gagtcagcaa    7200
caccttcttc acgaggcaga cctctcgacg gatcgttcca ctgagcgtca gaccccgtag    7260
aaaagatcaa aggatcttct tgagatcctt ttttctgcg cgtaatctgc tgcttgcaaa     7320
caaaaaaacc accgctacca gcggtggttt gtttgccgga tcaagagcta ccaactcttt    7380
ttccgaaggt aactggcttc agcagagcgc agataccaaa tactgtcctt ctagtgtagc    7440
cgtagttagg ccaccacttc aagaactctg tagcaccgcc tacataccc gctctgctaa     7500
tcctgttacc agtggctgct gccagtggcg ataagtcgtg tcttaccggg ttggactcaa    7560
gacgatagtt accggataag gcgcagcggt cgggctgaac ggggggttcg tgcacacagc    7620
ccagcttgga gcgaacgacc tacaccgaac tgagatacct acagcgtgag cattgagaaa    7680
gcgccacgct tcccgaaggg agaaaggcgg acaggtatcc ggtaagcggc agggtcggaa    7740
caggagagcg cacgagggag cttccagggg gaaacgcctg gtatctttat agtcctgtcg    7800
ggtttcgcca cctctgactt gagcgtcgat ttttgtgatg ctcgtcaggg gggcggagcc    7860
tatggaaaaa cgccagcaac gcggcctttt tacggttcct ggccttttgc tggccttttg    7920
ctcacatgtt ctttcctgcg ttatcccctg attctgtgga taaccgtatt accgcctttg    7980
agtgagctga taccgctcgc cgcagccgaa cgaccgagcg cagcgagtca gtgagcgagg    8040
aagcggaaga agctcgcaca ttcagcagcg ttttttcagcg cgttttcgat cagcgtttca   8100
atgttggtat caacaccagg tttaactttg aacttatcgg cactgacggt tactgatttt    8160
gaacttttgc tttgccacgg aacggtctgc gttgtcggga agatgcgtga tctgatcctt    8220
caactcagca aaagttcgcc aatacgcaaa ccgcctctcc ccgcgcgttg gccgattcat    8280
taatgcagct ggcacgacag gtttcccgac tggaaagcgg gcagtgagcg caacgcaatt    8340
aatgtgagtt agctcactca ttaggcaccc caggctttac actttatgct tccggctcgt    8400
atgttgtgtg gaattgtgag cggataacaa tttcacacag gaaacagcta tgaccatgat    8460
tacgccaagc ttgcatgcct gcaggtc                                        8487
```

<210> SEQ ID NO 100
<211> LENGTH: 8038
<212> TYPE: DNA
<213> ORGANISM: Artificial
<220> FEATURE:
<223> OTHER INFORMATION: pRET1003Rv

<400> SEQUENCE: 100

| | | | | | |
|---|---|---|---|---|---|
| ccgtccacca | cccggtgcct | ggtctgcgtc | tccctcggct | cgttcctcgc | ctatcctggt | 60 |
| gaccagacac | cggagcgagc | tatgcccagg | gttgcgcagt | gacttcgtca | ctgcgtaacc | 120 |
| ctgggcgctc | gcctcccatt | cgcttcgctc | acaggagggg | gccgtcgatg | ccgctgacg | 180 |
| ctgcatctga | cgaccggcgg | accgaggtcc | gcgccgctgc | ttcgcgggcc | gctgacgcgg | 240 |
| ccccggcgaa | gcgcacccgc | accgtggcgg | tgcggctgac | cgatggggag | gaggccgcgt | 300 |
| ggatcgacgc | cgcgctggcc | gatggccacc | ggcagctcgg | ggcgtgggtg | cgtgagcggg | 360 |
| cggtggccgg | ctatctcggg | aaggtccgcc | cgaagaccgg | cagtggaatg | tcggcggagg | 420 |
| cggccgcgga | ggtcgccgcg | atgcggcagc | agatgacgaa | ggtggggaac | aacctgaacc | 480 |
| agatcgcgag | ggcgatcaac | gccgggcagg | tgccgtcgca | gatggccgag | tccctgcaga | 540 |
| aggggtggct | ggagaggtgg | gggcaggagt | tgggcggat | ggcggatcgg | ctcgacgcgc | 600 |
| tcgacgacca | gggctgacgt | gatcgcgaag | atcagcacgg | gcagcgaccc | gaaggggttg | 660 |
| gcggcgtatc | tgcacgggcc | ggggaaggcc | accccgcaca | gctaccgcac | cgaggcgggc | 720 |
| cggctgattg | ccggcgggac | ggtgatcgcg | gatcggtgc | aggtcaccgc | caaaaacccg | 780 |
| acccggtggg | ggcgggactt | cgagcgggcc | gccgcgacga | acgcgcgggt | gggtaagccg | 840 |
| gtgtggcatt | gctcgctgcg | gtgcgcgccc | gggatcggc | ggctgaccga | taccgagttc | 900 |
| gcggacatcg | cgcagacggt | cgccgagcgg | atgggcttcg | agagtcatcc | gtgggtggcg | 960 |
| gtgcggcacg | acgacgacca | catccacctg | gctgtctccc | gggtcgattt | tcagggcgtg | 1020 |
| acctggaaga | acagcaacga | ccggtggaag | gtcgtcgagg | tgatgcgcga | ggtcgaacgc | 1080 |
| gcgcacggcc | tgatcgaggt | ggcgagcccg | agcgggccc | gtggccggca | agccagcagc | 1140 |
| ggcgagcaac | gccgcgcggt | gcggaccggc | aaggtggcgc | agcgggacgg | tctgagggaa | 1200 |
| attgtgaccg | ccgcccgcga | catcgccgca | ggccagggtg | tggggcgtt | cgaagtggcg | 1260 |
| ctcgtacaga | acccgattac | ccgagtgcag | gtgcggcgca | acgtcgcgaa | gacgggccgg | 1320 |
| atgaatggct | acagcttcaa | cctgcccggc | tacgtcgacg | ccgccgggga | gccgatctgg | 1380 |
| ttgccggcct | ccaaactcga | ccggggtttg | tcctggtcac | agctggaaaa | gacgctgacc | 1440 |
| agaccccgcc | cggaccgcct | cgccggcgag | gagacggtgc | cgcggaagcg | gctcgagcgc | 1500 |
| gccgccgcgt | gggagcagcg | ccgccgcgag | gtcggcggcg | agcagttcgc | agctgcccgc | 1560 |
| tgggagcagg | cccgcgcgaa | tgttggtgag | acggccgggc | ggatccgcgc | cgaacagtcc | 1620 |
| gcggacacga | agtggaagca | ggtgaacgag | gcgttgacca | gcaagaccgg | gccgaggag | 1680 |
| caggctgccg | aggcagcgcg | ggtcgcctcc | gctgtcatgg | gaggccaccc | gacaccgcta | 1740 |
| cgggacatgc | tcgccgccca | ggagcagcgc | cggaagccgt | ggactccgga | gcagaaacgc | 1800 |
| cagtacgcga | ccgcaaaagc | ccaagcagaa | cgcgccgcga | aggccaagga | cgccgcgaaa | 1860 |
| tggaccgagt | cgccggcgg | cggctaccag | cgggacgtgc | gcgggatgaa | cctgcgactg | 1920 |
| tgggtggctg | aggacggcgc | ctggtcgatc | acctcgaaga | aggaccccga | ccgccagtac | 1980 |
| gccgcaggtc | aggccgacac | cgtcgcgcag | gcccaagccg | cggccacggc | cacagcgaaa | 2040 |
| acgcaggccc | aggcgatgtg | gaagcaggtc | ccggccgaca | agcgcaccga | gtcagccacc | 2100 |

```
agagcggtcc ggcgcgtgat cgcggatctc accccacca aacccgccga ggtcaaaccc    2160
ccggcccgcc gccagggacc aaccatgccg cagtcggccc cggggtatca gccacccggc    2220
cgcgaccgag gtcgagaatc cggaatggga ctgtgagcag agagcgagaa ggctttcgtg    2280
gagcgtaggg aacagacgca ggcctggcga agcatgtcca agaacaccat cgatcgctag    2340
aaggtcggtc gtgcccaggg tgcccaggat gcgtacataa cgcgcgaaag gtgcatacct    2400
cccatagcat cggcgcgtat ggtagggaaa atgatcttca aacgtattgc tgtggtcgtg    2460
ctcgctggtg gggctttggt agtgggaggc agccaggttg ctggtgctac cacggtttca    2520
gctccacagc cgagtccttc agcagcggtg gtgccgacgg ttcttccacc agtcactttc    2580
accgccgctt ctgcgcactg cgaggccag tacgcgtcgg attcccggcg atgccgtctg     2640
attccacttc cacagggccg agcgatctgc tgggcggcag ccgctgcccg ttacgcagcg    2700
tgccgcgccg gaaactaggt agaacgtgag catggacgag cttcccacct tcatcgccga    2760
cgacatcgtg atggccagaa cgttcgacag ccctaacggc caggtggtgc tcgaggtgaa    2820
cactccgcgg ccgttcgatg ctgcggcccc ggagggtgac tactgctgca ccttccggat    2880
cagcgggaac atggatgccc cttacgacgg attcggtggc ggcgtcgacg cagtgcaggc    2940
gctgctactc gcattggcca tggcacacga ggaacttcgt caaacttcgc cagagttgac    3000
gtttctaggc gagacgaacc tcggtctacc ggtcttgaac atcaagcccg acaacgcgat    3060
cgaagccgtg gtctcattcc ccgctccctg atgtgacgca ctttcacccc tggcactcat    3120
gtaccgaagc tgggactgag aaagggctgc cgcgtcaccg cttcgcgttg acttgccact    3180
gaacgggggc gtgtcccggt cagggcgggg tgtgacctgg gttcatgaca ccgctaacac    3240
gctgcggaaa tgcggattga actagttcat ttggggaacg atgacctgat gaccggggat    3300
cgtgacctac ccatgctgac catcgccgag gcggtggacg cgacgcagac cagtgagagc    3360
acgatcaagc gccgcctgcg gtcgggcgcg ttcccgaacg cggtccgcac tgccgacggg    3420
aagtggatga ttcccctcgg tgacctatca gcggcagggc tgagaccagg gaaaatggcg    3480
aaacctgacc cggtgacccc ttcaaatgac cgggtccgtg acctggcagc tgagaacgcc    3540
gagctccgtc agcgcctggc cgtggccgaa gccctggcca gcgaacgcaa tcggatcatc    3600
gacgtgcagc aacagatgct ccggatgctc gaagcccggc cggtgtcggc cctggagccc    3660
gcggcggttc cagtggcggg tccgccgccg cccgtcccgg ccgccgatgg tcgggcagct    3720
acgggcgccc tggcccggat acgtcgacgg cttctcggct aggagctgac cgcgtacttg    3780
cgtgcgtcgt gcaggagctt tcccaccgtt ccggtggaga ttcccatctc ctcggcgatc    3840
tcgcggtact tcaggccctg ctcgcgcagc tcgacgcccc ggcgacggtt ctcggctgcc    3900
cgtgcgagga actggtcccg cggctcggcc atgatgcgct ggatcgtgcg cgtggaggcc    3960
cccatcttct cggccagctc gcgagctgtc tgcttgcggc ggatcggtcg ttcagcgccc    4020
acggtctgcc tcccacaatg cgttccggtc gaccttcgtc gctcgtttcc ggtttgcctc    4080
gcgcttcttc tcactcatct tgcgaccgcg tgcggcttgt atggcgatga atgtggcctc    4140
gtagacagca gggccgtcgg cccacatccg ggactttgta gtgatccagc gggtaatgga    4200
ggccgcgacg gcgcgtagct cgcttgctgg cagtggatcg ggcctgcctg tgaccgggtt    4260
cctgaacgtg gcgttgatct gtgcggcttc cgcatagatc gcggccccga ggccggtcgg    4320
gtcgccccag tggaagcgga tttgcgggta ggcccaggtg cgtgcggttt cgaacagggc    4380
gcagtttcgg ccgaggccga tcgggttctc acggcgcgat cgggtttgcc gccagcgcgt    4440
```

```
tggcggcatg tggatgccga gttccgcctc gagctcggcg agggatcgcc gctcggtgtg   4500
cagccaatgg gtgtcccagt caccgtgagt cgggttcttg gtcatcaggc ccgaatagcc   4560
cttgtccccc tggacggcgc gccggaggcc ttcggtgacg gcggccgcat aggcgagcgg   4620
cttacgacgg gcgtactcgg tgcgggtgaa cggctctgcc agcgcccaca cagcgtgtgc   4680
gtgcccgtta cggggttct  ccacgatcgc gttcggcaga ggatgattcc cggccgccga   4740
cagcgcccgc agcgcggcgt ccgggtggtc aacgtccacg acgagcaggt tgctcaatgc   4800
ctgcgggttc gactcgatgt agcggcgatc cagtgcgtct gatcgccgca tccggtagac   4860
gccgtcgagg aaatcgtcgg ttgccagtgg ccacagcggt agccacagct gttcccaggc   4920
gccgcctgtg tgctcttcca ccgcaaccat ggggaacaca ctcacacaca agatcgattt   4980
attccggtac gacacgccag ccaagtcaga tgtttcggtt tctggagcgg tcctccagac   5040
ctttgagatc cgctccagaa acgtccacaa attattgggg tacgtcgaac caagccttat   5100
caggtatccc ggggttccgg gggtgaacac caccctccga ccgtccaga  atccgtcgat   5160 ctcacctatc cgctcgaagt ccttgagtca gtgacaggac cactgctggg ctcccagcgc   5220
agaaggcaag tgaaggcaga cgactgcggg aggtaagtcg ggtacggcat gaggtccttc   5280
agaagcggcg tcgacgccag gcccacacgc acaatccgct tcccacgagg gacaccaccg   5340
gtagcgcccc ctgcaaccgg cgcagtgtca cgaggcgccg gtactgctcg tttgacagga   5400
actgcagggt cggtgagctc gcgctgggcg gatcccacca gtagctcccc gtgccggtaa   5460
ccgcttgggg ccaagcgaag acacccaccg cggcagcgat ggcaatgcac gtggatggga   5520
acaccaccca gaaccaggga atcctggtg  ccggcccgag acgatcccgg cgcggtaaga   5580
ccacaccggc caccatcgcc acggccccg  acgcaacaag caataaccac cccatgagcg   5640
gacggtacaa gcgccgacgc cgggtggccg ttaggtgcgc gccagcccgt gaccggaccg   5700
gcgaagcgtg ccgctgggcg gcccgccgtg gcgcccgtcc cgtgcccgtt ctgaccggtg   5760
gtctcggtcg ctcgttcctc gcgtcctcac ctgccggtca gcccgtgacc ggactctaga   5820
ggatccccgg gtaccgagct cgaattcgta atcatggtca tagctgtttc ctgtgtgaaa   5880
ttgttatccg ctcacaattc cacacaacat acgagccgga agcataaagt gtaaagcctg   5940
gggtgcctaa tgagtgagct aactcacatt aattgcgttg cgctcactgc ccgctttcca   6000
gtcgggaaac ctgtcgtgcc agctgcatta atgaatcggc caacgcgcgg ggagaggcgg   6060
tttgcgtatt ggagcttggc actgggccaa gctgaatttc tgccattcat ccgcttatta   6120
tcacttattc aggcgtagca ccaggcgttt aagggcacca ataactgcct taaaaaaatt   6180
acgccccgcc ctgccactca tcgcagtact gttgtaattc attaagcatt ctgccgacat   6240
ggaagccatc acagacggca tgatgaacct gaatcgccag cggcatcagc accttgtcgc   6300
cttgcgtata atatttgccc atggtgaaaa cggggcgaa  gaagttgtcc atattggcca   6360
cgtttaaatc aaaactggtg aaactcaccc agggattggc tgagacgaaa aacatattct   6420
caataaaccc tttagggaaa taggccaggt tttcaccgta acacgccaca tcttgcgaat   6480
atatgtgtag aaactgccgg aaatcgtcgt ggtattcact ccagagcgat gaaaacgttt   6540
cagtttgctc atggaaaacg gtgtaacaag ggtgaacact atcccatatc accagctcac   6600
cgtctttcat tgccatacga aattccggat gagcattcat caggcgggca agaatgtgaa   6660
taaaggccgg ataaaacttg tgcttatttt tctttacggt ctttaaaaag gccgtaatat   6720
ccagctgaac ggtctggtta taggtacatt gagcaactga ctgaaatgcc tcaaaatgtt   6780
ctttacgatg ccattgggat atatcaacgg tggtatatcc agtgattttt ttctccattt   6840
```

-continued

```
tagcttcctt agctcctgaa aatctcgata actcaaaaaa tacgcccggt agtgatctta    6900
tttcattatg gtgaaagttg gaacctctta cgtgccgatc aacgtctcat tttcgccaaa    6960
agttggccca gggcttcccg gtatcaacag ggacaccagg atttatttat tctgcgaagt    7020
gatcttccgt tcgacggagt tccactgagc gtcagacccc gtagaaaaga tcaaaggatc    7080
ttcttgagat cctttttttc tgcgcgtaat ctgctgcttg caaacaaaaa aaccaccgct    7140
accagcggtg gtttgtttgc cggatcaaga gctaccaact cttttccga aggtaactgg     7200
cttcagcaga gcgcagatac caaatactgt ccttctagtg tagccgtagt taggccacca    7260
cttcaagaac tctgtagcac cgcctacata cctcgctctg ctaatcctgt taccagtggc    7320
tgctgccagt ggcgataagt cgtgtcttac cgggttggac tcaagacgat agttaccgga    7380
taaggcgcag cggtcgggct gaacggggggg ttcgtgcaca cagcccagct tggagcgaac   7440
gacctacacc gaactgagat acctacagcg tgagcattga gaaagcgcca cgcttcccga    7500
agggagaaag gcggacaggt atccggtaag cggcagggtc ggaacaggag agcgcacgag    7560
ggagcttcca gggggaaacg cctggtatct ttatagtcct gtcgggtttc gccacctctg    7620
acttgagcgt cgattttgt gatgctcgtc aggggggcgg agcctatgga aaaacgccag     7680
caacgcggcc ttttacggt tcctggcctt ttgctggcct tttgctcaca tgttctttcc     7740
tgcgttatcc cctgattctg tggataaccg tattaccgcc tttgagtgag ctgataccgc    7800
tcgccgcagc cgaacgaccg agcgcagcga gtcagtgagc gaggaagcgg aagaagctca    7860
ttcgccattc aggctgcgca actgttggga agggcgatcg gtgcgggcct cttcgctatt    7920
acgccagctg gcgaaagggg gatgtgctgc aaggcgatta agttgggtaa cgccagggtt    7980
ttcccagtca cgacgttgta aaacgacggc cagtgccaag cttgcatgcc tgcaggtc     8038
```

PLASMIDS AND UTILIZATION THEREOF

TECHNICAL FIELD

The present invention relates to novel plasmids derived from any of microorganisms belonging to the genus *Rhodococcus* (hereinafter referred to as "the genus *Rhodococcus*") and to utilization thereof. More specifically, the invention relates to plasmids or their partial DNA fragments (hereinafter also referred to simply as "DNA fragments"), and to shuttle vectors, vectors, transformants, aminoketone asymmetric reductase production methods and optically active aminoalcohol production methods which utilize them.

BACKGROUND ART

The genus *Rhodococcus* is known to produce enzymes involved in nitrile metabolism and to produce enzymes which asymmetrically reduce aminoketones. In particular, *Rhodococcus erythropolis* is known to have very high aminoketone asymmetric reduction activity. Such microorganisms and enzymes act on α-aminoketones to high selectively produce optically active β-aminoalcohols at high yields (for example, Patent documents 1 and 5). Thus, it has long been desired to develop a host-vector system intended for mass production of useful enzymes and the like in the genus *Rhodococcus*. However, the development of vectors suitable for the genus *Rhodococcus* as hosts has lagged behind. Only a few strains of the genus *Rhodococcus* have been found with plasmids, namely *Rhodococcus* sp. H13-A (Non-patent document 1), *Rhodococcus rhodochrous* ATCC4276 (Patent document 2), *Rhodococcus rhodochrous* ATCC4001 (Patent document 3) and *Rhodococcus erythropolis* IFO12320 (Patent document 4).

[Patent document 1] WO01/73100
[Patent document 2] Japanese Unexamined Patent Publication HEI No. 4-148685
[Patent document 3] Japanese Unexamined Patent Publication HEI No. 4-330287
[Patent document 4] Japanese Unexamined Patent Publication HEI No. 9-28379
[Patent document 5] WO02/070714
[Non-patent document 1] J. Bacteriol., 170, 638, 1988

DISCLOSURE OF THE INVENTION

Problems to be Solved by the Invention

As mentioned above, it has been desired to develop new vectors for breeding and improve to industrially useful strains (mutant strains) from the genus *Rhodococcus*. In particular, self-cloning systems are preferred from the standpoint of safety of the recombinant DNA microbes and their products which may be used as foods and additives. It is an object of the present invention to provide novel plasmids that can be used as vectors for such a host-vector system.

It is desirable to create recombinant microbes suitable for industrial application from among *Rhodococcus erythropolis* which has aminoketone asymmetric reduction activity. In particular, it is a first object of the invention to provide novel plasmids or their partial DNA fragments which can be used to create such recombinant microbes.

If a plasmid such as described above can be obtained, it would become easy to construct a shuttle vector that is replicable even in other microbes. It is therefore a second object of the invention to provide nucleotide sequence data relating to DNA replication (replication region, etc.) necessary for construction of such a shuttle vector.

It is a third object of the invention to provide shuttle vectors that are replicable in both the genus *Rhodococcus* and *E. coli*.

It is a fourth object of the invention to apply the shuttle vectors to an aminoketone asymmetric reductase.

Means for Solving the Problems

The present inventors carefully screened plasmids for vector construction from among *Rhodococcus* strains, and as a result discovered several novel plasmids usable as vectors for host-vector systems.

Furthermore, the present inventors found that it is possible to construct shuttle vectors by transferring into the aforementioned plasmids a drug resistance gene and a gene region that is replicable in *E. coli*. As a result there were obtained nucleotide sequence data, plasmids and shuttle vectors that achieve the objects stated above, and the present invention has thereupon been completed.

Specifically, the present invention provides a DNA fragment, a DNA, a plasmid, a shuttle vector, a vector, a transformant, a method for production of an aminoketone asymmetric reductase, and a method for production of an optically active aminoalcohol, according to following (1) to (39).

(1) A DNA fragment having at least one nucleotide sequence selected from the group consisting of the nucleotide sequences set forth as SEQ ID NO: 35, SEQ ID NO: 36 and SEQ ID NO: 37.

(2) A plasmid or a partial DNA fragment thereof, characterized by comprising a DNA replication region having at least one nucleotide sequence selected from the group consisting of the nucleotide sequences set forth as SEQ ID NO: 35, SEQ ID NO: 36 and SEQ ID NO: 37.

(3) A DNA fragment having at least one nucleotide sequence selected from the group consisting of the nucleotide sequences set forth as SEQ ID NO: 1, SEQ ID NO: 4, SEQ ID NO: 14, SEQ ID NO: 17 and SEQ ID NO: 22.

(4) A plasmid or a partial DNA fragment thereof, characterized by comprising a coding region for a DNA replication-related protein having at least one nucleotide sequence selected from the group consisting of the nucleotide sequences set forth as SEQ ID NO: 1, SEQ ID NO: 4, SEQ ID NO: 14, SEQ ID NO: 17 and SEQ ID NO: 22.

(5) A plasmid or a partial DNA fragment thereof, characterized by comprising a coding region for a DNA replication-related protein having at least one nucleotide sequence selected from the group consisting of the nucleotide sequences set forth as SEQ ID NO: 1, SEQ ID NO: 4, SEQ ID NO: 14, SEQ ID NO: 17 and SEQ ID NO: 22 and comprising a DNA replication region having at least one nucleotide sequence selected from the group consisting of the nucleotide sequences set forth as SEQ ID NO: 35, SEQ ID NO: 36 and SEQ ID NO: 37.

(6) A DNA fragment having the nucleotide sequence set forth as SEQ ID NO: 76.

(7) A plasmid or a partial DNA fragment thereof, characterized by comprising a promoter region having the nucleotide sequence set forth as SEQ ID NO: 76.

(8) A plasmid or a partial DNA fragment thereof, characterized by comprising a coding region for a DNA replication-related protein having at least one nucleotide sequence selected from the group consisting of the nucleotide sequences set forth as SEQ ID NO: 1, SEQ ID NO: 4, SEQ ID NO: 14, SEQ ID NO: 17 and SEQ ID NO: 22, comprising a DNA replication region having at least one nucleotide sequence selected from the group consisting of the nucleotide sequences set forth as SEQ ID NO: 35, SEQ ID NO:

36 and SEQ ID NO: 37, and comprising a promoter region having the nucleotide sequence set forth as SEQ ID NO: 76.

(9) A circular plasmid characterized by comprising a plasmid or a partial DNA fragment according to any one of (1) to (8), wherein the numbers of restriction endonuclease cleavage sites are BamH I: 2, EcoR I: 2, Kpn I: 1, Pvu II: 1 Sac I: 1 and Sma I: 1, and the size is approximately 5.4 kbp.

(10) A plasmid having the nucleotide sequence set forth as SEQ ID NO: 73.

(11) A plasmid or a DNA fragment according to any one of (1) to (10), characterized by being derived from a bacterium belonging to the. genus *Rhodococcus*.

(12) A DNA fragment having at least one nucleotide sequence selected from the group consisting of the nucleotide sequences set forth as SEQ ID NO: 70, SEQ ID NO: 71 and SEQ ID NO: 72.

(13) A plasmid or a partial DNA fragment thereof, characterized by comprising a DNA replication region having at least one nucleotide sequence selected from the group consisting of the nucleotide sequences set forth as SEQ ID NO: 70, SEQ ID NO: 71 and SEQ ID NO: 72.

(14) A DNA fragment having at least one nucleotide sequence selected from the group consisting of the nucleotide sequences set forth as SEQ ID NO: 40, SEQ ID NO: 42, SEQ ID NO: 44, SEQ ID NO: 45, SEQ ID NO: 53, SEQ ID NO: 55, SEQ ID NO: 56, SEQ ID NO: 61, SEQ ID NO: 62 and SEQ ID NO: 69.

(15) A plasmid or a partial DNA fragment thereof, characterized by comprising a coding region for a DNA replication-related protein having at least one nucleotide sequence selected from the group consisting of the nucleotide sequences set forth as SEQ ID NO: 40, SEQ ID NO: 42, SEQ ID NO: 44, SEQ ID NO: 45, SEQ ID NO: 53, SEQ ID NO: 55, SEQ ID NO: 56, SEQ ID NO: 61, SEQ ID NO: 62 and SEQ ID NO: 69.

(16) A plasmid or a partial DNA fragment thereof, characterized by comprising a coding region for a DNA replication-related protein having at least one nucleotide sequence selected from the group consisting of the nucleotide sequences set forth as SEQ ID NO: 40, SEQ ID NO: 42, SEQ ID NO: 44, SEQ ID NO: 45, SEQ ID NO: 53, SEQ ID NO: 55, SEQ ID NO: 56, SEQ ID NO: 61, SEQ ID NO: 62 and SEQ ID NO: 69 and comprising a DNA replication region having at least one nucleotide sequence selected from the group consisting of the nucleotide sequences set forth as SEQ ID NO: 70, SEQ ID NO: 71 and SEQ ID NO: 72.

(17) A plasmid or a partial DNA fragment thereof, characterized by comprising a coding region for a DNA replication-related protein having at least one nucleotide sequence selected from the group consisting of the nucleotide sequences set forth as SEQ ID NO: 40, SEQ ID NO: 42, SEQ ID NO: 44, SEQ ID NO: 45, SEQ ID NO: 53, SEQ ID NO: 55, SEQ ID NO: 56, SEQ ID NO: 61, SEQ ID NO: 62 and SEQ ID NO: 69, comprising a DNA replication region having at least one nucleotide sequence selected from the group consisting of the nucleotide sequences set forth as SEQ ID NO: 70, SEQ ID NO: 71 and SEQ ID NO: 72, and comprising a promoter region having the nucleotide sequence set forth as SEQ ID NO: 76.

(18) A DNA fragment having at least one nucleotide sequence selected from the group consisting of the nucleotide sequences set forth as SEQ ID NO: 67 and SEQ ID NO: 47.

(19) A plasmid or a partial DNA fragment thereof, characterized by comprising a mobilization protein region having at least one nucleotide sequence selected from the group consisting of the nucleotide sequences set forth as SEQ ID NO: 67 and SEQ ID NO: 47.

(20) A DNA fragment having the nucleotide sequence set forth as SEQ ID NO: 75.

(21) A plasmid or a partial DNA fragment thereof, characterized by comprising a mobilization-related region having the nucleotide sequence set forth as SEQ ID NO: 75.

(22) A circular plasmid characterized by comprising a plasmid or DNA fragment according to any one of (12) to (21), wherein the numbers of restriction endonuclease cleavage sites are BamH I: 2, Pvu II: 4, Sac I: 3 and Sma I: 4, and the size is approximately 5.8 kbp.

(23) A plasmid having the nucleotide sequence set forth as SEQ ID NO: 74.

(24) A plasmid or a DNA fragment according to any one of (12) to (23), characterized by being derived from a bacterium belonging to the genus *Rhodococcus*.

(25) A DNA fragment having the nucleotide sequence set forth as SEQ ID NO: 77.

(26) A DNA fragment characterized by comprising a promoter region having the nucleotide sequence set forth as SEQ ID NO: 77.

(27) A shuttle vector replicable in bacteria belonging to the genus *Rhodococcus* and *E. coli*, and comprising a plasmid or partial DNA fragment thereof according to any one of (1) to (26) and a DNA region replicable in *E. coli*.

(28) A vector characterized by being constructed using a shuttle vector according to (27).

(29) A vector characterized by comprising a plasmid or DNA fragment according to any one of (6), (7), (25) or (26).

(30) A vector according to (28) or (29), characterized by having inserted therein an aminoketone asymmetric reductase gene.

(31) A vector according to (30), characterized in that the aminoketone asymmetric reductase gene is a nucleic acid coding for a protein consisting the amino acid sequence set forth as SEQ ID NO: 78, or a nucleic acid that codes for a protein having the amino acid sequence set forth as SEQ ID NO: 78 with a deletion, insertion, substitution or addition of one or a plurality of amino acids, and having aminoketone asymmetric reduction activity.

(32) A vector according to (30), characterized in that the aminoketone asymmetric reductase gene is a nucleic acid consisting the nucleotide sequence set forth as SEQ ID NO: 79, or a nucleic acid that hybridizes with nucleic acid having a nucleotide sequence complementary to the nucleotide set forth as SEQ ID NO: 79 under stringent conditions, and that codes for a protein having aminoketone asymmetric reduction activity.

(33) A transformant containing a vector according to (28) or (29).

(34) A transformant containing a vector according to any one of (30) to (32).

(35) A method for production of an aminoketone asymmetric reductase, which comprises a culturing step in which a transformant according to (34) is cultured in medium that allows growth of said transformant, and
a purification step in which the aminoketone asymmetric reductase is purified from said transformant obtained in said culturing step.

(36) A method for production of an optically active aminoalcohol, wherein an aminoketone asymmetric reductase obtained by the production method of (35) is reacted with an enantiomeric mixture of an α-aminoketone compound represented by the following general formula (1):

[Chemical Formula 1]

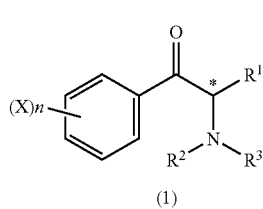

(1)

wherein X may be the same or different and represents at least one species selected from the group consisting of halogen, lower alkyl, hydroxyl optionally protected with a protecting group, nitro and sulfonyl;
n represents an integer of 0 to 3;
$R^1$ represents lower alkyl;
$R^2$ and $R^3$ may be the same or different and represent at least one species selected from the group consisting of hydrogen and lower alkyl; and
* represents asymmetric carbon,
or a salt thereof, to produce an optically active aminoalcohol compound represented by the following general formula (2):

[Chemical Formula 2]

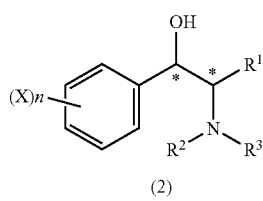

(2)

wherein X, n, $R^1$, $R^2$, $R^3$ and * have the same definitions as above, and having the desired optical activity.
(37) A method for production of an optically active aminoalcohol, wherein a transformant according to (34) is reacted with an enantiomeric mixture of an α-aminoketone compound represented by the following general formula (1):

[Chemical Formula 3]

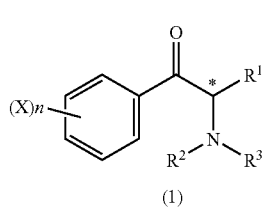

(1)

wherein X may be the same or different and represents at least one species selected from the group consisting of halogen, lower alkyl, hydroxyl optionally protected with a protecting group, nitro and sulfonyl;
n represents an integer of 0 to 3;
$R^1$ represents lower alkyl;
$R^2$ and $R^3$ may be the same or different and represent at least one species selected from the group consisting of hydrogen and lower alkyl; and
* represents asymmetric carbon,
or a salt thereof, to produce an optically active aminoalcohol compound represented by the following general formula (2):

[Chemical Formula 4]

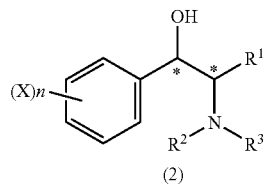

(2)

wherein X, n, $R^1$, $R^2$, $R^3$ and * have the same definitions as above, and having the desired optical activity.
(38) A production method for an optically active aminoalcohol according to (37), wherein the production method for the optically active aminoalcohol is carried out with further addition of a compound represented by the following general formula (3):

[Chemical Formula 5]

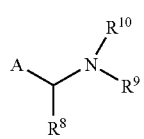

(3)

wherein A represents the following formula (Y) or (Z):

[Chemical Formula 6]

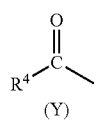

(Y)

wherein $R^4$ represents hydrogen, optionally substituted C1-3 alkyl, a C5-10 hydrocarbon ring which is bonded to $R^8$ or a 5- to 8-membered heterocyclic skeleton containing 1-3 heteroatoms which is bonded to $R^8$,

[Chemical Formula 7]

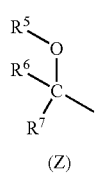

(Z)

wherein $R^5$ represents hydrogen, C1-3 alkyl or a 5- to 8-membered heterocyclic skeleton containing 1-3 heteroatoms which is bonded to $R^6$ or $R^9$;
$R^6$ represents hydrogen, optionally substituted C1-3 alkyl, a C5-10 hydrocarbon ring which is bonded to $R^8$ or a 5- to 8-membered heterocyclic skeleton containing 1-3 heteroatoms which is bonded to $R^5$ or $R^9$;
$R^7$ represents hydrogen or optionally substituted C1-6 alkyl;
$R^8$ represents hydrogen, carboxyl, optionally substituted C1-6 alkyl, a 5- to 8-membered heterocyclic skeleton containing 1-3 heteroatoms which is bonded to $R^4$ or a C5-10 hydrocarbon ring which is bonded to $R^6$;

R⁹ represents hydrogen, optionally substituted C1-6 alkyl, optionally substituted C1-6 alkyloxycarbonyl, optionally substituted acyl or a 5- to 8-membered heterocyclic skeleton containing 1-3 heteroatoms which is bonded to R⁵ or R⁶; and R¹⁰ represents hydrogen or optionally substituted C1-6 alkyl, or a pharmaceutically acceptable salt or solvate thereof, for production of an optically active aminoalcohol.

(39) A shuttle vector according to (27), having a nucleotide sequence selected from the group consisting of the nucleotide sequences set forth as SEQ ID NO: 89 to SEQ ID NO: 100.

EFFECT OF THE INVENTION

The plasmids of the invention are novel plasmids unknown to the prior art, and are valuable as vectors for host-vector systems belonging to the industrially useful the genus *Rhodococcus*. They are of particular utility in the creation of recombinant microbes capable of industrial asymmetric reduction of aminoketones. An example of asymmetric reduction of an aminoketone to which such microbes may contribute is a reaction for production of d-(1S, 2S)-pseudoephedrine from 1-2-methylamino-1-phenyl-1-propanone.

The plasmids of the invention can coexist in single *Rhodococcus* cell and therefore can be used not only alone for their replicating function, but also as compatible plasmids. That is, by inserting different protein (for example, enzyme) genes into the different plasmids, it is possible to express the proteins simultaneously in the same cell.

The shuttle vectors of the invention are useful for creation of industrially useful recombinant microbes of the genus *Rhodococcus* and *Escherichia coli*.

The nucleotide sequence data relating to DNA replication obtained from the plasmids of the invention may serve as the basis for construction of the aforementioned shuttle vectors, and specifically they provide DNA fragments as constituent elements of the vectors.

BEST MODE FOR CARRYING OUT THE INVENTION

Preferred embodiments of the invention will now be explained.

The first plasmid of the invention is a plasmid isolated from the genus *Rhodococcus*, or a derivative thereof. Specifically, it may be isolated from, for example, *Rhodococcus erythropolis* IAM1400, IAM1503, JCM2893 and JCM2894 strains, has a size of approximately 5.4 kbp and is a circular plasmid cleavable by the restriction enzymes shown in Table 1. The plasmids isolated from each of these strains are designated as pRET1100, pRET1300, pRET1500 and pRET1700, respectively. Plasmids of the invention may be prepared from these sample strains by publicly known methods (for example, boiling, alkali dissolution, cesium chloride density gradient ultracentrifugation: Lab Manual Idenshi Kogaku, 3rd Edition, Chapter 10, pp. 55-59, Maruzen).

TABLE 1

| Restriction enzyme | Number of cleavage sites | Fragment sizes (kbp) |
|---|---|---|
| BamH I | 2 | 0.4, 5.0 |
| EcoR I | 2 | 0.3, 5.1 |
| Kpn I | 1 | 5.4 |
| Pvu II | 1 | 5.4 |
| Sac I | 1 | 5.4 |
| Sma I | 1 | 5.4 |

Figure 1:
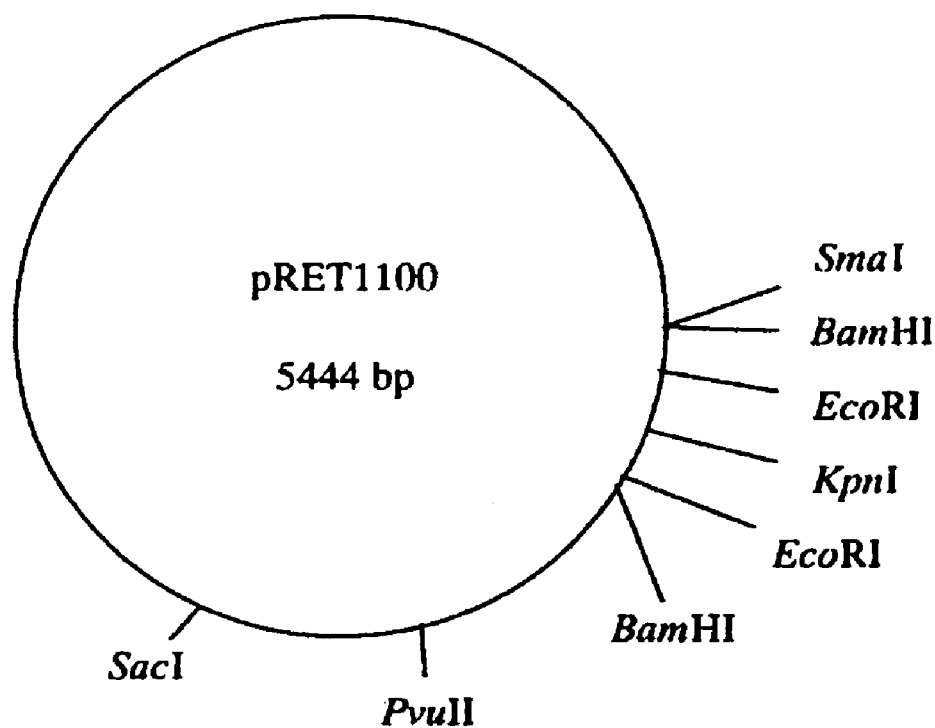
FIG. 1 is a restriction enzyme cleavage map of plasmid pRET1100.

FIG. 1 shows a restriction enzyme cleavage map for pRET1100. This plasmid was sequenced by a publicly known method (using a fluorescent automatic sequencer, for example) and its full nucleotide sequence was revealed to be 5444 bp set forth as SEQ ID NO: 73 of the Sequence Listing.

The second plasmid of the invention is also a plasmid isolated from the genus *Rhodococcus*, or its derivative. Specifically, it may be isolated from, for example, *Rhodococcus rhodnii* JCM3203, has a size of approximately 5.8 kbp and is a circular plasmid cleavable by the restriction enzymes shown in Table 2. This plasmid is designated as pRET1000.

TABLE 2

| Restriction enzyme | Number of cleavage sites | Fragment sizes (kbp) |
|---|---|---|
| BamH I | 2 | 2.0, 3.8 |
| Pvu II | 4 | 0.1, 1.4, 2.0, 2.3 |
| Sac I | 3 | 0.9, 1.0, 3.9 |
| Sma I | 4 | 0.1, 1.2, 1.6, 2.9 |

Figure 2:
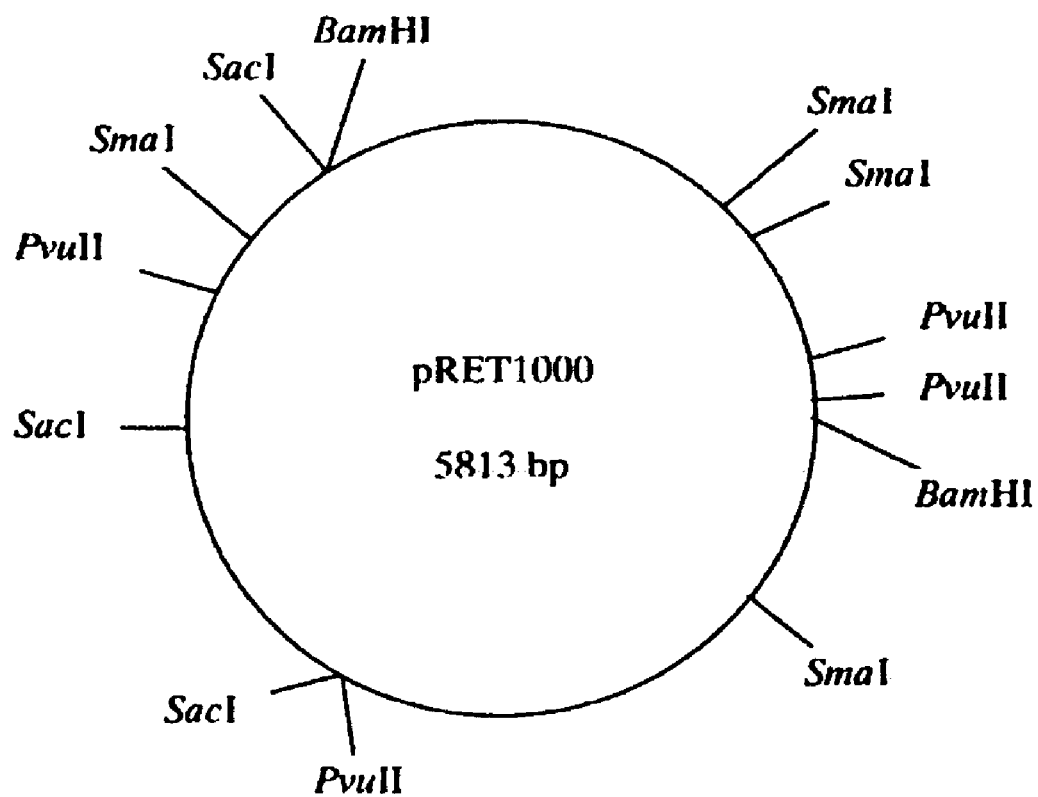
FIG. 2 is a restriction enzyme cleavage map of plasmid pRET1000.

FIG. 2 shows a restriction enzyme cleavage map for pRET1000. This plasmid was also sequenced by a publicly known method and its full nucleotide sequence was revealed to be 5813 bp set forth as SEQ ID NO: 74 of the Sequence Listing.

The plasmids of the invention (natural- or wild-types) are circular plasmids that can also be defined by the restriction enzyme cleavage patterns shown in Tables 1 and 2. Thus, the present invention encompasses the following two types of circular plasmids.

(1) A circular plasmid derived from a *Rhodococcus* strain, characterized by having a size of approximately 5.4 kbp and possessing the following restriction enzyme cleavage sites: BamH I:2, EcoR I:2, Kpn I:1, Pvu II:1, Sac I:1 and Sma I:1.

(2) A circular plasmid derived from a *Rhodococcus* strain, characterized by having a size of approximately 5.8 kbp and possessing the following restriction enzyme cleavage sites: BamH I:2, Pvu II:4, Sac I:3 and Sma I:4.

As a result of analysis of the nucleotide sequences of plasmids pRET1100 and pRET1000 (i.e., SEQ ID NO: 73 and SEQ ID NO: 74), there is predicted the existence of a group of nucleotide sequences (open reading frames, hereinafter "orf") coding for proteins for DNA replication or other functions.

In the relevant technical field, "DNA replication" refers to using DNA itself as template to form two double-stranded DNA molecules exactly identical to existing double-stranded DNA (parent DNA). The replication mechanism consists of three stages: initiation from the starting point of replication (replication origin), DNA chain elongation and termination.

During replication, a portion of the DNA double strand is unraveled and new DNA strands are synthesized complementary to each single strand. The double strand is unraveled by DNA helicase and helix destabilizing proteins (also known as single-strand DNA-binding protein), and the unraveled portion is referred to as the replication fork. The template DNA in the direction from 3' to 5' toward the replication fork is the "leading strand", and the one in the direction from 5' to 3' is the "lagging strand". DNA polymerase extends the DNA strand in the direction from 5' to 3'. Therefore when the leading strand is the template, DNA is synthesized in the direction of the replication fork. However when the opposite lagging strand is the template, the DNA strand must be extended in the opposite direction from the replication fork. Consequently, replication of the lagging strand is accomplished in fragments of about 200 bases, known as Okazaki fragments. Every approximately 200 bases, RNA primer is used with DNA as template to synthesize 10 bases of RNA in the direction from 5' to 3'. From this RNA as primer, DNA polymerase synthesizes a DNA strand in the direction from 5' to 3' on the lagging strand as template. The replicated DNA fragment of approximately 200 bases then binds to the single-stranded DNA from which RNA is removed. In this replication mechanism, several proteins including DNA helicase and helix-destabilizing protein work together to form the replicating machinery. Other proteins involved include DNA topoisomerase (which prevents twisting during the DNA replication), replication initiation proteins and replication termination proteins. The DNA replication mechanism is described in detail in, for example, "Saibou no Bunshiseibutsugaku [Molecular Biology of the Cell]", 3rd Edition, translated by Keiko Nakamura et al., pp. 251-262, Kyoikusha, 1996.

Upon analysis of the nucleotide sequences of the plasmids pRET1100 and pRET1000, they were found to include sequences of AT-rich homologous or analogous repeats and a sequence thought to have a DNA secondary structure, i.e. a nucleotide sequence predicted to be a DNA replication region (a nucleotide sequence region recognized by proteins involved in DNA replication or a region including the DNA replication origin), in the vicinity of the aforementioned orf relating to DNA replication.

DNA replication requires a DNA replication region and a region coding for a protein involved in DNA replication (hereinafter referred to as "DNA replication-related protein"). According to the present invention it is possible to obtain data relating to the nucleotide sequences of these regions for both plasmids pRET1100 and pRET1000.

First, the nucleotide sequences set forth as SEQ ID NO: 35-37 were identified as DNA replication regions for plasmid pRET1100. As regions coding for proteins related to DNA replication there were identified the nucleotide sequences set forth as SEQ ID NO: 1-3 (orf1), the nucleotide sequence set forth as SEQ ID NO: 4 (orf2), the nucleotide sequences set forth as SEQ ID NO: 5-16 (orf3), the nucleotide sequences set forth as SEQ ID NO: 17-21 (orf4), the nucleotide sequences set forth as SEQ ID NO: 22-26 (orf5), the nucleotide sequence set forth as SEQ ID NO: 27 or 28 (orf6), the nucleotide sequence set forth as SEQ ID NO: 29 or 30 (orf7), the nucleotide sequence set forth as SEQ ID NO: 31 or 32 (orf8), and the nucleotide sequence set forth as SEQ ID NO: 33 or 34 (orf9).

Construction of a plasmid capable of DNA replication from pRET1100 requires that the recombinant plasmid have at least one DNA replication region and at least one coding region (orf) for a DNA replication-related protein. Thus, the (recombinant) plasmids of the invention are characterized by comprising at least one DNA replication region and at least one coding region for a DNA replication-related protein. The coding region for a DNA replication-related protein preferably has a nucleotide sequence selected from the group consisting of the nucleotide sequences set forth as SEQ ID NO: 1, 4, 14, 17 and 22.

The region of the nucleotide sequence set forth as SEQ ID NO: 76 has been suggested as a promoter involved in expression of replication-related proteins, and the plasmids of the invention preferably comprise a promoter region having the nucleotide sequence set forth as SEQ ID NO: 76.

For plasmid construction, the DNA fragments are appropriately selected based on the aforementioned nucleotide sequence data. The present invention also encompasses derivatives or functional (DNA-replicating) fragments of the plasmids.

Next, the nucleotide sequences set forth as SEQ ID NO: 70-72 were identified as DNA replication regions for plasmid pRET1000. As regions coding for proteins related to DNA replication there were identified the nucleotide sequences set forth as SEQ ID NO: 38-41 (orf10), the nucleotide sequence set forth as SEQ ID NO: 42 or 43 (orf11), the nucleotide sequence set forth as SEQ ID NO: 44 (orf12), the nucleotide sequence set forth as SEQ ID NO: 45 or 46 (orf13), the nucleotide sequences set forth as SEQ ID NO: 48-50 (orf14), the nucleotide sequence set forth as SEQ ID NO: 51 or 52 (orf15), the nucleotide sequence set forth as SEQ ID NO: 53 or 54 (orf16), the nucleotide sequence set forth as SEQ ID NO: 55 (orf17), the nucleotide sequences set forth as SEQ ID NO: 56-60 (orf18), the nucleotide sequence set forth as SEQ ID NO: 61 (orf19), the nucleotide sequence set forth as SEQ ID NO: 62 (orf20), and the nucleotide sequences set forth as SEQ ID NO: 63-69 (orf21).

Construction of a plasmid capable of DNA replication from pRET1000 requires that the recombinant plasmid have at least one DNA replication region and at least one coding region (orf) for a DNA replication-related protein. Thus, the (recombinant) plasmids of the invention are characterized by comprising at least one DNA replication region and at least one coding region for a DNA replication-related protein. The coding region for a DNA replication-related protein preferably has a nucleotide sequence selected from the group consisting of the nucleotide sequences set forth as SEQ ID NO: 40, 42, 44, 45, 53, 55, 56, 61, 62 and 69.

The regions with the nucleotide sequences set forth as SEQ ID NO: 67 and 47 are homologous with mobilization proteins, and have been implicated in mobilization. The region with the nucleotide sequence set forth as SEQ ID NO: 75 has been implicated in gene expression of mobilization protein and suggested as a recognition site for an expressed protein. Thus, the plasmids of the invention preferably include mobilization protein regions having the nucleotide sequences set forth as SEQ ID NO: 67 and 47, or include a region involved in mobilization having the nucleotide sequence set forth as SEQ ID NO: 75.

For plasmid construction, the DNA fragments are appropriately selected based on the aforementioned nucleotide sequence data. The present invention also encompasses derivatives or functional (DNA-replicating) fragments of the plasmids.

The plasmids or DNA fragments of the invention may also contain nucleotide sequences with a substitution, deletion or insertion of one or a plurality of nucleotides in a DNA replication region, DNA replication-related protein coding region, promoter region, mobilization protein region or mobilization-related region, or a portion thereof, so long as the function of each region is not impaired.

The shuttle vectors of the invention may be any which comprise a plasmid or DNA fragment having a DNA replication region, DNA replication-related protein coding region, promoter region, mobilization protein region or mobilization-related region, and a DNA region that is replicable in *E. coli*, and which are replicable in the genus *Rhodococcus* and *E. coli*, such as those having the nucleotide sequences set forth as SEQ ID NO: 89 to 100. The shuttle vectors of the invention may also have nucleotide sequences with one or a plurality of nucleotide substitutions, deletions or insertions in the aforementioned nucleotide sequences, so long as they are replicable in the genus *Rhodococcus* and *E. coli*.

The "plurality" referred to above will differ depending on the type of region, and specifically may be 2-1100, preferably 2-800, more preferably 2-300, even more preferably 2-100, yet more preferably 2-20 and most preferably 2-10.

As a plasmid or DNA fragment having substantially the same nucleotide sequence as the aforementioned DNA replication region, DNA replication-related protein coding region, promoter region, mobilization protein region or mobilization-related region, or a portion thereof, there may be mentioned specifically, a nucleotide sequence which hybridizes with a DNA replication region, DNA replication-related protein coding region, promoter region, mobilization protein region or mobilization-related region, or a portion thereof, under stringent conditions. Here "stringent conditions" are conditions under which specific hybrids are formed and non-specific hybrids are not formed. While it is difficult to precisely quantify the conditions, one example is a set of conditions that permit hybridization of DNA with high homology, such as 80% or greater, preferably 90% or greater or more preferably 95% or greater homology, while not permitting hybridization of DNA with lower homology. More specifically, there may be mentioned hybridization conditions with ordinary Southern hybridization washing at 60° C., 1×SSC, 0.1% SDS or preferably Southern hybridization washing at 0.1× SSC, 0.1% SDS corresponding salt concentration. When a DNA fragment with a length of approximately 300 bp is used as a portion of the DNA replication region, DNA replication-related protein coding region, promoter region, mobilization protein region or mobilization-related region, the hybridization washing conditions may be 50° C., 2×SSC, 0.1% SDS.

The aforementioned plasmid or DNA fragment having substantially the same nucleotide sequence as the aforementioned DNA replication region, DNA replication-related protein coding region, promoter region, mobilization protein region or mobilization-related region, or a portion thereof, may be obtained by for example, modification of a DNA replication region, DNA replication-related protein coding region, promoter region, mobilization protein region or mobilization-related region, or a portion thereof, by site-directed mutagenesis so as to have a substitution, deletion or insertion of nucleotides at a specific site. Such modified DNA may also be obtained by mutation treatment known in the prior art. As mutation treatments there may be mentioned methods of in vitro treatment of DNA including a DNA replication region, DNA replication-related protein coding region, promoter region, mobilization protein region or mobilization-related region, or a portion thereof, with hydroxylamine or the like, and methods of treating a microbe possessing the DNA above, such as the genus *Escherichia*, with ultraviolet rays or with a mutagenic agent ordinarily used for mutagenesis such as N-methyl-N'-nitro-N-nitrosoguanidine (NTG) or EMS.

Nucleotide substitutions, deletions or insertions as mentioned above include those found in naturally occurring mutants or variants due to differences in *Rhodococcus* strains.

A shuttle vector of the invention includes a DNA fragment (A) as the aforementioned plasmid or portion thereof, and a DNA region (B) which is replicable in *E. coli*. In some cases it is preferred for the shuttle vector to comprise a DNA region including a drug resistance gene. In the relevant technical field, a "shuttle vector" is a vector which comprises the DNA replication mechanism for two different cell types, and preferably also a drug resistance gene or the like as a selective marker, allowing its auto-replication in the two different cell-types. The DNA fragment (A) as the aforementioned plasmid or portion thereof is a DNA region that is replicable in the genus *Rhodococcus*. The DNA region (B) which is replicable in *E. coli* may be a full plasmid or a portion thereof, so long as it can be replicated and amplified in *E. coli*. As such DNA regions that are replicable in *E. coli* there may be used, for example, the plasmids pUC18, pHSG299 and pHSG398.

When the shuttle vector of the invention includes a drug resistance gene, the preferred ones are ampicillin resistance gene, kanamycin resistance gene and chloramphenol resistance gene, but there are no particular restrictions on the manner of drug so long as the gene is expressed in the genus *Rhodococcus* and *E. coli* as hosts and confers drug resistance to the host cells, in order to allow verification of the presence of plasmids in the two genera based on resistance to the drug. Also, a plurality of such drug resistance genes may be used in combination.

The shuttle vector preferably contains multiple cloning sites (multicloning sites), and the cloning sites and drug resistance gene may be induced from, for example, an *E. coli* plasmid. That is, a publicly known *E. coli* plasmid such as one listed above may be cleaved with an appropriate restriction endonuclease and a DNA region containing the cloning sites and drug resistance gene constructed and ligated with another DNA fragment (a DNA region which is replicable in the genus *Rhodococcus*).

Figure 3:
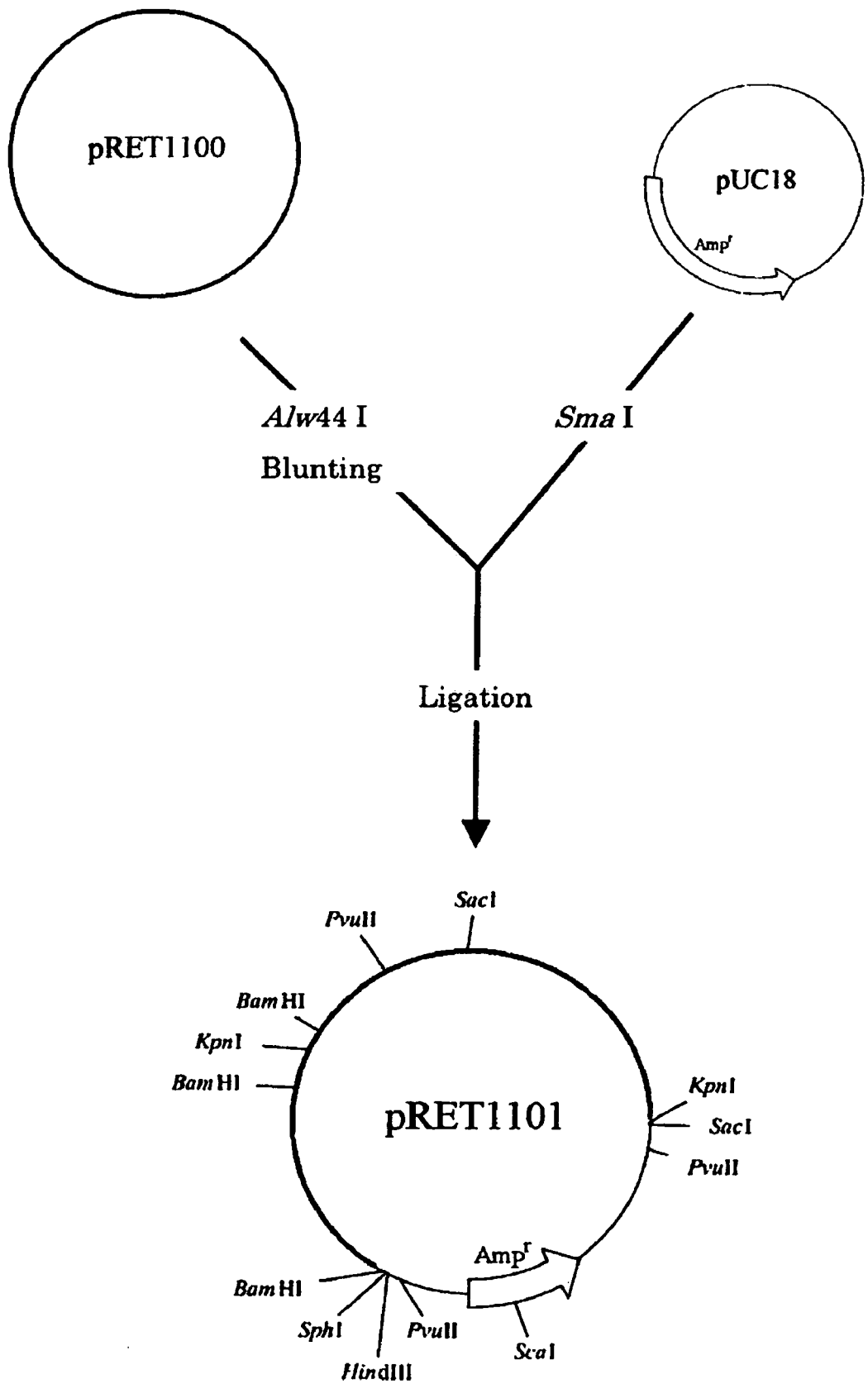
FIG. 3 is a summary illustration for construction of shuttle vector pRET1101.
Figure 4:
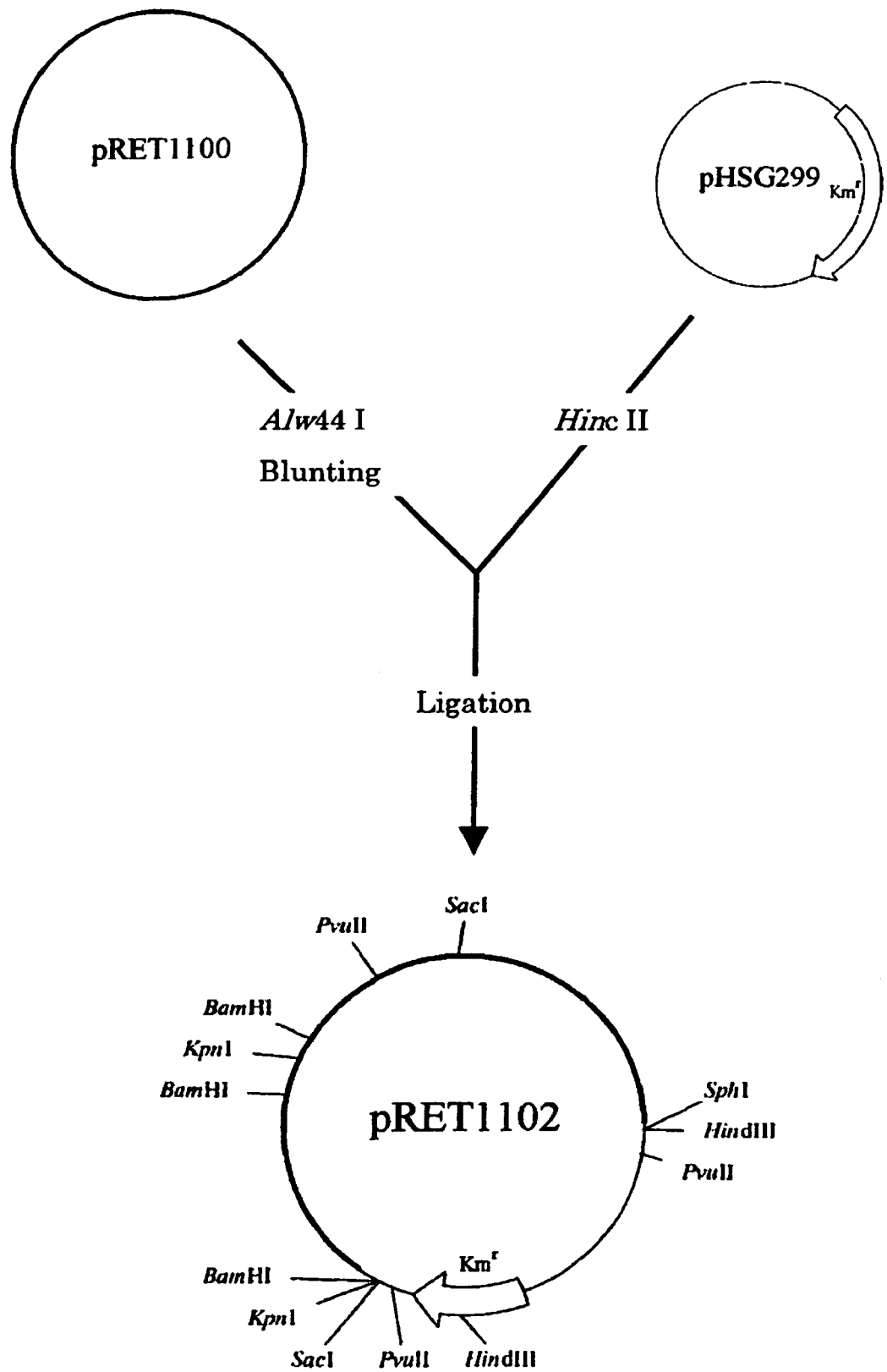
FIG. 4 is a summary illustration for construction of shuttle vector pRET1102.
Figure 5:
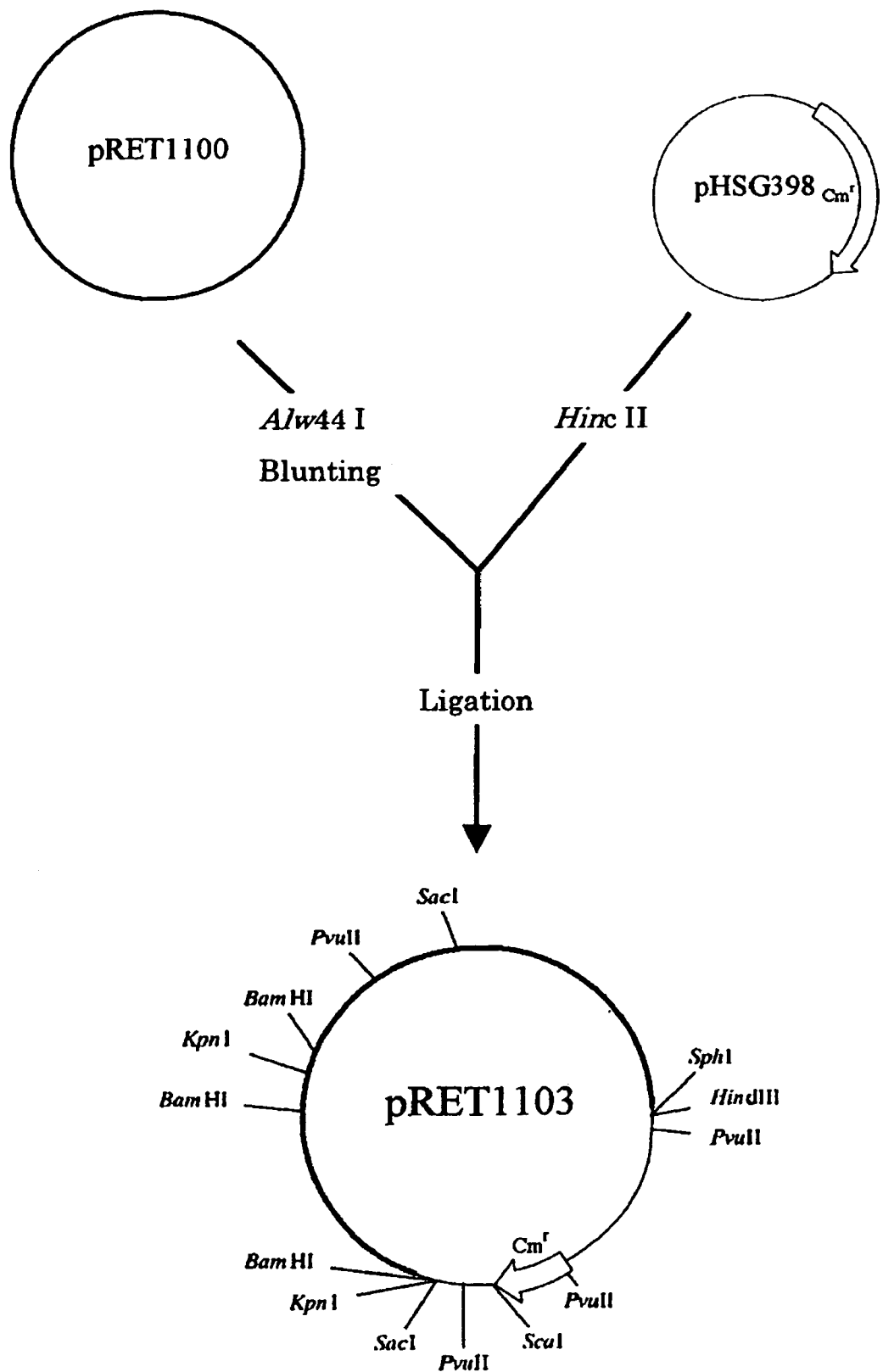
FIG. 5 is a summary illustration for construction of shuttle vector pRET1103.

As an illustration, outline of shuttle vector constructions is shown in FIGS. 3 to 5. The shuttle vectors may be constructed by treating the aforementioned plasmids and *E. coli* plasmids With suitable restriction endonucleases and then ligating them. In this manner, the present inventors constructed 18 shuttle vectors (Table 5) using the *Rhodococcus* plasmids pRET1000, pRET1100 or pRET1200, and the *E. coli* plasmids pUC18, pHSG299 or pHSG398.

The shuttle vectors of the invention are replicable in the genus *Rhodococcus* and *E. coli* as hosts, and are industrially useful. The *Rhodococcus* and *E. coli* strains transformed by the shuttle vectors of the invention, as well as other microbial transformants, are useful in this way and such transformants are also encompassed by the scope of the invention.

A vector of the invention is characterized by being constructed using a shuttle vector of the invention. Specifically, it is a vector having target DNA inserted therein which is to be introduced into the shuttle vector of the invention. The DNA to be introduced and the shuttle vector of the invention are treated with appropriate restriction endonucleases and then ligated them to construct the vector. The vector may then be used to obtain transformants having the desired DNA transferred therein.

As examples of DNA to be inserted there may be mentioned aminoketone asymmetric reductase genes and coenzyme-regenerating system enzyme genes. Aminoketone asymmetric reductase genes are genes coding for aminoketone asymmetric reductases as described in WO02/070714, and more specifically, DNA coding for a protein comprising the amino acid sequence set forth as SEQ ID NO: 78 (aminoketone asymmetric reductase derived from *R. erythropolis* MAK-34), and particularly DNA comprising the nucleotide sequence set forth as SEQ ID NO: 79. The entirety of the content described in WO02/070714 is incorporated herein by reference.

An aminoketone asymmetric reductase is any having the properties described in WO02/070714, and includes a protein having the amino acid sequence set forth as SEQ ID NO: 78 of the Sequence Listing, as well as proteins having amino acid sequences obtained by deletion, insertion, substitution or addition of one or more amino acids in the aforementioned amino acid sequence, and exhibiting aminoketone asymmetric reduction activity. Aminoketone asymmetric reduction activity is activity of producing an optically active aminoalcohol represented by general formula (2) above using an α-aminoketone represented by general formula (1) above as the substrate.

There are no particular restrictions on the methods of deletion, insertion, substitution and addition, and any publicly known methods may be employed. For example, there may be mentioned the methods described in "Zoku Seikagaku Jikken Kouza 1, Idenshi Kenkyuhou II", edited by the Japanese Biochemical Society, p 105 (Hirose, S.), Tokyo Kagaku Dojin (1986); "Shin Seikagaku Jikken Kouza 2, Kakusan III (Recombinant DNA Technology)", edited by the Japanese Biochemical Society, p. 233 (Hirose, S.), Tokyo Kagaku Dojin (1992); R. Wu, L. Grossman ed., "Methods in Enzymology", Vol. 154, p. 350 & p. 367, Academic Press, New York (1987); R. Wu, L. Grossman, ed., "Methods in Enzymology", Vol. 100, p. 457 & p. 468, Academic Press, New York (1983); J. A. Wells et al., "Gene", Vol. 34, p. 315 (1985);. T. Grundstroem et al., "Nucleic Acids Res", Vol. 13, p. 3305 (1985); J. Taylor et al., "Nucleic Acids Res.", Vol. 13, p. 8765 (1985); R. Wu, ed., "Methods in Enzymology", Vol. 155, p. 568, Academic Press, New York (19.87); and A. R. Oliphant et al., "Gene", Vol. 44, p. 177 (1986). As specific examples, there may be mentioned the site-directed mutagenesis method (site-specific mutagenesis method) utilizing synthetic oligonucleotides, the Kunkel method, the dNTP[αS] method (Eckstein method), and the region-directed mutagenesis method using sulfurous acid or nitrous acid.

Sugar chains are attached to the majority of proteins, and substitution of one or a plurality of amino acids can modify the attachment of sugar chains. Thus, the aminoketone asymmetric reductases of the invention also include proteins having the amino acid sequence set forth as SEQ ID NO: 78 of the Sequence Listing and having modifications of sugar chains, so long as they exhibit the aforementioned aminoketone asymmetric reduction activity.

The aminoketone asymmetric reductases of the invention may also have modifications of their amino acid residues by chemical methods, or their derivatives may be enhanced by modification or partial degradation using peptidase enzymes such as pepsin, chymotrypsin, papain, bromelain, endopeptidase and exopeptidase.

When the aminoketone asymmetric reductases of the invention are produced by a gene recombinant method, a fusion protein may be expressed and then converted or processed into a protein having biological activity which is substantially equivalent to a natural aminoketone asymmetric reductase either in vivo or ex vivo. In this case, a fusion production method ordinarily employed for genetic engineering may be used, and the fusion protein may be purified by affinity chromatography or the like, utilizing the fused portion thereof. Modification and enhancement of protein structures may be carried out with reference to "Shin Seikagaku Jikken Kouza 1, Tanpakushitsu VII, Tanpakushitsu Kogaku", edited by the Japanese Biochemical Society, Tokyo Kagaku Dojin (1993), by the methods described therein, the methods described in literature cited therein, or methods which are essentially equivalent thereto.

The aminoketone asymmetric reductase of the invention may also differ from naturally occurring forms in the identities of one or more of the amino acid residues or in the positions of one or more of the amino acid residues. The present invention also encompasses deletion analogues with deletion of one or more (for example, 1-80, preferably 1-60, more preferably 1-40, even more preferably 1-20 and especially 1-10) amino acid residues, substitution analogues with substitution of one or more (for example, 1-80, preferably 1-60, more preferably 1-40, even more preferably 1-20 and especially 1-10) amino acid residues or addition analogues with addition of one or more (for example, 1-80, preferably 1-60, more preferably 1-40, even more preferably 1-20 and especially 1-10) amino acid residues peculiar to natural aminoketone asymmetric reductases. Also encompassed are enzymes having the domain structure characteristic of natural aminoketone asymmetric reductases. There may also be mentioned isomers of the aminoketone asymmetric reductases.

So long as the domain structure characteristic of natural aminoketone asymmetric reductases is maintained, all mutants above are also encompassed among the aminoketone asymmetric reductases of the invention. In addition, it is assumed that enzymes having a primary structural conformation substantially equivalent to natural aminoketone asymmetric reductases of the invention, or a portion thereof, as well as enzymes having biological activity substantially equivalent to natural aminoketone asymmetric reductases, may also be included. Naturally occurring mutants may also be mentioned. The aminoketone asymmetric reductases of the invention may be separated and purified in the manner explained below. The present invention encompasses DNA fragments coding for the aforementioned polypeptides, polypeptides of aminoketone asymmetric reductases having all or some of the natural features, and DNA fragments coding for analogues or derivatives thereof. The nucleotides of the aminoketone asymmetric reductases may be modified (for example, with addition, deletions or substitutions), and such modified forms are also encompassed by the invention.

An aminoketone asymmetric reductase gene according to the invention is a nucleic acid coding for any of the aforementioned aminoketone asymmetric reductases. As representative examples there may be mentioned nucleic acid coding for a protein having the amino acid sequence set forth as SEQ ID NO: 78 of the Sequence Listing, and especially nucleic acid having the nucleotide sequence set forth as SEQ ID NO: 79, but since several nucleotide sequences (codons) can code for each amino acid, there exist numerous nucleic acids coding for a protein having the amino acid sequence set forth as SEQ ID NO: 78. Thus, all such nucleic acids are also encompassed among the aminoketone asymmetric reductase genes of the invention. Here, "coding for a protein" means that, when the DNA consists of two strands, one of the two complementary strands has a nucleotide sequence coding for the protein, and therefore the nucleic acids of the invention include nucleic acids comprising nucleotide sequences directly coding for the amino acid sequence set forth as SEQ ID NO: 78 and nucleic acids comprising nucleotide sequences which are complementary thereto. In addition, the aminoketone asymmetric reductase genes of the invention may be nucleic acids which hybridize with nucleic acid comprising a nucleotide sequence complementary to SEQ ID NO: 79 under stringent conditions, and which code for proteins with aminoketone asymmetric reduction activity. Here, "stringent conditions" has the same definition as explained above.

The coenzyme-regenerating system enzyme gene may be one for various dehydrogenases, specifically, glucose dehydrogenase, glucose-6-phosphate dehydrogenase, aldehyde dehydrogenases, alcohol dehydrogenases, organic acid dehydrogenases and amino acid dehydrogenases. More specifically, there may be suitably used acetaldehyde dehydrogenase, ethanol dehydrogenase, propanol dehydrogenase, glycerol dehydrogenase, formate dehydrogenase, acetate dehydrogenase, butyrate dehydrogenase, lactate dehydrogenase, maleate dehydrogenase and glutamate dehydrogenase.

A transformant according to the invention is characterized by comprising the aforementioned vector. The transformant is obtained by introducing the vector into host cells. The vector introduction method may be a publicly known method, such as the calcium phosphate method, lipofection, electroporation, microinjection or the like.

For example, a transformant of the invention comprising a vector having an aminoketone asymmetric reductase gene inserted therein has aminoketone asymmetric reduction activity, and may be applied for an aminoketone asymmetric reductase production method or optically active aminoalcohol production method as described below.

The method for production of an aminoketone asymmetric reductase of the invention is characterized by comprising a culturing step in which transformants containing a vector having an aminoketone asymmetric reductase gene inserted therein are cultured in medium which allows growth of the transformants, and a purification step in which the aminoketone asymmetric reductase is purified from the transformants obtained in the culturing step.

The method for culturing may be a publicly known method with no particular restrictions so long as it permits growth of the cells used, and ordinarily a liquid medium containing a carbon source, nitrogen source and other nutrients is used. As carbon sources for the medium there may be used any of those that can be utilized by the cells. Specifically, there may be mentioned sugars such as glucose, fructose, sucrose, dextrin, starch and sorbitol, alcohols such as methanol, ethanol and glycerol, organic acids such as fumaric acid, citric acid, acetic acid and propionic acid, and their salts, hydrocarbons such as paraffin, and mixtures thereof. As nitrogen sources there may be used any of those that can be utilized by the cells. Specifically, there may be mentioned ammonium salts of inorganic acids such as ammonium chloride, ammonium sulfate and ammonium phosphate; ammonium salts of organic acids such as ammonium fumarate and ammonium citrate; nitric acid salts such as sodium nitrate and potassium nitrate; and inorganic or organic nitrogenous compounds such as meat extract, yeast extract, malt extract and peptone, as well as mixtures thereof. The medium may also contain appropriately added nutrient sources ordinarily used for culturing, such as inorganic salts, trace metal salts and vitamins; When necessary, there may also be added to the medium substances that promote cell growth and buffering substances effective for maintaining the pH of the medium.

The culturing of the cells may be carried out under conditions suitable for growth. Specifically, the medium pH may be 3-10, preferably 4-9, and the temperature may be 0-50° C., preferably 20-40° C. The cell culturing may be conducted either under aerobic or anaerobic conditions. The culturing time is preferably 10-150 hours, but should be appropriately determined for the type of cells used.

The culture solution of the cells cultured in the manner described above is filtered or centrifuged and the cells are rinsed with water or buffer solution. The rinsed cells are suspended in a suitable amount of buffer solution for disruption of the cells. The method of disruption is not particularly restricted but as examples there may be mentioned mechanical disruption with a mortar, Dynomill, French press, ultrasonic cell disrupter or the like. The aminoketone asymmetric reductase in the cell-free extract obtained by filtration or centrifugation of the solid matter from the cell disruptate is recovered by an ordinary enzyme isolating method.

There are no particular restrictions on the method for isolation of the enzyme and any publicly known method may be employed, but as examples there may be mentioned purification by salting out such as ammonium sulfate precipitation; gel filtration methods using Sephadex and the like; ion-exchange chromatography methods using carriers with diethylaminoethyl groups or carboxymethyl groups; hydrophobic chromatography using carriers with hydrophobic groups such as butyl, octyl and phenyl; dye gel chromatography methods; electrophoresis methods; dialysis; ultrafiltration methods; affinity chromatography methods; high performance liquid chromatography methods and the like.

The enzyme may also be used as an immobilized enzyme. There are no particular restrictions on the method and any publicly known method may be employed, among which there may be mentioned immobilization of the enzyme or the enzyme-producing cells, and the immobilization may be accomplished by a carrier bonding method such as a covalent bonding method or adsorption method, a crosslinking method, entrapment method or the like. A condensing agent such as glutaraldehyde, hexamethylene diisocyanate or hexamethylene diisothiocyanate may also be used if necessary. Other immobilizing methods include: a monomer method in which a monomer is gelled by polymerizing reaction; a prepolymer method in which molecules larger than monomers are polymerized; a polymer method in which a polymer is gelled; immobilization using polyacrylamide; immobilization using natural polymers such as alginic acid, collagen, gelatin, agar and κ-carrageenan; and immobilization using synthetic polymers such as photosetting resins and urethane polymers.

The enzyme purified in this manner is judged as having been adequately purified if a single band is confirmed in electrophoresis (SDS-PAGE, etc.).

A method for production of an optically active aminoalcohol according to the invention is characterized to produce an optically active aminoalcohol compound represented by the following general formula (2), which compound exhibits the desired optical. activity, by reacting an aminoketone asymmetric reductase obtained by the production method of the invention with an enantiomeric mixture of an α-aminoketone compound represented by the following general formula (1) or a salt thereof.

[Chemical Formula 8]

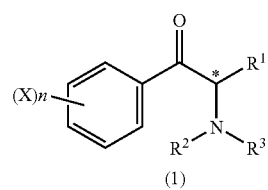

(1)

wherein X may be the same or different and represents at least one species selected from the group consisting of halogen, lower alkyl, hydroxyl optionally protected with a protecting group, nitro and sulfonyl;

n represents an integer of 0 to 3;

$R^1$ represents lower alkyl;

$R^2$ and $R^3$ may be the same or different and represent at least one species selected from the group consisting of hydrogen and lower alkyl; and

* represents asymmetric carbon.

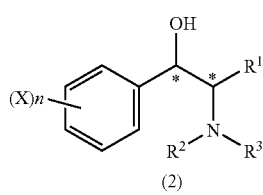

[Chemical Formula 9]

(2)

wherein X, n, $R^1$, $R^2$, $R^3$ and * have the same definitions as above.

First, the α-aminoketone compound represented by general formula (1) according to the invention will be explained.

The substituent X is as follows. As the aforementioned halogen there may be mentioned fluorine, chlorine, bromine and iodine.

As lower alkyl there are preferred C1-6 alkyl, among which there may be mentioned methyl, ethyl, propyl, isopropyl, butyl, isobutyl, s-butyl, t-butyl, pentyl, isopentyl, hexyl and the like. These may have straight-chain or branched structures. As substituents they may contain halogens such as fluorine or chlorine, or hydroxyl, alkyl, amino, alkoxy and the like.

As protecting groups for hydroxyl optionally protected with a protecting group there may be mentioned groups that can be removed by treatment with water, groups that can be removed by acid or weak base treatment, groups that an be removed by hydrogenation or groups that can be removed with Lewis acid catalysts and thiourea, and such protecting groups include optionally substituted acyl, optionally substituted silyl, alkoxyalkyl, optionally substituted lower alkyl, benzyl, p-methoxybenzyl, 2,2,2-trichloroethoxycarbonyl, allyloxycarbonyl, trityl and the like.

The aforementioned acyl groups include acetyl, chloroacetyl, dichloroacetyl, pivaloyl, benzoyl, p-nitrobenzoyl and the like. They may contain hydroxyl, alkyl, alkoxy, nitro, halogen and the like as substituents. The aforementioned silyl groups include trimethylsilyl, t-butyldimethylsilyl, triarylsilyl and the like. They may contain alkyl, aryl, hydroxyl, alkoxy, nitro, halogen and the like as substituents. The aforementioned alkoxyalkyl groups include methoxymethyl, 2-methoxyethoxymethyl and the like. The aforementioned lower alkyl include C1-6 alkyl, among which there may be mentioned methyl, ethyl, propyl, isopropyl, butyl, isobutyl, s-butyl, t-butyl, pentyl, isopentyl, hexyl and the like. These may have straight-chain or branched structures. As substituents they may contain halogen such as fluorine or chlorine, or hydroxyl, alkyl, amino, alkoxy and the like.

X may be nitro or sulfonyl, and specifically there may be mentioned methylsulfonyl and the like.

The number "n" for X is an integer of 0-3, and is preferably 0.

$R^1$ in general formula (1) above represents lower alkyl. As lower alkyl there are preferred C1-6 alkyl, among which there may be mentioned methyl, ethyl, propyl, isopropyl, butyl, isobutyl, s-butyl, t-butyl, pentyl, isopentyl, hexyl and the like. These may have straight-chain or branched structures.

Each of $R^2$ and $R^3$ represent hydrogen or lower alkyl. The lower alkyl include C1-6 alkyl, among which there may be mentioned methyl, ethyl, propyl, isopropyl, butyl, isobutyl, s-butyl, t-butyl, pentyl, isopentyl, hexyl and the like. These may have straight-chain or branched structures.

As salts of the aforementioned α-aminoketone compounds there may be mentioned salts of inorganic acids such as hydrochloride, sulfate, nitrate, phosphate and carbonate, and salts of organic acids such as acetic acid and citric acid.

The α-aminoketone can be easily synthesized by halogenation (for example, bromination) of the α-carbon of a corresponding 1-phenylketone derivative, followed by replacement of the halogen such as bromine with an amine (Ger. (East), 11, 332, Mar. 12, 1956).

The optically active aminoalcohol represented by general formula (2) above according to the invention will now be explained. In general formula (2), X, n, $R^1$, $R^2$, $R^3$ and * have the same definitions as in general formula (1) above. As β-aminoalcohols having the desired optical activity there may be mentioned (1S, 2S)aminoalcohols. As specific examples of (1S, 2S)aminoalcohols there may be mentioned d-threo-2-methylamino-1-phenylpropanol (d-pseudoephedrine), d-threo-2-dimethylamino-1-phenylpropanol (d-methylpseudoephedrine), (1S, 2S)-α-(1-aminoethyl)-benzyl alcohol (d-norpseudoephedrine), (1S, 2S)-1-(p-hydroxyphenyl)-2-methylamino-1-propanol, (1S, 2S)-α-(1-aminoethyl)-2,5-dimethoxy-benzyl alcohol, (1S, 2S)-1-(m-hydroxyphenyl)-2-amino-1-propanol, (1S, 2S)-1-(p-hydroxyphenyl)-2-amino-1-propanol, (1S, 2S)-1-phenyl-2-ethylamino-1-propanol, (1S, 2S)-1-phenyl-2-amino-1-butanol, (1S, 2S)-1-phenyl-2-methylamino-1-butanol and the like.

The conditions for reaction of the aminoketone asymmetric reductase are not particularly restricted so long as an optically active aminoalcohol represented by general formula (2) having the desired optical activity is produced, but since the enzyme optimum pH is 8.1 and the optimum temperature is 55° C., the reaction is preferably carried out under conditions of pH 7-9 and 30-65° C. temperature.

A method for production of an optically active aminoalcohol according to the invention is also characterized to produce an optically active aminoalcohol compound represented by the following general formula (2), which compound exhibits the desired optical activity, by reacting a transformant of the invention with an enantiomeric mixture of an α-aminoketone compound represented by the following general formula (1) or a salt thereof.

[Chemical Formula 10]

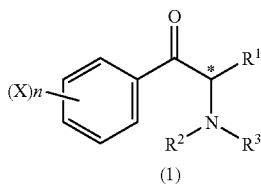

(1)

[Chemical Formula 11]

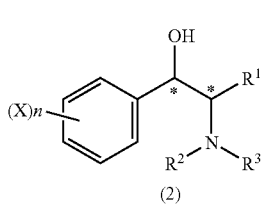

(2)

As the reaction conditions for the reaction described above, for example, the transformants shake cultured in liquid medium may be collected, an aqueous aminoketone solution (0.1-10% concentration) added to the obtained cells, and reaction conducted at a temperature of 20-40° C. for a period of several hours to one day while regulating the pH to between 6-8. Upon completion of the reaction, the cells may be separated and the product in the reaction solution isolated to obtain an optically active aminoalcohol. The reaction may be conducted in the same manner for treated transformant cells (dry cells or immobilized cells) or the enzyme or immobilized enzyme obtained from the transformants.

In the production method for an optically active aminoalcohol of the invention, the reaction may be carried out with further addition of a compound represented by the following general formula (3) or a pharmaceutically acceptable salt or solvate thereof, for more efficient production of the optically active aminoalcohol.

[Chemical Formula 12]

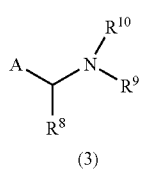

(3)

(wherein A represents the following formula (Y) or (Z))

[Chemical Formula 13]

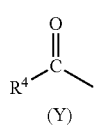

(Y)

(wherein $R^4$ represents hydrogen, optionally substituted C1-3 alkyl, a C5-10 hydrocarbon ring which is bonded to $R^8$ or a 5- to 8-membered heterocyclic skeleton containing 1-3 heteroatoms which is bonded to $R^8$)

[Chemical Formula 14]

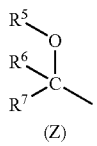

(Z)

(wherein $R^5$ represents hydrogen, C1-3 alkyl or a 5- to 8-membered heterocyclic skeleton containing 1-3 heteroatoms which is bonded to $R^6$ or $R^9$, $R^6$ represents hydrogen, optionally substituted C1-3 alkyl, a C5-10 hydrocarbon ring which is bonded to $R^8$ or a 5- to 8-membered heterocyclic skeleton containing 1-3 heteroatoms which is bonded to $R^5$ or $R^9$, and $R^7$ represents hydrogen or optionally substituted C1-6 alkyl); $R^8$ represents hydrogen, carboxyl, optionally substituted C1-6 alkyl, a 5- to 8-membered heterocyclic skeleton containing 1-3 heteroatoms which is bonded to $R^4$ or a C5-10 hydrocarbon ring which is bonded to $R^6$; $R^9$ represents hydrogen, optionally substituted C1-6 alkyl, optionally substituted C1-6 alkyloxycarbonyl, optionally substituted acyl or a 5- to 8-membered heterocyclic skeleton containing 1-3 heteroatoms which is bonded to $R^5$ or $R^6$; and $R^{10}$ represents hydrogen or optionally substituted C1-6 alkyl)

In general formula (3) above, C1-3 alkyl may be straight-chain or branched, and specifically there may be mentioned methyl, ethyl, n-propyl, isopropyl and the like. C1-6 alkyl may be straight-chain or branched, and specifically there may be mentioned methyl, ethyl, n-propyl, isopropyl, n-butyl, i-butyl, s-butyl, t-butyl, pentyl, hexyl and the like. As C5-10 hydrocarbon rings there may be mentioned cyclopentyl, cyclohexyl, cycloheptyl, cyclooctyl, cyclononyl, cyclodecanyl and the like.

As heteroatoms for the 5- to 8-membered heterocyclic skeleton containing 1-3 heteroatoms there may be mentioned nitrogen, oxygen, sulfur and the like, among which nitrogen and oxygen are particularly preferred, and as 5- to 8-membered heterocyclic skeletons there may be mentioned pyrrolidine, piperidine, imidazolidine, piperazine, tetrahydrofuran, tetrahydropyran, tetrahydrothiophene, morpholine and the like.

As C1-6 alkyloxycarbonyl there may be mentioned methyloxycarbonyl, ethyloxycarbonyl, isopropyloxycarbonyl, isobutyloxycarbonyl, t-butyloxycarbonyl and the like. As acyl there may be mentioned formyl, acetyl, propionyl, butyryl, isobutyryl, pivaloyl, benzoyl, valeryl and the like. When the aforementioned C1-3 or C1-6 alkyl, C1-6 alkyloxycarbonyl or acyl have substituents there are no particular restrictions on the types, positions and numbers of substituents, and as examples of substituents there may be mentioned halogen such as fluorine and chlorine, hydroxyl, alkyl, carboxyl, amino, alkoxy, nitro, aryl and the like. As pharmaceutically acceptable salts there may be mentioned salts of inorganic acids such as hydrochloric acid, sulfuric acid, nitric acid and phosphoric acid, salts of organic acids such as acetic acid and citric acid, salts of inorganic bases such as Na, K, Mg, Ca and ammonia, and salts of organic bases such as triethylamine and cyclohexylamine.

As examples of compounds represented by general formula (3) above there may be mentioned 1-acetylamino-2- hydroxypropane, 1-methylamino-2-hydroxypropane, 1-amino-2-oxopropane, 1-amino-2-hydroxycyclopentane, 1-amino-2,3-dihydroxypropane, L-threonine, 4-amino-3-hydroxybutanoic acid, 1-amino-2-oxocyclohexane, morpholine, 3-hydroxypyrrolidine, 3-hydroxypiperidine, 2-aminomethyl-tetrahydrofuran, 1-(2-hydroxypropyl)amino-2-hydroxypropane, 1-t-butyloxycarbonylamino-2-hydroxypropane, 2-amino-3-hydroxybutane, DL-serine, 1-amino-2-hydroxypropane, 1-amino-2-hydroxybutane and 1-amino-2-hydroxycyclohexane. Compounds among these having asymmetric carbons may be optically active forms or racemic forms, unless otherwise specified.

Addition of such activity inducers to the medium can induce cellular activity and thus more efficiently promote production of the optically active β-aminoalcohol than when no such activity inducers are added. The activity inducers may be used alone, or several such activity inducers may be used in admixture. The amount of such activity inducers is preferably 0.01-10 wt% with respect to the medium.

The reaction method for production of the β-aminoalcohol of the invention is not particularly restricted so long as it is a method in which the cells or the cell-produced enzyme is reacted with an enantiomeric mixture of an α-aminoketone compound represented by general formula (1) above or its salt, to produce the corresponding optically active β-aminoalcohol compound represented by general formula (2), and the reaction is initiated by mixing the cells rinsed with buffer solution or water with the α-aminoketone aqueous solution used as the starting material.

The reaction conditions may be selected within a range that does not impede production of the optically active β-aminoalcohol compound represented by general formula (2). The cell volume is preferably 1/100 to 1000-fold and more preferably 1/10 to 100-fold in terms of dry weight with respect to the racemic aminoketone. The concentration of the racemic aminoketone substrate is preferably 0.01-20% and more preferably 0.1-10%. The pH of the reaction solution is preferably 5-9 and more preferably 6-8, and the reaction temperature is preferably 10-50° C. and more preferably 20-40° C. The reaction time is preferably 5-150 hours, but this may be appropriately determined depending on the cell type.

In order to more efficiently promote the reaction, there may be added sugars such as glucose, organic acids such as acetic acid and energy sources such as glycerol. These may be added alone or as mixtures. The amount of addition is preferably 1/100 to 10-fold with respect to the substrate. Coenzymes and the like may also be added. As coenzymes there may be used nicotinamide adenine dinucleotide (NAD), reduced nicotinamide adenine dinucleotide (NADH), nicotinamide adenine dinucleotide phosphate (NADP), reduced nicotinamide adenine dinucleotide phosphate (NADPH) and the like, either alone or in mixtures, added in amounts of preferably 1/1000 to 1/5 with respect to the racemic aminoketone. In addition to such coenzymes, there may be added coenzyme-regenerating enzymes such as glucose dehydrogenase, in amounts of 1/1000 to 1/5 with respect to the racemic aminoketone. Also, substrates for coenzyme-regenerating enzymes, such as glucose, may be added, in amounts of 1/100 to 10-fold with respect to the racemic aminoketone. There may also be used combinations of sugars such as glucose, organic acids such as acetic acid, energy sources such as glycerol, coenzymes, coenzyme-regenerating enzymes and coenzyme-regenerating enzyme substrates. These usually accumulate in the cells but if necessary they may be added to increase the reaction speed or yield, and therefore may be added as appropriate.

If the reaction solution is reacted with addition of the specific salts described above under the aforementioned conditions, racemization of the unreacted α-aminoketone isomers will be aided, thus more efficiently promoting conversion to the enantiomer which will serve as the substrate of the cells or cell-produced enzyme. This will tend to yield the target aminoalcohol from the starting material at a high yield of 50% or greater.

As salts that promote racemization of unreacted α-aminoketones there may be used weak acid salts such as acetate, tartarate, benzoate, citrate, malonate, phosphate, carbonate, paranitrophenol salt, sulfite and borate, but there are preferably used phosphate (for example, sodium dihydrogen phosphate, potassium dihydrogen phosphate, ammonium dihydrogen phosphate), carbonate (for example, sodium carbonate, sodium hydrogen carbonate, potassium carbonate, ammonium carbonate) and citrate (for example, sodium citrate, potassium citrate, ammonium citrate). Mixtures thereof may also be used, with a buffer solution with a pH of 6.0-8.0 added to a final concentration of preferably 0.01-1 M. In the case of a phosphate, for example, sodium dihydrogen phosphate and sodium monohydrogen phosphate may be mixed in a proportion of between 9:1 and 5:95.

The optically active α-aminoalcohol produced by the reaction may be purified by ordinary separation and purification means. For example, the optically active β-aminoalcohol may be obtained directly from the reaction solution or after separation of the cells, by being subjected to a common purification process such as membrane separation, extraction with an organic solvent (for example, toluene, chloroform, etc.), column chromatography, vacuum concentration, distillation, crystallization, recrystallization or the like. The optical purity of the produced optically active β-aminoalcohol can be measured by high performance liquid chromatography (HPLC).

EXAMPLES

The present invention will now be explained in greater detail through examples, with the understanding that these examples in no way limit the technical scope of the invention.

Example 1

Isolation and Purification of Plasmids (1) Method

*Rhodococcus* strains were inoculated to 5 mL of GPY medium (1% glucose, 0.5% bactopeptone, 0.3% yeast extract) and cultured with shaking at 25° C. After adding 250 μL of a 100 mg/mL ampicillin solution in the logarithmic growth phase, culturing was continued at 25° C. for 2 hours with shaking. The cells were harvested by centrifugation (12 krpm, 5 min), and after removing off the supernatant, they were suspended in 1 mL of 50 mM Tris (pH 7.5), the cells were again harvested by centrifugation (12 krpm, 5 min) and the supernatant was removed off. They were then suspended in 250 μL of a 10 mg/mL lysozyme solution dissolved in TE solution (10 mM Tris (pH 7.5), 1 mM EDTA), and the suspension was allowed to stand at 37° C. for 30 minutes. Next, 100 μL of 3 M sodium chloride and 25 μL of 10% SDS were added and the mixture was allowed to stand at −20° C. overnight. To the supernatant from centrifugation (12 krpm, 5 min) there were added 0.5 μL each of 50 μg/mL Proteinase K and 50 μg/mL RNase A, and the mixture was allowed to stand at 37° C. for 15 minutes. An equivalent of phenol/chloroform/isoamyl alcohol solution was added and centrifugation was performed (12 krpm, 5 min). A 2.5-fold amount of ethanol was added to the supernatant, the mixture was centrifuged (12 krpm, 5 min), and the precipitate was dissolved in 50 μL of sterilized water. Confirmation of plasmids was accomplished by electrophoresis with 0.8% agarose gel and staining with ethidium bromide, followed by UV irradiation.

(2) Test Bacteria Strains and Results

Throughout the examples, the presence or absence of plasmids was screened from available strains belonging to the genus *Rhodococcus* and its related genus *Mycobacterium* followed the method described in (1) above.

Table 3 shows the screened strains confirmed to contain plasmids. Specifically, *Rhodococcus erythropolis* (IAM1400, IAM1503, JCM2893, JCM2894 and JCM2895) and *Rhodococcus rhodnii* (JCM3203) were confirmed to contain plasmids of approximately 5.4 kbp and 5.8 kbp, respectively. These plasmids were designated according to the names listed in Table 3: pRET1100, pRET1200, pRET1300, pRET1400, pRET1500, pRET1600, pRET1700, pRET1800, pRET0500, pRET1000 (see Table 3).

*R. erythropolis* IAM1400 and IAM1503 are described in "IAM Catalogue of Strains, Third Edition, 2004" published by the Institute of Molecular and Cellular Biosciences, The University of Tokyo, and are available from the institute. Also, *R. erythropolis* JCM2893, JCM2894 and JCM2895 and *R. rhodnii* JCM3203 are described in "JCM Catalogue of Strains, Eighth Edition 2002" published by RIKEN, Japan, and are available from the institute.

TABLE 3

| Strain | No. | Size (kbp) | Name |
| --- | --- | --- | --- |
| *Rhodococcus erythropolis* | IAM 1400 | 5.4 | pRET1100 |
| | | 5.4 | pRET1200 |
| " | IAM 1503 | 5.4 | pRET1300 |
| | | 5.4 | pRET1400 |
| " | JCM 2893 | 5.4 | pRET1500 |
| | | 5.4 | pRET1600 |
| " | JCM 2894 | 5.4 | pRET1700 |
| | | 5.4 | pRET1800 |
| " | JCM 2895 | 5.4 | pRET0500 |
| *Rhodococcus rhodnii* | JCM 3203 | 5.8 | pRET1000 |

Example 2

Identification of Restriction Endonuclease Sites

Various restriction endonucleases were used to determine restriction endonuclease sites, for classification of the plasmids shown in Table 3. Each plasmid was isolated by the method described in Example 1, and then digested with EcoR I, Hind III, Pvu II, Sca I, Sph I, Sma I, Sac I, BamH I and Kpn I, and electrophoresed on 0.8% agarose gel for confirmation of the DNA fragments. The size marker used was Loading Quick DNA size Marker λ/EcoR I+Hind III double digest (Toyobo). The numbers of sites cleaved by the restriction endonucleases and the sizes of the fragments were determined based on the size marker. The results are shown in Table 4.

TABLE 4

| | *R. erythropolis* | | | | | | | | | *R. rhodnii* |
| --- | --- | --- | --- | --- | --- | --- | --- | --- | --- | --- |
| | IAM 1400 | | IAM 1503 | | JCM 2893 | | JCM 2894 | | JCM 2895 | JCM 3203 |
| | pRET1100 | pRET1200 | pRET1300 | pRET1400 | pRET1500 | pRET1600 | pRET1700 | pRET1800 | pRET0500 | pRET1000 |
| BamH I | 2(0.4, 5.0) | 1(5.4) | same as pRET1100 | same as pRET1200 | same as pRET1100 | same as pRET1200 | same as pRET1100 | same as pRET1200 | same as pRET1200 | 2(2.0, 3.8) |
| EcoR I | 2(0.3, 5.1) | 1(5.4) | | | | | | | | 0 |
| Hind III | 0 | 0 | | | | | | | | 0 |
| Kpn I | 1(5.4) | 0 | | | | | | | | 0 |
| Pvu II | 1(5.4) | 2(0.9, 4.5) | | | | | | | | 4(0.1, 1.4, 2.0, 2.3) |
| Sac I | 1(5.4) | 1(5.4) | | | | | | | | 3(0.9, 1.0, 3.9) |
| Sca I | 0 | 0 | | | | | | | | 0 |
| Sph I | 0 | 0 | | | | | | | | 0 |
| Sma I | 1(5.4) | 2(0.4, 0.5) | | | | | | | | 4(0.1, 1.2, 1.6, 2.9) |

Values in parentheses indicate sizes (kbp)

Based on the analysis results shown above, the plasmids in Table 3 were classified into three types: plasmids possessing the same restriction endonuclease sites as pRET1100, plasmids possessing the same restriction endonuclease sites as pRET1200, and pRET1000.

Example 3

Plasmid Sequencing and Homology Search

As the plasmids were classified into three types, i.e. pRET1000, pRET1100 and pRET1200 based on the results of Example 2, it was attempted to sequence each of the plasmids.

First, the DNA fragments of the plasmids were cloned for determination of the nucleotide sequences. For *Rhodococcus erythropolis* (IAM1400), the plasmids (pRET1100, pRET1200) were isolated and digested with Sma I and Sac I. Upon electrophoresis on 0.8% agarose gel, DNA fragments with sizes of approximately 0.5 kbp, approximately 1.7 kbp, approximately 3.7 kbp and approximately 4.9 kbp were confirmed. The respective DNA fragments were recovered from the agarose gel using a GFX™ PCR DNA and Gel Band Purification Kit (Amersham Bioscience) and used as insert DNA. Separately, pBluescript II KS(−) was used after digesting with Sma I alone or with Sma I and Sac I, as vector DNA. The insert DNA and vector DNA were ligated with Ligation High (Toyobo) and used to transform *E. coli* JM109. The obtained transformants were screened using a GFX Micro Plasmid Prep Kit (Amersham Bioscience) to obtain different clones.

For *Rhodococcus rhodnii* (JCM3203), the plasmid (pRET1000) was isolated and then digested with BamH I. Upon electrophoresis on 0.8% agarose gel, DNA fragments with sizes of approximately 2.0 kbp and approximately 3.8 kbp were confirmed. The respective DNA fragments were recovered from the gel using the aforementioned Kit and used as insert DNA. The vector DNA used was pBluescript II KS(−) digested with BamH I.

Determination of the nucleotide sequences of the plasmid inserts was accomplished by the primer walking method. The apparatus used was an ABI PRISM™310NT Genetic Analyzer, and the enzyme used was a BigDye Terminator v3.1 Cycle Sequencing Kit (ABI).

First, P7 (M13 forward, Toyobo) and P8 (M13 reverse, Toyobo) primers were used for partial decoding of the insert nucleotide sequences. Next, primers were designed within the decoded sequence (using the sequence analyzing software DNASIS Pro; Hitachi Software Corp.), and the designed primers (synthetic oligo DNA) were used for further decoding of the nucleotide sequence. This procedure was repeated until decoding of the entirety of each insert nucleotide sequence. Upon completion of the insert nucleotide sequence decoding, primers were designed for reaction from the ends of each insert to the vector direction in order to analyze how the inserts were linked, and PCR was conducted (using KOD -plus-), using the plasmid isolated from *Rhodococcus erythropolis* (IAM1400) as template. The PCR product was purified using a GFX™ PCR DNA and Gel Band Purification Kit, and sequencing was carried out using the same primers used for PCR, to analyze the arrangement of the inserts.

The results of sequencing showed that pRET1100 consisted of 5444 bp, with a G+C content of 59%. The full determined nucleotide sequence is set forth as SEQ ID NO: 73 of the Sequence Listing. Plasmid pRET1200 consisted of 5421 bp and had a G+C content of 62%. Plasmid pRET1000 consisted of 5813 bp and had a G+C content of 67%. The full determined nucleotide sequence is set forth as SEQ ID NO: 74 of the Sequence Listing.

A homology search for the determined nucleotide sequences using DNASIS Pro revealed that pRET1000 and pRET1100 were novel plasmids. On the other hand, pRET1200 had approximately 99.6% homology with pN30 (GenBank accession no. AF312210) (calculated based on pRET1200).

For pRET1000 and pRET1100, comparison was made with publicly known plasmids based on the determined nucleotide sequences, using DNASIS Pro. As a result, neither of the plasmids were found to have completely matching restriction endonuclease sites with other plasmids.

Example 4

Nucleotide Sequence Analysis

The results of analysis of the nucleotide sequences of pRET 1100 and pRET1000 are shown below.

The following orfs were found in pRET1100:
  orf1 (SEQ ID NO: 1, SEQ ID NO: 2 or SEQ ID NO: 3) consisting of the nucleotide sequence from bases 202, 238 or 337 to 480 of the nucleotide sequence set forth as SEQ ID NO: 73;,
  orf2 (SEQ ID NO: 4) consisting of the nucleotide sequence from bases 477 to 758 of the nucleotide sequence set forth as SEQ ID NO: 73;
  orf3 (SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15 or SEQ ID NO: 16) consisting of the nucleotide sequence from bases 862, 1294, 1450, 1462, 1486, 1489, 1513, 1630, 1645, 1687, 2224 or 2227 to 2409 of the nucleotide sequence set forth as SEQ ID NO: 73;
  orf4 (SEQ ID NO: 17, SEQ ID NO: 18, SEQ ID NO: 19, SEQ ID NO: 20 or SEQ ID NO: 21) consisting of the nucleotide sequence complementary to the nucleotide sequence from bases 1875, 1734, 1701, 1674 or 1581 to 1444 of the nucleotide sequence set forth as SEQ ID NO: 73;
  orf5 (SEQ ID NO: 22, SEQ ID NO: 23, SEQ ID NO: 24, SEQ ID NO: 25 or SEQ ID NO: 26) consisting of the nucleotide sequence complementary to the nucleotide sequence from bases 2828, 2792, 2747, 2594 or 2540 to 2406 of the nucleotide sequence set forth as SEQ ID NO: 73;
  orf6 (SEQ ID NO: 27 or SEQ ID NO: 28) consisting of the nucleotide sequence from bases 2971 or 3049 to 3306 of the nucleotide sequence set forth as SEQ ID NO: 73;
  orf7 (SEQ ID NO: 29 or SEQ ID NO: 30) consisting of the nucleotide sequence complementary to the nucleotide sequence from bases 3577 or 3571 to 3053 of the nucleotide sequence set forth as SEQ ID NO: 73;
  orf8 (SEQ ID NO: 31 or SEQ ID NO: 32) consisting of the nucleotide sequence from bases 3339 or 3648 to 3902 of the nucleotide sequence set forth as SEQ ID NO: 73; and
  orf9 (SEQ ID NO: 33 or SEQ ID NO: 34) consisting of the nucleotide sequence from bases 4366 or 4477 to 5034 of the nucleotide sequence set forth as SEQ ID NO: 73.

The following orfs were found in pRET1000:
  orf10 (SEQ ID NO: 38, SEQ ID NO: 39, SEQ ID NO: 40 or SEQ ID NO: 41) consisting of the nucleotide sequence complementary to the nucleotide sequence from bases 3350, 3251, 2945 or 2849 to 2412 of the nucleotide sequence set forth as SEQ ID NO: 74;

orf11 (SEQ ID NO: 42 or SEQ ID NO: 43) consisting of the nucleotide sequence complementary to the nucleotide sequence from bases 2365 or 2332 to 2159 of the nucleotide sequence set forth as SEQ ID NO: 74;

orf12 (SEQ ID NO: 44) consisting of the nucleotide sequence from bases 3197 to 3526 of the nucleotide sequence set forth as SEQ ID NO: 74;

orf13 (SEQ ID NO: 45 or SEQ ID NO: 46) consisting of the nucleotide sequence complementary to the nucleotide sequence from bases 4035 or 3996 to 3679 of the nucleotide sequence set forth as SEQ ID NO: 74;

orf14 (SEQ ID NO: 48, SEQ ID NO: 49 or SEQ ID NO: 50) consisting of the nucleotide sequence from bases 4621, 4654 or 4666 to 4830 of the nucleotide sequence set forth as SEQ ID NO: 74;

orf15 (SEQ ID NO: 51 or SEQ ID NO: 52) consisting of the nucleotide sequence complementary to the nucleotide sequence from bases 5161 or 5062 to 4709 of the nucleotide sequence set forth as SEQ ID NO: 74;

orf16 (SEQ ID NO: 53 or SEQ ID NO: 54) consisting of the nucleotide sequence from bases 2331 or 2334 to 2618 of the nucleotide sequence set forth as SEQ ID NO: 74;

orf17 (SEQ ID NO: 55) consisting of the nucleotide sequence from bases 2907 to 3242 of the nucleotide sequence set forth as SEQ ID NO: 74;

orf18 (SEQ ID NO: 56, SEQ ID NO: 57, SEQ ID NO: 58, SEQ ID NO: 59 or SEQ ID NO: 60) consisting of the nucleotide sequence from bases 1650, 1689, 1713, 1827 or 1875 to 2162 of the nucleotide sequence set forth as SEQ ID NO: 74;

orf19 (SEQ ID NO: 61) consisting of the nucleotide sequence from bases 1906 to 2169 of the nucleotide sequence set forth as SEQ ID NO: 74;

orf20 (SEQ ID NO: 62) consisting of the nucleotide sequence complementary to the nucleotide sequence from bases 810 to 553 of the nucleotide sequence set forth as SEQ ID NO: 74;

orf21 (SEQ ID NO: 63, SEQ ID NO: 64, SEQ ID NO: 65, SEQ ID NO: 66, SEQ ID NO: 67, SEQ ID NO: 68 or SEQ ID NO: 69) consisting of the nucleotide sequence from bases 117, 147, 306, 456, 5144, 5276 or 5534 to 656 of the nucleotide sequence set forth as SEQ ID NO: 74.

The DNA replication region of pRET1100 is the region represented by the nucleotide sequence set forth as SEQ ID NO: 35 (from bases 2410 to 3200), the nucleotide sequence set forth as SEQ ID NO: 36 (from bases 1000 to 1500) or the nucleotide sequence set forth as SEQ ID NO: 37 (from bases 5000 to 500). The DNA replication region of pRET1000 is the region represented by the nucleotide sequence set forth as SEQ ID NO: 70 (from bases 3355 to 3507), the nucleotide sequence set forth as SEQ ID NO: 71 (from bases 4290 to 4350) or the nucleotide sequence set forth as SEQ ID NO: 72 (from bases 3570 to 3894).

The region of the nucleotide sequence from bases 5144 to 656 (SEQ ID NO: 67) and the region of the nucleotide sequence from bases 4381 to 4830 (SEQ ID NO: 47) of the nucleotide sequence of pRET1000 (SEQ ID NO: 74) are homologous with mobilization proteins, suggesting that they are involved in mobilization.

A DNA secondary structure is predicted for the region of the nucleotide sequence from bases 4260 to 4339 (SEQ ID NO: 75) of the nucleotide sequence of pRET1000 (SEQ ID NO: 74), and it is presumably involved in expression of the mobilization protein gene or is the recognition site of the expressed protein.

On the other hand, it was suggested that the region of the nucleotide sequence from bases 761 to 868 (SEQ ID NO: 76) of the nucleotide sequence of pRET1100 (SEQ ID NO: 73) is a promoter involved in expression of a protein related to replication.

Example 5

Construction of Shuttle Vectors

For construction of a shuttle vector between *Rhodococcus* strains and *E. coli*, the *Rhodococcus* plasmids pRET1000, pRET1100 and pRET1200 and the *E. coli* plasmids pUC18, pHSG299 and pHSG398 were used for the following experiment.

First, DNA fragments were prepared from *R. erythropolis* plasmids. Specifically, plasmids pRET1100 and pRET1200 were obtained from *R. erythropolis* (IAM1400), and then Alw44 I was used for digestion of pRET1100 at 37° C. for 2 hours and Blunting High (Toyobo) was used for blunting of the ends, while BspLU11 I was used for digestion of pRET1200 at 48° C. for 2 hours and Blunting High (Toyobo) was used for blunting of the ends, to obtain DNA fragments of *R. erythropolis* plasmid. Each of the DNA fragments was dissolved in TE solution.

For pRET1000, plasmid pRET1000 was obtained from *R. rhodnii* (JCM3203), and then Drd I was used for digestion of pRET1000 at 37° C. for 2 hours and Blunting High was used for blunting of the ends, to obtain pRET1000 DNA fragments, which were dissolved in TE solution.

Next, DNA fragments were prepared from the *E. coli* plasmids. Specifically, pUC18 (containing the ampicillin-resistance gene (Amp$^r$)) was digested with Sma I at 30° C. for 2 hours, and pHSG299 (containing the kanamycin-resistance gene (Km$^r$)) and pHSG398 (containing the chloramphenicol-resistance gene (Cm$^r$)) were digested with Hinc II at 37° C. for 2 hours to obtain DNA fragments of *E. coli* plasmid, which were dissolved in TE.

After ligating the DNA fragments from the *Rhodococcus* and *E. coli* plasmids prepared in the manner described above, they were used for transformation in *E. coli* DH5α, which were plated on LB (1% tryptophan, 0.5% yeast extract, 1% sodium chloride; pH 7.2) agar medium containing 100 μg/mL kanamycin, 100 μg/mL ampicillin or 30 μg/mL chloramphenicol, coated with 30 μL of 0.1 M IPTG (isopropyl-β-galactoside) and 4% X-gal (5-bromo-4-chloro-3-indole-β-D-galactopyranoside) and allowed to stand at 30° C. for 60 hours. White colonies were selected from among the appearing colonies, and were cultured with shaking in LB liquid medium containing 100 μg/mL kanamycin, 100 μg/mL ampicillin or 30 μg/mL chloramphenicol, at 30° C. for 60 hours. The DNA was purified from the obtained culture solution using a GFX™ Micro Plasmid Prep Kit (Amersham Bioscience, with purification under the manufacturer's specified conditions). The obtained DNA was confirmed by electrophoresis on 0.8% agarose gel. The obtained shuttle vectors are shown in Table 5, and the methods for constructing each of the shuttle vectors using pRET1100 are shown in FIGS. 3 to 5.

TABLE 5

| Constructed shuttle vectors | Origin Rhodococcus | E. coli |
|---|---|---|
| pRET1001, pRET1001Rv | pRET1000 | pUC18 |
| pRET1002, pRET1002Rv | pRET1000 | pHSG299 |
| pRET1003, pRET1003Rv | pRET1000 | pHSG398 |
| pRET1101, pRET1101Rv | pRET1100 | pUC18 |
| pRET1102, pRET1102Rv | pRET1100 | pHSG299 |
| pRET1103, pRET1103Rv | pRET1100 | pHSG398 |
| pRET1201, pRET1201Rv | pRET1200 | pUC18 |
| pRET1202, pRET1202Rv | pRET1200 | pHSG299 |
| pRET1203, pRET1203Rv | pRET1200 | pHSG398 |

The shuttle vectors constructed with pRET1100 and pUC18, pHSG299 or pHSG398 were designated respectively as pRET1101 (SEQ ID NO: 89), pRET1102 (SEQ ID NO: 90) or pRET1103 (SEQ ID NO: 91), respectively. Of the shuttle vectors, pRET1101 exhibits ampicillin resistance, pRET1102 exhibits kanamycin resistance and pRET1103 exhibits chloramphenicol resistance. Also, the shuttle vectors pRETI 101 to 1103 wherein the *E. coli* gene and pRET1100 were linked in reverse (Rv) were designated respectively as pRET1101Rv (SEQ ID NO: 92), pRET1102Rv (SEQ ID NO: 93) and pRET1103Rv (SEQ ID NO: 94).

Similarly, the shuttle vectors constructed using pRET1000 and pRET1200 were designated as pRET1001-pRET1003 (SEQ ID NO: 95-SEQ ID NO: 97) and pRET1001Rv-pRET1003Rv (SEQ ID NO: 98-SEQ ID NO: 100), and as pRET1201-pRET1203 and pRET1201Rv-pRET1203Rv (Table 5).

Example 6

Examining Method of Transformation to *R. erythropolis*

The *Rhodococcus-E. coli* shuttle vectors obtained in Example 5 were used for transformation of *R. erythropolis* MAK-34 strain (MAK-34; deposited at the National Institute of Bioscience and Human-Technology, National Institute of Advanced Industrial Science and Technology, Ministry of Economy, Trade and Industry, (currently: International Patent Organism Depositary, National Institute of Advanced Industrial Science and Technology) on Feb. 15, 2001 as FERM BP-7451). Electroporation was investigated as the method of gene transfer.

First, *R. erythropolis* MAK-34 strain was inoculated to 5 mL of GPY medium and cultured with shaking at 30° C. for 36 hours. After seeding 1 mL of culture solution in 100 mL of LB medium, culturing was continued at 200 rpm at 30° C. for 10 hours. The cultured cells were harvested by centrifugation (12 krpm, 5 min, 4° C.) and the harvested cells were rinsed twice with ultrapurified water. The rinsed cells were harvested by centrifugation (12 krpm, 5 min, 4° C.) and suspended in 2.4 mL of a 10% glycerol solution. The suspension was dispensed into 300 µl portions and frozen at −80° C. as competent cells.

A 90 µL portion of the prepared competent cells and a 5 µL portion of the shuttle vector (pRET1001, pRET1002, pRET1003, pRET1101, pRET1102, pRET1103, pRET1201, pRET1202 or pRET1203) were mixed on ice. The mixed solution was gently poured into a 0.1 cm cuvette which had been cooled on ice, and was set in a Gene Pulser II Electroporation System (BIO-RAD). After pulsing at 20 kV/cm, 400Ω, 25 µF, the mixed solution was added with 300 µL of LB medium immediately and was allowed to stand at 25° C. for 3 hours.

A portion of the cell suspension was plated on an antibiotic-containing LB plate (100 µg/mL kanamycin, 100 µg/mL ampicillin or 30 µg/mL chloramphenicol). As a result, colonies were obtained when using pRET1002, pRET1102 and pRET1202 containing the kanamycin resistance gene. In order to confirm that the obtained colonies contained the plasmids, the plasmids were isolated and all were verified to contain the shuttle vector.

This suggested that *R. erythropolis* can be transformed by electroporation and that pRET1002, pRET1102 and pRET1202 function as shuttle vectors.

Example 7

Obtaining Aminoketone Asymmetric Reductase Gene (Mak Gene)

The mak gene was isolated from *R. erythropolis* MAK-34 strain for insertion of the mak gene into the shuttle vector shown in FIG. 5.

First, genomic DNA was obtained from *R. erythropolis* MAK-34 strain. After inoculating *R. erythropolis* MAK-34 strain to 5 mL of GPY medium, culturing with shaking was performed at 30° C. for 48 hours, and then the culture solution was seeded in 100 mL of GPY medium and subcultured at 200 rpm at 30° C. for 10 hours. The genomic DNA was obtained using a Genomic DNA Buffer set and Genomic-tip 500/G (QIAGEN).

The obtained genomic DNA was used as template for PCR using KOD -plus-. The primers used were MAKF1 (5'-GAATCTTCTCGTTGATGCAGATCAGGTC-3'; SEQ ID NO: 80) and MAKR[2] (5'-CTGACTCCGTAGTGTTCTGC-CAGTTC-3'; SEQ ID NO: 81), for PCR at an annealing temperature of 68° C. and extension reaction for 1 minute and 50 seconds. The obtained PCR product was subjected to phenol/chloroform treatment and ethanol precipitation, and then mixed with pUC18 that had been digested with Sma I for 2 hours at 30° C., and ligated therewith using Ligation High. Competent High (Toyobo) was used for transformation of *E. coli* DH5α, which was then plated on LB agar medium (containing 100 µg/mL ampicillin) that had been coated with 30 µL of 0.1 M IPTG and 4% X-gal, and was allowed to stand at 30° C. for 60 hours. White colonies were selected from among the appearing colonies, and were cultured with shaking in LB liquid medium containing 100 µg/mL ampicillin at 30° C. for 60 hours. The DNA was purified from the obtained culture solution using a GFX™ Micro Plasmid Prep Kit. The obtained DNA was confirmed by electrophoresis on 0.8% agarose gel. The obtained clone was designated as pMAK-1.

Example 8

Construction of Expression Vector-1

A promoter and aminoketone asymmetric reductase gene (mak gene) were inserted into the shuttle vector shown in Table 5.

First, an expression vector (without exogenous promoter) containing approximately 400 bp upstream from the mak gene was constructed.

pMAK-1 was digested with Sma I at 30° C. for 2 hours, and then with Pst I at 37° C. for 2 hours. The solution was supplied for 0.8% agarose gel electrophoresis. The DNA size marker used was Loading Quick DNA size Marker λ/EcoR I+Hind III double digest. After electrophoresis, an approximately 1.4 kbp DNA fragment was purified using a GFX™ PCR DNA and Gel Band Purification Kit, and used as the insert DNA. On the other hand, the vector used was pRET1102 digested with Hinc II and Pst I at 37° C. for 2 hours. The DNA fragments were ligated with Ligation High and Competent High was used for transformation of E. coli DH5α. The cells were plated on LB agar medium containing 100 µg/mL kanamycin and allowed to stand at 30° C. for 60 hours.

The appearing colonies were cultured with shaking on LB liquid medium containing 100 µg/mL kanamycin at 30° C. for 60 hours. The DNA was purified from the obtained cultured medium using a GFX™ Micro Plasmid Prep Kit. The obtained DNA was confirmed by 0.8% agarose gel electrophoresis.

For screening, the obtained DNA without restriction endonuclease treatment and the DNA after digestion with Pst I at 37° C. for 2 hours were subjected to 0.8% agarose gel electrophoresis, and the target plasmid was obtained based on the size of the DNA. The size marker used was Loading Quick DNA size Marker λ/EcoR I+Hind III double digest, pRET1102 and pRET1102 that had been digested with Pst I at 37° C. for 2 hours. The plasmid obtained in this manner was designated as pRET1104.

Example 9

Construction of Expression Vector-2

The shuttle vectors were reduced, since reduction of shuttle vectors is effective for expression vector enhancement, gene modification, transformation efficiency improvement and replication in cells.

First, shuttle vector pRET1102 was reduced. After digesting pRET1102 with BamH I and Hinc II for 2 hours, it was electrophoresed on 0.8% agarose gel and an approximately 2.7 kbp DNA fragment was recovered using a GFX™ PCR DNA and Gel Band Purification Kit to prepare a pRET1102 DNA fragment. The size marker used was Loading Quick DNA size Marker λ/EcoR I+Hind III double digest.

Separately, a DNA fragment replicable in E. coli was prepared by digesting pHSG299 with BamH I and Hinc II for 2 hours, subjecting it to 0.8% agarose gel electrophoresis, and recovering an approximately 2.7 kbp DNA fragment using a GFX™ PCR DNA and Gel Band Purification Kit.

The DNA fragments were ligated with Ligation High and Competent High was used for transformation of E. coli JM109 cells, which were then plated on LB agar medium, containing 100 µg/mL kanamycin, that had been coated with 30 µL of 0.1 M IPTG and 4% X-gal, and was allowed to stand at 30° C. for 48 hours.

White colonies were selected from among the appearing colonies, and were cultured with shaking in LB liquid medium containing 100 µg/mL kanamycin at 30° C. for 48 hours. The DNA was purified from the obtained culture solution using a GFX™ Micro Plasmid Prep Kit. The reduced shuttle vector of pRET1102 obtained in this manner was designated as pRET1123 (approximately 5.3 kbp).

Next, shuttle vector pRET1202 was reduced. The Rhodococcus-derived DNA fragment was prepared by digesting pRET1202 with EcoR I for 2 hours and then with Dra III for 2 hours, using Blunting High for blunting of the ends, performing 0.8% agarose gel electrophoresis, and then recovering an approximately 3.7 kbp DNA fragment using a GFX™ PCR DNA and Gel Band Purification Kit. The size marker used was Loading Quick DNA size Marker λ/EcoR I+Hind III double digest. The DNA fragment was inserted at the Hinc II site of pHSG299. After ligation, Competent High was used for transformation of E. coli DH5α, which was then plated on LB agar medium, containing 100 µg/mL kanamycin, that had been coated with 30 µL of 0.1 M IPTG and 4% X-gal, and was allowed to stand at 30° C. for 72 hours. White colonies were selected from among the appearing colonies, and were cultured with shaking in LB liquid medium containing 100 µg/mL kanamycin at 30° C. for 72 hours. The DNA was purified from the obtained culture solution using a GFX™ Micro Plasmid Prep Kit. When the plasmid obtained by screening was digested with Sac I, BamH I, Pst I or EcoR I for 2 hours, all of the clones had approximately 500 bp clipped at the side of EcoR I site of the Rhodococcus-derived region. The plasmid was designated as pRET1204 (approximately 5.9 kbp). It was not possible to obtain a clone with no clipping of the genus Rhodococcus replication region.

The shuttle vector pRET1002 was reduced in a similar manner to obtain pRET1006 (approximately 4.9 kbp).

R. erythropolis was transformed with these three reduced plasmids, pRET1006, pRET1123 and pRET1204, and upon confirming the presence or absence of shuttle vector by the method described in Example 6, all the shuttle vectors were detected in the transformed cells. This suggested that the three reduced plasmids pRET1006, pRET1123 and pRET1204 are replicated in R. erythropolis.

Example 10

Construction of Expression Vector-3

An expression vector was constructed by having the mak gene inserted into the shuttle vector constructed in Example 9.

The Pst I site of pRET1123 constructed in Example 9 was deleted for cloning of the promoter in the single step. After digesting pRET1123 with Pst I for 2 hours, Blunting High was used for blunting of the ends and Ligation High was used for ligation. The solution was used to transform E. coli JM109 using Competent High, and culturing was performed on an LB plate containing 100 µg/mL kanamycin at 30° C. for 36 hours. The formed colonies were inoculated on LB liquid medium containing 100 µg/mL kanamycin and cultured at 30° C. for 24 hours, and then the DNA was purified using a GFX™ Micro Plasmid Prep Kit to obtain pRET1132

The obtained pRET1132 was digested with Pst I for 1 hour and then electrophoresed on 0.8% agarose, which resulted in confirming lack of cleavage of pRET1132 by Pst I. As controls there were used pRET1123 and pRET1132 not digested with Pst I, and pRET1123 digested with Pst I.

Example 11

Construction of Expression Vector-4

A clone was constructed having a promoter and the mak gene inserted in the aforementioned shuttle vector.

A clone was constructed having a Pst I site upstream from the mak gene, for insertion of a promoter. The procedure was carried out in the following manner to obtain a clone having His-Tag added to the C-terminus of the aminoketone asymmetric reductase. PCR was conducted with KOD -plus- using the pMAK-1 obtained in Example 7 as template, MAKPstF (5'-GACCACTGCAGATCAATCAACTCTGAT-GAGGTCC-3'; SEQ ID NO: 82) and MAKHisBglIIR (5'-CGCTTAGATCTCAGTTCGCCGAGCGCCATCGCCG-3'; SEQ ID NO: 83) as primers, with an annealing temperature of 68° C. and extension reaction for 1 minute and 50 seconds. A PCR fragment (insert) produced by digesting the obtained PCR product with Bgl II at 37° C. for 2 hours was ligated with pQE70 (digested with Sph I at 37° C. for 2 hours, blunted with Blunting High and digested with Bgl II at 37° C. for 2 hours) using Ligation High, and then Competent High was used for transformation of *E. coli* DH5αcells, which were plated on LB agar medium containing 100 μg/mL ampicillin and allowed to stand at 30° C. for 60 hours. The appearing colonies were cultured with shaking on LB liquid medium containing 100 μg/mL ampicillin at 30° C. for 60 hours. The DNA was purified using a GFX™ Micro Plasmid Prep Kit. The obtained DNA was confirmed by 0.8% agarose gel electrophoresis.

For screening, the DNA without restriction endonuclease treatment and the DNA after digestion with Pst I and Bgl II at 37° C. for 2 hours were subjected to 0.8% agarose gel electrophoresis, and the target plasmid was obtained based on the size of the DNA. The plasmid obtained in this manner was designated as pMAK-2. The size marker used was Loading Quick DNA size Marker λ/EcoR I+Hind III double digest, pQE70, and pQE70 that had been digested with Bgl II at 37° C. for 2 hours.

A clone was constructed by inserting the pRET1200 repA promoter (obtained by PCR amplification using as template a clone of pRET1204 wherein the orientation of repA encoded by the *Rhodococcus*-derived DNA fragment was in the same orientation as the kanamycin resistance gene encoded by pHSG299, and using as primers P1200rep-Pst5195 (5'-AGC-CGCTGCAGAAGCAACACCGCATCCGCCCATTG-3'; SEQ ID NO: 84) and P7 (5'-CGCCAGGGTTTTCCCAGT-CACGAC-3'; SEQ ID NO: 85), with an annealing temperature of 60° C. and extension reaction for 1 minute, followed by digestion with EcoR I and Pst I at 37° C. for 2 hours) at the EcoR I-Pst I site of pMAK-2 (designated as pMAK-19).

Next, PCR was conducted with KOD -plus- using as template pMAK-19 and as primers pQE7OF1 (5'-GGCGTAT-CACGAGGCCCTTTCGTCTTCACC-3'; SEQ ID NO: 86) and pQE70R1135Bm (5'-GGTTGGATCCGTCATCAC-CGAAACGCGCGAGGCAG-3'; SEQ ID NO: 87), with an annealing temperature of 60° C. and extension reaction for 3 minutes. The PCR product was purified from the reaction solution by using a GFX™ PCR DNA and Gel Band Purification Kit and after digestion of the purified PCR product with EcoR I and BamH I for 2 hours, it was electrophoresed on 0.8% agarose gel and the DNA fragment was purified by using a GFX™ PCR DNA and Gel Band Purification Kit. The DNA fragment was used as an insert DNA.

Separately, a vector to be used as the expression shuttle vector was obtained by digesting pRET1132 with EcoR I and BamH I for 2 hours, subjecting the DNA fragment to 0.8% agarose gel electrophoresis and purifying the DNA fragment by using a GFX™ PCR DNA and Gel Band Purification Kit. After mixing the insert DNA and vector, Ligation High was used for ligating them and Competent High was used for transformation of *E. coli* JM109 cells, which were plated on an LB plate containing 100 μg/mL kanamycin. The obtained colonies were cultured on LB liquid medium containing 100 μg/mL kanamycin, and then the plasmid DNA was recovered by using a GFX™ Micro Plasmid Prep Kit and subjected to 0.8% agarose gel electrophoresis for screening. The size markers used were Loading Quick DNA size Marker λ/EcoR I+Hind III double digest and pRET1132. The obtained expression vector was designated as pRET1133.

Also, pMAK-19 was digested with EcoR I and Hind III at 37° C. for 2 hours, blunted with Blunting High and subjected to 0.8% agarose gel electrophoresis, and the approximately 1.6 kbp DNA fragment was purified by using a GFX™ PCR DNA and Gel Band Purification Kit. The clone having this fragment inserted at the Hinc II site of pRET1102 was designated as pRET1114.

The pRET1133 promoter was also modified. The mak gene-expressing promoter encoded in pRET1133 is the repA gene promoter of pRET1200 and has a length of approximately 800 bp, and a plasmid was constructed by having approximately 200 bp clipped off from this promoter. The promoter used for the cloning was prepared by PCR. Plasmid pRET1200 was used as template, P1204rep-Ec2958 (5'-CGCGGAATTCGACCACCACGCACGCACACCGCAC-3'; SEQ ID NO: 88) and P1200rep-Pst5195 (5'-AGCCGCT-GCAGAAGCAACACCGCATCCGCCCATTG-3'; SEQ ID NO: 84) were used as primers, and KOD -plus- was used as the PCR enzyme for PCR at an annealing temperature of 60° C. and extension reaction for 50 seconds. The PCR product was purified by using a GFX™ PCR DNA and Gel Band Purification Kit, digested with the restriction endonucleases EcoR I and Pst I for 2 hours, and subjected to 1.6% agarose gel electrophoresis, and the DNA fragment Was purified by using a GFX™ PCR DNA and Gel Band Purification Kit. The DNA fragment was used as the insert DNA. The nucleotide sequence of the promoter region in the DNA fragment is set forth as SEQ ID NO: 77.

Separately, for the vector, pRET1133 was digested with restriction endonucleases EcoR I and Pst I for 2 hours and subjected to 0.8% agarose gel electrophoresis, and an approximately 7.2 kbp DNA fragment was purified by using a GFX™ PCR DNA and Gel Band Purification Kit. The size marker used was Loading Quick DNA size Marker λ/EcoR I+Hind III double digest.

The insert DNA and vector obtained in this manner were ligated by using Ligation High, and Competent High was used for transformation of *E. coli* JM109 cells, which were plated on an LB plate containing 100 μg/mL kanamycin. The obtained colonies were cultured on LB liquid medium containing 100 μg/mL kanamycin, and then the plasmid DNA was recovered by using a GFX™ Micro Plasmid Prep Kit and subjected to 0.8% agarose gel electrophoresis for screening. The size markers used were Loading Quick DNA size Marker λ/EcoR I+Hind III double digest and pRET1133.

Also, after digesting the obtained DNA with restriction endonucleases EcoR I and Pst I for 2 hours, it was subjected to 1.6% agarose gel electrophoresis and a DNA fragment corresponding to the approximately 600 bp insert DNA was confirmed. The size marker used was a 100 bp DNA Ladder. The expression vector obtained in this manner was designated as pRET1138.

Example 12

Preparation of Recombinant *R. erythropolis* and Measurement of Enzyme Activity

The aforementioned expression vectors pRET1102, pRET1104, pRET1114 and pRET1138 were used for transformation of *R. erythropolis* MAK-34 strain and *R. erythropolis* JCM2895 (provided by RIKEN Japan), and the enzyme activity was measured. The aminoketone asymmetric reductase purified from MAK-34 strain has the abilities to react with 1-2-methylamino-1-phenyl-1-propanone as described in International Patent Publication WO02/070714, and to produce d-(1S, 2S)-pseudoephedrine. It was also reacted with 1-2-dimethylaminopropiophenone, 1-amino-2-butanone, etc. and production of each corresponding β-aminoalcohol was confirmed.

The activity assay was conducted by preparing a reaction solution with a cell density O.D.=5, 2% glucose and 0.2 M sodium phosphate buffer (pH 6.0), and 3% (1S, 2S)-2-(N-ethylamino)-1-phenyl-1-propanol (EAM) was contained in the reaction as substrate. A synthesis method for EAM is described in J. Am. Chem. Soc., Vol. 50, pp. 2287-2292, 1928. The reaction solution was incubated with shaking at 30° C. for 16 hours. Confirmation of (1S, 2S)-2-(N-ethylamino)-1-phenyl-1-propanol (EPE), which was β-aminoalcohol as the reaction product, was accomplished by HPLC. The column used was an Inertsil Ph-3 3.0×75 mm, the eluent was aqueous 7% acetonitrile and 0.05 M sodium phosphate buffer (pH 6.0), and the detection was carried out with UV (220 nm).

The results of the activity assay carried out in this manner are shown in Table 6. The pRET1104-introduced recombinant cells lacking the exogenous promoter region exhibited about the same activity as the pRET1102-introduced recombinant cells lacking the mak gene used as the control, and no recombinant enzyme expression was found.

With transformation of pRET1114 into MAK-34 strain, high specific activity was found compared to pRET1104. This indicated that the pRET1200 repA promoter region inserted into the vector functions as a promoter.

With transformation of pRET1138, the specific activity of the recombinant R. erythropolis MAK-34 strain was 37.7 µg/h·mL/O.D. while the specific activity of the recombinant R. erythropolis JCM2895 was 34.9 µg/h·mL/O.D., and therefore expression of the enzyme in R. erythropolis strain was confirmed.

TABLE 6

| Vector | MAK-34 | JCM2895 |
| --- | --- | --- |
| pRET1102 | 1.0 | 1.0 |
| pRET1104 | 0.7 | 2.0 |
| pRET1114 | 17.2 | not tested |
| pRET1138 | 37.7 | 34.9 |

Specific activity (units: µg/h·mL/O.D.)

Example 13

Purification of Enzyme

The recombinant cells obtained in Example 12 were cultured at 30° C. for 4 days in 100 mL of LB medium containing 100 µg/mL kanamycin, the cells were harvested by centrifugation at 12,000 rpm for 5 minutes and the protein having His-tag was purified with The QIAexpressionist Kit (Qiagen). Specifically, the cells were disrupted by ultrasonic treatment, the supernatant was obtained by centrifugation, and the protein was purified with a nickel chelate column. Upon applying the obtained protein to SDS-PAGE, a band of protein, which molecular weight is approximately 28,000, was observed. This molecular weight is roughly equivalent to the molecular weight of the aminoketone asymmetric reductase described in International Patent Publication WO02/070714, thus indicating that the aminoketone asymmetric reductase was produced in the recombinant Rhodococcus strains.

Example 14

Enzymatic Production of β-aminoalcohol

A 0.5 mL portion of reaction solution containing the purified enzyme (0.5 µg/mL) obtained in Example 13, 5 mM NADPH, 120 mM Tris-HCl (pH 7.5) and 5 mM EAM was reacted at 37° C. for 16 hours. The substrate and product (EPE) were analyzed by HPLC. The column used was an Inertsil Ph-3 3.0×75 mm, the eluent was aqueous 7% acetonitrile and 0.05 M sodium phosphate buffer (pH 6.0), and the detection was carried out with UV (220 nm). The results confirmed production of EPE.

Similarly, the purified enzyme or the crude enzyme extract obtained from the recombinant cells cultured as described in Example 13 was reacted with 1-2-dimethylaminopropiophenone and 1-amino-2-butanone, etc. and production of the corresponding β-aminoalcohols was confirmed.

INDUSTRIAL APPLICABILITY

As explained above, the plasmids and shuttle vectors of the invention are derived from Rhodococcus strains (especially Rhodococcus erythropolis and Rhodococcus rhodnii), and when utilized them for modification of the same bacteria by recombination, they allow creation of bacterial strains that more efficiently produce aminoketone asymmetric reductases. They also permit mass production of useful enzymes including aminoketone asymmetric reductases in transformants.

---

The invention claimed is:

1. An isolated DNA fragment having the nucleotide sequence set forth as SEQ ID NO: 35.

2. An isolated plasmid or an isolated partial DNA fragment thereof, comprising a DNA replication region having the nucleotide sequence set forth as SEQ ID NO: 35.

3. An isolated plasmid or an isolated partial DNA fragment thereof, comprising an ORF of SEQ ID NO: 1, 4, 5, 17, 22, 27, 29, 31 or 33 and a DNA replication region having the nucleotide sequence set forth as SEQ ID NO: 35.

4. An isolated plasmid or an isolated partial DNA fragment thereof, comprising an ORF of SEQ ID NO: 1, 4, 5, 17, 22, 27, 29, 31 or 33, a DNA replication region having the nucleotide sequence set forth as SEQ ID NO: 35, and a promoter region.

5. An isolated circular plasmid comprising the DNA fragment according to claim 1 and one or more restriction endonuclease cleavage sites selected from the group consisting of BamH I, EcoR I, Kpn I, Pvu II, Sac I, and Sma I, wherein the size of the isolated circular plasmid is approximately 5.4 kbp.

6. An isolated shuffle vector replicable in bacteria belonging to the genus *Rhodococcus* and *E. coli*, and comprising the DNA fragment according to claim 1 and a DNA region replicable in *E. coli*.

* * * * *